US012564589B2

(12) United States Patent
Gunjan

(10) Patent No.: US 12,564,589 B2
(45) Date of Patent: *Mar. 3, 2026

(54) METHODS FOR TREATING CANCER, REDUCING SIDE EFFECTS OF CANCER TREATMENT, AND PREVENTING THE RECURRENCE OF CANCER

(71) Applicant: Florida State University Research Foundation, Inc., Tallahassee, FL (US)

(72) Inventor: Akash Gunjan, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/082,283

(22) Filed: Mar. 18, 2025

(65) Prior Publication Data

US 2025/0288582 A1 Sep. 18, 2025

Related U.S. Application Data

(60) Provisional application No. 63/566,424, filed on Mar. 18, 2024.

(51) Int. Cl.
A61K 31/502 (2006.01)
A61K 31/167 (2006.01)
(Continued)

(52) U.S. Cl.
CPC .......... A61K 31/502 (2013.01); A61K 31/167 (2013.01); A61K 31/19 (2013.01); (Continued)

(58) Field of Classification Search
CPC .... A61K 31/502; A61K 31/167; A61K 31/19; A61K 31/37; A61K 31/437; (Continued)

(56) References Cited

U.S. PATENT DOCUMENTS

2021/0369725 A1 12/2021 Gunjan

FOREIGN PATENT DOCUMENTS

WO WO-2024081910 A1 * 4/2024 ........... A61K 31/506

OTHER PUBLICATIONS

Chen T et al. DNA damage response inhibition-based combination therapies in cancer treatment: Recent advances and future directions. Aging Cancer. 2022; 3: 44-67. https://doi.org/10.1002/aac2.12047 (Year: 2022).*

(Continued)

*Primary Examiner* — Savitha M Rao
*Assistant Examiner* — Elena Vladimirovna Vishnyakova
(74) *Attorney, Agent, or Firm* — Thomas |Horstemeyer, LLP

(57) ABSTRACT

The disclosure, in one aspect, relates to methods for treating cancer in a subject, the methods including at least the steps of administering at least one drug from each of at least two classes selected from an inhibitor of poly-ADP ribose polymerase (PARP inhibitor), an inhibitor of DNA-dependent protein kinase catalytic subunit (DNA-PKcs inhibitor), an inhibitor of wild-type isocitrate dehydrogenase (IDH inhibitor), an inhibitor of histone acetyltransferase (HAT inhibitor), an inhibitor of histone deacetylase (HDAC inhibitor), an inhibitor of DNA polymerase Θ (POLΘ inhibitor), an inhibitor of platelet-derived growth factor receptor (PDGFR inhibitor), and a DNA alkylating agent to the subject. In any of these aspects, the disclosed method allows for administering lower doses of the drugs in combination compared to administration as single drugs while preventing the recurrence of the cancer, preventing drug resistance of the cancer, and reducing side effects associated with cancer treatment.

13 Claims, 71 Drawing Sheets

(51) Int. Cl.

| | |
|---|---|
| *A61K 31/19* | (2006.01) |
| *A61K 31/37* | (2006.01) |
| *A61K 31/437* | (2006.01) |
| *A61K 31/444* | (2006.01) |
| *A61K 31/454* | (2006.01) |
| *A61K 31/495* | (2006.01) |
| *A61K 31/53* | (2006.01) |
| *A61K 31/5377* | (2006.01) |
| *A61N 5/10* | (2006.01) |
| *A61P 35/00* | (2006.01) |

(52) U.S. Cl.
CPC ............ *A61K 31/37* (2013.01); *A61K 31/437* (2013.01); *A61K 31/444* (2013.01); *A61K 31/454* (2013.01); *A61K 31/495* (2013.01); *A61K 31/53* (2013.01); *A61K 31/5377* (2013.01); *A61N 5/10* (2013.01); *A61P 35/00* (2018.01)

(58) Field of Classification Search
CPC .. A61K 31/444; A61K 31/454; A61K 31/495; A61K 31/53; A61K 31/5377; A61N 5/10; A61P 35/00
See application file for complete search history.

(56) References Cited

OTHER PUBLICATIONS

Zhang, H., et al. Mapping combinatorial drug effects to DNA damage response kinase inhibitors. Nat Commun. 14, 8310 (2023). https://doi.org/10.1038/s41467-023-44108-y (Year: 2023).*

Baxter, U.S., et al. (2022), Resistance to DNA repair inhibitors in cancer. Mol Oncol, 16: 3811-3827. https://doi.org/10.1002/1878-0261.13224 (Year: 2022).*

International Search Report for PCT/US2025/020317 dated Sep. 29, 2025.

Pratt, G., et al., A multi-centre phase I trial of the PARP inhibitor olaparib in patients with relapsed chronic lymphocytic leukaemia, T-prolymphocytic leukaemia or mantle cell lymphoma. Br J Haematol. Aug. 2018;182(3):429-433. doi: 10.1111/bjh.14793. Epub Jun. 23, 2017. PMID: 28643365.

Zeng, L., et al.,Combining PARP and DNA-PK Inhibitors With Irradiation Inhibits HPV-Negative Head and Neck Cancer Squamous Carcinoma Growth. Front Genet. Sep. 10, 2020;11:1036. doi: 10.3389/fgene.2020.01036. PMID: 33133138; PMCID: PMC7511754.

* cited by examiner

SF188 (WT H3.3)        KNS42 (H3.3 G34V)

PALB2 recruitment efficiency

Olaparib Treatment

Day 0     Day 19     Day 62

SF8628 H3.3K27M cells

Untreated control mice
Tumor upon engraftment

Side view          Belly view

Disseminated tumor after 2 months

Side view          Belly view

IDH1-H3 interaction in pcGBM2 wild type pediatric glioblastoma cells

IDH1-H3 interaction in DIPG IV H3.1K27M mutant pediatric glioblastoma cells

IDH1-H3 interaction in SF7761 H3.3K27M mutant pediatric glioblastoma cells

H3K27me3 levels

H3K27me3

H4 (Loading control)

Expt. #1     Expt. #2

SF7761 H3.3K27M cells

1

METHODS FOR TREATING CANCER, REDUCING SIDE EFFECTS OF CANCER TREATMENT, AND PREVENTING THE RECURRENCE OF CANCER

CROSS-REFERENCE TO RELATED APPLICATIONS

This application claims the benefit of U.S. Provisional Application Ser. No. 63/566,424, filed Mar. 18, 2024, which is incorporated herein by reference in its entirety.

BACKGROUND

Mutations in the DNA packaging and regulatory protein histone H3 and its primary sequence variants drive specific types of cancers, including pediatric cancers such as the incurable pediatric high-grade gliomas (pHGG) known as Diffuse Intrinsic Pontine Gliomas (DIPG) that occur in the brain stem, and Diffuse Midline Gliomas (DMG); these are responsible for about half of all childhood brain cancer fatalities. Around 80% of DIPG tumors carry the lysine 27 to methionine (K27M) mutation in histone H3 variants, usually the histone H3.3 variant. H3 K27M mutant high-grade pediatric gliomas such as DIPG and DMG do not currently have any approved therapies and are 100% fatal. Patients mostly receive experimental and/or palliative therapy until they pass away. FDA-approved drugs including AG120, Olaparib, and vorinostat used individually have been shown to be ineffective against DIPG. Additionally, H3.3 G34R/V (glycine 34 to arginine or valine) mutations are also found in about 20% of all the non-brain stem pHGG. Driver H3.3 K36M (lysine 36 to methionine) mutations in the H3F3B gene and H3.3 G34W/L (glycine 34 to tryptophan or leucine) mutations in the H3F3A gene encoding H3.3 are found in nearly all cases of skeletal tumors known as chondroblastomas and giant cell tumors of the bone (GCTB) respectively, and these also occur primarily in children and young adults. Although chondroblastomas and GCTB are non-fatal, they are primarily treated by surgery and have very high recurrence rates resulting in multiple surgeries, including mutilating and disfiguring limb amputations. Finally, about 10% of secondary Acute Myeloid Leukemia (s-AML) cases diagnosed per year also carry H3 mutations, including the H3K27M/I (lysine 27 to methionine or isoleucine). It would be advantageous to have available a therapeutic approach that targets specific molecular pathways that are aberrant only in the mutant tumor cells but not the wild type cells, i.e., a therapy in which only the H3 mutant tumor cells would be eliminated specifically, while the normal cells carrying wild type H3 would be largely spared.

Recurrence rates can vary by cancer type as well as within cancer type due to various factors including genetics, stage of cancer, patient lifestyle factors, treatments used, and others. Chondroblastomas and GCTB are particularly prone to recur, as are glioblastomas; ovarian, breast, prostate, bladder, and pancreatic cancers; melanomas; and soft tissue sarcomas. Cancer cells may mutate and become resistant to treatments that were previously effective if the same therapy is administered for a length of time. Additionally, standard dosages of many cancer therapies lead to numerous systemic side effects that negatively affect patient quality of life.

Despite advances in cancer treatment research, there is still a scarcity of cancer therapies that are effective in the treatment of cancers associated with H3 mutations, as well as homologous recombination deficient (HRD) subtypes of breast, ovarian, prostate, and pancreatic cancers; and melanomas, while reducing side effects and preventing or greatly limiting cancer recurrence. These needs and other needs are satisfied by the present disclosure.

SUMMARY

In accordance with the purpose(s) of the present disclosure, as embodied and broadly described herein, the disclosure, in one aspect, relates to methods for treating cancer in a subject, the methods including at least the steps of administering at least one drug from each of at least two classes selected from an inhibitor of poly-ADP ribose polymerase (PARP inhibitor), an inhibitor of DNA-dependent protein kinase catalytic subunit (DNA-PKcs inhibitor), an inhibitor of wild-type isocitrate dehydrogenase (IDH inhibitor), an inhibitor of histone acetyltransferase (HAT inhibitor), an inhibitor of histone deacetylase (HDAC inhibitor), an inhibitor of DNA polymerase $\Theta$ (POL$\Theta$ inhibitor), a platelet derived growth factor receptor inhibitor (PDGFR inhibitor), and a DNA damaging agent such as radiation or an alkylating agent such as Temozolomide to the subject. In one aspect, the PARP inhibitor can be Olaparib or another FDA approved PARP inhibitor, such as the brain penetrant niraparib and the DNA-PKcs inhibitor can be a pre-clinical drug such as, for example, NU7441 or the brain penetrant VX-984. In one aspect, VX-984 may be more soluble, more available, and better tolerated compared to NU7441; however, either drug may be of use in the disclosed compositions and methods at low doses designed to minimize side effects. Additionally, any of the disclosed drug combinations can be combined with the precise delivery of radiation to the tumor cells to generate DNA breaks and promote more tumor cell killing. In any of these aspects, due to the synergistic effects of these drugs when used in combination, both with and without radiation or other agents that induce DNA damage, the disclosed method allows for administering lower doses of the drugs in combination compared to administration as single drugs while preventing the recurrence of the cancer, preventing drug resistance of the cancer, and reducing side effects associated with cancer treatment.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A: Histone variant H3.3 is rapidly recruited to sites of laser induced DNA damage in living cells. HCT116 human colon carcinoma cells were transiently co-transfected with expression constructs for H3.3-mEmerald and RFP-PCNA. Laser microirradiation using a 405 nm laser that causes a variety of DNA damage was carried out within the area enclosed within the circle and rectangle as described in the Methods, and results in the robust recruitment of PCNA at the DNA damage sites as has been shown previously. Rapid recruitment of H3.3 within 45 seconds of DNA damage was observed, soon after the start of PCNA recruitment, and usually persisted for about ~45-60 mins. Qualitatively similar results were obtained with SVGp12 human embryonic glial cell line and RPE retinal pigment epithelial cells. Percent recruitment was calculated by dividing the number of cells recruiting H3.3 by the number of cells recruiting PCNA in the same cells. n=number of cells analyzed. Scale bar=5 μm. Time stamp is in hours:minutes:seconds:milliseconds. FIG. 1B: Canonical replication-coupled histone H3.1 is not recruited to sites of laser induced DNA damage. HCT116 cells expressing H3.1-GFP and Cerulean-PCNA (Cer-PCNA) were treated as in (FIG. 1A) to cause DNA damage. Laser irradiation results in photobleaching of existing fluorescent molecules in the damaged area which appears dark due to the nearly immobile nature of canonical core histones. No recruitment of H3.1 was observed, while PCNA was clearly recruited to DNA damage site. Identical results were obtained for histone H3.2-GFP. FIG. 1C: Stable knockdown of H3.3 in human cells. Whole cell extracts from individual clones exhibiting different degrees of H3.3 knockdown following lentiviral mediated transduction of shRNAs targeting both the genes encoding histone H3.3 were assayed using histone H3.3 specific antibodies (Millipore Sigma). Total levels of histone H3 and H4 were not appreciably affected. The percentage knockdown for each clone shown at the bottom of the lanes was quantitated by measuring fluorescence intensity of the H3.3 band relative to the signal from the H4 band on a Li-Cor Odyssey imager. The cell line ("H3.3KD") corresponding to the clone that shows a ~90% reduction in H3.3 levels was selected for all subsequent studies involving H3.3 knockdown cells. The control cell line ("LUC") was stably transduced with luciferase shRNAs. FIG. 1D: Reduction of H3.3 levels results in the accumulation of high levels of spontaneous endogenous DSBs. The presence of endogenous damage in H3.3KD and control LUC cells was determined by Western blotting of whole cell extracts using the indicated antibodies. FIG. 1E: Knockdown of H3.3 results in greatly enhanced sensitivity to DNA damage by the alkylating agent methyl methane sulfonate (MMS). Indicated cells were treated with or without 0.0175% MMS for 2 hours after which the MMS was washed away and the cells allowed to recover. 48 hours after MMS treatment, the viability of the cells was scored by flow cytometry using the violet fluorescent Live/Dead cell staining kit (Invitrogen) following the manufacturer's instructions. The error bars represent the standard error of the mean from 3 independent experiments. Significant differences between treatments are indicated by p values determined using a t-test. FIG. 1F: H3.3 knockdown results in sensitivity to ionizing radiation. The H3.3KD and control LUC cells were treated with 2 Gy of ionizing radiation (IR) using an X-RAD320 irradiator and allowed to form colonies for 2-3 weeks to determine viability. FIG. 1G: H3.3KD cells are sensitive to the replication inhibitor Mimosine (Mimo). Cells were treated with 0.5 mM Mimo and processed as described in FIG. 1E.

FIG. 2A: Cancer-associated H3.3 mutants mostly fail to be recruited to sites of laser induced DNA damage. HCT116 cells expressing the indicated mutant H3.3-mEmerald and RFP-PCNA were treated as in (FIG. 1A) to cause DNA damage within the areas indicated in red. Although PCNA was recruited in nearly all cases, recruitment of mutant H3.3 was not observed for most cells. The few cells showing recruitment of mutant H3.3 exhibited weak recruitment to the DNA damage sites, or failed to retain the signal at the damage sites for longer than a few minutes compared to the WT H3.3. The number of cells recruiting mutant H3.3 relative to PCNA to the damage sites are indicated for each mutant. Scale bar=10 μm. FIG. 2B: Cancer-associated histone H3.3 mutant cells accumulate high levels of endogenous DNA damage. The H3.3KD cell line was reconstituted with either wild type or the indicated mutant H3.3 tagged with a FLAG epitope and the presence of γH2A.X foci was measured in unperturbed cells by immunofluorescence (IF) as described in the Methods. Images were acquired under identical conditions for all the samples. Scale bar=25 μm. FIG. 2C: Quantitation of the γH2A.X foci in cells expressing the H3.3K27M mutation shown in FIG. 2D. FIG. 2D: Pediatric patient-derived glioblastoma cells carrying the H3.3G34V mutation (KNS42) accumulates high levels of spontaneous DSBs compared to cells carrying WT H3.3 (SF188). γH2A.X foci were measured in the patient derived cells as described above in 2B. Scale bar=25 μm.

FIG. 3A: H3.3KD cells are defective in the recruitment of HR factor PALB2 to DSBs in living cells. LUC and H3.3KD cells were co-transfected with PALB2-YFP and RFP-PCNA and their recruitment to sites of DNA damage in living cells was measured as described in FIG. 1A. The number of cells recruiting PALB2-YFP relative to RFP-PCNA are shown. p-values were derived using the Fisher's Exact test. n=number of cells. FIG. 3B: H3.3KD cells are much slower in the recruitment of single strand DNA binding protein RPA70 to DSBs that LUC cells. Cells were co-transfected with RPA70-GFP its recruitment kinetics were measured as described in FIG. 1A. The time taken to accumulate a GFP signal higher than the pre-damage GFP signal at the DNA damage sites was recorded. FIG. 3C: NHEJ promoting DSB repair pathway choice factor 53BP1 is recruited faster to DSBs in H3.3KD cells. Time taken for the recruitment of 53BP1-GFP to DSBs was measured as described in FIG. 3B. FIG. 3D: H3.3KD cells exhibit slower DSB repair kinetics. H3.3KD and LUC cells were exposed to a low 0.25 Gy dose of ionizing radiation (IR) to induce DSBs, following which cells were fixed at 15 min, 1 h and 4 h and processed for IF to measure γH2A.X foci as described in the Methods. Images were acquired under identical conditions for all the samples. LUC cells had completed most of their DSB repair by 4h but H3.3KD still exhibited high numbers of γH2A.X foci. Scale bar=25 μm. FIG. 3E: H3.3KD cells are severely defective in HR mediated DSB repair. Fluorescence based assay for HR mediated DSB repair was performed in DR-GFP carrying LUC and H3.3KD cells as described previously. GFP positive cells were scored by flow cytometry. FIG. 3F: H3.3KD cells exhibit high levels of mutagenic- NHEJ. Fluorescence based mutagenic-NHEJ assay was performed in EJ-RFP based LUC and H3.3KD cells by the addition of 1 µM Shield1 reagent and 100 nM Triamcinolone Acetonide to induce the DSB as described previously. FIG. 3G: H3.3KD cells have higher plasmid rejoining efficiency. LUC and H3.3KD cells were co-transfected with a mCherry expressing plasmid as a control for transfection efficiency and a NHEJ substrate in the form of an eGFP-C1 plasmid linearized with Age I restriction endonuclease that cleaves between the promoter and the eGFP open reading frame. NHEJ mediated re-ligation of the DSB created by Age I results in green fluorescence. Green fluorescing cells were quantitated by flow cytometry and the data was normalized to red fluorescence from mCherry.

FIG. 4A: H3.3KD cells are sensitive to NHEJ inhibition. H3.3KD cells are sensitive to inhibition of alt-NHEJ using the PARP inhibitor (PARPi) Olaparib (OLA) and c-NHEJ using the DNA-PKcs inhibitor NU7441, both at 1 µM. Concomitant induction of DSBs using 2Gy IR synergizes strongly with NHEJ inhibition to selectively eliminate H3.3KD cells. For this assay, equal number of cells were seeded in triplicate at low density in multi-well plates and treated with the indicated drugs with or without radiation. Surviving cells were dissociated and counted one week later, before the untreated cells reached confluency. FIG. 4B: Pediatric patient-derived H3.3 mutant glioblastoma cells are sensitive to Olaparib in vitro. Mutant cells were significantly sensitive to combination treatment with OLA+IR, whereas glioblastoma cells carrying WT H3.3 remained largely unaffected. The assay was performed as described above for FIG. 4A. p-values were derived from an ANOVA with a post hoc Tukey Honest Significant Difference test. FIG. 4C: Mice harboring patient derived H3.3K27M mutant tumors survive longer upon Olaparib treatment. A Kaplan-Meier plot depicting the relative survival data for the vehicle versus drug treated mice is shown. Immunocompromised R2G2 mice (Invigo) were engrafted with luciferase expressing SF8628 H3.3K27M mutant cells and treated with the vehicle DMSO or OLA+IR according to the following schedule. For the first two weeks of treatment, the mice received either the vehicle (5% DMSO+95% PBS) or 50 mg/kg of OLA in DMSO+PBS by intraperitoneal injections (IP) along with 2 Gy of IR using a two day on followed by one day off schedule, for a total of 10 sessions to deliver 20 Gy. After this, the mice received either DMSO or only 37.5 mg/kg of OLA 5 days (Monday-Friday) per week until the humane or clinical end point was met and the animal was euthanized. FIG. 4D: Example of a mouse harboring SF8628 H3.3K27M tumor cells where monotherapy with PARPi such as OLA resulted in initial regression of the tumor, but a subsequent rebound of the tumor. Bioluminescent imaging of the mice was performed as described in the Methods on the indicated days since the start of treatment. FIG. 4E: Variable sensitivity of SF8628 H3.3K27M mutant tumor cells following passage through mice treated with OLA. Once clinical or humane endpoints were reached, tumors were removed following euthanasia of mice that had been treated with DMSO or OLA plus 20 Gy IR (total). Cells were cultured from these tumors and their sensitivity to OLA was tested again as described in FIG. 4A. Although the tumor cells were still sensitive to OLA, the magnitude of their sensitivity was variable, suggestive of possible development of OLA resistance in some tumors. FIG. 4F: Patient derived H3.3 mutant glioblastoma cells are very sensitive to combination treatment with inhibitors of multiple NHEJ pathways in vitro. Cells were treated with the indicated combinations of alt-NHEJ and c-NHEJ inhibitors either with or without 1 Gy IR as described in FIG. 4A. All patient derived H3.3 mutant cells tested were very sensitive to the combination treatment while the cells carrying WT H3.3 remained unaffected. p-values were derived from an ANOVA with a post hoc Tukey Honest Significant Difference test. FIG. 4G: Combination treatment with c-NHEJ and alt-NHEJ inhibitor along with radiation blocks the growth of KNS42 H3.3G34V mutant tumors in mice. Immunocompromised NIH III Nude mice (Charles River) were engrafted with the pediatric patient derived KNS42 H3.3G34V mutant tumors and were treated as described in 4C except that the drug treated mice received 25 mg/kg OLA and 5 mg/kg NU7441.

FIG. 5A: DSBs accumulate predominantly in heterochromatin in H3.3KD cells. Unperturbed LUC and H3.3KD cells were processed for IF as described in methods using the indicated antibodies. Nuclei were stained with DAPI. The plot on the right shows quantitation of the microscopy data performed using ImageJ. p-values were derived using the Fisher's Exact test. Scale bar=5 µm. FIG. 5B: RFP-PCNA is excluded from the nucleoli of non-S phase cells. LUC cells were co-transfected with the indicated expression constructs and live cell imaging was performed 24 hours post-transfection. Nucleoli are located within the areas enclosed by the dashed white lines and exclude RFP-PCNA, while colocalizing with both Cerulean fluorescent protein-tagged Fibrillarin (Fibrillarin-CER, a nucleolar marker) and HP1β-GFP (a marker for heterochromatin). Identical results were obtained with H3.3KD cells. Scale bar=5 µm. FIG. 5C: H3.3KD cells exhibit weak recruitment of PCNA to DNA damage sites in rDNA heterochromatin within nucleoli. DNA damage using a 405 nm laser was inflicted within rDNA heterochromatin (within the nucleoli) or in euchromatin (outside the nucleoli) in LUC and H3.3KD cells transiently transfected with RFP-PCNA as described in FIG. 1A. The recruitment of PCNA to DNA damage sites within rDNA heterochromatin versus euchromatin was measured over time and still images from before and 10 minutes after the DNA damage are shown. Notice the weak PCNA signal in H3.3KD nucleolus compared to the LUC nucleolus. Scale bar=5 µm. FIG. 5D: Recruitment of PCNA to DNA damage sites in euchromatin (outside nucleoli) is not significantly different between LUC and H3.3KD cells. Cells were transfected with RFP-PCNA and processed as described in 5C. Data of PCNA recruitment from the indicated number of cells (n) is plotted here and p values for time points at 203 seconds as well as 603 seconds are provided. FIG. 5E: H3.3KD cells exhibit a severe delay in the recruitment of RFP-PCNA to DNA damage sites within rDNA heterochromatin. LUC and H3.3KD cells were transfected with RFP-PCNA and processed as described in FIG. 5D. FIG. 5F: Sensing of DSBs is unaffected in H3.3 deficient cells. LUC and H3.3KD cells were transiently transfected with MRE11-YFP and processed as described in FIG. 5C to measure the time taken for the recruitment to DSBs in euchromatin versus rDNA heterochromatin. FIG. 5G: Recruitment of HR factor PALB2 is inefficient in H3.3KD cells in both euchromatin and heterochromatin. Recruitment of PALB2-YFP at laser induced DSBs was measured essentially as described in FIG. 5C. p-values were derived using the Fisher's Exact test. FIG. 5H: 53BP1 is precociously recruited to DSBs in rDNA heterochromatin in H3.3KD cells. 53BP1-GFP recruitment to DSBs in euchromatin versus rDNA heterochromatin in LUC and H3.3KD cells was measured as in 5C. p-values were derived using the Fisher's Exact test.

FIG. 6A: RNF168 recruits faster to DSBs in H3.3KD cells. LUC and H3.3KD cells were transiently transfected with RNF168-GFP and its timing of recruitment to DSBs was assayed as described in FIG. 1A. FIG. 6B: Histone H1.0 recovers faster and to a greater extent in H3.3KD cells in the absence of DNA damage. FRAP was used to measure the recovery of H1.0-GFP in LUC and H3.3KD cells after photobleaching using a 488 nm laser (which does not cause DNA damage under the conditions used) as described previously. Error bars were omitted for clarity. n=number of cells analyzed. FIG. 6C: Histone H1.0 recovers to a greater extent in H3.3KD cells at DNA damage sites. The recovery of H1.0-GFP in LUC and H3.3KD cells after simultaneous DNA damage and photobleaching using a 405 nm laser was followed as in FIG. 6B. Histone H1.2 recovers to a greater extent in H3.3KD cells at DNA damage sites. The dynamics of H1.2-GFP was followed as in FIG. 6C.

(FIG. 8A) Enhanced rate of micronuclei formation in H3.3KD cells. Micronuclei score was determined as described previously from 1000 LUC and H3.3KD cells. The difference between LUC and H3.3 was trending towards significance (p=0.12). (FIG. 8B) Increased incidence of lagging chromosomes during mitosis in H3.3KD cells. Quantitation of lagging chromosomes from 100 anaphases in LUC and H3.3KD cells is shown. (FIG. 8C) Flies deficient in H3.3 accumulate endogenous DNA damage. Western blot showing the levels of γH2A.v (the fly homolog of mammalian γH2A.X) in adult flies of the indicated genotypes: wild-type (WT; Oregon-R), heterozy-gous (het, with just one H3.3 allele) and rescue (res, which completely lacks H3.3, but its sterility is rescued by an extra copy of H3.2 driven by the H3.3B promoter). A sample from flies treated with 10 Gy IR is included as a positive control for γH2A.v signal. Histone H4 levels are shown as loading control for blot. (FIG. 8D) Flies deficient in H3.3 are hypersensitive to DNA damaging agents. 100 third instar

*Drosophila* larvae from WT and heterozygous (H3.3 Het) genotype carrying just one out of four alleles of H3.3 were exposed to either IR or ultra violet (UV) light and their development into adult flies was monitored for over two weeks. The difference in DNA damage sensitivity between WT and H3.3 Het was trending towards significance. (FIG. 8E) Flies expressing H3.3K27M lose viability rapidly upon exposure to ionizing radiation. Adult flies carrying the H3.3K27M mutant under the control of UAS and driven by heat shock inducible GAL4 driver were exposed to 37° C. for 2 hours prior to delivery of 30 Gy IR. Viable flies remaining were scored daily for a week. There was no loss of viability in any of the flies that did not receive either heat shock, IR or both. (FIG. 8F) Budding yeast strains carrying H3G34R mutant are sensitive to genotoxic agents. Expo-nentially growing yeast strains carrying either WT or G34R mutant H3 were treated with or without the indicated amounts of the indicated genotoxic agents for 90 minutes prior to plating 1000 cells on rich media plates in triplicate to determine viability by colony enumeration. (FIG. 8G) Budding yeast strains carrying H3K27M mutant are sensi-tive to the DNA stand breakage reagent Bleocin. Yeast cells carrying the H3K27M mutant were treated with Bleocin for 60 minutes and processed as described in FIG. 8F.

(FIG. 9A) Characterization of the expression of epitope tagged mutant H3.3 in HCT116 cells. HCT116 derived H3.3KD cells were stably reconstituted with FLAG-tagged WT or the indicated mutant H3.3. Western blotting using the indicated antibodies was performed on whole cell lysates prepared from the cells. Histone H4 levels are shown as a loading control. (FIG. 9B) The association of mutant H3.3 with chromatin is indistinguishable from that of WT H3.3 as determined by high salt washes. Crude nuclear pellets from cells expressing the epitope tagged WT or mutant H3.3 shown in FIG. 9A were washed with buffer containing increasing amount of salt for 30 minutes on ice with tap mixing every 5 minutes. The supernatant was discarded and the pellet boiled in SDS gel loading buffer and resolved on an 18% polyacrylamide gel prior to processing for Western blotting using FLAG or H3 antibodies.

(FIG. 10A) H3.3KD cells express nor-mal amounts of major DNA repair factors. Western blotting using the indicated antibodies was performed on whole cell lysates prepared from LUC and H3.3KD cells. Histone H4 levels serve as a loading control. (FIG. 10B) The checkpoint responses upon replication arrest are fully intact in H3.3KD cells. Cells were treated with 0.5 mM mimosine (Mimo), 2 mM thymidine (Thy), and 2.5 mM hydroxyurea (HU) for 8 hours prior to preparing whole cell lysates in the presence of protease and phosphatase inhibitors and Western blotting using the indicated antibodies. (FIG. 10C) The DNA damage checkpoint is fully functional in response to ionizing radia-tion in cells expressing H3.3 mutants. Cells expressing the WT or mutant H3.3 were treated with 2 Gy IR and harvested at the indicated time points. Whole cell lysates were pre-pared and Western blotting performed as described in FIG. 10B using the indicated antibodies. (FIG. 10C) H3.3KD cells exhibit high levels of mutagenic-NHEJ mediated DSB repair. Whole cell extracts were prepared from the cells used for the mutagenic-NHEJ assay shown in FIG. 3F and analyzed by Western blotting using the indicated antibodies.

The level of the DsRed protein correlates with the degree of mutagenic-NHEJ mediated DSB repair in the cells.

Figure 11:
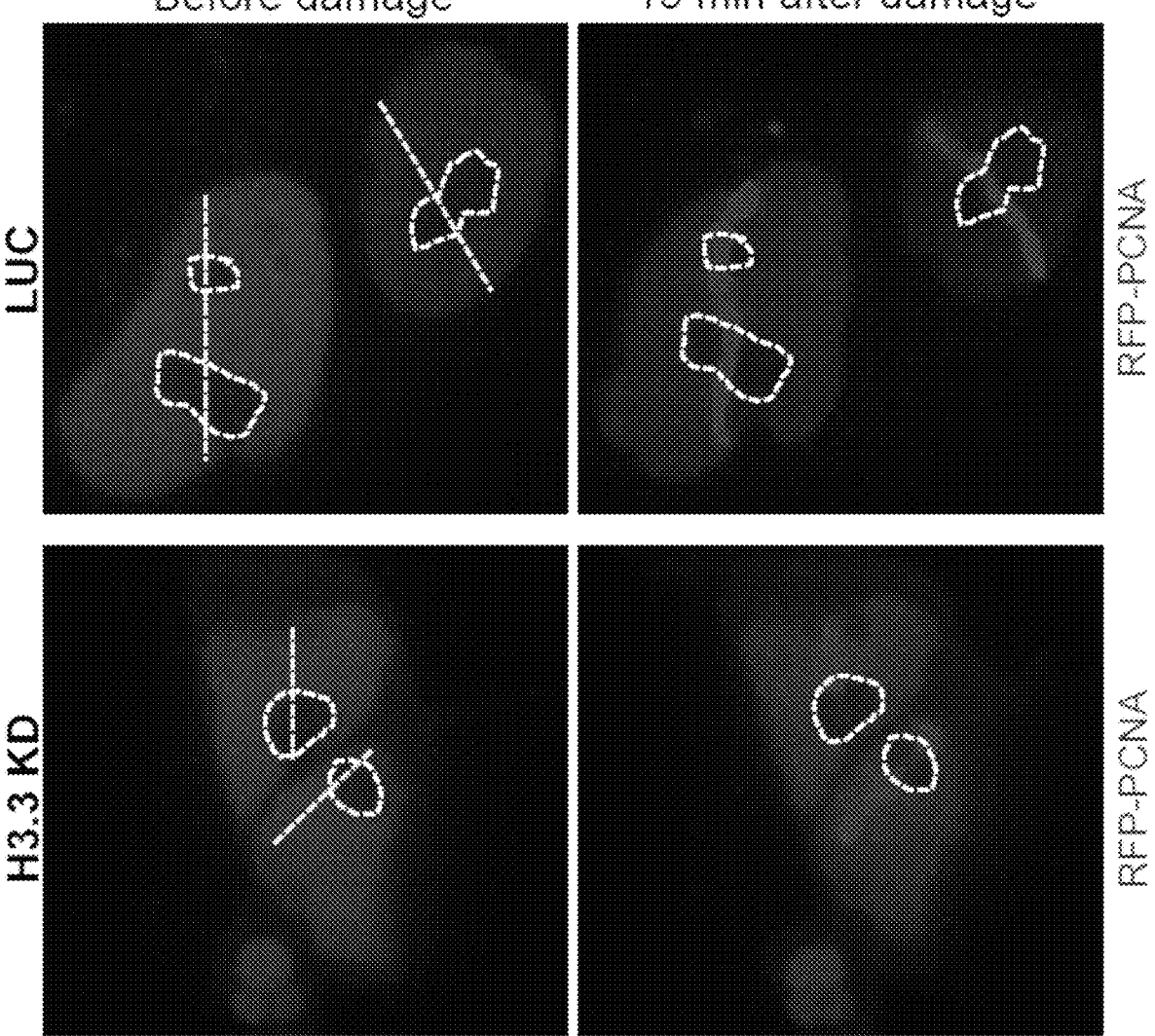

FIG. 11 shows H3.3 deficiency results in poor recruitment of PCNA to DNA damage sites within rDNA heterochromatin in nucleoli even at later time points, indicating that H3.3 deficiency may specifically impair DNA repair within heterochromatin. Cells were processed as described for FIG. 5C.

Figure 12A:
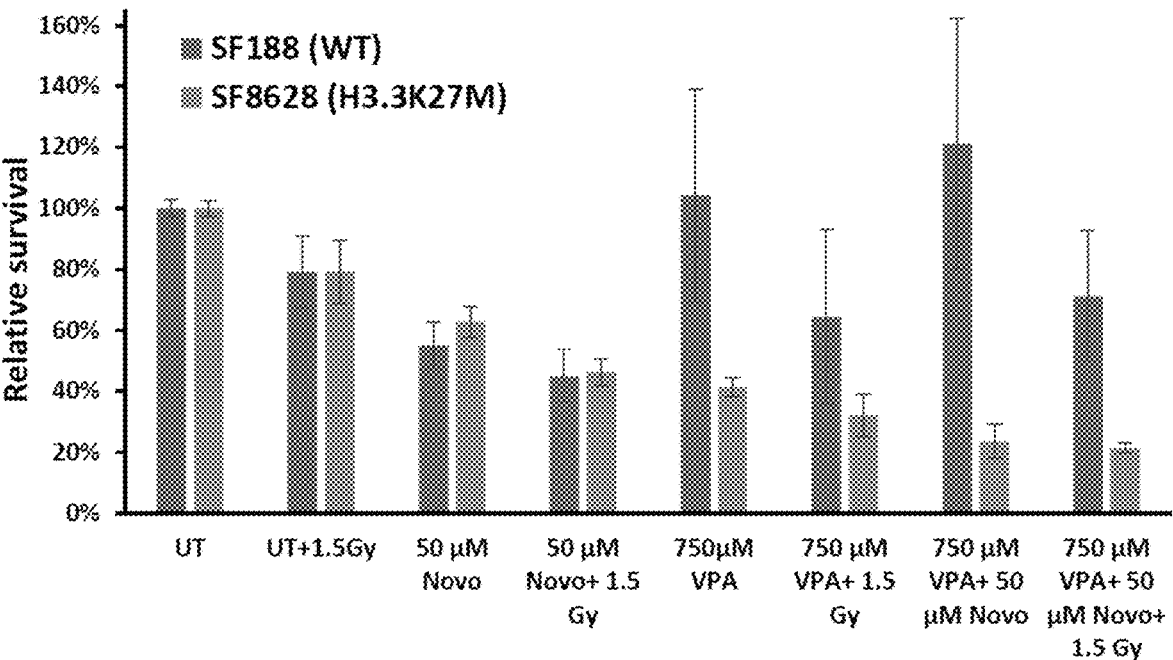
Figure 12B:
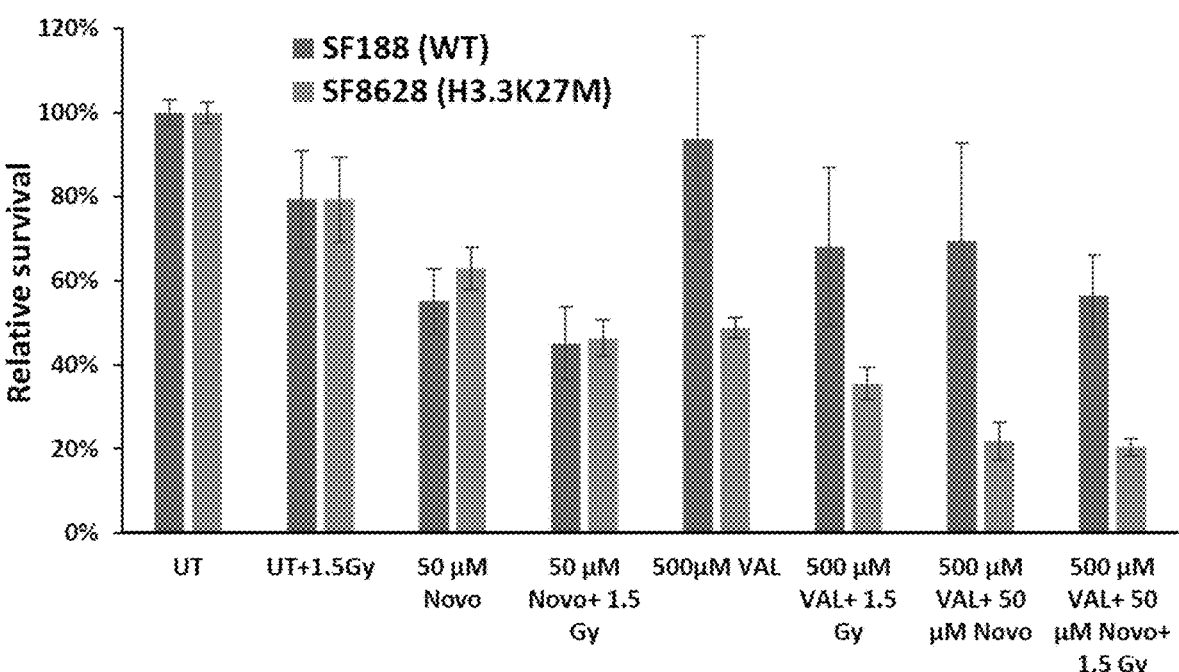

FIGS. 12A-12B show that only H3 mutant pediatric high-grade glioma (pHGG) cells are specifically sensitive to combinations of older FDA-approved drugs such as histone deacetylase (HDAC) inhibitors valproic acid or sodium valproate, and DNA Polymerase theta (POLΘ) inhibitor Novobiocin in combination with ionizing radiation (IR). Wild-type (WT) or H3.3K27M mutant pediatric high grade glioma cells were treated with the indicated concentrations of the different inhibitors with or without 1.5 Gy IR treatment prior to counting surviving cells after 7 days. Error bars represent standard deviation. VPA=Valproic Acid and VAL=Sodium Valproate, both of which are HDAC inhibitors; Novo=Novobiocin, a POLΘ inhibitor. This data clearly shows that HDAC inhibitors specifically target the H3.3K27M mutant pediatric high grade glioma cells, while the pediatric gliomas carrying wild-type H3.3 are not appreciably affected. Furthermore, although both the WT and H3.3K27M mutant cells showed similar sensitivity to the POLΘ inhibitor, a synergistic killing effect was only observed for the H3.3K27M mutant cells when POLΘ and HDAC inhibitors were combined. Note that this assay cannot accurately determine cell survival below ~20% due to the presence of significant numbers of senescent cells that are still alive, but which are not capable of proliferating or dividing any more.

Figure 13:
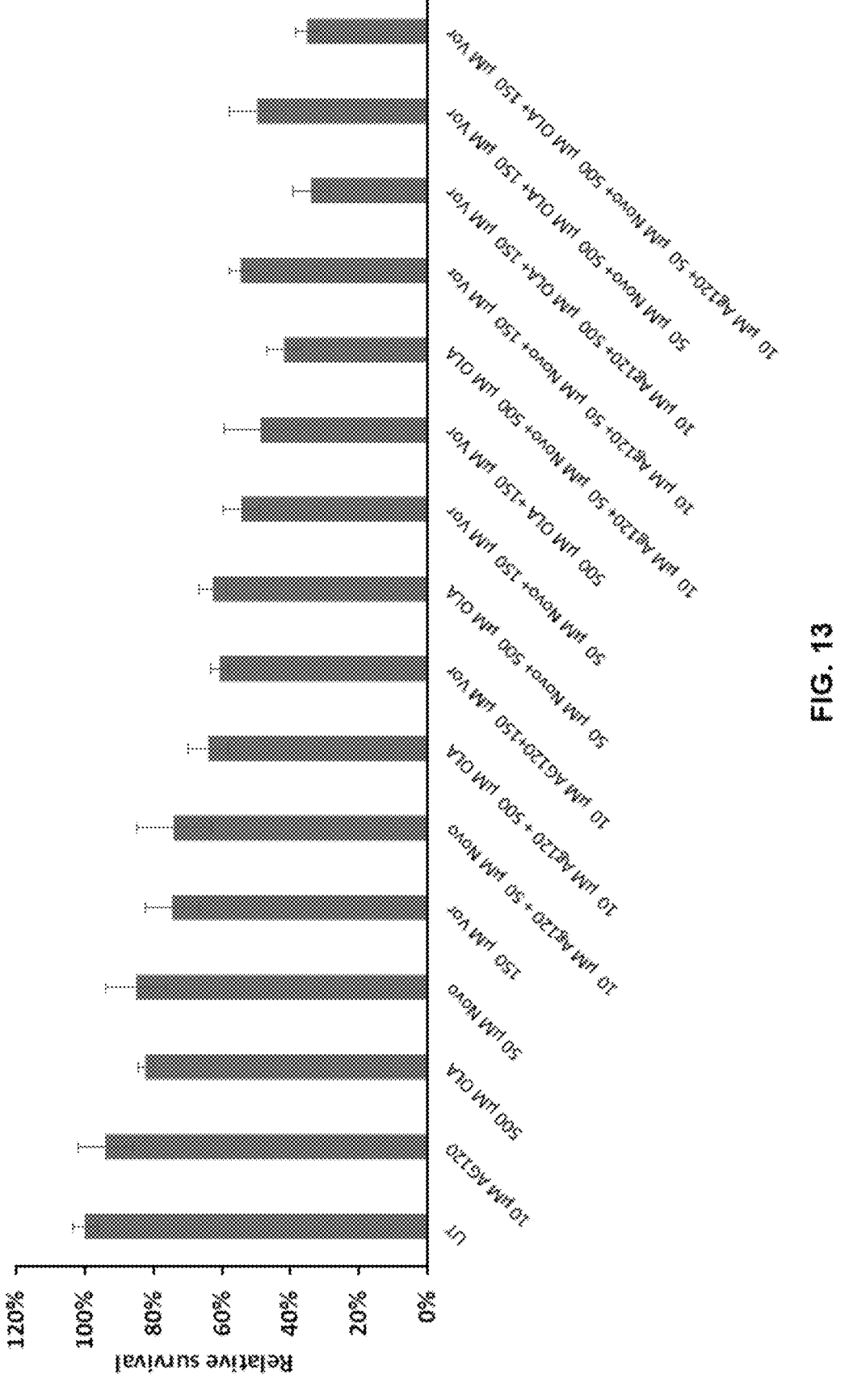

FIG. 13 shows that H3.3K27M mutant pediatric high grade glioma (pHGG) cells are increasingly sensitive to combinations of different classes of FDA-approved drugs. H3.3K27M mutant SF8628 pHGG cells were treated with the indicated concentrations of the different inhibitors for 7 days prior to counting the surviving cells. Error bars represent standard deviation. Ag120=Ivosidenib, an Isocitrate Dehydrogenase 1 (IDH1) inhibitor; Ola=Olaparib, a Poly-ADP Ribose Polymerase (PARP) inhibitor; Novo=Novobiocin, a DNA Polymerase Theta (POLΘ) inhibitor; Vor=Vorinostat, a histone deacetylase (HDAC) inhibitor. This data clearly shows that, in general, H3.3K27M mutant cells show increasing sensitivity to treatment with each additional inhibitor from a different class, for combinations of at least three, and possibly four, different inhibitors.

Figure 14:
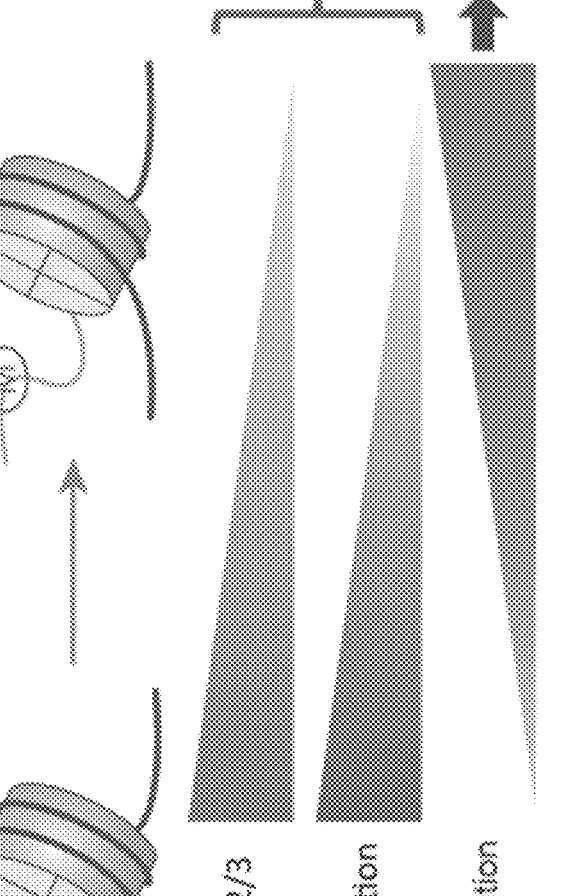

FIG. 14 shows targeting aberrant epigenetic pathways in the 100% fatal H3K27M mutant pediatric High-Grade Gliomas (pHGG) including Diffuse Intrinsic Pontine Gliomas (DIPG) using combination therapeutics. Normal wild type (wt) cells carry a lysine (K) amino acid at position 27 in all the major histone H3 proteins that can be trimethylated (indicated by the three circles). This lysine is mutated to a methionine (M) amino acid upon which it cannot be methylated and serves to drive the vast majority of pHGG cancers by dramatically reducing the levels of repressive DNA and histone H3K27 di- and trimethylation (H3K27me2/3), while increasing the levels of histone acetylation. These epigenetic changes can be exploited for therapeutic purposes and targeting defects in histone acetylation and histone methylation (but not DNA methylation) individually for treating pHGG has been suggested previously in the literature. However, the combined approach of targeting histone acetylation along with histone and DNA methylation simultaneously is far superior, especially when combined with targeted radiation of the tumor for the following three reasons. First, the simultaneous inhibition of multiple pathways makes it nearly impossible for the cancer cells to mutate multiple pathways at the same time and survive to give rise to drug resistance. Next, since the targeted pathways are independent of each other, drugs that inhibit them act additively or synergistically with each other when used in combination and require lower doses, resulting in minimal side effects. Finally, targeted radiation ensures high levels of DNA double strand breaks (DSBs) specifically in the tumor cells to further enhance the effects of the drugs, rather than relying on naturally occurring DSBs in the tumor cells when the drugs are used by themselves in the absence of radiation. The combination therapy described here would mostly involve drugs that are Food and Drug Administration (FDA) approved for treating other conditions but have been neither suggested nor tested previously for treating these fatal childhood brain tumors.

Figure 15:
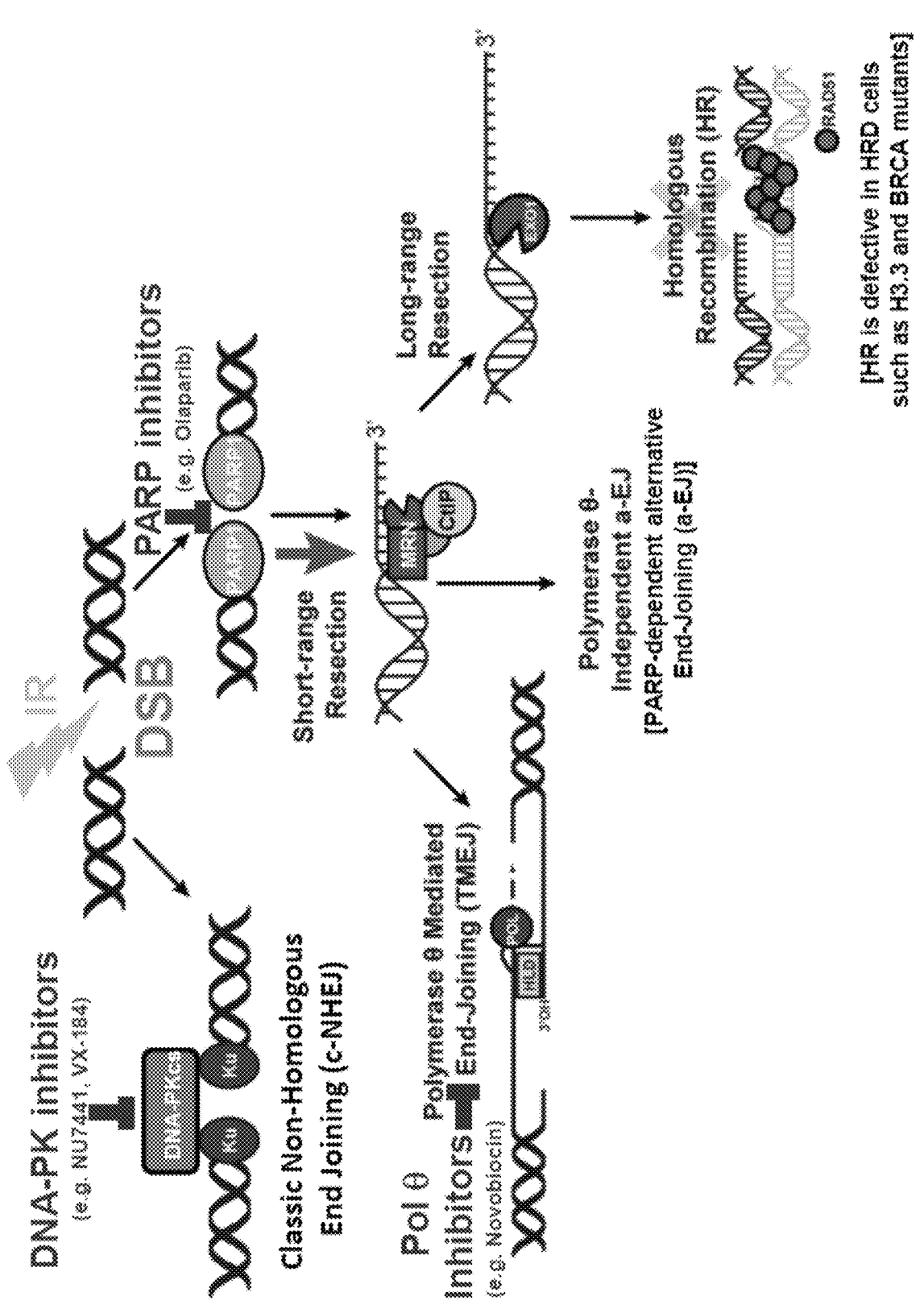

FIG. 15 shows a highly simplified view of DNA Double Strand Break (DSB) repair by Homologous Recombination (HR), classic Non-Homologous End Joining (c-NHEJ), Alternative-End Joining (a-EJ) pathways, Theta Mediated End Joining (TMEJ), and their inhibitors. In the absence of HR, cells can repair DSBs via one of the three error-prone NHEJ pathways that largely function independently of each other. Blocking all three pathways in HRD cells such as those carrying cancer-associated H3.3 or Homologous Recombination (HR) pathway mutations in genes such as BRCA1 or BRCA2 will preclude all DSB repair in these cells.

Figure 16A:
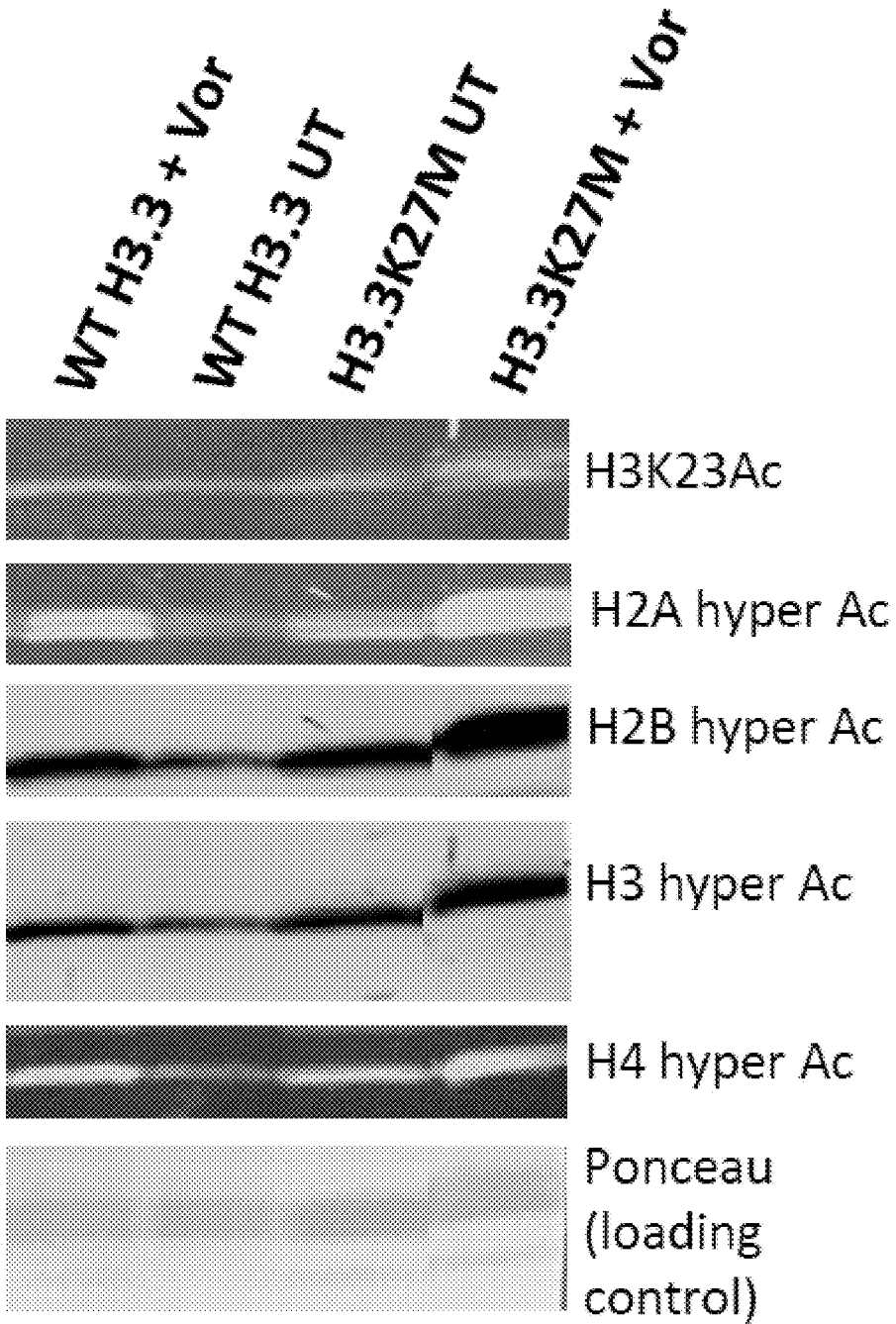
Figure 16B:
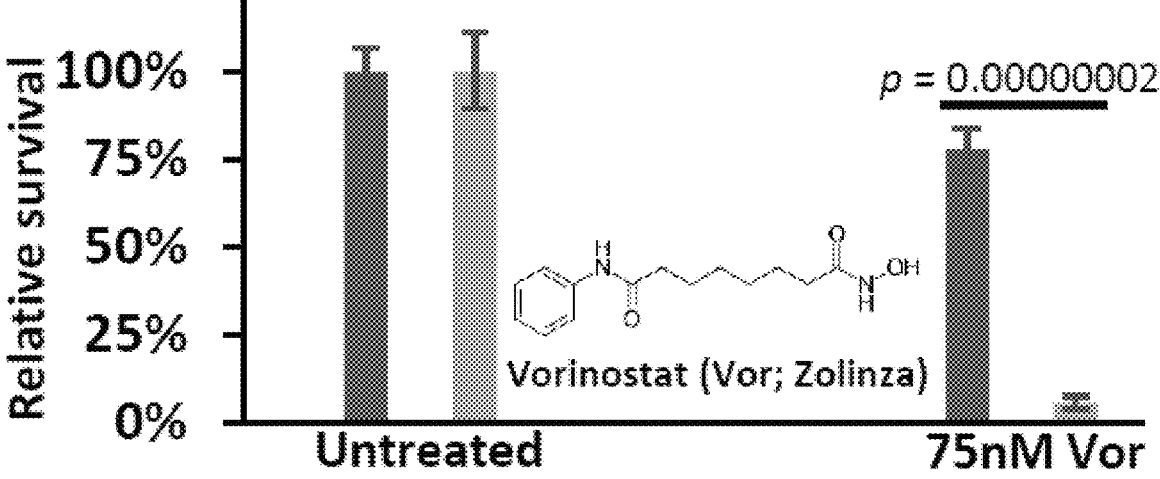
Figure 16C:
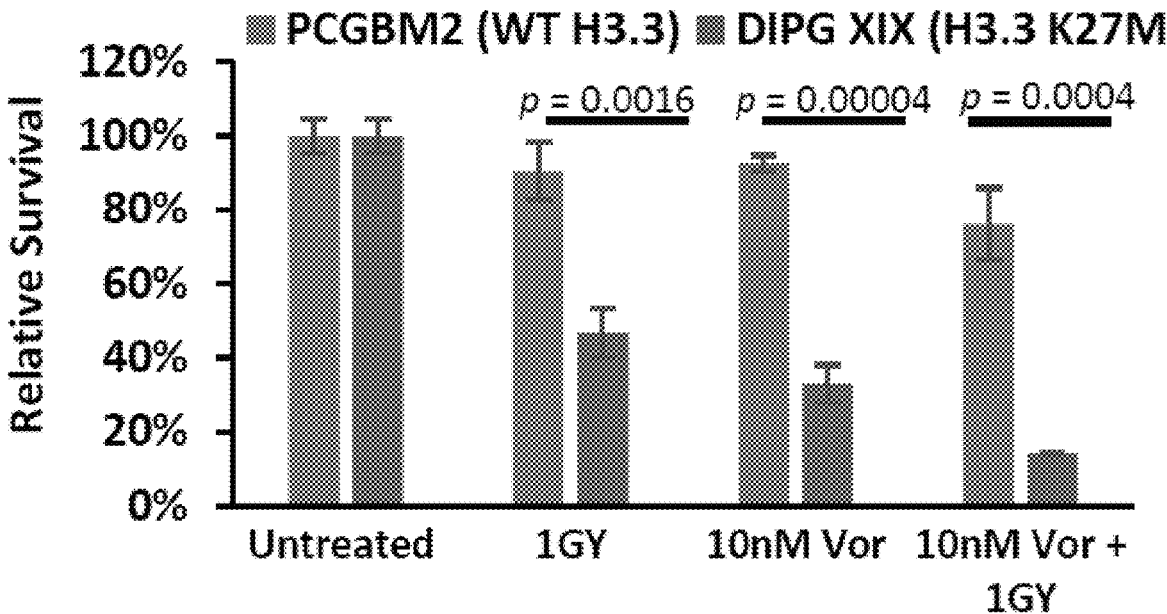

FIGS. 16A-16C show Patient derived H3.3 K27M mutant Diffuse Intrinsic Pontine Glioma (DIPG) cells exhibit high levels of histone acetylation and can be specifically eliminated following treatment with histone deacetylase inhibitors (HDACi). (FIG. 16A) H3.3 K27M mutant DIPG cells exhibit high levels of acetylation that can be enhanced even further to cytotoxic levels upon treatment with HDACi. Patient derived glioblastoma cells carrying either wild type (WT) H3.3 or the H3.3 K27M mutant were either left untreated (UT) or treated with 75 nM Vorinostat (Vor) for 16 hours before harvesting them, acid extracting total histones and processing them for Western blotting using antibodies specific to the indicated acetylated (Ac) histones. Ponceau staining of the total histones is shown as a loading control. (FIG. 16B) Treatment of cells with HDACi specifically kills the H3.3 K27M mutant DIPG cells, while largely sparing the cells carrying WT H3.3. The indicated cells were either left untreated or treated with 75 nM of the FDA approved HDACi Vorinostat (Vor; trade name Zolinza) for 7 days before counting the surviving cells. The structure of Vor is also shown. (FIG. 16C) The cytotoxic effects of HDACi synergizes with radiation in specifically eliminating H3.3K27M mutant DIPG cells. The indicated cells were either left untreated or treated with a very low dose of Vor (10 nM) either with or without a low 1 Gy dose of radiation and surviving cells were counted one week later. Error bars represent standard deviation and significant differences between treatments are indicated by the p values.

Figure 17A:
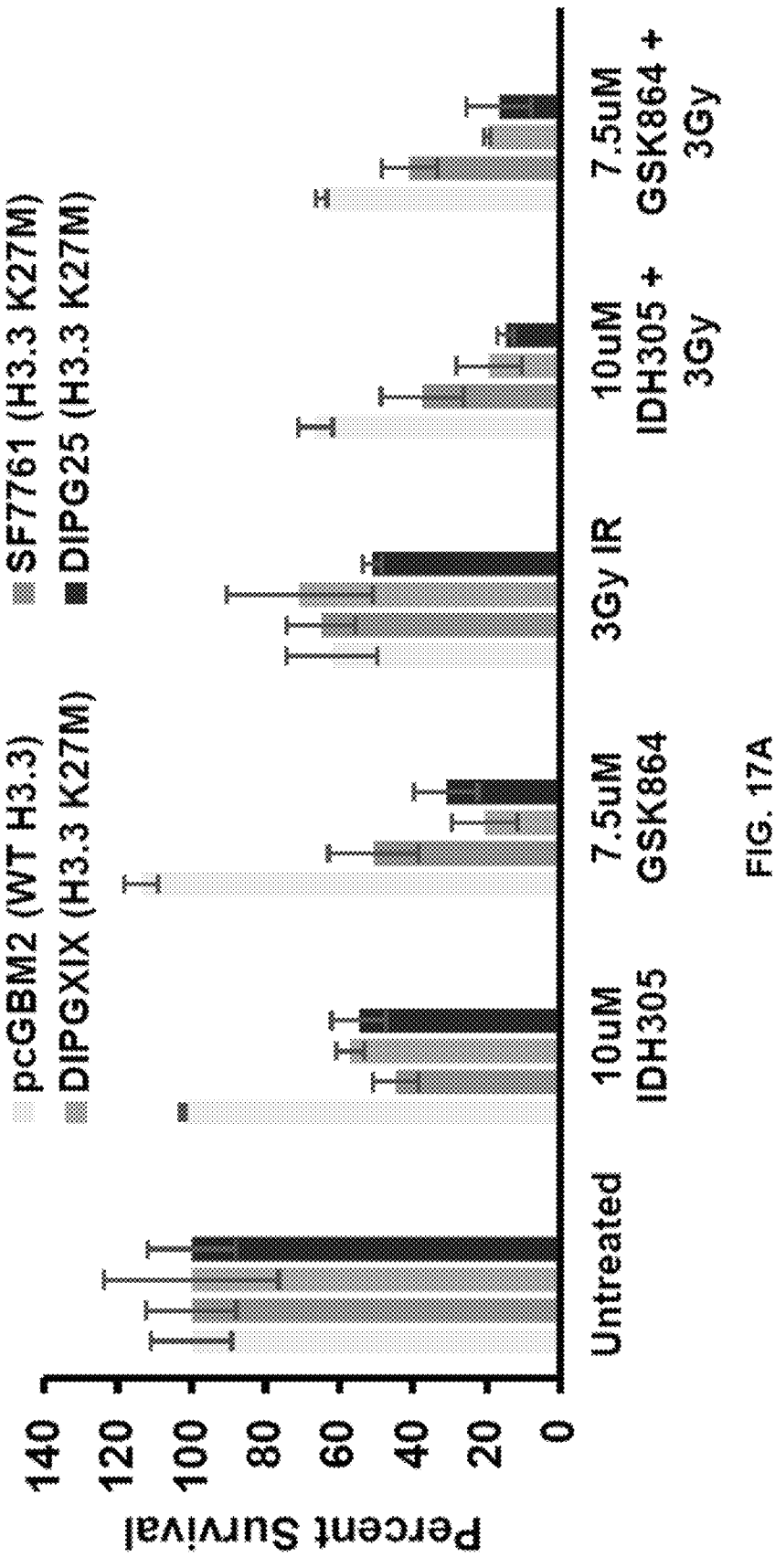
Figure 17B:
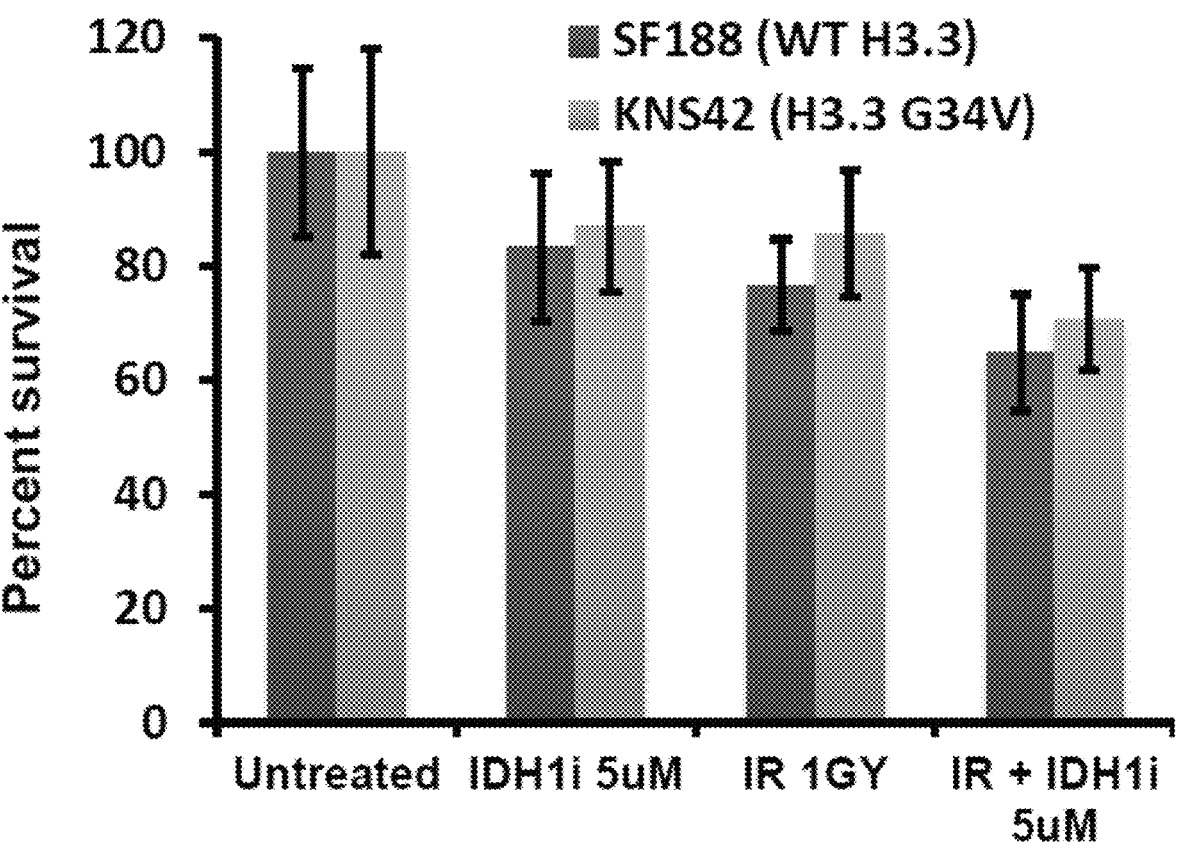

FIGS. 17A-17B show only H3.3K27M mutant pediatric glioma cells are specifically sensitive to IDH1 inhibitors. (FIG. 17A) Patient derived H3.3K27M mutant Diffuse Intrinsic Pontine Glioma (DIPG) cells are sensitive to treatment with IDH1 inhibitors (IDHi) in a manner that is synergistic with ionizing radiation (IR). The indicated human patient derived WT or H3.3K27M mutant pediatric high grade glioma cells were exposed for 7 days to the indicated concentrations of the IDH inhibitors with or without IR treatment prior to measuring survival as described in FIGS. 16A-16C. Error bars represent standard deviation. (FIG. 17B) Pediatric glioblastoma cells such as KNS42 carrying the H3.3G34V mutant or SF188 cells carrying wild type H3.3 are not sensitive to IDH inhibition. Experiment was performed as in FIG. 17A. IDH1i=IDH1 inhibitor. This data clearly shows that IDH1 inhibitors specifically target the H3.3K27M mutant pediatric high grade glioma cells, while the pediatric gliomas carrying H3.3G34V or wild type H3.3 are not appreciably affected. On the other hand, combinations of DNA repair inhibitors that target non-homologous end-joining (NHEJ) pathways eliminate all H3.3 mutant pediatric high grade gliomas.

Figure 18A:
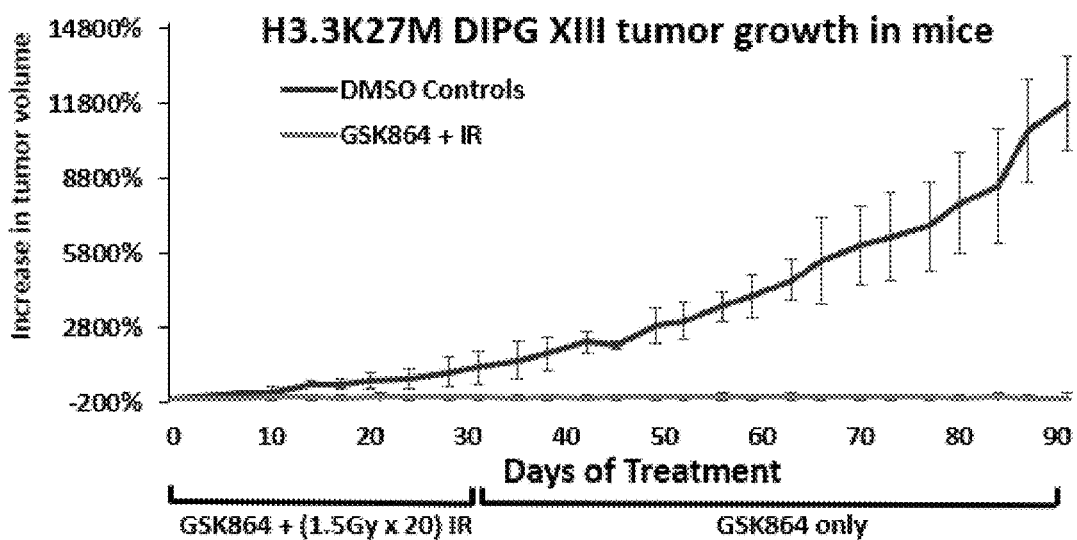
Figure 18B:
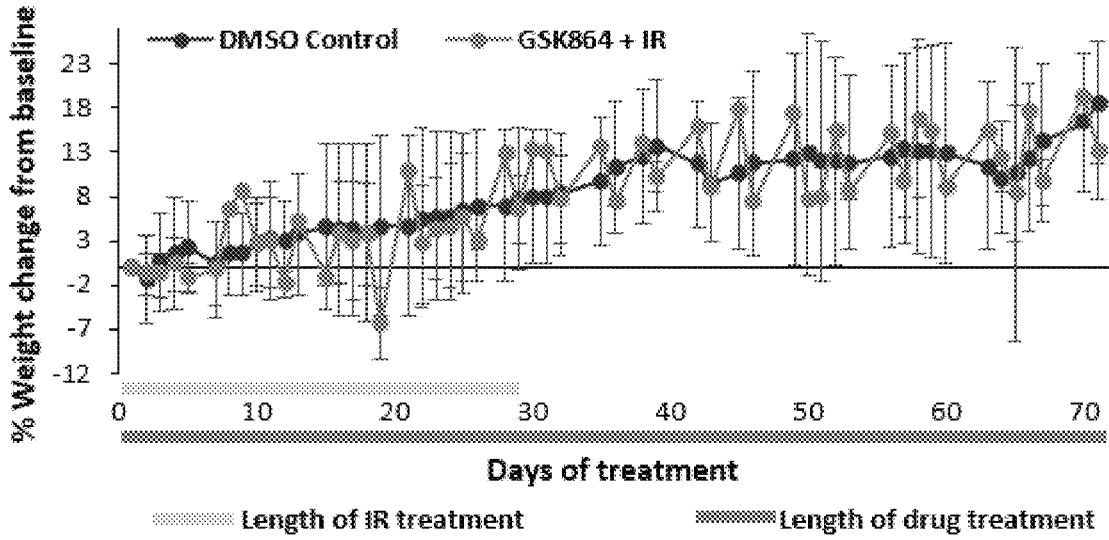

FIGS. 18A-18B show IDH1 inhibitors plus radiation completely blocks the growth of H3.3K27M mutant DIPG XIII tumors xenografted in mice in vivo. (FIG. 18A) IDH1 inhibition with GSK864 combined with radiation blocks the growth of H3.3K27M mutant human DIPG xenografts in mice. R2G2 mice (Envigo) were engrafted subcutaneously with human DIPGXIII cells carrying the H3.3K27M mutation. Once tumors were palpable, treatments were initiated. Mice were injected intraperitoneally with 75 mg/kg/day of the preclinical IDH1 inhibitor GSK864 and 20 fractions of 1.5Gy IR delivered over 4 weeks, following which only GSK864 administration was continued. Control mice received DMSO. Tumors were measured at least twice per week using microcalipers. (FIG. 18B) Long term treatment with a combination of IDH1 inhibitor GSK864 along with radiation is very well tolerated in mice. The body weight of mice is unaffected even after 20 fractions of radiation plus 70 days of IDH1 inhibition.

Figure 19A:
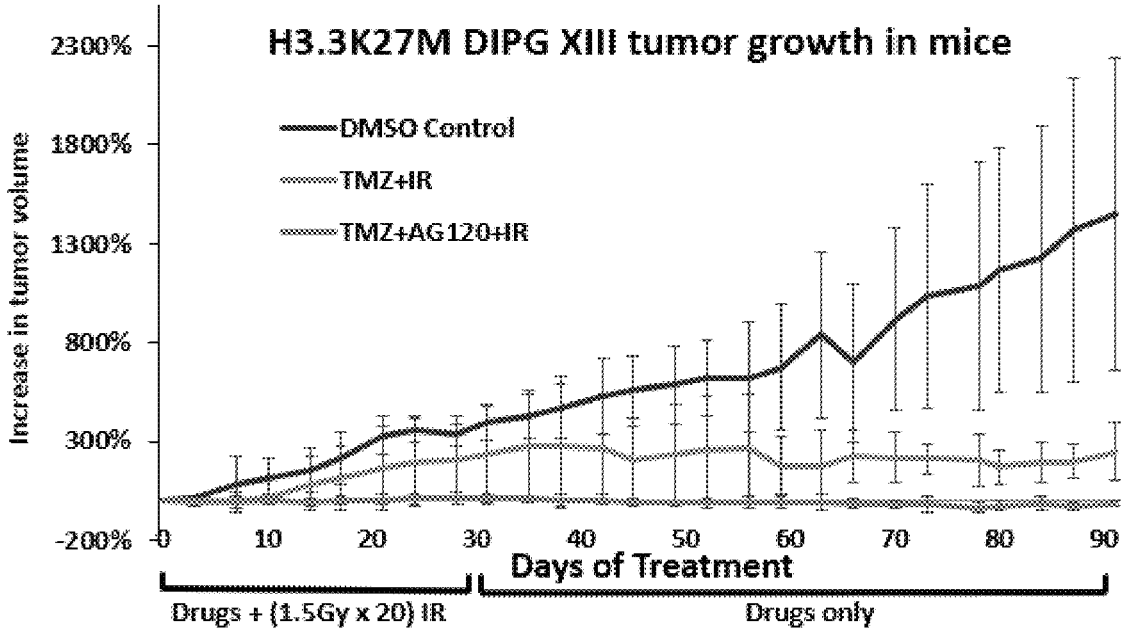
Figure 19B:
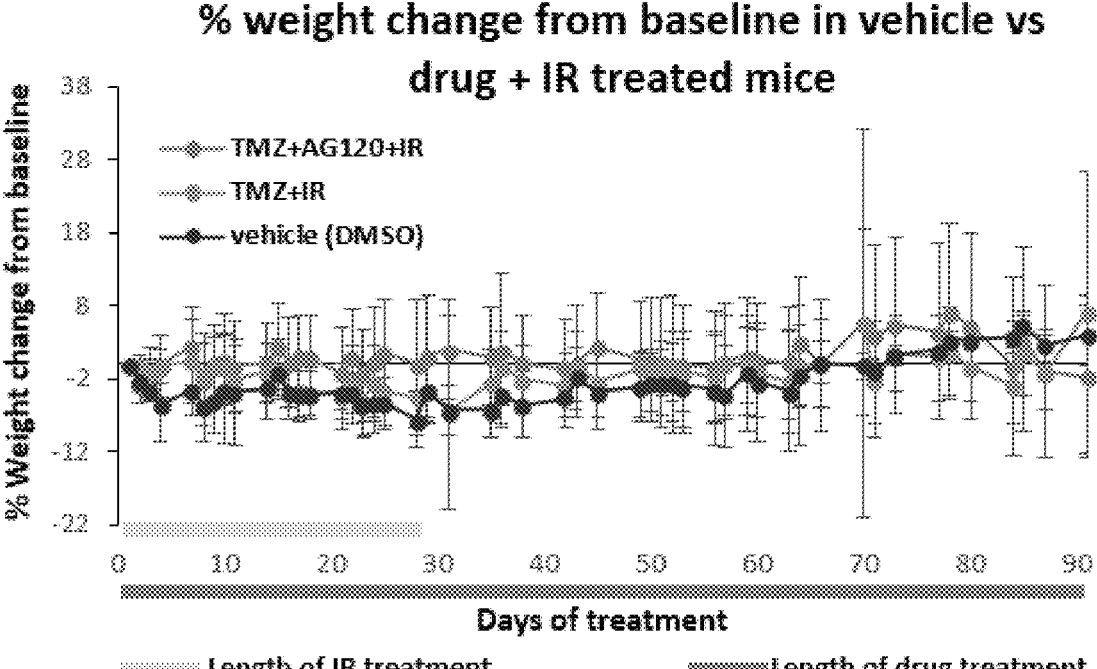

FIGS. 19A-19B show IDH1 inhibitors plus radiation completely blocks the growth of H3.3K27M mutant DIPG XIII tumors xenografted in mice in vivo. (FIG. 19A) IDH1 inhibition using AG120 is superior to Temozolomide (TMZ) plus radiation in blocking the growth of H3.3K27M mutant human DIPG xenografts in mice. RAG2/IL2RG double knockout mice (Taconic) were engrafted subcutaneously with human DIPGXIII cells and treated as described above in FIG. 18A except that the IDH1 inhibitor used was AG120 at 75 mg/kg/day. TMZ was used at 15 mg/kg/day. Error bars are omitted to clearly show the difference between TMZ and AG120. (FIG. 19B) Long term treatment with a combination of IDH1 inhibitor AG120 along with radiation does not affect body weight and is very well tolerated by mice.

Figure 20:
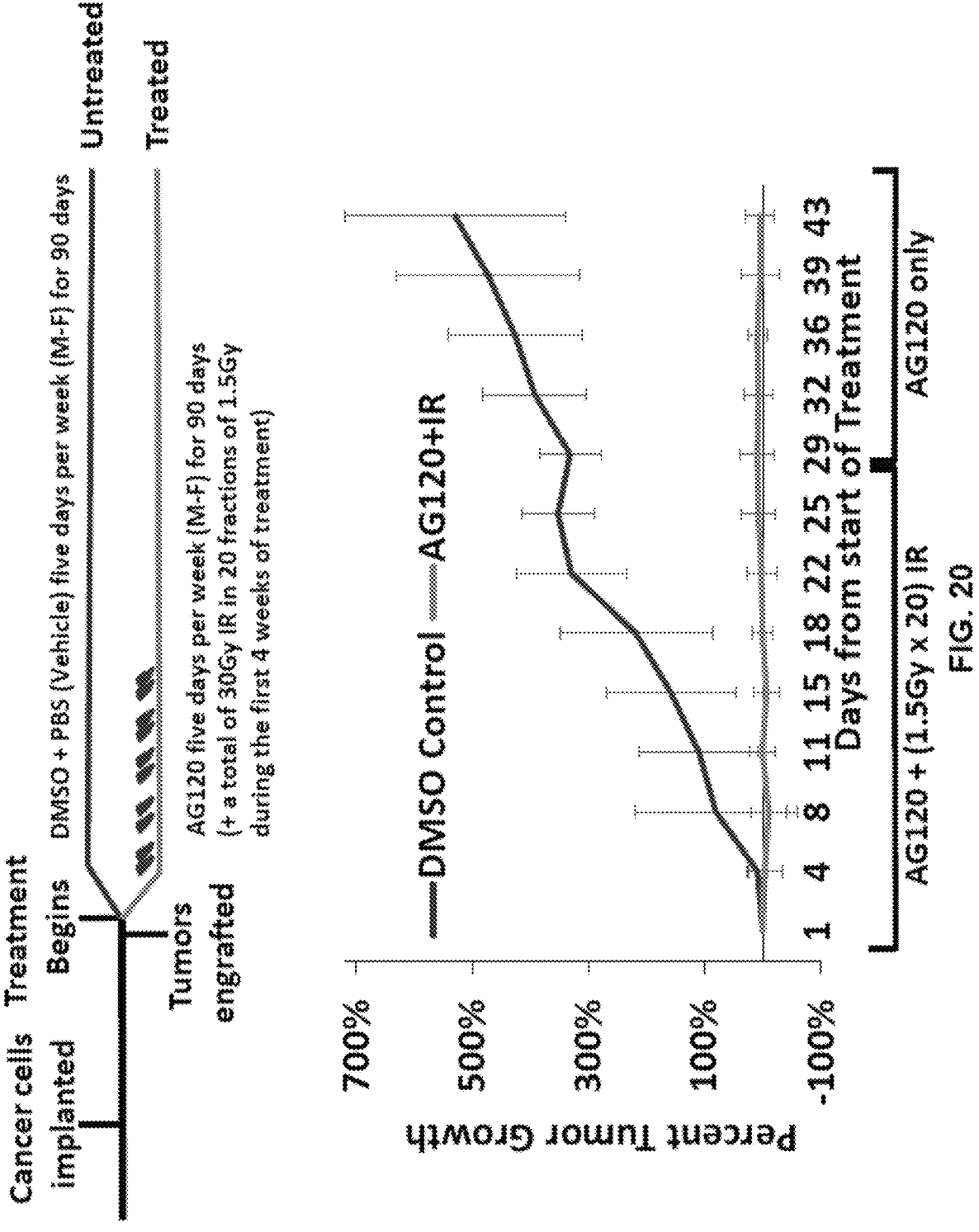

FIG. 20 shows inhibition of IDH1 using the FDA approved inhibitor AG120 (Ivosidenib) in combination with radiation completely blocks the growth of H3.3K27M mutant human DIPG XIII tumors xenografted in mice. Immunocompromised Rag2/IL2rg double knockout mice (Taconic) were engrafted subcutaneously in the flank with the pediatric patient derived DIPGXIII H3.3K27M mutant tumors and were treated as described in and scheme shown at top, except that the drug treated mice received 75 mg/kg AG120 plus 30 Gy radiation (delivered over the first four weeks of treatment in twenty 1.5 Gy fractions indicated by lightning bolts) following which only drug administration was continued until the humane or clinical endpoint was met. Microcaliper measurement based relative tumor volumes are plotted. Error bars show standard deviation.

Figure 21:
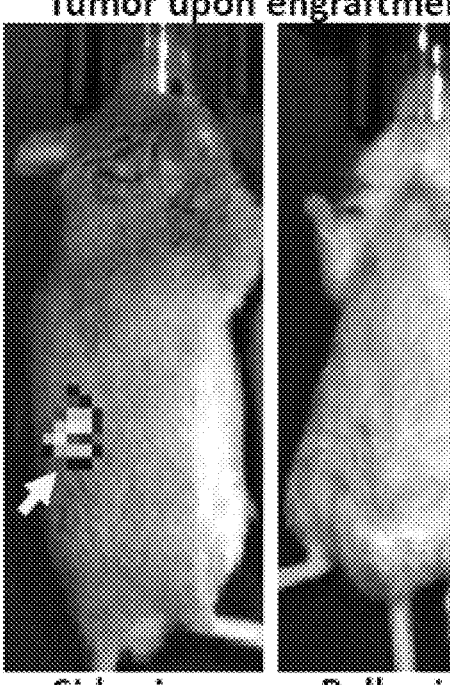
Figure 21:
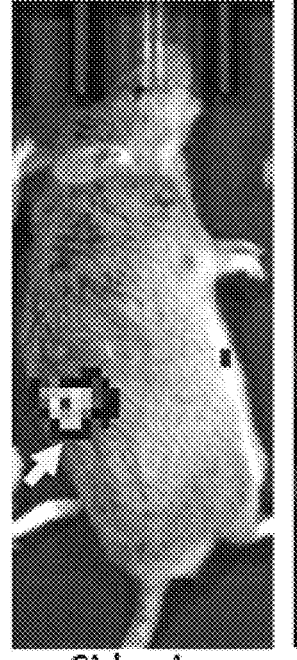
Figure 21:
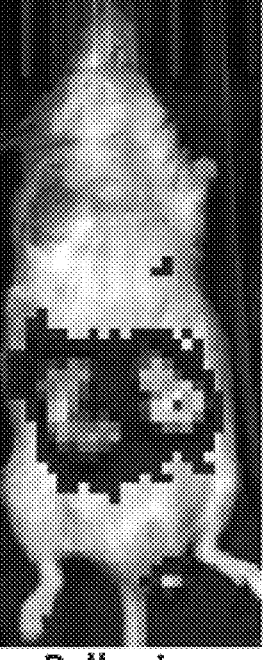

FIG. 21 shows dissemination of human patient derived DIPG XIII H3.3K27M cancer cells in untreated mice. Bioluminescence images of the side and belly of a representative mouse at the time of engraftment with H3.3K27M mutant tumor on the flank, followed by vehicle injections for two months by which time the tumor had disseminated extensively in the abdominal area and elsewhere (DIPG tumors within the brain are not typically known to metastasize). The original site of engraftment in the flank is indicated by the arrow. Overall, up to 30% of the mice in multiple untreated groups developed disseminated tumors compared to none in the treatment groups so far. Up to 30% of the untreated mice also developed lower body paralysis presumably due to invasion of the spinal cord by the human DIPG tumor cells engrafted in the flank. The poor outcomes in untreated mice harboring human H3.3 mutant DIPG tumors further highlight the effectiveness of the disclosed therapeutic approaches.

Figure 22A:
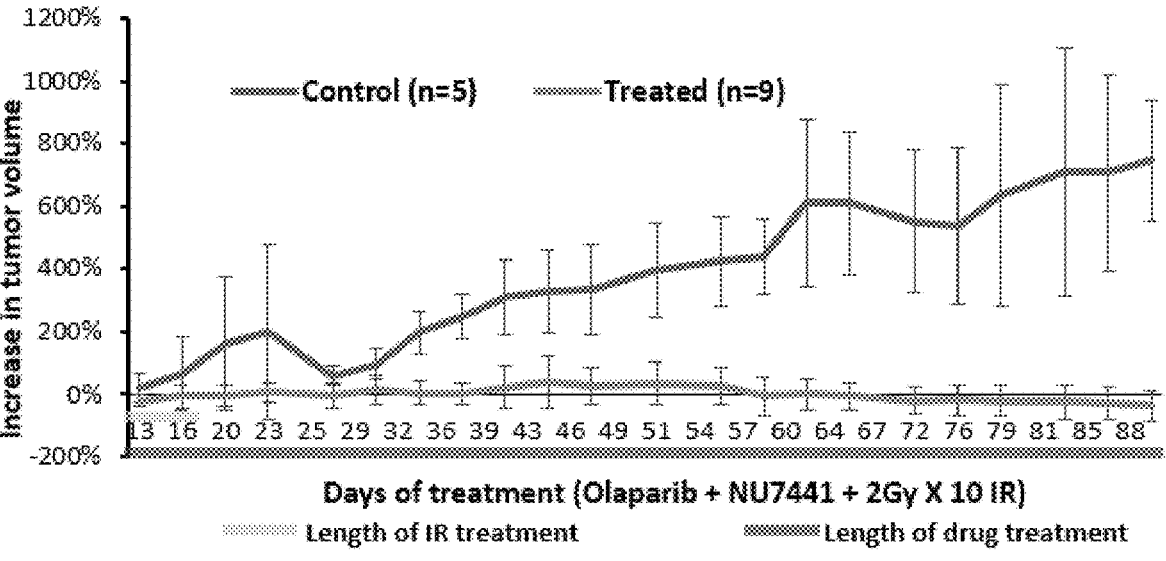
Figure 22B:
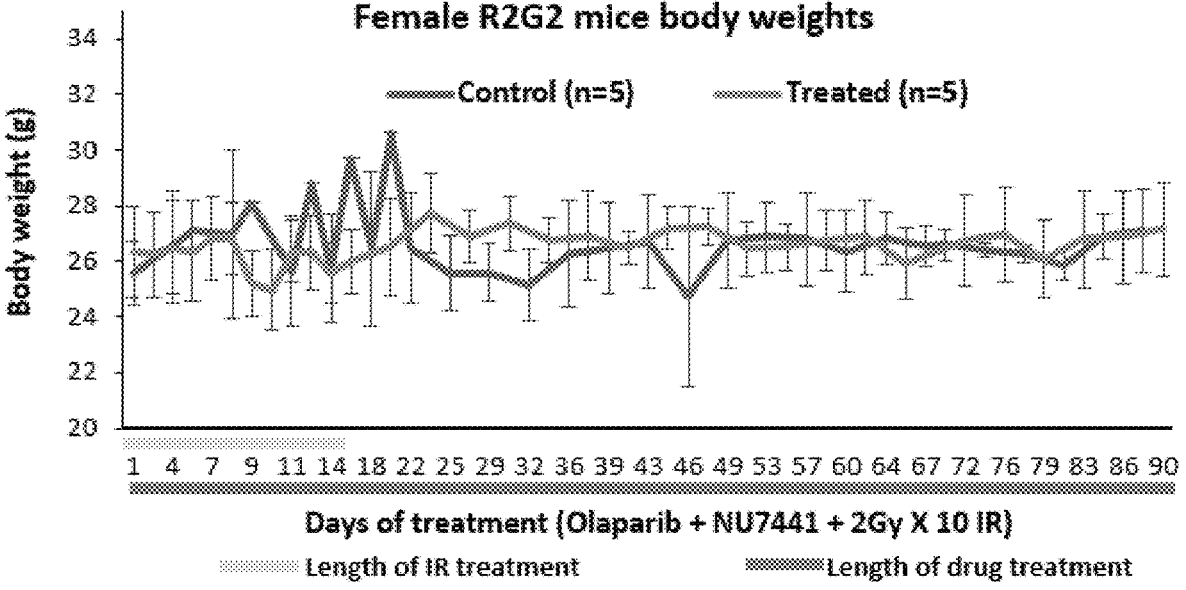

FIGS. 22A-22B SHOW In vivo effects of treatment of H3.3K27M mutant DIPG cancer cells engrafted in mice with the PARP inhibitor Olaparib in combination treatment with NHEJ inhibitor NU7441 and radiation. (FIG. 22A) Combination treatment with NHEJ inhibitors and radiation blocks the growth of H3.3K27M mutant DIPG tumors engrafted in mice. R2G2 mice (Envigo) were engrafted subcutaneously with bioluminescent human SF8628 cells carrying the H3.3K27M mutation. Once tumors were palpable (longest dimension ~5 mm, tumor volume 25-35 cubic mm), mice were divided into two groups that were injected intraperitoneally daily with either the vehicle (15% DMSO), or 37.5 mg/kg/day OLA plus 5 mg/kg/day of the DNA-PK inhibitor NU7441. Mice treated with OLA+NU7441 also received 20Gy of IR in ten fractions of over 2 weeks at the beginning of the treatment, following which only OLA administration was continued. Tumor size was measured every 3-4 days using digital microcalipers. (FIG. 22B) Long term treatment with a combination of NHEJ inhibitors along with radiation is very well tolerated in mice. The body weight of female mice used in the data shown above in panel A is plotted here. The weight of treated mice was unaffected even after 10 fractions of radiation plus 90 days of treatment with two NHEJ inhibitors, which would be roughly the equivalent of almost 10 years in human lifespan.

Figure 23:
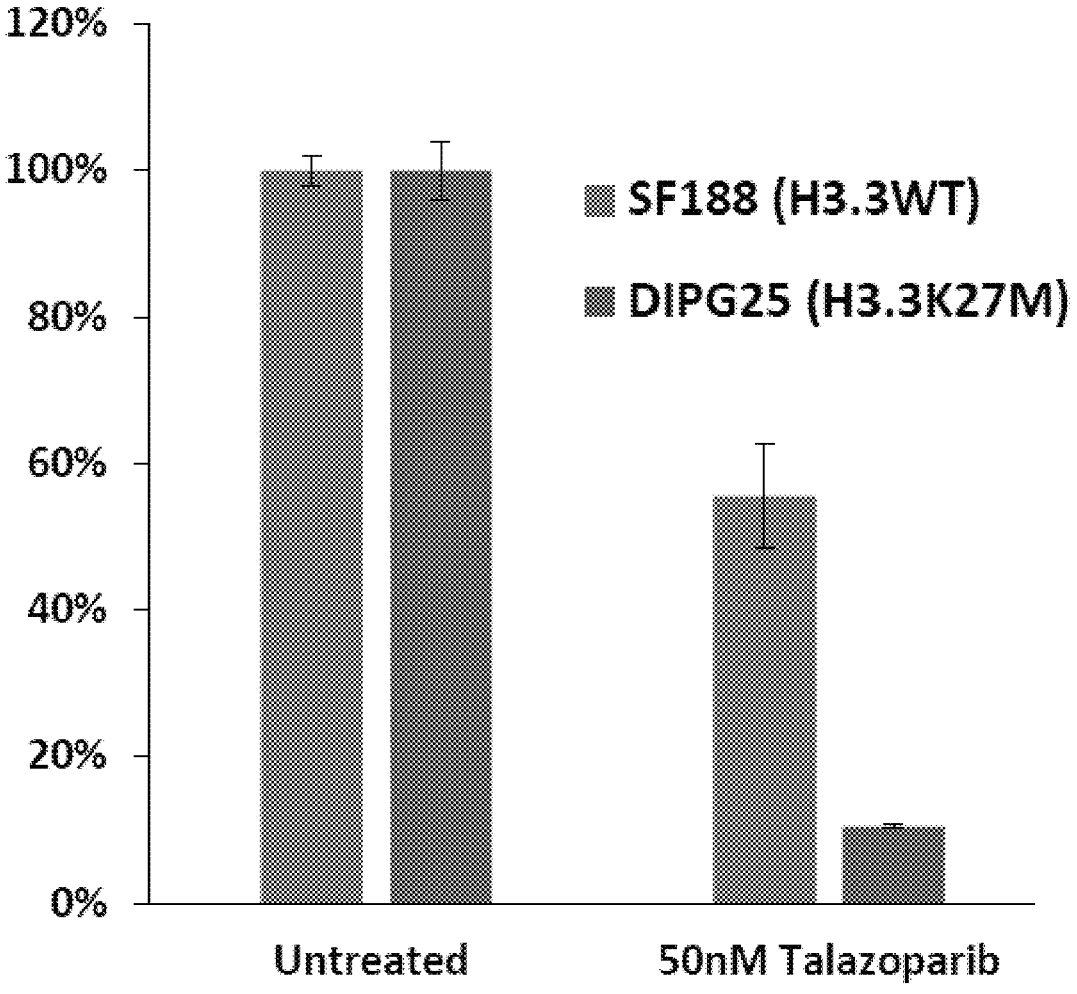

FIG. 23 shows patient derived H3.3K27M mutant DIPG cells are exquisitely sensitive to treatment with another FDA approved PARP inhibitor Talazoparib (Talzenna). The indicated human patient derived WT or H3.3K27M pediatric glioblastoma cells were exposed to a triple combination of the indicated concentration of the FDA approved PARP inhibitor drug Talazoparib for 7 days prior to measuring survival by counting viable cells. The H3.3 K27M mutant cancer cells are very sensitive to Talazoparib. Error bars represent standard deviation.

Figure 24:
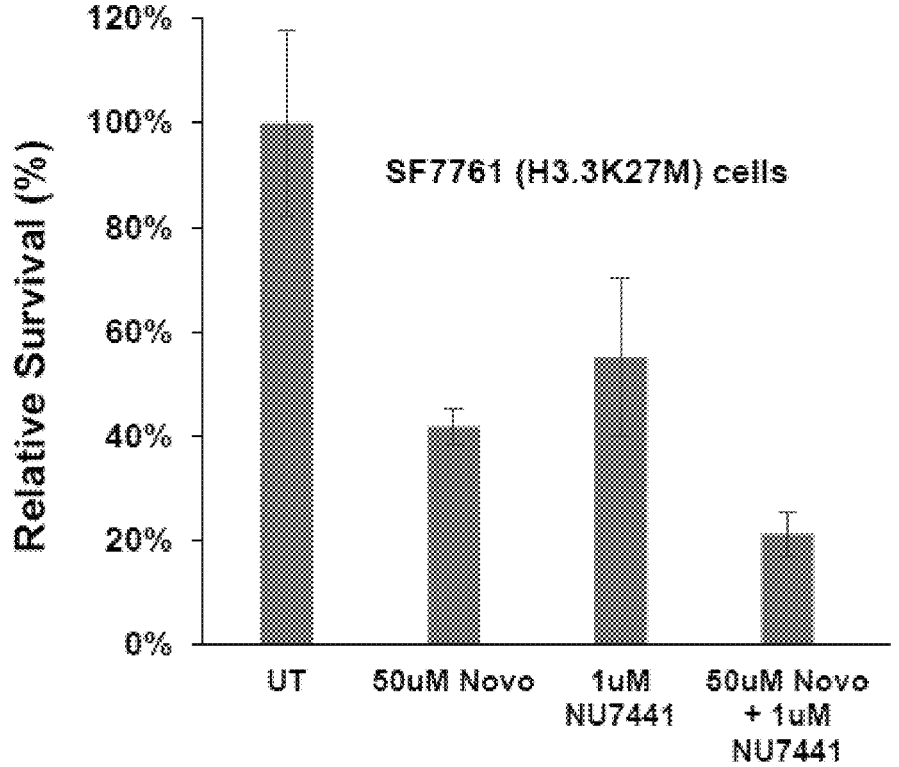

FIG. 24 shows DNA polymerase Theta inhibitor Novobiocin synergizes with c-NHEJ inhibitor NU7441 in killing patient derived SF7761 H3.3K27M mutant DIPG cells in culture. The indicated human patient derived H3.3K27M pediatric glioblastoma cells were exposed to the indicated concentration of the FDA approved Pole inhibitor Novobiocin (Novo) or the DNA-PK inhibitor NU7441 for 7 days prior to measuring survival by counting viable cells. Error bars represent standard deviation.

Figure 25:
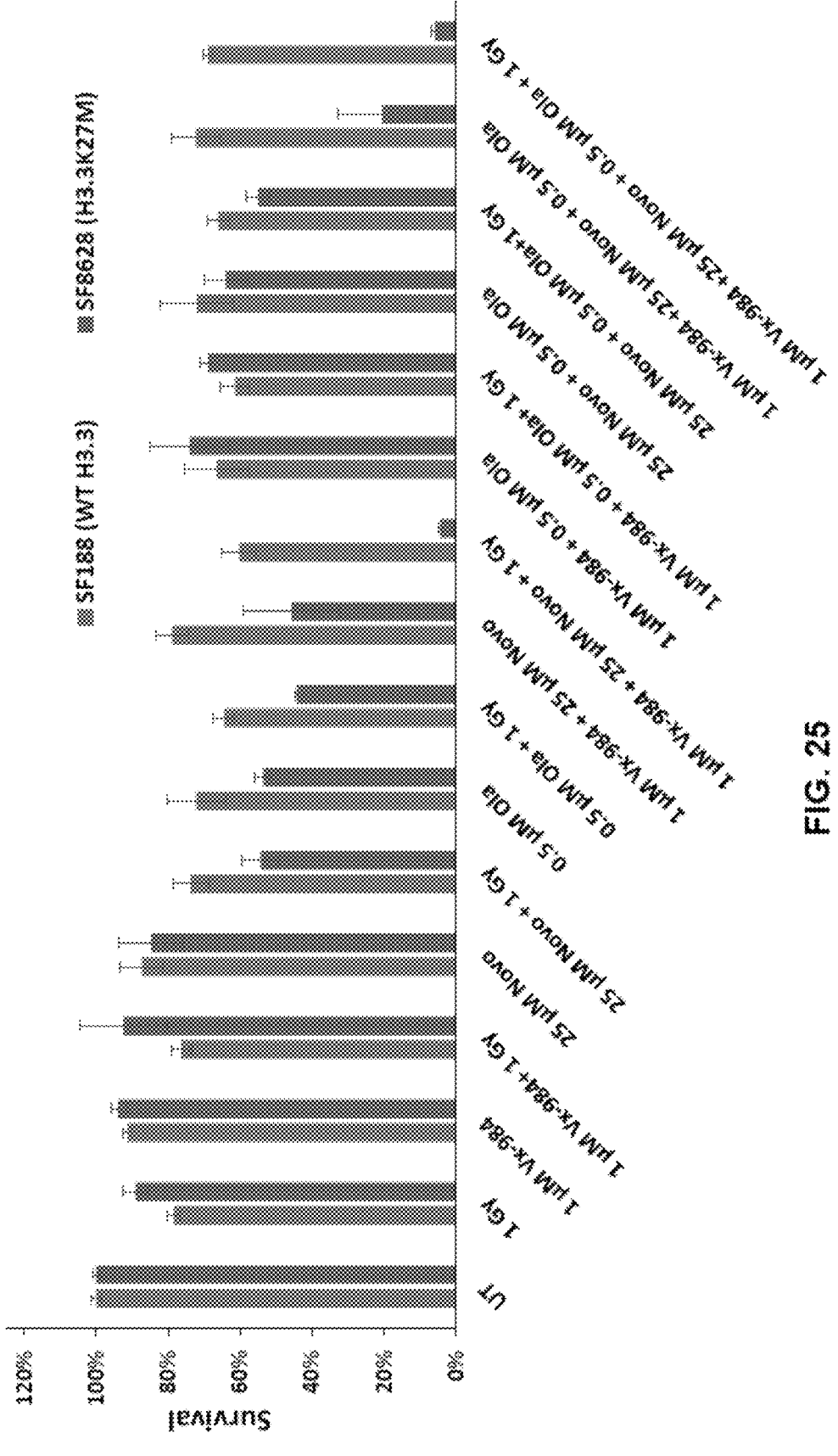

FIG. 25 shows patient derived H3.3K27M mutant DIPG cells are exquisitely sensitive to combination treatment with FDA approved NHEJ inhibiting drugs. The indicated human patient derived WT or H3.3K27M pediatric glioblastoma cells were exposed to a triple combination of the indicated concentrations of the FDA approved drugs Olaparib (OLA), Novobiocin (Novo) and the preclinical, brain permeable DNA-PK inhibitor Vx-984 for 7 days prior to measuring survival as described in FIGS. 16A-16C. Additive/synergistic effects are clearly visible when the drugs are used in combination. Error bars represent standard deviation.

Figure 26:
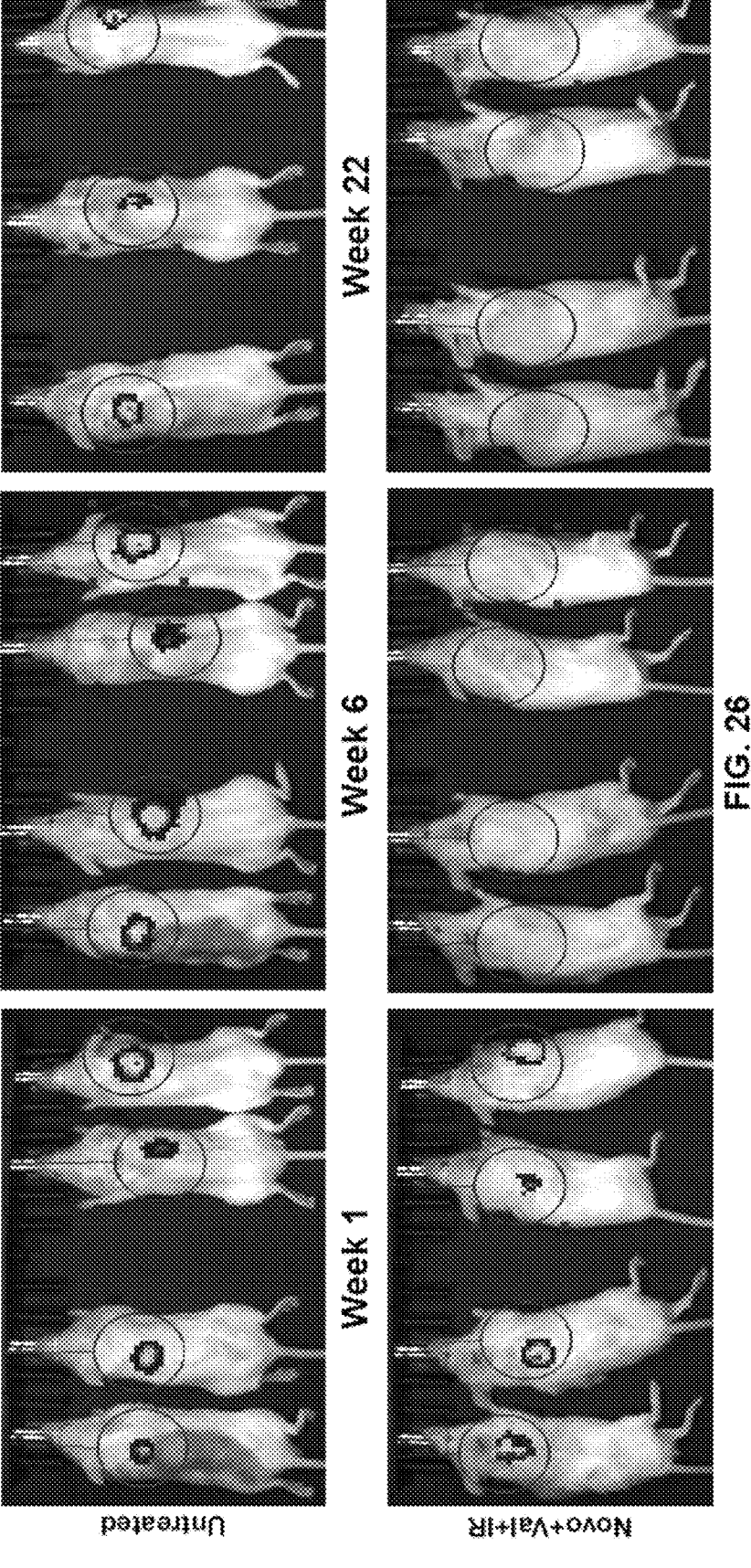

FIG. 26 shows combination treatment with c-NHEJ inhibitor Olaparib and alt-NHEJ inhibitor NU7441 along with radiation completely blocks the growth of DIPG XIII H3.3K27M mutant tumors in mice. Immunocompromised BRG mice (Jackson Laboratories) were engrafted subcutaneously in the flank with the pediatric patient derived, luciferase carrying H3.3K27M mutant SF7761 DIPG tumor cells. The drug treated mice received 100 mg/kg of Novobiocin (Novo) and Sodium Valproate (Val), plus 30 Gy ionizing radiation (IR, delivered over the first four weeks of treatment in twenty 1.5 Gy fractions indicated by lightning bolts), following which only drug administration was continued 5 days per week (Monday through Friday, with no treatments on weekends) for a total of 90 days (~13 weeks), after which all treatments were stopped. Bioluminescent images of the mice from the indicated weeks are shown. Note that one of the untreated mice succumbed to the tumor disseminating into the lungs by week 10 of the treatment, while all the treated mice are still alive and healthy more than a year after the implantation of the human DIPG tumor cells. Since no signals from tumor cells have been detected in the treated mice for over 24 weeks now, which is roughly equivalent to 20 years in human lifespan, it is believed that this treatment was curative for these mice.

Figure 27:
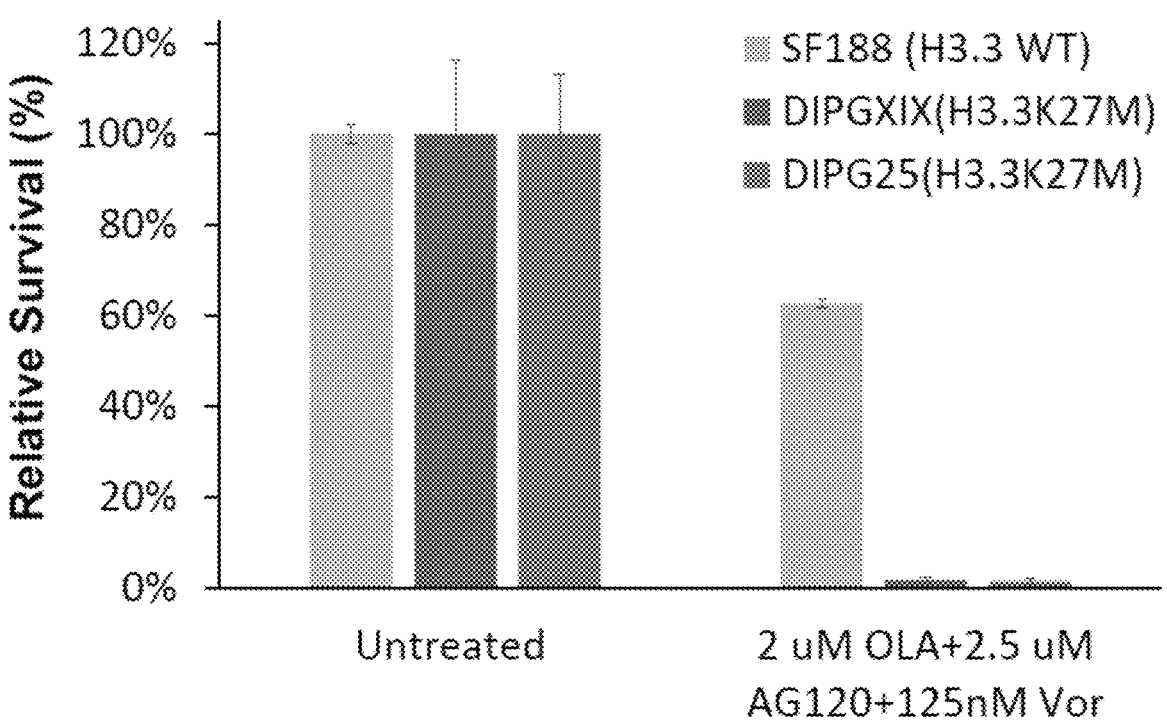

FIG. 27 shows patient derived H3.3K27M mutant DIPG cells are exquisitely sensitive to combination treatment with FDA approved drugs. The indicated human patient derived WT or H3.3K27M pediatric glioblastoma cells were exposed to a triple combination of the indicated concentrations of the FDA approved drugs Olaparib (OLA), AG120 (Ivosidenib) and Vorinostat (Vor) for 7 days prior to measuring survival as described in FIGS. 16A-16C. Error bars represent standard deviation.

Figure 28:
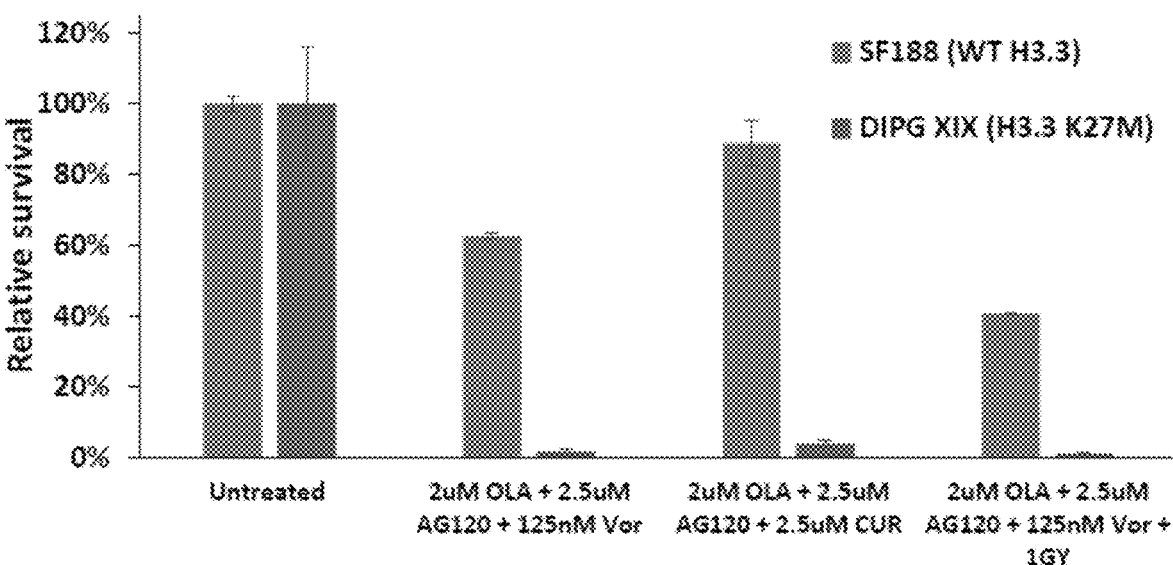

FIG. 28 shows patient derived H3.3K27M mutant DIPG cells are exquisitely sensitive to combination treatment with FDA approved drugs Olaparib (Lynparza), AG120 (Ivosidenib, Tibsovo) and Vorinostat (Zolinza), or health supplements like Curcumin. The indicated human patient derived WT or H3.3K27M pediatric glioblastoma cells were exposed to a triple combination of the indicated concentrations of the FDA approved drugs Olaparib (OLA), AG120 (Ivosidenib, Tibsovo) and Vorinostat (Vor), or the commonly used health supplement Curcumin (Cur, which is a natural inhibitor of histone acetyltransferases) for 7 days prior to measuring survival as described in FIGS. 16B-16C. Error bars represent standard deviation.

Figure 29:
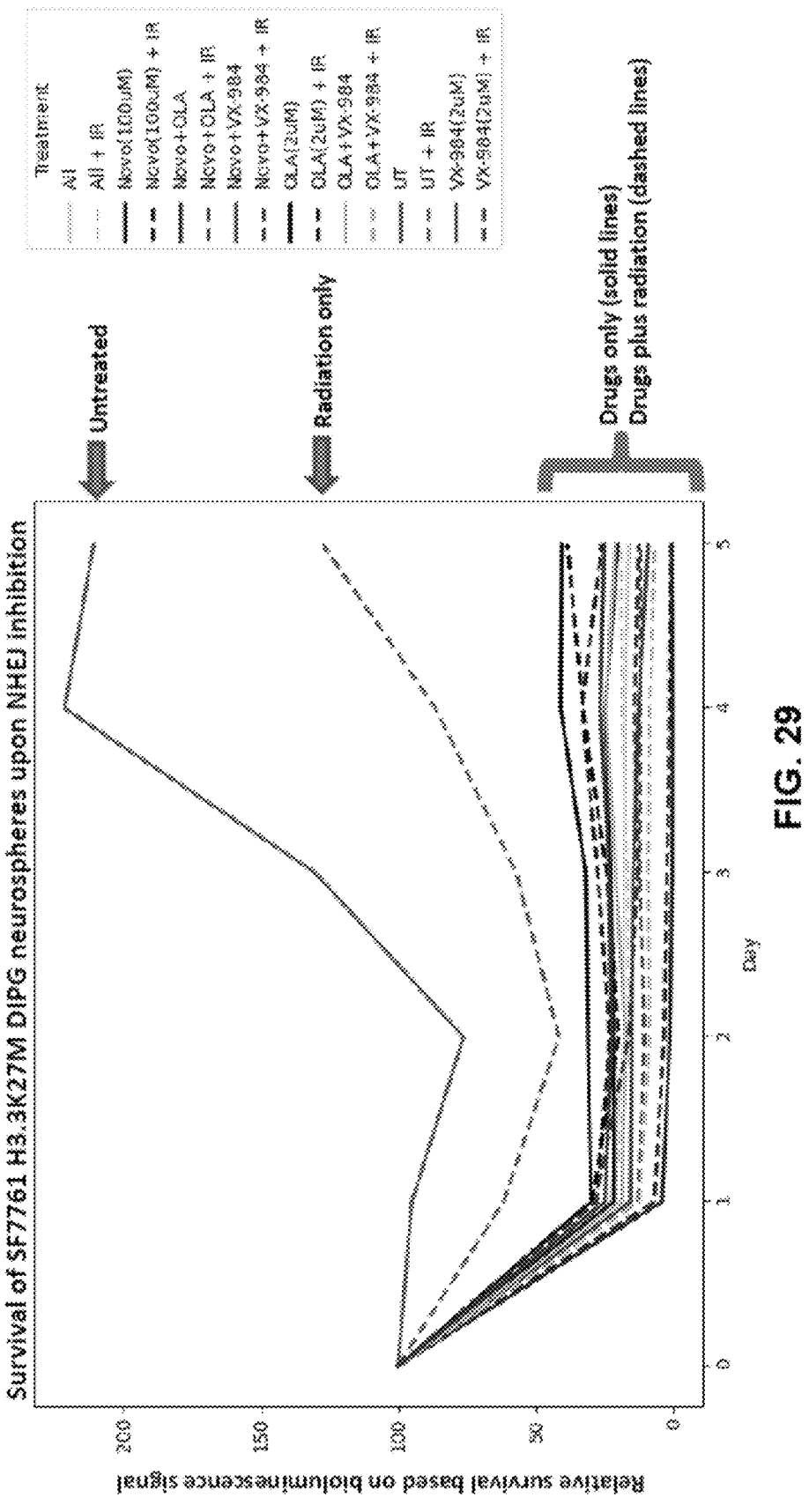

FIG. 29 shows inhibition of NHEJ pathways kills H3.3K27M mutant human tumor cells within 3D neurospheres. Compared to 2D cultures of cells in vitro, cultured 3D tumor spheroids, organoids or neurospheres are much better mimics of the 3D tumors in vivo. H3.3K27M mutant SF7761 DIPG neurospheres expressing luciferase were cultured in vitro. Bioluminescence from the organoids was measured daily to determine survival upon treatment with or without a combination of 100 UM Novobiocin (Novo) to block Pole mediated Theta Mediated End Joining (TMEJ), 2 μM OLA (Olaparib) to block Poly-ADP Ribose Polymerase 1 (PARP1) mediated alternative-End Joining (a-EJ), and 2 μM VX-984, a DNA-PK inhibitor to block classic Non-Homologous End Joining (c-NHEJ).

Figure 30:
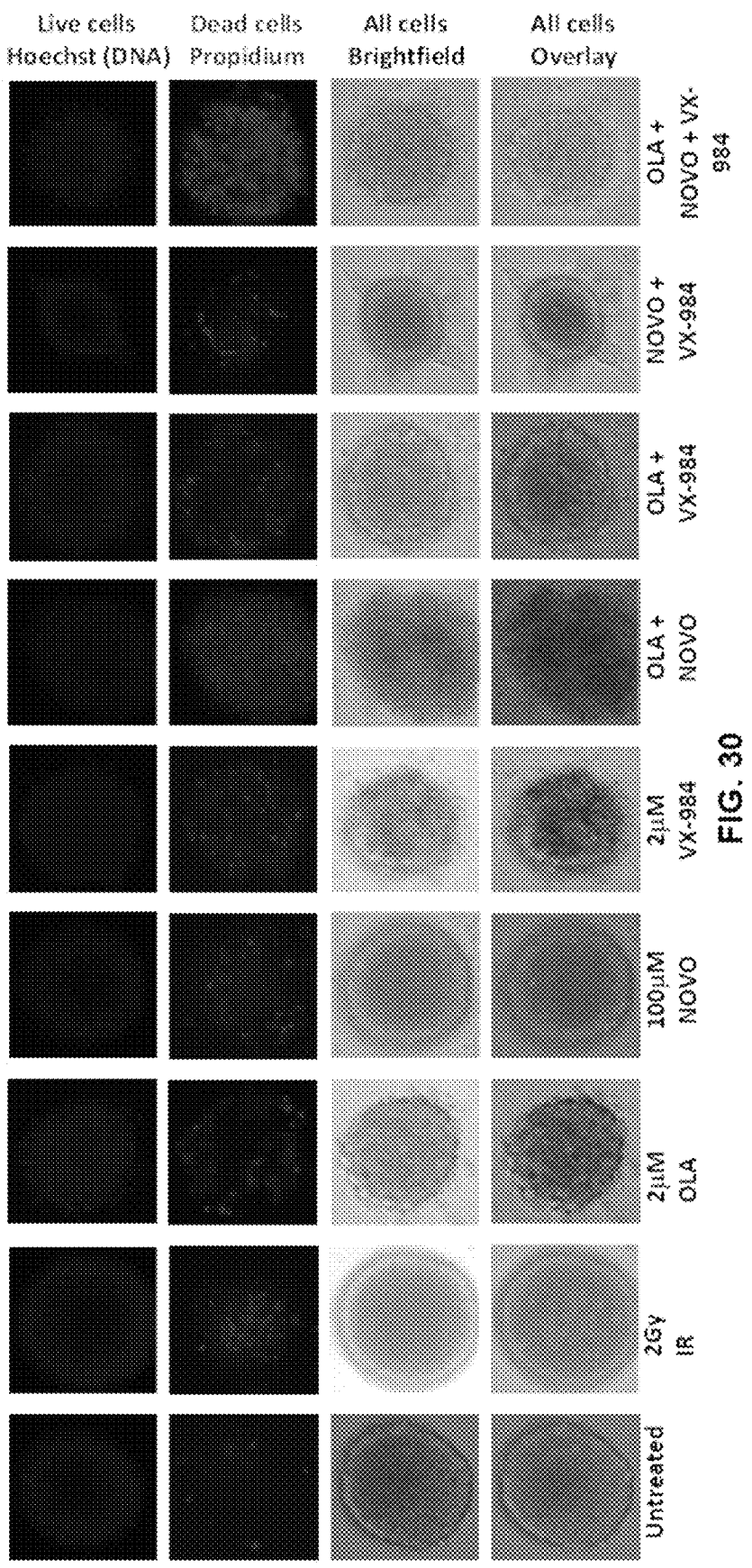

FIG. 30 shows inhibition of NHEJ pathways kills H3.3K27M mutant human tumor cells within 3D neurospheres. H3.3K27M mutant SF7761 DIPG neurospheres expressing luciferase were cultured in vitro and treated with or without a combination of 100 UM Novo to block Pole mediated TMEJ, 2 μM OLA to block PARP1 mediated a-EJ, and 2 μM VX-984, a DNA-PK inhibitor to block c-NHEJ.

On day 5 of treatment, organoids were stained with the live cell permeable dye Hoechst 33342 (blue, to stain DNA in all cells) and live-cell impermeable propidium iodide (red, to stain nucleic acids in dead or dying cells only). Images were collected at 10× magnification on a Keyence microscope. Bioluminescence measurements from an experiment performed in triplicate is plotted. Composite overlay of images including brightfield of representative organoids are shown. Unlike the bioluminescence data shown previously in FIG. 29, the microscopy images shown here provide data from individual cells within the neurospheres, which is more informative regarding the relative efficacy of single and combination treatments.

Figure 31:
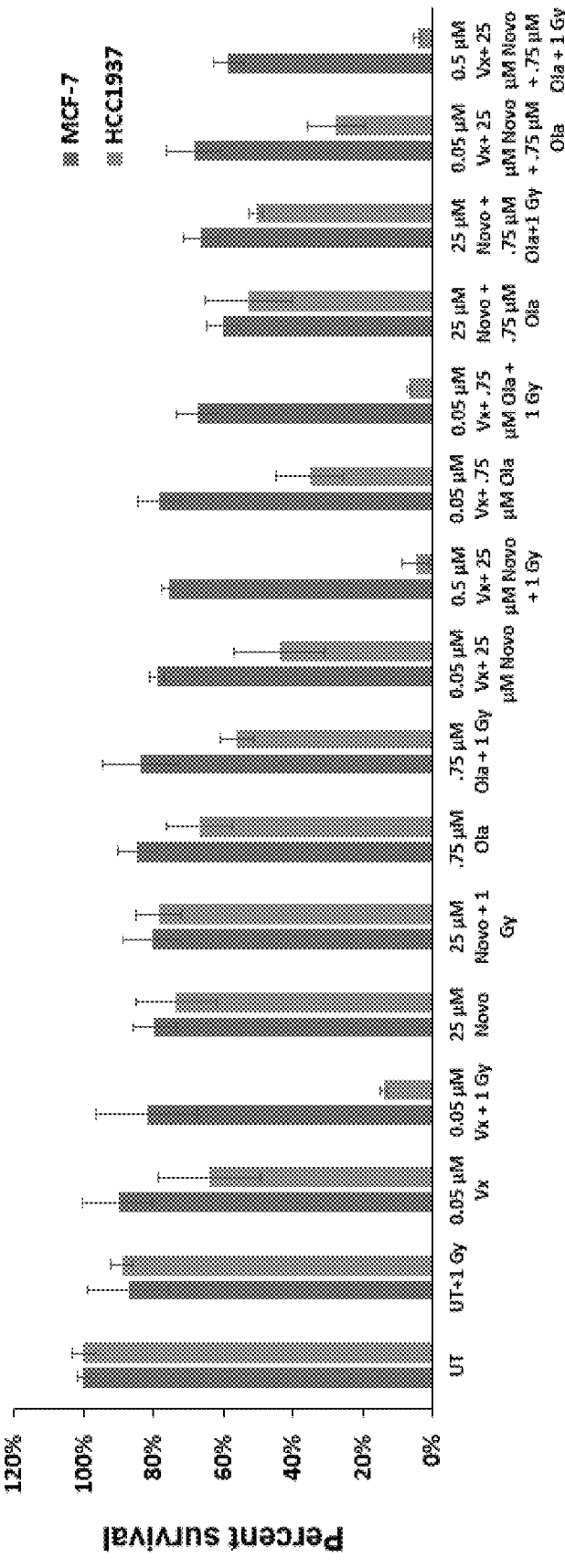

FIG. 31 shows breast cancer cells deficient in homologous recombination (HR) due to mutations in the BRCA1 gene are very sensitive to inhibition of Non-Homologous End Joining (NHEJ) pathways by simultaneous treatment with both DNA-PKcs, PARP and Pol☐ inhibitors. Wild type (WT) breast cancer (MCF7), BRCA1 mutant breast cancer (HCC1937) cells were either left untreated or treated with the DNA-PKcs inhibitor Vx-984 (Vx, 0.5 ☐M), FDA approved PARP inhibitor Olaparib (Ola, 0.5 ☐M), and the Pol☐ inhibitor Novobiocin (Novo, 25 ☐M) and surviving cells were counted one week later. Additive/synergistic effects can be seen when the drugs are used in combination. Error bars represent standard deviation.

Figure 32:
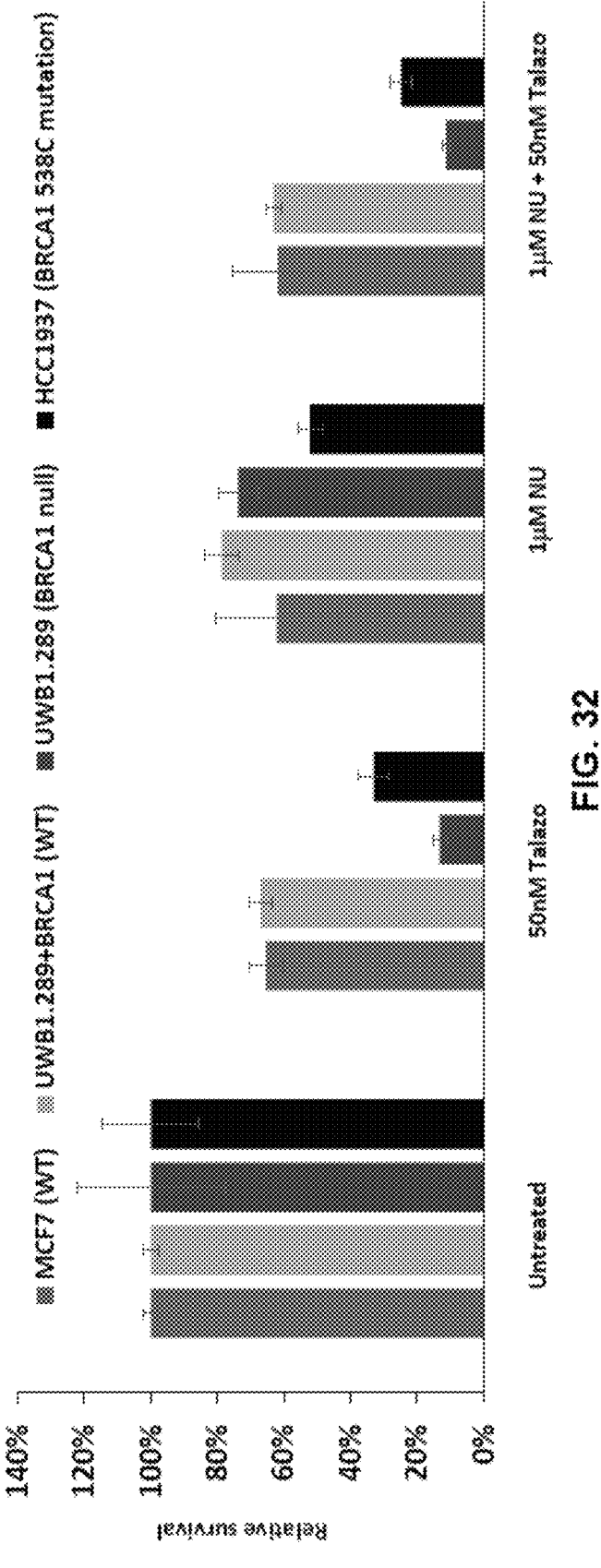

FIG. 32 shows breast and ovarian cancer cells deficient in homologous recombination (HR) due to mutations in the BRCA1 gene are very sensitive to inhibition of Non-Homologous End Joining (NHEJ) pathways by simultaneous treatment with both DNA-PKcs and PARP inhibitors. Wild type (WT) breast cancer (MCF7), BRCA1 mutant breast cancer (HCC1937), BRCA1 mutated ovarian cancer (UWB1.289) and its isogenic WT reconstituted control (UWB1.289+BRCA1) cells were either left untreated or treated with the DNA-PKcs inhibitor NU7441 (NU, 1 mM) or the FDA approved PARP inhibitor Talazoparib (Talazo, 50 nM) and surviving cells were counted one week later. Error bars represent standard deviation. This data suggests that the use of lower doses of Talazoparib will allow for better visualization of the synergistic effect on cell killing when combined with NU7441, which is predicted to increase even further when combined with radiation to cause DNA strand breaks.

Figure 33:
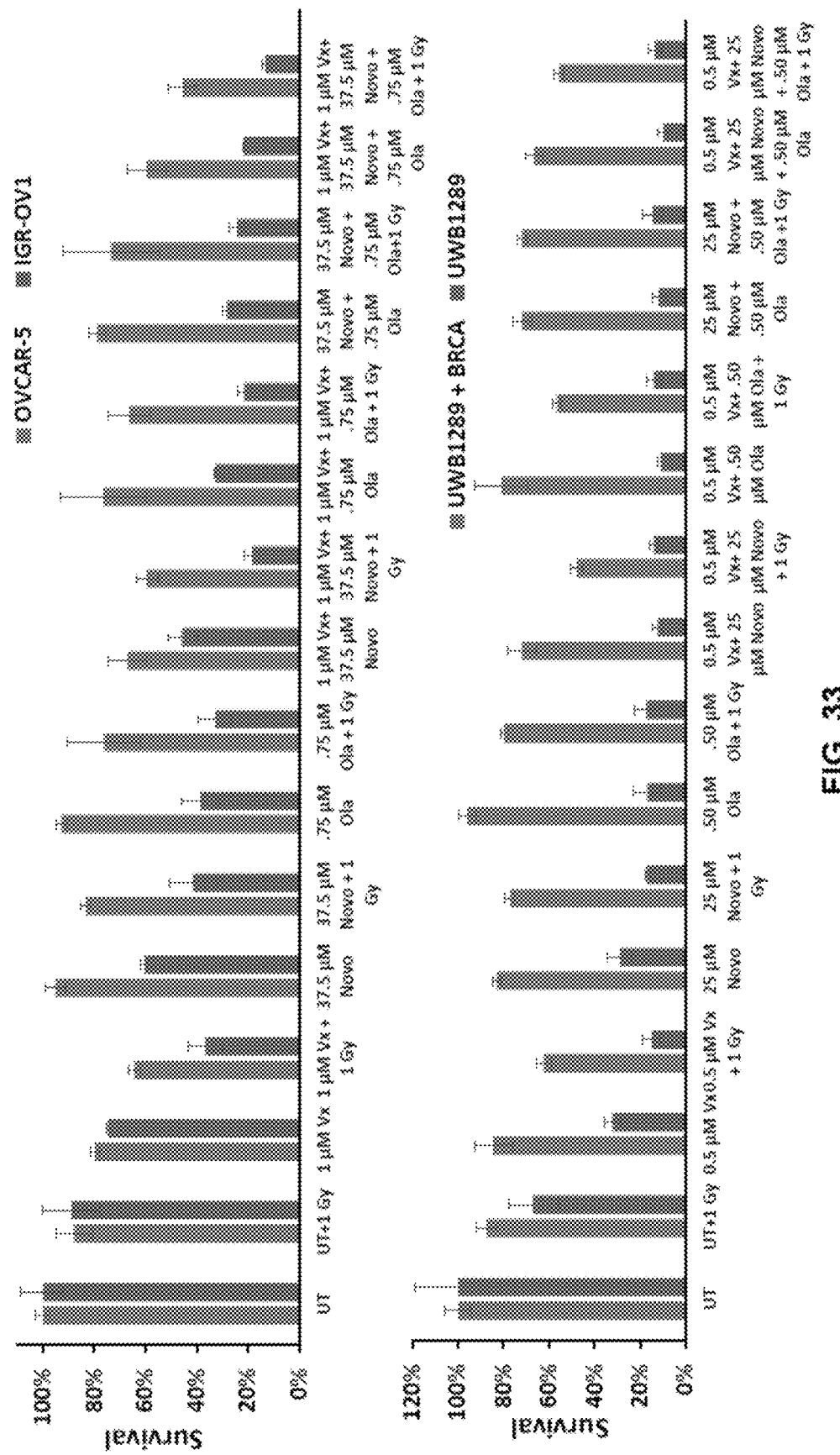

FIG. 33 shows ovarian cancer cells deficient in homologous recombination (HR) due to mutations in the BRCA1 gene are very sensitive to inhibition of Non-Homologous End Joining (NHEJ) pathways by simultaneous treatment with combinations of DNA-PKcs, PARP inhibitors and Pole inhibitors. Wild type (WT) ovarian cancer OVCAR-5, hemizygous (IGR-OV1) and homozygous (UWB1.289) BRCA1 mutated ovarian cancer, and its isogenic WT reconstituted control (UWB1.289+BRCA1) cells were either left untreated or treated with the DNA-PKcs inhibitor Vx-984 (Vx, 0.5 UM), FDA approved PARP inhibitor Olaparib (Ola, 0.5 UM), and the Pole inhibitor Novobiocin (Novo, 25 μM) and surviving cells were counted one week later. Error bars represent standard deviation. Note: The lower detection limit of this assay is about 10% survival. Nevertheless, additive/synergistic effects are apparent when the drugs are used in combination.

Figure 34:
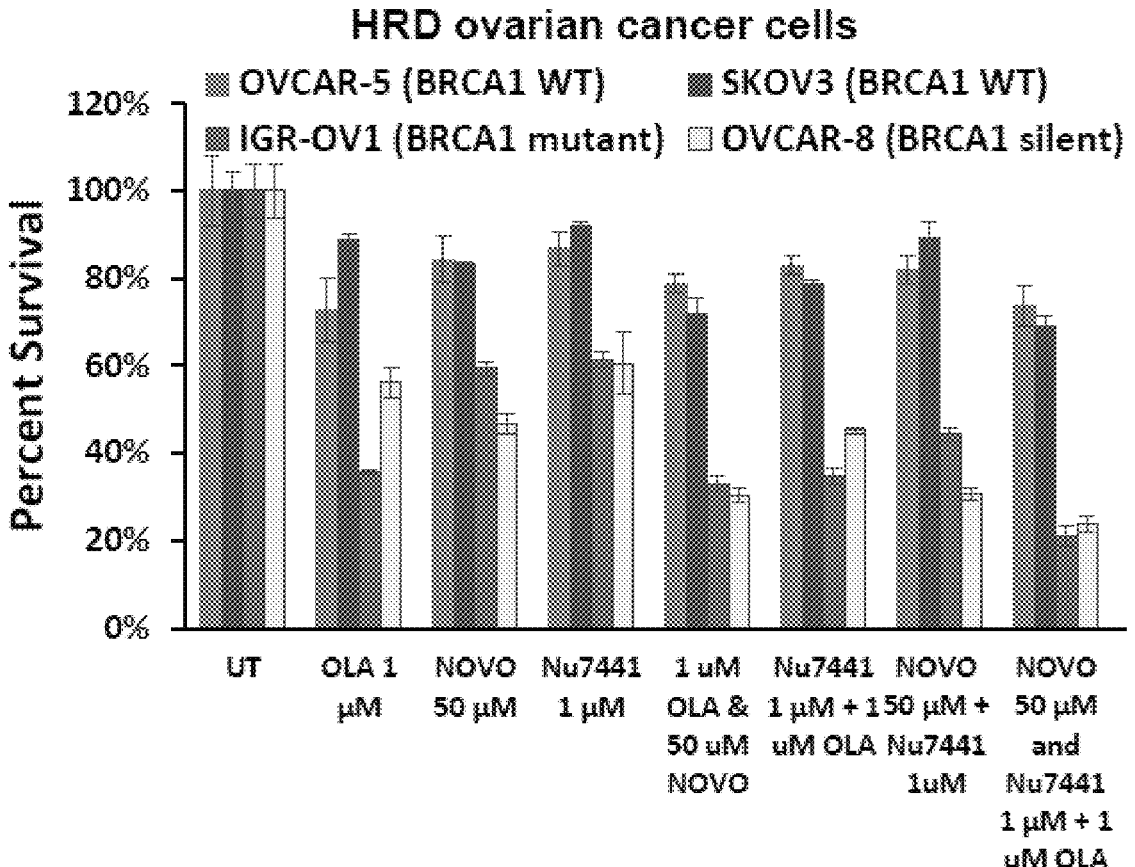

FIG. 34 shows homologous recombination deficient (HRD) ovarian cancer cells that carry either a mutant or epigenetically silenced BRCA1 gene are very sensitive to inhibition of Non-Homologous End Joining (NHEJ) pathways upon combination treatment with PARP, DNA-PK and Pole inhibitors. The indicated WT or BRCA1 deficient ovarian cancer cells were either left untreated (UT) or treated with different combinations of the DNA-PK inhibitor Nu7441 (1 µM), the FDA approved PARP inhibitor Olaparib (OLA; 1 µM), and the FDA approved antibiotic Novobiocin (NOVO; 50 µM) which is also a Pole inhibitor. Surviving cells were counted one week later. Error bars represent standard deviation.

Figure 35:
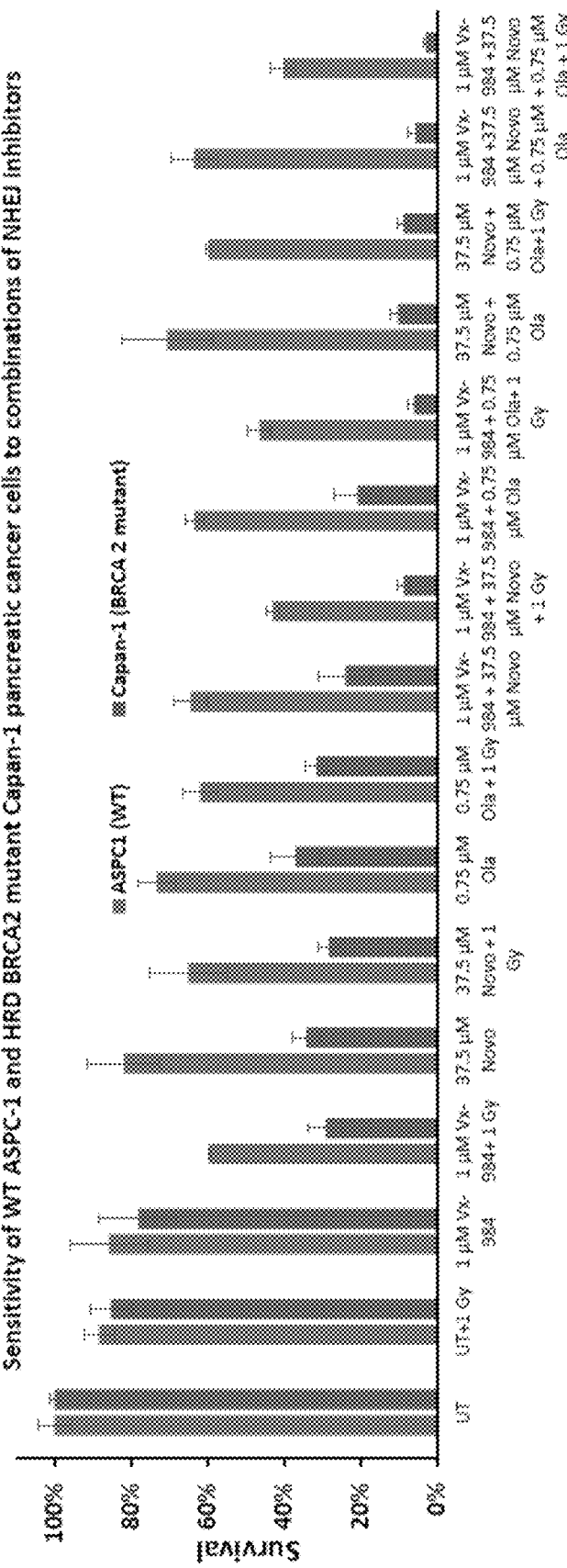

FIG. 35 shows pancreatic cancer cells deficient in homologous recombination (HR) due to mutations in the BRCA2 gene are very sensitive to inhibition of Non-Homologous End Joining (NHEJ) pathways by simultaneous treatment with both DNA-PKcs, PARP and Pole inhibitor inhibitors in the presence of radiation. The indicated wild type or BRCA2 mutant pancreatic cancer cells were either left untreated or treated with the DNA-PKcs inhibitor Vx-984 (1 µM), the FDA approved PARP inhibitor Olaparib (0.75 UM), and the Pole inhibitor Novobiocin (Novo, 37.5 UM), either with or without a low 1 Gy dose of radiation to cause DNA stand breaks and surviving cells were counted one week later. Additive/synergistic effects are clear when the drugs are used in combination. Error bars represent standard deviation.

Figure 36:
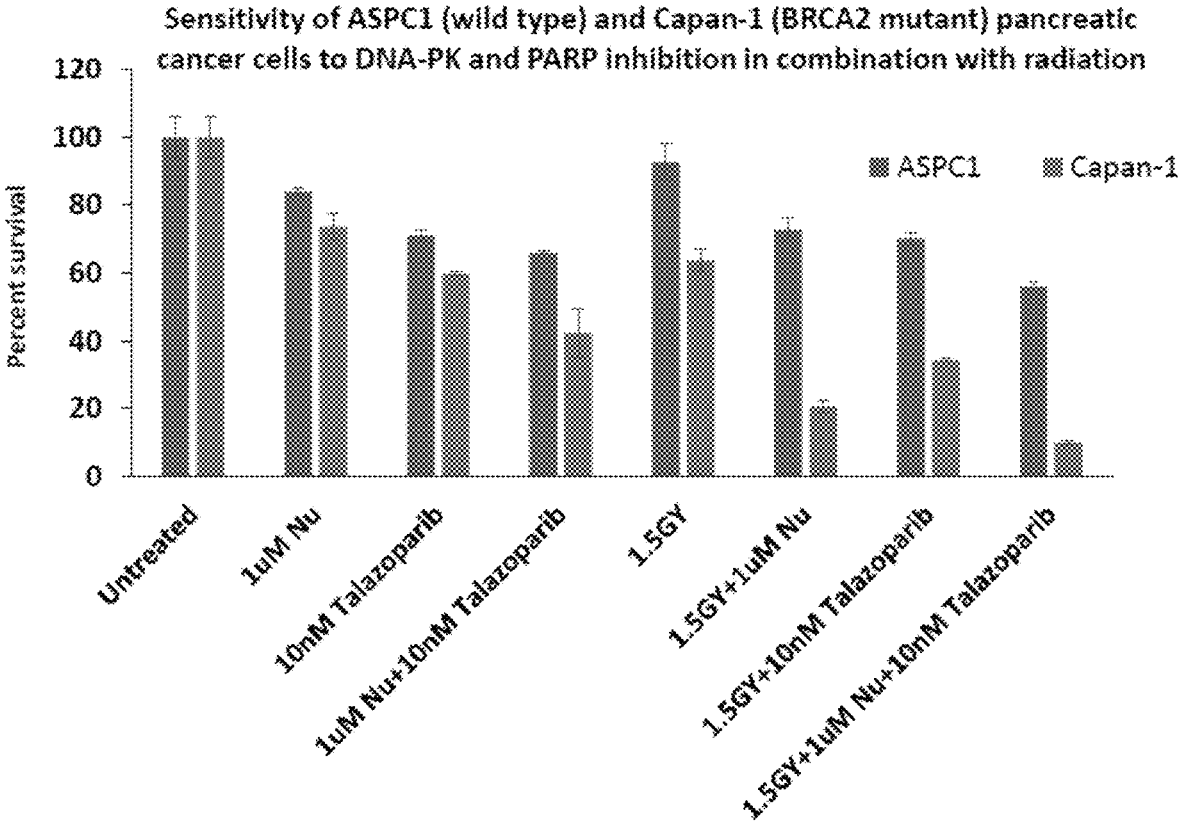

FIG. 36 shows pancreatic cancer cells deficient in homologous recombination (HR) due to mutations in the BRCA2 gene are very sensitive to inhibition of Non-Homologous End Joining (NHEJ) pathways by simultaneous treatment with both DNA-PKcs and PARP inhibitors in the presence of radiation. The indicated wild type or BRCA2 mutant pancreatic cancer cells were either left untreated or treated with the DNA-PKcs inhibitor NU7441 (Nu; 1 µM), a very low dose of the FDA approved PARP inhibitor Talazoparib (10 nM), either with or without a low 1.5 Gy dose of radiation to cause DNA stand breaks and surviving cells were counted one week later. Error bars represent standard deviation.

Figure 37A:
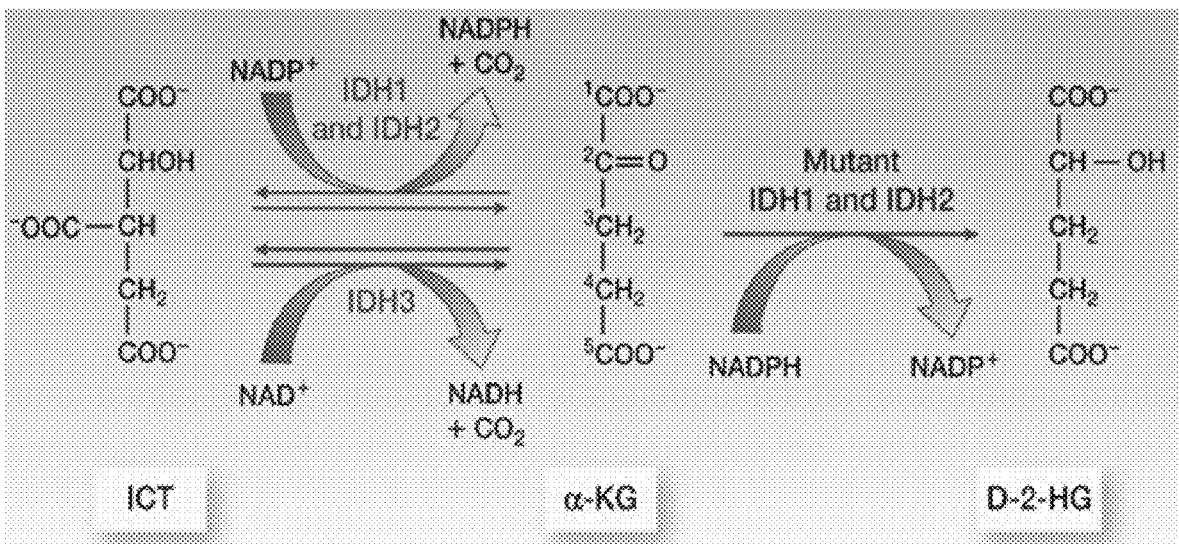
Figure 37B:
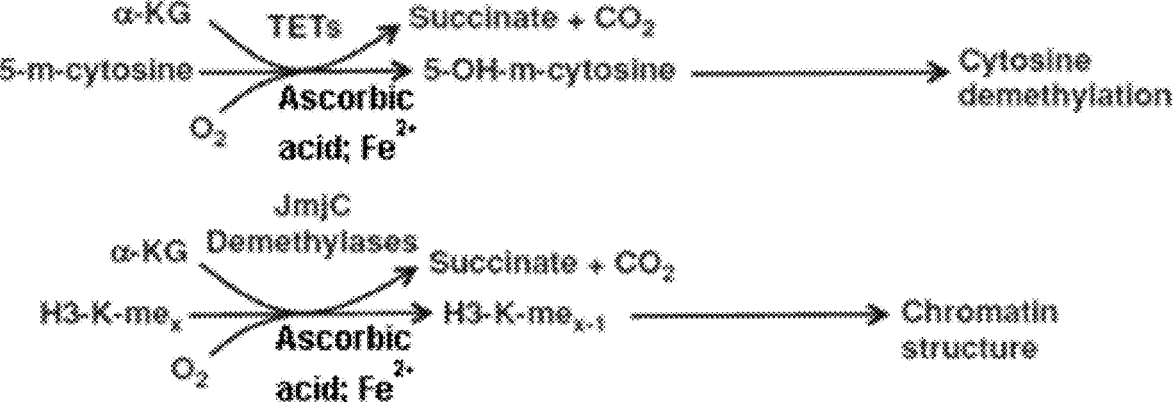

FIGS. 37A-37B show Reactions catalyzed by wild type/mutant human IDH enzymes, and DNA/histone demethylation reactions driven by alpha-ketoglutarate (α-KG). (FIG. 37A) Reactions catalyzed by wild type and mutant human IDH enzymes. (FIG. 37B) Alpha-ketoglutarate (α-KG) dependent DNA and histone demethylation reactions catalyzed by the dioxygenase family of demethylase enzymes.

Figure 38:
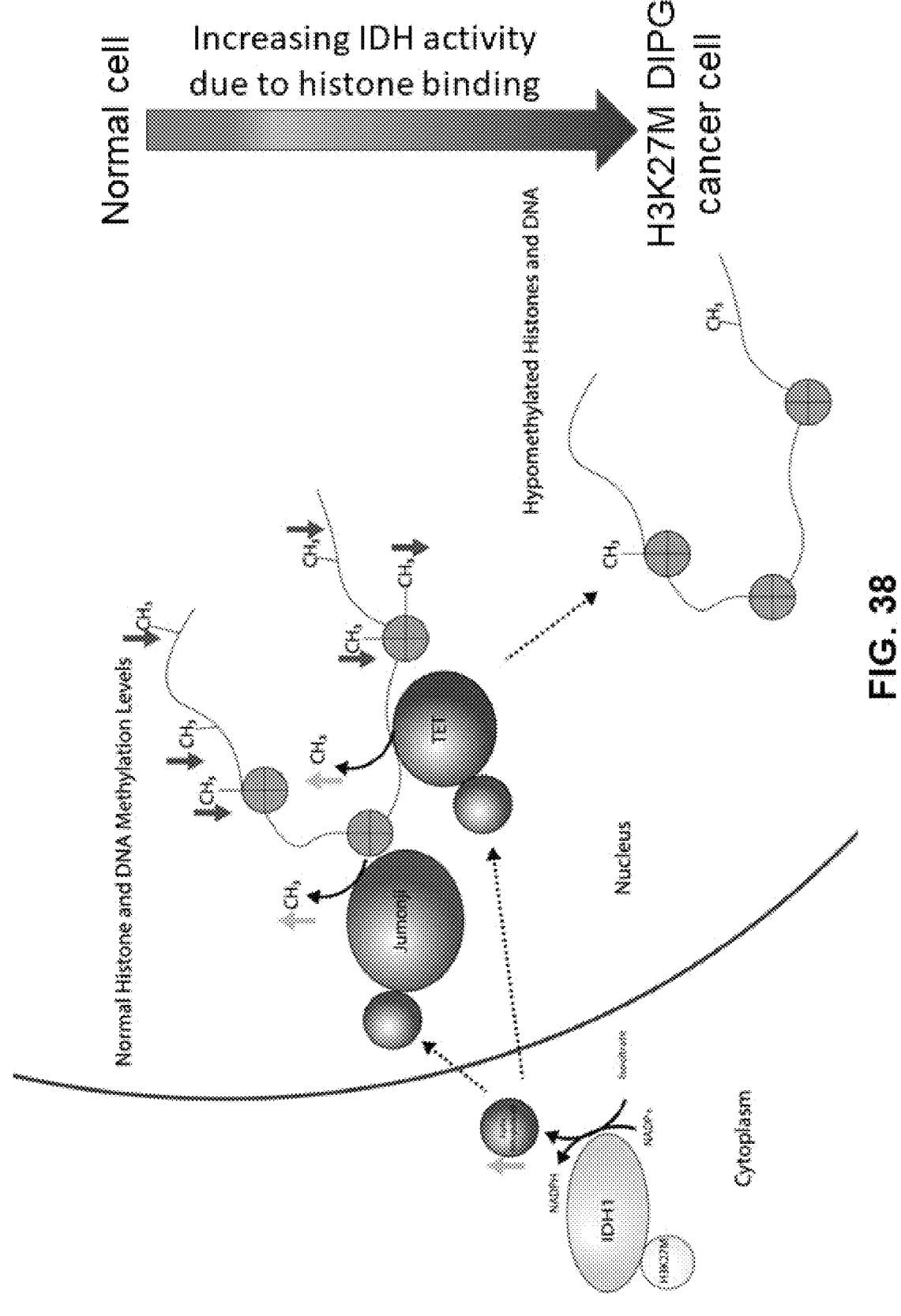
Figure 39A:
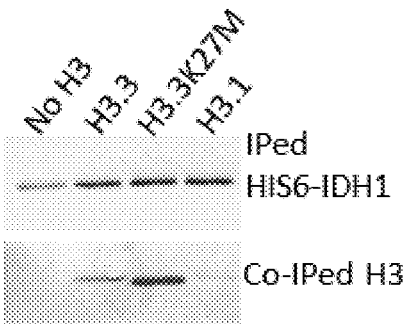
Figure 39B:
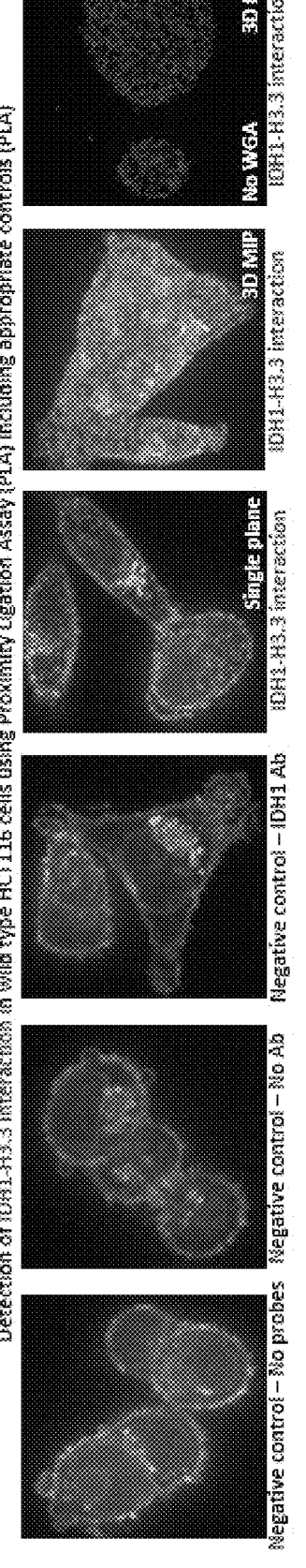
Figure 39C:
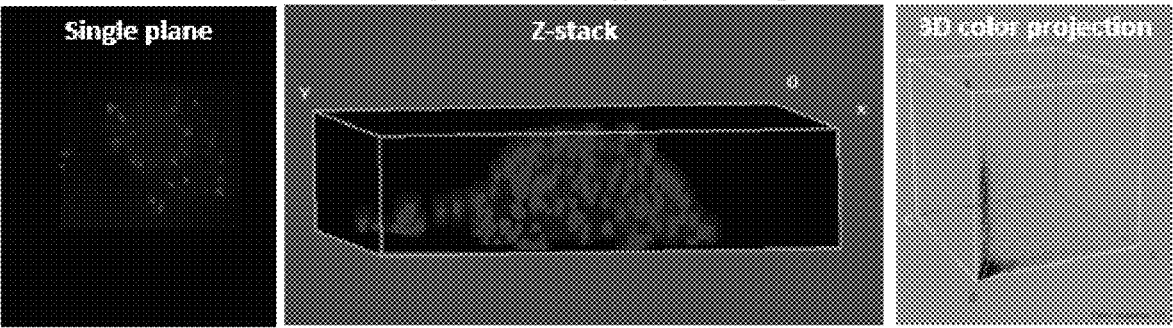
Figure 39D:
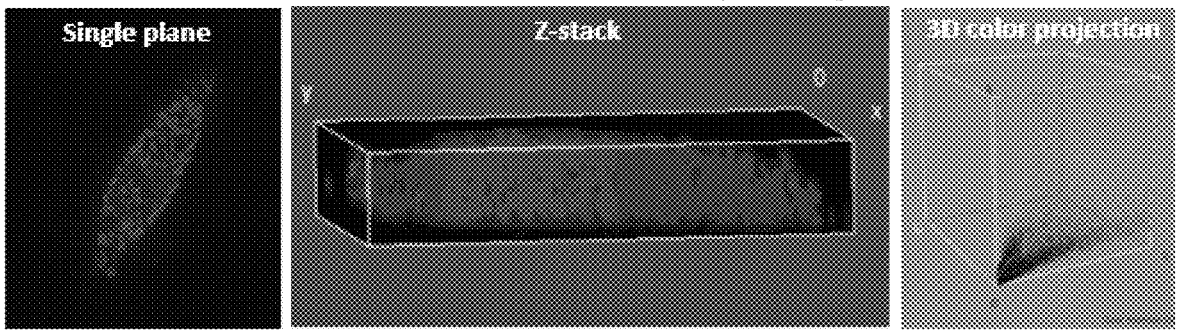
Figure 39E:
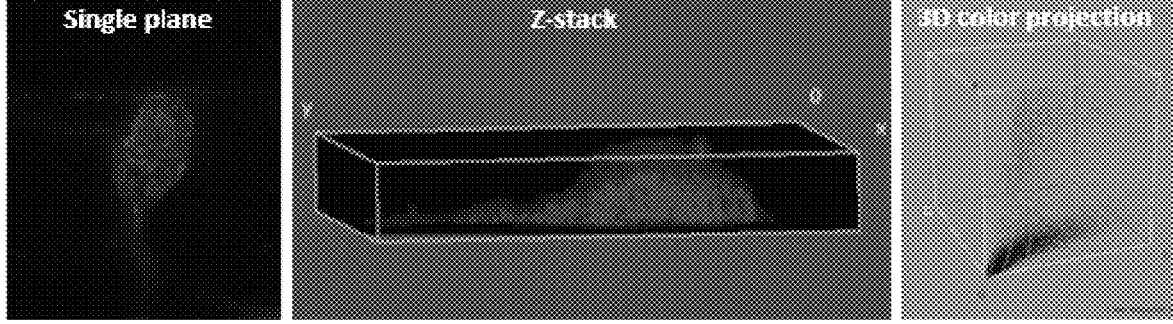
Figure 39F:
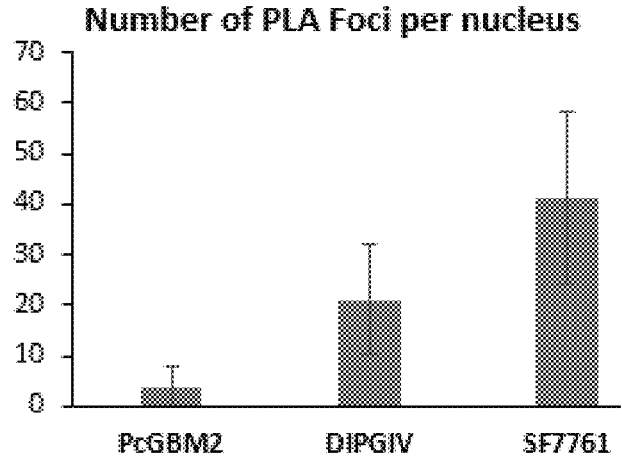
Figure 40A:
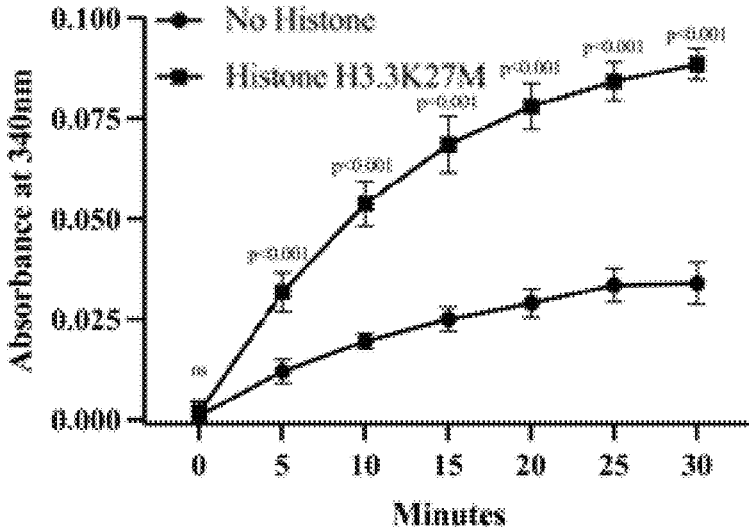
Figure 40B:
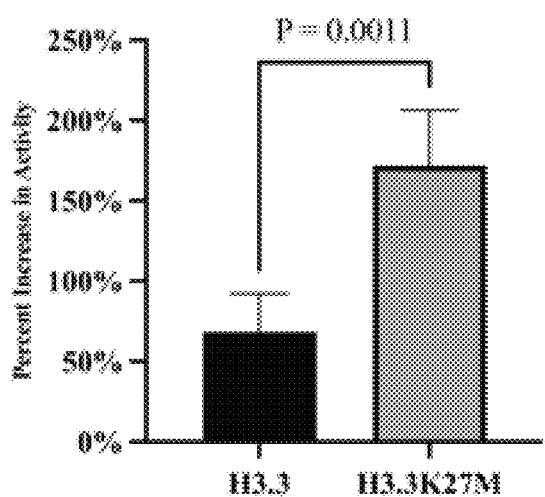
Figure 40C:
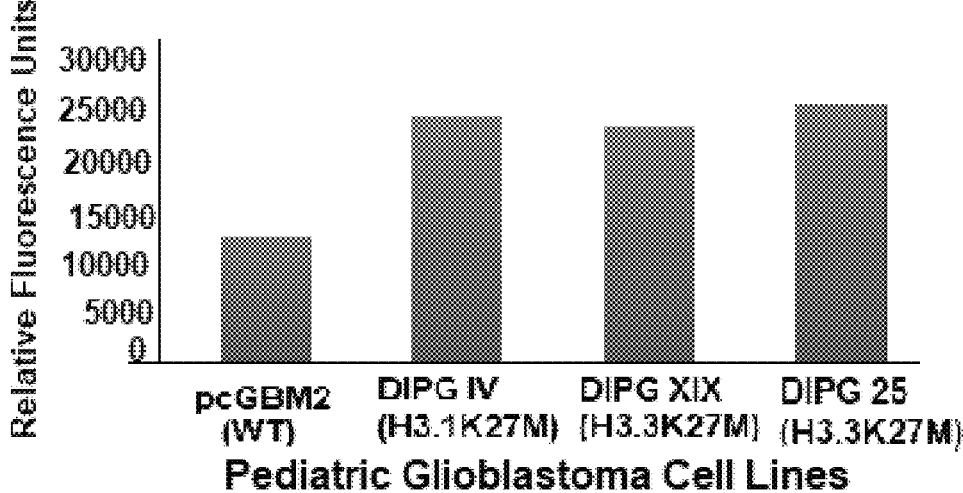
Figure 40D:
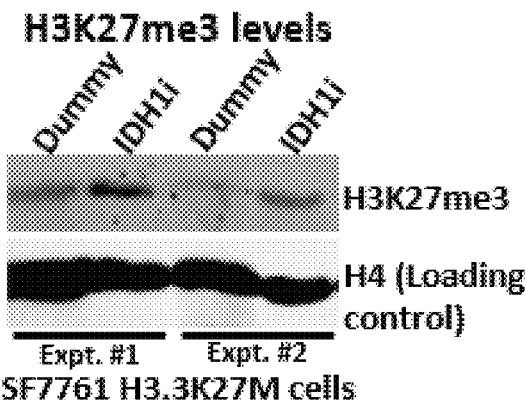
Figure 40E:
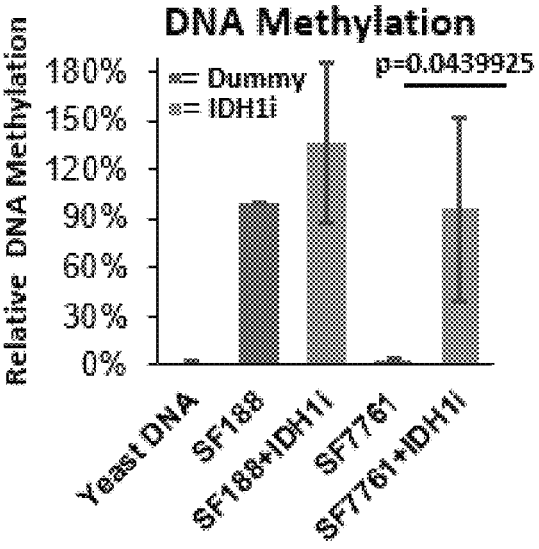
Figure 40F:
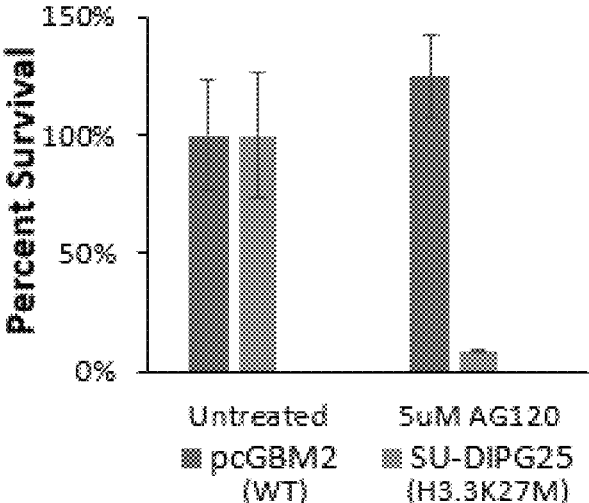

FIG. 38 shows a model illustrating the proposed role of H3K27M mutant in regulating IDH enzyme activity, α-KG production and DNA/histone methylation levels. Newly synthesized histones, especially the H3.3K27M mutant, interact with IDH1 enzyme in the cytoplasm and upregulate its activity resulting in the production of elevated levels of α-KG. High levels of α-KG then enter the nucleus where it drives excessive histone demethylation (via Jumonji domain demethylases) as well as DNA demethylation (via TET demethylases) reactions in H3.3K27M mutant DIPG cells, resulting in the hypomethylation phenotype observed in these cells. Reversing the observed hypomethylation in H3.3K27M mutant DIPG cells using inhibitors of wild type IDH1 to block excessive α-KG production would provide therapeutic benefits. α-KG is shown as circles, arrows denote excessive demethylation reactions and/or indicate the resulting reduction in the levels of DNA and histone methylation.

FIGS. 39A-39F show Wild type (WT) and K27M mutant H3 associates with IDH1 in vitro and in cells, especially in the nucleus. (FIG. 39A) Mutant histone H3.3K27M binds IDH1 with a greater affinity than wild type H3.3 or H3.1. Purified recombinant epitope-tagged human IDH1 and histones were used to assay their binding in vitro by first immobilizing 1 microgram of HIS6-tagged IDH1 onto Talon beads (GE) and incubating them with equal amounts of the indicated histones in a total volume of 20 microliters. Following incubation at room temperature for 10 minutes, the beads were recovered by centrifugation, washed 3 times with the binding buffer to remove unbound proteins. The beads were then boiled in SDS gel loading buffer to recover bound proteins prior to resolving them by 18% PAGE and transferring to a nitrocellulose membrane for Western blotting. A monoclonal HIS-tag antibody (Novagen) was used to quantitate immobilized IDH1, while the bound histones were measured using H3 antibodies. (FIG. 39B) IDH1 interacts with H3.3 in human cells. Proximity Ligation Assay (PLA) was performed using the Duolink kit (Sigma-Aldrich) according to the manufacturer's instructions in HCT116 cells to detect the interaction between IDH1 and H3.3 using highly specific monoclonal antibodies to each protein. The DNA within the nuclei is stained using DAPI, while the cell membranes and some cytosolic structures such as the Golgi apparatus are stained using Wheat Germ Agglutinin (WGA) to show the cell boundaries. Negative controls exhibiting the absence of PLA signals when no probes or no antibody (Ab) or only the IDH1 Ab is used. When both H3.3 and IDH1 Ab are used, multiple foci corresponding to positive PLA signals are observed both in a single plane, but especially on a Maximum Intensity Projection (MIP) rendering of a stack of 30 confocal images showing the abundance of dots indicating interaction between IDH1 and H3.3 with a nucleocytoplasmic signal distribution. The last panel on the far right has the WGA signal removed to allow better visualization of the PLA signals. (FIG. 39C) PLA signals showing the H3.3-IDH1 interaction in pCGBM2 pediatric glioblastoma cells carrying WT H3.3. The Z-stack rendered in 3D shows very little overlap between the PLA signal and the signal from the nucleus in WT cells. (FIG. 39D) PLA signals showing the H3-IDH1 interaction in H3.1K27M mutant DIPGIV pediatric glioblastoma cells. The Z-stack rendered in 3D shows considerable overlap between the PLA signal and the signal from the nucleus, which is confirmed by the 3D color projection, suggesting enrichment of H3-IDH12 interaction in the nucleus. (FIG. 39E) PLA signals showing the H3-IDH1 interaction in H3.3K27M mutant SF7761 pediatric glioblastoma cells. The Z-stack rendered in 3D shows considerable overlap between the PLA signal and the signal from the nucleus. (FIG. 39F) Quantitation of the average number of PLA foci per nucleus. The average number of PLA foci per nucleus was determined using Image J and plotted.

FIGS. 40A-40F show binding of histone H3.3K27M mutant to IDH1 enhances its activity, leading to a-ketoglutarate overproduction and hypomethylation in H3.3K27M mutant cells, which can be reversed using IDH inhibitors, and to which these cells are very sensitive (FIG. 40A) Binding of histone H3.3K27M enhances IDH1 activity in vitro. A binding reaction between purified H3.3K27M and IDH1 was set up using 0.1 microgram of IDH1 with or without the same amount of histone H3.3K27M as described above, except that the Talon beads were omitted from the reaction. Citrate and NADP+ was added to initiate the reaction. The generation of NADPH from NADP+ during the IDH1 mediated conversion of isocitrate to α-KG in the absence or presence of H3.3K27M in the reaction was monitored spectrophotometrically. Error bars indicate standard deviation from the mean in three independent experiments. (FIG. 40B) Quantitation of the increase in IDH1 activity due to WT or K27M mutant H3.3. Increase in IDH1 activity determined as described in panel A in the presence of WT or mutant H3.3 is plotted. (FIG. 40C) Pediatric DIPG cancer cells carrying the H3 K27M mutant exhibit high levels of α-KG. A fluorogenic assay was performed to measure α-KG levels in whole cell extracts prepared from the indicated pediatric glioblastoma cells carrying either the WT H3 or the H3K27M mutant as indicated. The data was normalized based on cell counts. All the three different patient derived H3 K27M mutant DIPG cells exhibited α-KG levels that were at least twice as high as the WT H3 carrying pediatric glioblastoma cells. (FIG. 40D) Treatment with the NCATS IDH1 inhibitor increases H3 K27me3 levels in the SF7761 H3.3K27M mutant DIPG cells. Western blotting of acid extracted histones following a 5-day treatment of SF7761 pediatric DIPG tumor cells carrying the H3.3K27M mutant with or without 5 micromolar of the novel NCATS IDH1 inhibitor (IDH1i) using the indicated antibodies was performed. Histone H4 levels serve as a loading control. Two biological replicates are shown and the average increase in H3 K27Me3 levels in these cells following IDH1 inhibition after normalization to H4 levels is ~470%. (FIG. 40E) IDH1 inhibition increases DNA methylation in H3.3K27M mutant DIPG cells. DNA methylation in the indicated cells was measured following treatment with 5 micromolar IDH1 inhibitor for 5 days. Data from multiple experiments is plotted here and significant differences are indicated by p values. (FIG. 40F) H3.3K27M mutant cells are sensitive to IDH1 inhibitors. Patient derived childhood glioblastoma cells carrying WT H3.3 (pCGBM2) or the H3.3K27M mutant (DIPG25) were treated in triplicate with or without 5 μM of the FDA approved mutant IDH1 inhibitor AG120 (trade name Ivosidenib). Cell viability was measured after 7 days (where applicable, the IDH1 inhibitor was added one day prior to IR exposure and maintained throughout the experiment).

Figure 41:
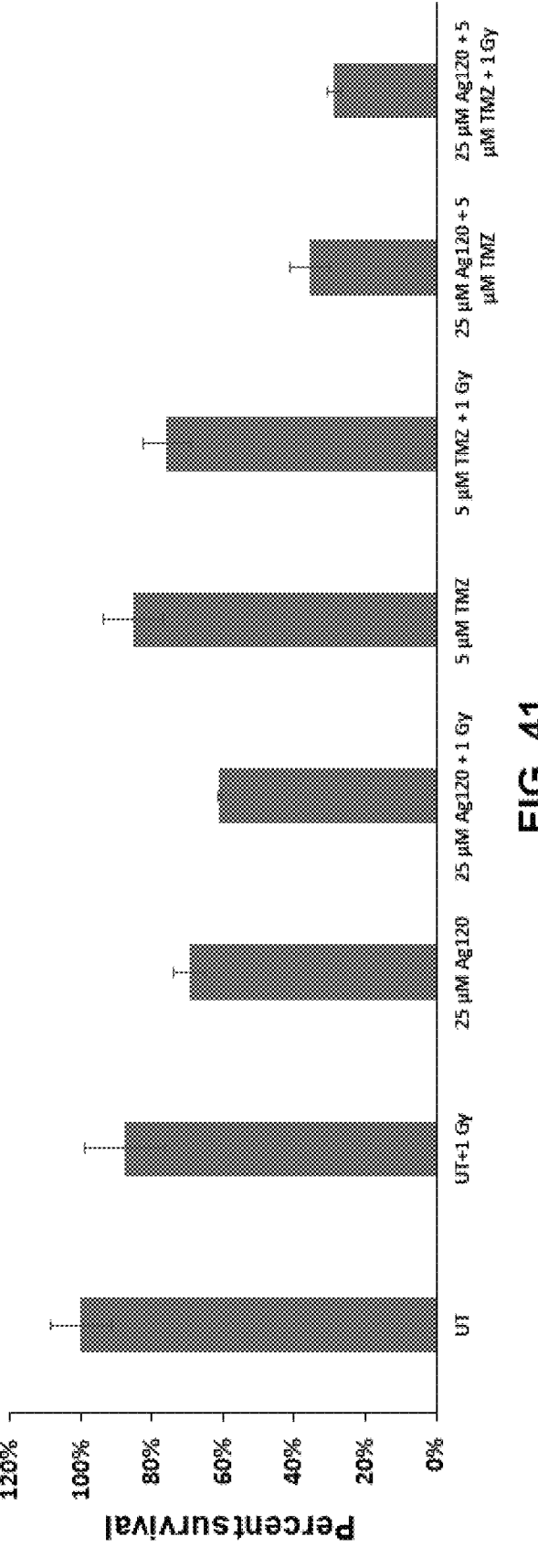

FIG. 41 shows FDA approved alkylating drug Temozolomide (TMZ) and IDH1 inhibitor AG120 show synergistic effects in killing H3.3K27M mutant DIPG cancer cells. H3.3K27M mutant SF7761 DIPG cells were treated with 5 μM TMZ for 3 days to increase DNA and histone methylation levels before treatment with 25 UM AG120 and 1Gy radiation, following which cells were incubated for 4 more days in the continued presence of TMZ. Surviving cells were then counted to determine percent survival. Error bars represent standard deviation.

Figure 42:
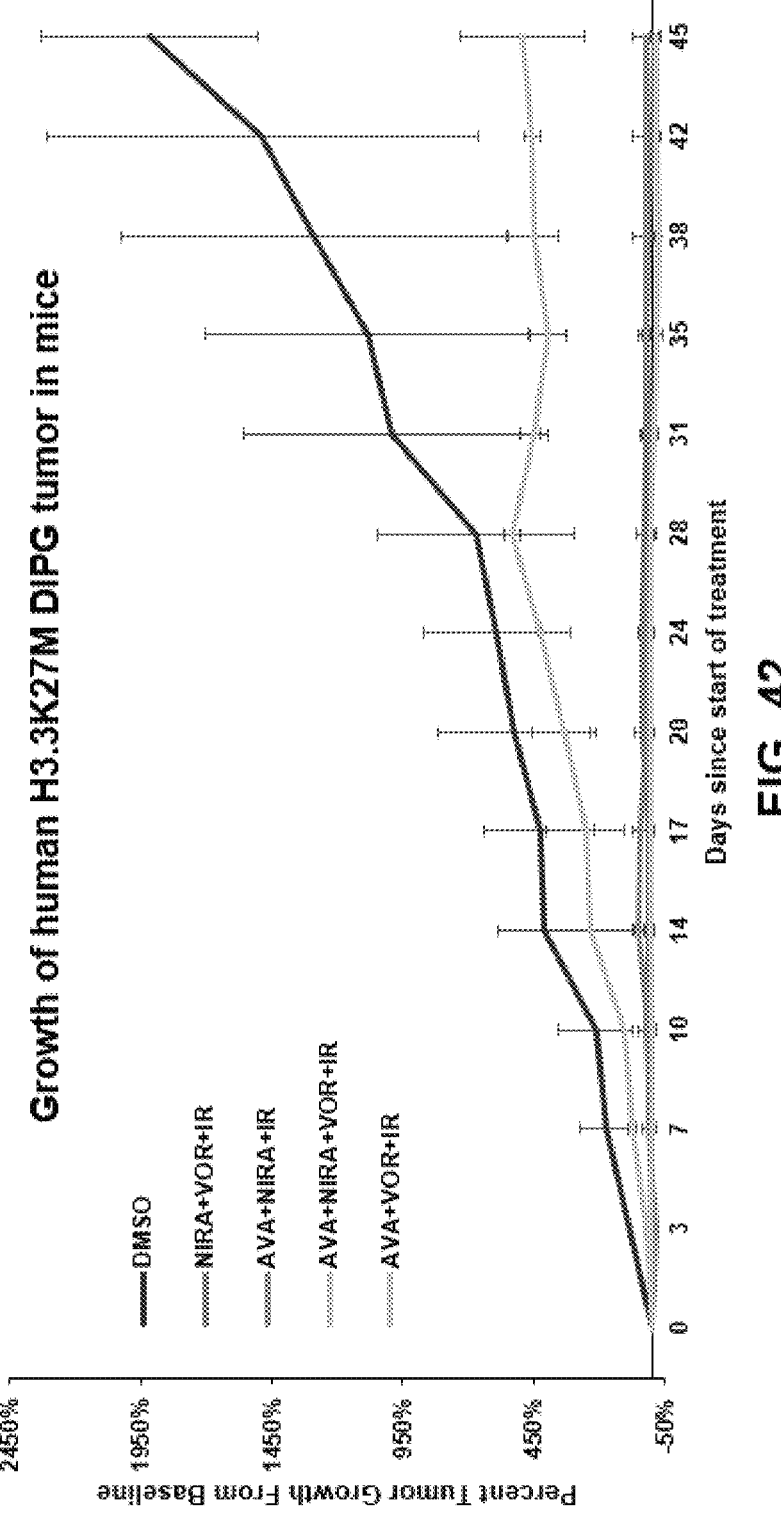

FIG. 42 shows combination therapies using brain penetrant FDA approved drugs targeting different pathways are very effective in blocking the growth of human H3.3K27M DIPG tumors in mice. R2G2 mice (Envigo) were engrafted subcutaneously with human DIPG XIII cells carrying the H3.3K27M mutation. Once tumors were palpable, mice were divided into the indicated treatment groups that were injected intraperitoneally Monday to Friday with either the vehicle (DMSO) or the indicated combinations of 15 mg/kg/day each of the PDGFR inhibitor Avapritinib (Ava), PARP1 inhibitor Niraparib (Nira) and the HDAC inhibitor Vorinostat (Vor). Mice treated with drugs also received 30Gy of ionizing radiation (IR) in twenty fractions of over 4 weeks at the beginning of the treatment, following which only drug administration was continued for 45 days. Tumor size was measured every 3-4 days using digital microcalipers.

Figure 43:
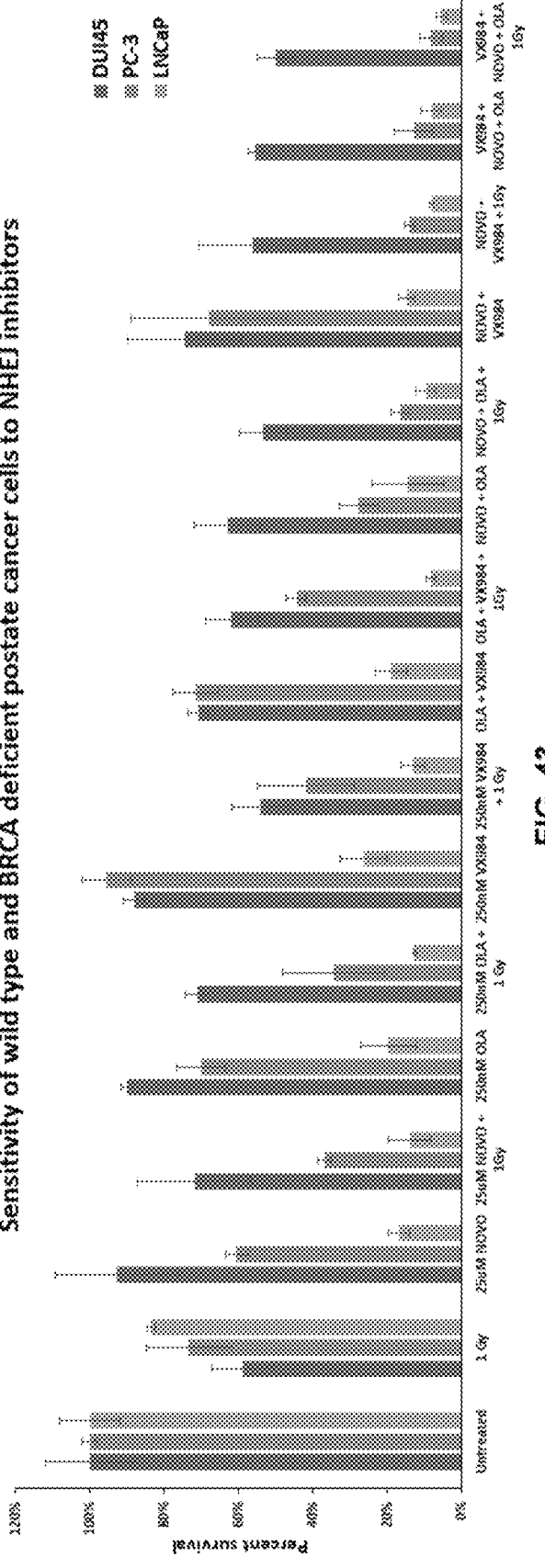

FIG. 43 shows prostate cancer cells deficient in homologous recombination (HR) due to mutations in the BRCA2 gene are very sensitive to inhibition of Non-Homologous End Joining (NHEJ) pathways by simultaneous treatment with NHEJ inhibitors in the presence of radiation. DU145 cells lack pathogenic BRCA mutations and serve as a wild type control. PC-3 cells exhibit reduced BRCA1 expression and mimic homologous recombination deficient (HRD) phenotype. LNCaP cells carry pathogenic BRCA2 mutation that results in an HRD phenotype. The indicated wild type or BRCA mutant/deficient prostate cancer cells were either left untreated or treated with the DNA-PKcs inhibitor VX984 (250 nM), the FDA approved PARP inhibitor Olaparib (OLA, 250 nM), and the FDA approved antibiotic Novobiocin (NOVO; 25 mM) which also inhibits Pole, either with or without a low 1 Gy dose of ionizing radiation to cause DNA stand breaks and surviving cells were counted one week later. Note: The lower detection limit of this assay is about 10% survival. Error bars represent standard deviation.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Two molecules each of the canonical core histones H4, H3, H2A and H2B form an octameric protein core around which 147 base pairs of DNA is wrapped to form a nucleosome. In most eukaryotes, one molecule of linker histone H1 is believed to bind close to the entry and exit sites of the DNA around the nucleosome core particle to form the nucleosome. This structure is repeated to package all DNA into filaments called chromatin, which then regulates access to the genetic information contained in DNA. All aspects of DNA metabolism, including DNA repair are modulated by chromatin structure. Chromatin structure in turn is regulated by posttranslational histone modifications and non-allelic primary sequence variants of the canonical histones found at specific loci or under certain conditions. Canonical histones H3.1 and H3.2 are deposited genome-wide during S-phase, while the replacement variant H3.3 (which differs from H3.1 and H3.2 at 5 and 4 of 135 residues respectively) is deposited throughout the cell cycle in transcriptionally active regions, where it forms unstable nucleosomes relative to canonical H3 variants. Histone H3.3 is enriched at the promoters of transcriptionally active genes and at telomeres. Deposition of H3.3 into these varying chromatin structures is dependent on two H3.3 specific chaperones, Histone Regulator (HIRA) and Alpha-Thalassemia Mental Retardation X-linked protein/Death domain Associated protein (ATRX/DAXX), which are responsible for its incorporation in euchromatin and heterochromatin respectively. Interestingly, a lysine (K) to methionine (M) mutation at position 27 (K27M) or a glycine (G) to arginine (R)/valine (V) mutation at position 34 (G34R/V) in H3.3 are found in a majority of childhood glioblastoma brain tumors. Additionally, H3.3G34 is mutated to Tryptophan (W) or Leucine (L) in nearly all giant cell tumors of bone, while the K36M mutation occurs in the vast majority of chondroblastomas. The K27M mutation results in a global reduction in H3K27 methylation which is important for gene repression. The G34R/V mutation affects the pattern of the gene activating H3K36 methylation, thereby altering transcription and causing upregulation of the MYCN oncogene. Together, these studies suggest that transcriptional and epigenetic defects may drive cancer in H3.3 mutant cells.

Although transcription independent roles of H3.3 and their potential relevance to tumorigenesis have not been investigated in depth, several studies have suggested a role for H3.3 in DNA repair. The exact role of H3.3 in DNA repair from these studies is far from clear, in part due to the discrepancies between some of the studies. Initially, H3.3 was shown to be recruited to sites of UV damage where it is required for replication fork progression in a HIRA-dependent manner in mammalian and chicken cells. These findings suggest that H3.3 may play a role in the nucleotide excision repair (NER) pathway during chromatin reconstitution following DNA repair synthesis. Another study at the time reported the deposition of H3.3 at sites of DSBs in a HIRA-dependent manner, following which H3.3 was acetylated to facilitate RAD51 recruitment for repair by the HR pathway. However, a subsequent study suggested an ATRX/DAXX-dependent role for H3.3 in HR downstream of RAD51 removal in reconstituting chromatin during the DNA repair synthesis step, prior to double Holiday junction formation. Yet another study suggested that H3.3 is deposited at DSBs in a Chromodomain Helicase DNA Binding Protein 2 (CHD2) and Poly-ADP Ribose Polymerase 1 (PARP1)-dependent manner to facilitate repair via the c-NHEJ pathway. However, data from this study should be interpreted with caution since the U2OS cancer cells used therein lack functional ATRX chaperone as well as the tumor suppressor, p53 and relied on transient knockdown of H3.3 for weeks-long assays. Furthermore, the U2OS cells also exhibit the Alternative Lengthening of Telomeres (ALT) phenotype and show highly aberrant H3.3S31 phosphorylation patterns. Taken together, the data so far suggests that H3.3 may be required for chromatin reconstitution during the DNA repair synthesis step that is involved in multiple DNA repair pathways. However, the precise role of H3.3 in DSB repair via both HR and NHEJ pathways is unclear and requires further investigation.

To clarify the role of H3.3 in DNA repair, herein are described assays using live cell microscopy approaches and stable H3.3 knockdown cells to show the direct recruitment of H3.3 to DNA damage sites in living cells. Both patient-derived pediatric high-grade glioma cells carrying wild type (WT) or mutant H3.3 and heterologous cells derived from the HCT116 cell line that have a stable near diploid karyotype, have been used in these assays, with histone chaperones, p53, and relevant DNA repair pathways intact. It is shown herein that H3.3 makes a major contribution to DSB repair via the HR pathway, which may be particularly important for the repair of DSBs within condensed heterochromatin. Consistent with this, cells deficient in H3.3 rely heavily on NHEJ pathways for DSB repair. Based on this evidence, a synthetic lethality based therapeutic strategy has been developed using NHEJ inhibitors that selectively targets patient-derived H3.3 mutant tumor cells in vitro and in vivo, thus providing an effective and novel therapeutic avenue for these cancers. Data reported herein indicates that H3.3 may be playing an upstream role as a HR promoting DSB repair pathway choice factor, by preventing H1 binding at DSBs which normally promotes NHEJ.

Shortcomings of Current Treatments

Current chemotherapeutic treatment options for H3.3 mutant cancers including, but not limited to, childhood glioblastomas are ineffective and surgery is often precluded due to the diffuse nature of the tumor and the involvement of the brain stem in many cases, resulting in 100% fatality. On the other hand, treatment of chondroblastomas and large cell tumors of the bone often requires surgical amputation of limbs, resulting in lifelong disability. A recently proposed therapeutic option targets the epigenetic and transcriptional alterations in H3.3K27M mutant cells and involves inhibiting the H3K27 histone demethylase JMJD3. However, this strategy works only for H3.3K27M tumors and is likely to affect normal cells that require JMJD3 function as well. In contrast, the disclosed approach targets NHEJ pathways concomitant with DSB induction as a therapeutic strategy for all cancers associated H3.3 mutations (K27M, G34R/V/W/L and K36M) since all of these are defective in HR-mediated DNA repair. Further, the disclosed strategy would spare normal cells as they would be able to use their functional HR pathway for DSB repair and survive. Finally, the disclosed approach targeting NHEJ pathways in the H3 mutant cancer cells deficient in HR can be combined with the modulation of epigenetic pathways such as histone acetylation using HDAC inhibitors, as well as modulation of DNA and histone methylation pathways by inhibiting IDH.

Currently, the FDA approved PARP inhibitor Olaparib is being used with mixed results for the treatment of specific HR defective cancers, such as BRCA1 or BRCA2 mutated ovarian and breast cancers, and in a more limited manner for prostate and pancreatic cancers. However, Olaparib only inhibits the alt-NHEJ pathway and single-strand break repair via the base excision repair pathway, leaving the classic NHEJ as well as Pole-dependent Theta Mediated End Joining (TMEJ) pathway functional, which can still repair DSBs in HR-defective tumor cells, thereby allowing some of these cancer cells to survive. In contrast, the disclosed strategy involves simultaneously inhibiting both alt- and classic-NHEJ pathways, as well as TMEJ for treating HR defective tumors and this should be much better at killing HR-defective cancer cells compared to PARP inhibitors alone. In one aspect, homologous recombination deficient (HRD) prostate cancer cells with BRCA mutations can also be treated using the same combination strategy as breast cancers with BRCA mutations. In another aspect, the data presented herein represent the first time that a significant subset of several different seemingly unrelated adult onset cancers (HRD breast, ovarian, prostate and pancreatic cancers, as well as some melanomas), that all share a common molecular defect (HRD) can be targeted effectively using the same combination therapy.

Furthermore, Olaparib treatment alone has also been shown to result in Olaparib-resistant tumors in patients and in mice (FIG. 4D) over time. In contrast, the disclosed approach involving the use of two different inhibitors to block both classic and alt-NHEJ, as well as a third inhibitor to block TMEJ in HR defective cancer cells, and can greatly minimize or eliminate the generation of resistant tumors as simultaneous acquisition of mutations that make a tumor cell resistant to all three classes of drugs targeting the three NHEJ pathways would be a much rarer event.

Method for Treating Cancer

In one aspect, disclosed herein is a method for treating cancer in a subject, the method including at least the steps of (a) administering at least one drug from each of at least two classes selected from an inhibitor of poly-ADP ribose polymerase (PARP inhibitor), an inhibitor of DNA-dependent protein kinase catalytic subunit (DNA-PKcs inhibitor), an inhibitor of wild-type isocitrate dehydrogenase (IDH inhibitor), an inhibitor of histone acetyltransferase (HAT inhibitor), an inhibitor of histone deacetylase (HDAC inhibitor), an inhibitor of DNA polymerase $\Theta$ (POL$\Theta$ inhibitor), a platelet-derived growth factor receptor inhibitor (PDGFR inhibitor), and a DNA alkylating agent to the subject and (b) administering radiation to the subject.

In an aspect, the cancer is associated with an H3.3 mutation such as, for example, an H3.3K27M mutation, an H3.1K27M mutation, or an H3.2K27M mutation, an H3.3G34V mutation, an H3.3G34R mutation, an H3.3G34W mutation, an H3.3G34L mutation, an H3.3K36M mutation, or any combination thereof.

In another aspect, the cancer can be selected from H3 mutant or HRD subtypes of acute lymphoblastic leukemia, acute myeloid leukemia, adrenocortical carcinoma, anal cancer, astrocytoma, basal cell carcinoma, bladder cancer, BRCA1 breast cancer, BRCA2 breast cancer, hormone receptor positive breast cancer, Burkitt's lymphoma, carcinoid tumor, cervical cancer, chondroblastoma, chronic lymphocytic leukemia, chronic myelogenous leukemia, colon cancer, cutaneous t-cell lymphoma, endometrial cancer, ependymoma, esophageal cancer, extrahepatic bile duct cancer, gallbladder cancer, a giant cell tumor of the bone, glioblastoma, another high-grade glioma, hairy cell leukemia, head and neck cancer, Hodgkin's lymphoma, hypopharyngeal cancer, intraocular melanoma, islet cell carcinoma, Kaposi's sarcoma, laryngeal cancer, lip and oral cavity cancer, liver cancer, medulloblastoma, melanoma (including BRCA1- or BRCA2-associated melanoma), Merkel cell carcinoma, mesothelioma, multiple myeloma, nasopharyngeal cancer, neuroblastoma, non-Hodgkin's lymphoma, non-small cell lung cancer, oropharyngeal cancer, osteosarcoma, ovarian cancer including BRCA1- or BRCA2-associated ovarian cancer, pancreatic cancer (including BRCA1- or BRCA2-associated pancreatic cancer), parathyroid cancer, penile cancer, pheochromocytoma, pituitary tumor, pleuropulmonary blastoma, primary central nervous system lymphoma, prostate cancer (including BRCA1- or BRCA2-associated prostate cancer), rectal cancer, renal cell cancer, retinoblastoma, rhabdomyosarcoma, salivary gland cancer, secondary acute myeloid leukemia (s-AML), small cell lung cancer, small intestine cancer, soft tissue sarcoma, squamous cell carcinoma, stomach cancer, testicular cancer, thymoma, thyroid cancer, uterine sarcoma, vaginal cancer, vulvar cancer, Waldenström's macroglobulinemia, Wilms' tumor, or any combination thereof. In one aspect, the cancer is a glioblastoma, another high-grade glioma, or any combination thereof. In one aspect, the glioblastoma can be pediatric glioblastoma. In an aspect, the s-AML, or any other cancer, can have an H3.3 mutation as discussed herein such as, for example, H3.3K27M.

In one aspect, steps (a) and (b) of the method are performed simultaneously. In an alternative aspect, steps (a) and (b) of the method are performed sequentially in any order (e.g., (a) can be performed before (b) or after (b)).

In one aspect, the two classes can be a PARP inhibitor and a DNA-PKcs inhibitor.

In an aspect, the PARP inhibitor can be selected from olaparib, rucaparib, niraparib, talazoparib, veliparib, BGB-290 (pamiparib), CEP 9722, E7016, 3-aminobenzamide, or any combination thereof. In another aspect, the DNA-PKcs inhibitor can be selected from NU7441 (2-N-morpholino-8-dibenzothiophenyl-chromen-4-one), NU7026 (2-(morpholin-4-yl)-benzo[h]chromen-4-one), SU11752, NK314, AZD7648, M3814, VX-984, CC-115, or any combination thereof. In some aspects, niraparib and veliparib may be of particular importance to DIPG as they are both brain penetrant. In another aspect, any PARP inhibitor can be used in combination with other drugs for treating other homologous recombination deficient tumors where brain penetrance is not required.

In any of these aspects, the combined dosages for the at least one drug from at least two different classes are lower than dosages for the individual drugs when administered separately.

In one aspect, the PARP inhibitor can be administered at a dosage of less than 600 mg per day, or from about 50 mg per day to about 550 mg per day, about 100 mg per day to about 500 mg per day, about 150 mg per day to about 450 mg per day, or about 50, 100, 150, 200, 250, 300, 350, 400, 450, 500, or about 550 mg per day, or a combination of any of the foregoing values, or a range encompassing any of the foregoing values, or can be administered at 25 mg or less per kg of subject body weight, or from about 1 to about 24 mg, about 5 to about 20 mg, about 10 to about 15 mg per kg of subject body weight, or about 1, 2, 5, 10, 15, or about 20 mg per kg of subject body weight. In another aspect, the DNA-PKcs inhibitor can be administered at a dosage of less than 400 mg per day, or from about 50 mg per day to about 350 mg per day, about 100 mg per day to about 300 mg per day, or about 150 mg per day to about 250 mg per day, or about 50, 100, 150, 200, 250, 300, 350, or about 400 mg per day, or can be administered at 5 mg or less per kg of subject body weight, or from about 1 to about 4.5 mg, about 1.5 to about 4 mg, or about 2 to about 3 mg, or at about 0.5, 1, 1.5, 2, 2.5, 3, 3.5, 4, or about 4.5 mg per kg of subject body weight. These values can, of course, vary, depending on the drug, patient age or body weight, and the like. In an aspect, if a typical vorinostat dose is 400 mg once per day, a dose for a child would be about 200 mg per day. In another aspect, a typical sodium valproate dose is about 10 to about 15 mg per kg of patient body weight per day, not to exceed 60 mg per kg per day. In some aspects, 125 mg, 250 mg, or 500 mg is administered up to 3 times per day in tablet or syrup form. In some aspects, sodium valproate can be given in amounts of up to 2 grams or 2.5 grams per day.

In one aspect, the PARP inhibitor is Olaparib and the DNA-PKcs inhibitor is NU7441.

In any of these aspects, the PARP inhibitor and the DNA-PKcs inhibitor, or any members of any other classes of drugs used in step (a) of the method, can be administered orally, intravenously, or both orally and intravenously. In still another aspect, some disclosed drugs do not normally cross the blood-brain barrier. In a further aspect, for the treatment of brain tumors, it can be especially important to cross the blood-brain barrier in order to reach the tumors. Either particular drugs administered or methods of administration can be altered to accomplish this goal. In one example, the PARP inhibitor niraparib shows better brain penetrance than Olaparib and may be especially suitable for treating brain tumors, while in other tumor types, most PARP inhibitors would be expected to perform similarly.

In one aspect, performing the method results in a reduction or elimination of at least one side effect relative to a cancer treatment not including each of steps (a) and (b). In a further aspect, the at least one side effect can be myelodysplastic syndrome (MDS), acute myeloid leukemia (AML), bone marrow suppression, a low white blood cell count, weakness, weight loss, fever, frequent infections, blood in urine, blood in stool, shortness of breath, fatigue, bruising more easily, bleeding more easily, shortness of breath, fever, cough, wheezing, pneumonitis, blood clots, nausea, vomiting, tiredness, weakness, low red blood cell count, diarrhea, loss of appetite, headache, changes in food taste, dizziness, indigestion, heartburn, low platelet count, or any combination thereof.

In a further aspect, performing the method does not induce drug resistance in the cancer. In another aspect, performing the method induces partial or complete remission of the cancer. In one aspect, various factors are believed to be responsible for drug resistance in cancer including, but not limited to, growth rate of a tumor, heterogeneity within a tumor, and others. In another aspect, combination chemotherapy has been attempted but success of this approach has plateaued, in part because combination chemotherapy tends to use drug combinations where the different drugs target different pathways in tumor cells, allowing resistance to individual drugs to arise. In one aspect, the synergism of targeting by drugs in the present combinations eliminates at least one pathway for drug resistance to emerge.

Likewise, systemic side effects of chemotherapeutic drugs at standard dosage levels, alone or in combination, can be too great for patients to tolerate, thus requiring a reduction in dosage or longer time periods between treatments, which can contribute to drug resistance. In one aspect, the present approach allows for lower dosages of individual drugs, thus reducing or eliminating side effects and enabling regular administration without interruption, contributing to patient toleration of therapy and not allowing tumors to mutate and evolve resistance to individual drugs.

In another aspect, radiation therapy can have side effects including, but not limited to, fatigue, headache, hair loss, localized swelling or tenderness, skin changes, difficulty swallowing, nausea and/or vomiting, diarrhea, sexual dysfunction, urinary or bladder problems, and/or other localized changes depending on the area to which radiation is administered. In one aspect, the present methods allow for lower doses of radiation than current recommendations, thus reducing the occurrence and side effects of radiation therapy while still providing effective cancer treatment.

In one aspect, when an initial cancer treatment does not fully destroy all cancer cells, cancer can recur. In an aspect, under traditional treatment regimens, some cancers have a particularly high recurrence rate, including childhood cancers, chondroblastomas, GCTB, Hodgkin lymphoma, glioblastomas, some soft tissue sarcomas, bladder cancer, breast cancer, ovarian cancer, prostate cancer, colorectal cancer, and pancreatic cancer, among others. In an aspect, fast-growing and/or advanced cancers, as well as cancers that have metastasized, are particularly likely to be recurring. In a further aspect, recurrent cancer can be a local recurrence in the same place, a regional recurrence wherein a tumor has grown into nearby lymph nodes or other tissues, a distant recurrence due to metastasis, or any combination thereof. In another aspect, the disclosed methods can prevent recurrent cancers by destroying more cancer cells and by preventing drug resistance, thereby allowing continued treatment with effective drug combinations.

In one aspect, the subject is a mammal such as, for example, a human, cat, dog, guinea pig, rat, mouse, rabbit, horse, cattle, swine, sheep, or goat.

In one aspect, when a drug of any class disclosed herein is described as being administered, it is to be understood that a composition or treatment provided to the subject to whom the treatment is administered contains a non-zero amount of the drug. As one non-limiting example, if a POLΘ inhibitor is administered at a dosage of less than 1 gram per day, "less than 1 gram" includes all nonzero amounts that are less than 1 gram per day. Further in this non-limiting example, if a POLΘ inhibitor is administered at 20 mg or less per kg of subject body weight, "20 mg or less" includes all nonzero amounts per kg of subject body weight up to or including 20 mg per kg. In an alternative aspect, if a POLΘ inhibitor is explicitly described as not being included in a composition, or if broad "comprising" style language is used to refer to other drugs but POLΘ inhibitors are not mentioned, then a composition or treatment containing 0 mg of the POLΘ inhibitor is contemplated. The same logic can be extended to all other listed classes of molecules including PARP inhibitors, DNA-PKcs inhibitors, IDH inhibitors, HAT inhibitors, HDAC inhibitors, and the like.

Selective Elimination of Cancer Cells Carrying H3 K27M Mutation Using Inhibitors of Wild-Type Isocitrate Dehydrogenase Enzyme In some aspects, the disclosed method additionally includes administering an inhibitor of wild-type isocitrate dehydrogenase (IDH inhibitor) to the subject, wherein the IDH inhibitor is administered in an effective amount to decrease wild-type IDH activity in cells of the cancer, and wherein the cancer carries a histone H3.3 K27M mutation, H3.1 K27M mutation, or H3.2 K27M mutation, and/or the cancer has low DNA methylation and/or low histone methylation. Optionally, the method further includes administering radiation therapy to the subject before, during, and/or after administering the IDH inhibitor to the subject.

In some aspects, depending on the concentration, the wild-type IDH inhibitor inhibits or blocks both wild-type IDH and mutant IDH. In other aspects, the wild-type IDH inhibitor is specific or selective such that it does not also inhibit mutant IDH. The wild-type IDH inhibitor can inhibit, for example, wild-type IDH1, IDH2, or both IDH1 and IDH2. The wild-type IDH inhibitor can include, for example, AG120, IDH305, GSK321, GSK864, or a combination thereof. In some aspects, the cancer to be treated is a glioblastoma, chondroblastoma, or giant cell tumor of bone (GCTB). In one aspect, the disclosed IDH inhibitors inhibit mutant IDH1 at low concentrations, but also inhibit wild type IDH1 at higher concentrations. In a further aspect, GSK321 and its derivatives specifically block wild type IDH1.

Subjects having a cancer with a histone H3 K27M mutation, low DNA methylation, and/or low histone methylation can be identified by assaying a sample of cancer cells obtained from the subjects. For example, the presence of a histone H3 mutation can be assayed using an antibody specific to H3 K27M, or using PCR to amplify the H3 gene from the cells and performing Sanger sequencing to confirm the mutations. An assay such as a Dot Blot can be used to identify cancer cells with low DNA methylation. Instead of using an antibody to recognize another protein, an antibody to recognize methylated DNA antigen is used. An assay can be used to identify cancer cells having low histone methylation using a Western blot assay.

Cancers such as pediatric glioblastomas driven by the histone H3 K27M mutation exhibit very low levels of DNA and histone methylation (particularly at the H3 K27 residue) and are refractory to currently available therapeutic strategies. However, it is possible that alleviation of the low DNA and histone methylation in these cancer cells, such as by pharmaceutical intervention, can sensitize them to killing by standard ionizing radiation (IR) treatment. Disclosed herein is a strategy for the selective elimination of these H3 K27M mutant cancer cells relative to normal cells carrying wild-type H3. This strategy involves the use of inhibitors of wild-type IDH enzymes to block the conversion of isocitrate to alpha-ketoglutarate ($\alpha$-KG), thereby inhibiting the demethylation reactions carried out by the dioxygenase family of demethylating enzymes that require $\alpha$-KG for activity. This will increase the DNA and histone methylation levels in the H3 K27M cancer cells. Optionally, the IDH inhibitor treated cells can then be selectively eliminated by radiation therapy. In an aspect, the disclosed method is superior to therapeutic approaches that inhibit histone methylase alone and should thus result in greater tumor cell killing.

IDH are evolutionarily conserved enzymes involved in converting isocitrate to alpha-ketoglutarate ($\alpha$-KG) in the Kreb's tricarboxylic acid (TCA) cycle. $\alpha$-KG, in turn, is an essential co-factor for the dioxygenase family of enzymes, which includes both histone and DNA demethylases that regulate methylation marks on chromatin. While many cases of pediatric glioblastomas are caused by mutations in histone H3, a majority of adult glioblastomas are associated with mutations in IDH1 and IDH2, two of the three such enzymes found in humans. Specific "gain of function" point mutations in IDH1 and IDH2 alter their catalytic properties such that $\alpha$-KG production is inhibited while the oncometabolite D-2-hydroxyglutarate (D-2-HG) accumulates. Although the exact process by which D-2-HG promotes carcinogenesis is unknown, it presumably competes with $\alpha$-KG and inhibits the activities of $\alpha$-KG dependent dioxygenases, thereby reducing demethylation reactions. Consistent with this idea, adult gliomas carrying IDH mutations are associated with a hypermethylation phenotype. Tremendous efforts are currently underway to develop highly specific small molecule inhibitors to block the activity of mutant IDH1 and IDH2 for use in treatment of IDH mutant cancers and the initial results are very promising. A byproduct of these inhibitor screens is the discovery of inhibitors of wild type IDH1 and IDH2, which are usually not studied any further as there is no need for drugs that can inhibit the wild type versions of these enzymes that are involved in the normal functioning of cells.

Primary brain tumors account for about 20% of childhood cancers and are a leading cause of cancer related mortality in children. The most common type of malignant brain tumor is glioblastoma, which arises from glial cells that form the supportive tissue of the brain and is associated with very poor prognosis. Following whole genome sequencing, H3.3 K27M, H3.1 K27M and H3.3 G34R/V mutations were found in over a third of all the non-brain stem pediatric glioblastomas and nearly 80% of pediatric Diffuse Intrinsic Pontine Glioma (DIPG) tumors. DIPG tumors are localized in the brain stem and hence cannot be surgically excised, resulting in 100% fatality since there are no approved therapies available. The methylation mimetic K27M mutation has been shown to sequester and inhibit the activity of PRC2 complex, which methylates H3 K27, resulting in reduced levels of the repressive H3 K27me3, which in turn leads to aberrant transcription and is believed to drive tumor formation. However, a weakness in these studies is that the sequestration of PRC2 by H3 K27M does not explain DNA hypomethylation observed in the same cells. Further, these studies do not provide any insight as to why these H3.3 mutations result in specific tumors primarily in children.

In one aspect, it is believed that additional non-transcriptional roles of H3.3 contribute to protection from cancer. Indeed, a few recent studies have suggested novel roles for H3.3 in genome maintenance. Here, it is shown that the H3 K27M mutation can promote DNA and histone demethylation by binding to IDH1 and enhancing its activity leading to high $\alpha$-KG levels in the cells, which in turn drives excessive dioxygenase mediated demethylation reactions, eventually resulting in the hypomethylation of both DNA and histones. More importantly, it is also shown that IDH1 inhibition can reverse this hypomethylation, thereby potentially rendering these cells amenable to treatment using well established cancer therapies such as radiotherapy. Hence, a potential use has now been found for inhibitors of wild type IDH enzymes as they can direct a therapeutic strategy for childhood glioblastomas carrying the H3 K27M mutation that exhibit a hypomethylation phenotype.

Apart from causing pediatric glioblastomas, H3.3 mutations also drive cartilage tumors known as chondroblastomas primarily in children and young adults. Interestingly, IDH1 and IDH2 mutations have been found to be associated with certain types of cartilage tumors as well, prompting speculation that H3.3 and IDH mutant tumors can have more molecular features and aberrant pathways in common, especially DNA and histone methylation related pathways. Hence, the results herein are likely to provide new insights into the potential connections between the molecular pathways that give rise to both adult and pediatric glioblastomas, as well as other H3.3 and IDH mutant malignancies.

In one aspect, the method includes administering an IDH inhibitor such as, for example, AG120, IDH305, GSK321, GSK864, or any combination thereof. In one aspect, the IDH inhibitor is administered at a dosage of less than 500 mg per day, or at a dosage of from about 50 mg to about 450 mg per day, about 100 mg per day to about 400 mg per day, or about 150 mg per day to about 300 mg per day, or about 50, 100, 150, 200, 250, 300, 350, 400, or about 450 mg per day, or at 150 mg or less per kg of subject body weight, or at from about 25 to about 125 mg, about 50 to about 100 mg, or about 50 to about 75 mg per kg of subject body weight, or at about 25, 50, 75, 100, or about 125 mg per kg of subject body weight. In an aspect, the IDH inhibitor such as, for example, AG120, is an inhibitor of wild-type isocitrate dehydrogenase 1.

Use of Histone Acetylase Inhibitors for Treating Histone H3.3K27M Mutant Cancers and Other Cancers Exhibiting High Levels of Histone Acetylation In some aspects, the disclosed method includes administering an inhibitor of histone acetyltransferase (HAT inhibitor or HATi) to the subject, wherein the cancer carries a histone H3.3 K27M mutation, and/or high histone acetylation. In some aspects, the HAT inhibitor is a natural compound, such as curcumin, garcinol, or anacardic acid. In other aspects, the HAT inhibitor is a synthetic compound, such as A485, C646, or CPTH2. In some aspects, the HAT inhibitor (natural or synthetic) is administered to the subject orally as an edible food or beverage. Optionally, the method further includes administering radiation therapy to the subject before, during, and/or after administering the HAT inhibitor.

Subjects having a cancer with a histone H3 K27M mutation and/or high histone acetylation can be identified by assaying a sample of cancer cells obtained from the subjects. For example, the presence of a histone H3 mutation can be assayed using a mutation specific antibody or by using PCR to amplify the H3 gene from the cells and performing Sanger sequencing to confirm the mutations. An assay such as a Western Blot can be used to identify cancer cells having high histone acetylation.

Mutations in the DNA packaging and regulatory protein histone H3 drives specific types of predominantly pediatric cancers, including DIPG. Up to 80% of DIPG tumors carry the lysine 27 to methionine (K27M) mutation in histone H3 variants, usually the histone H3.3 variant. Cancer cells carrying the H3 K27M mutation are known to have very low levels of repressive epigenetic marks such as H3 K27 trimethylation (H3 K27me3) as well as low levels of DNA methylation. Since the levels of repressive methylation on histones and DNA are generally anti-correlated with the levels of activating epigenetic marks such as histone acetylation, it was hypothesized that the H3 K27M mutant cancer cells would have higher than normal levels of histone acetylation.

Cancer cells with high levels of histone acetylation are likely to be addicted to the high acetylation levels which would be necessary for driving the expression of genes required for carcinogenesis and keeping the cancer cells alive. Hence, it was hypothesized that cancer cells having high levels of histone acetylation can be eliminated by treating them with natural or artificial compounds that block the activity of histone acetylase (HAT) enzymes. H3 K27M mutant cells indeed have high levels of acetylation compared to normal cells carrying wild type H3. Furthermore, it was determined that natural (Curcumin, Garcinol and Anacardic acid) as well as synthetic (A485, C646, CPTH2) HAT inhibitors can specifically eliminate patient derived cancer cells carrying the H3 K27M mutation in a manner that was also synergistic with ionizing radiation, while sparing the majority of cells carrying either the wild type H3 or a different H3.3 G34V mutation.

Based on these research findings, it is suggested that HATi can be used for treating H3 K27M mutant cancers, as well as other cancers that exhibit higher than normal levels of histone acetylation. Although potent synthetic HATi are not yet available, patients with currently incurable H3 K27M mutant DIPG and other cancers with high levels of histone acetylation can benefit from using the natural HATi compounds that are an integral part of the diet in several countries and are widely available as health supplements.

In another aspect, the method includes administering an HAT inhibitor such as, for example, curcumin, garcinol, anacardic acid, A485, C636, CPTH2, or any combination thereof. In one aspect, the HAT inhibitor is administered at a dosage of less than 400 mg per day, or from about 50 mg per day to about 350 mg per day, about 100 mg per day to about 300 mg per day, or about 150 mg per day to about 250 mg per day, or about 50, 100, 150, 200, 250, 300, 350, or about 400 mg per day, or can be administered at 5 mg or less per kg of subject body weight, or from about 1 to about 4.5 mg, about 1.5 to about 4 mg, or about 2 to about 3 mg, or at about 0.5, 1, 1.5, 2, 2.5, 3, 3.5, 4, or about 4.5 mg per kg of subject body weight.

Strategy for Treating Histone H3.3 K27M Mutant Cancers and Other Cancers Exhibiting High Levels of Histone Acetylation by Using Histone Deacetylase Inhibitors to Further Elevate their Acetylation to Cytotoxic Levels In some aspects, the disclosed method includes administering an inhibitor of histone deacetylase (HDAC inhibitor) to the subject, wherein the cancer carries a histone H3 K27M mutation, and/or has high histone acetylation. Examples of HDAC inhibitors include vorinostat, valproic acid, sodium valproate, romidepsin, Panobinostat, belinostat, or a combination thereof. In some aspects, sodium valproate and/or valproic acid may be more brain penetrant than vorinostat and may be of particular use when targeting tumors of the central nervous system. Optionally, the method further includes administering radiation therapy to the subject before, during, and/or after administering the HDAC inhibitor to the subject. In some aspects, in previous clinical trials, HDAC inhibitors were found to be ineffective for treating DIPG. Thus, herein, it is unexpectedly discovered that when HDAC inhibitors are paired with other drugs as disclosed herein as well as with radiation, HDAC exerts an effect in a relatively low dose on DIPG and other brain tumors.

Subjects having a cancer with a histone H3 K27M mutation and/or high histone acetylation can be identified by assaying a sample of cancer cells obtained from the subjects.

For example, the presence of a histone H3 mutation can be assayed using a mutation specific antibody or by using PCR to amplify the H3 gene from the cells and performing Sanger sequencing to confirm the mutations. An assay such as a Western Blot can be used to identify cancer cells having high histone acetylation.

As indicated above, the levels of repressive methylation on histones and DNA are generally anti-correlated with the levels of activating epigenetic marks such as histone acetylation; therefore, it was hypothesized that the H3 K27M mutant cancer cells would have higher than normal levels of histone acetylation. Cancer cells with high levels of histone acetylation are likely to be addicted to the high acetylation levels which would be necessary for driving the expression of genes required for carcinogenesis and keeping the cancer cells alive. Therefore, it was hypothesized that cancer cells that have high levels of histone acetylation can be eliminated by treating them with histone deacetylase inhibitors (HDACi) that inhibit or block the activity of the HDAC enzymes, thus leading to even higher levels of acetylation that are cytotoxic. H3 K27M mutant cells indeed have high levels of acetylation compared to normal cells carrying wild type H3. Furthermore, it has been determined that potent HDACi such as Vorinostat (Zolinza), Sodium Valproate (Depacon), divalproex sodium (Depakote, Depakote CP, and Depakote ER) and Valproic Acid (Depakene and Stavzor) can specifically eliminate hyperacetylated cancer cells carrying the H3 K27M mutation in a manner that was also synergistic with ionizing radiation, while sparing the majority of cells carrying the wild type H3 with normal levels of acetylation.

Based on these research findings, herein is a proposed a method of using HDACi as part of a combination therapy to treat H3 mutant cancers, including H3 K27M mutant cancers, as well as other cancers that exhibit higher than normal levels of histone acetylation. There are several HDACi that are FDA approved (Zolinza, Istodax, Farydak, Beleodaq, Depacon, Depakote and Depakene) for treating a very narrow subtype of rare cancers. Patients with currently incurable H3 K27M mutant DIPG and other cancers with high levels of histone acetylation can benefit from the off-label use of these FDA approved HDACi.

This therapeutic strategy would be one of the first for H3 K27M mutant cancer cells that is rationale based, rather than based on a large drug screen where the mechanism of action is usually unknown. Furthermore, this approach specifically targets a molecular pathway that is aberrant only in the mutant tumor cells but not the wild type cells. Finally, HDACi can be combined with precise radiation delivery to the tumors for synergistic killing of these tumor cells. Hence, the HDACi should specifically eliminate the H3 K27M mutant tumor cells while sparing normal cells with wild type H3, thus minimizing the potential for adverse effects, especially when used in combination with radiation.

In still another aspect, the method includes administering an HDAC inhibitor such as, for example, vorinostat, valproic acid, sodium valproate, romidepsin, Panobinostat, belinostat, or any combination thereof. In one aspect, the HDAC inhibitor is administered at a dosage of less than 400 mg per day, or from about 50 mg per day to about 350 mg per day, about 100 mg per day to about 300 mg per day, or about 150 mg per day to about 250 mg per day, or about 50, 100, 150, 200, 250, 300, 350, or about 400 mg per day, or is administered at 50 mg or less per kg of subject body weight, or from about 1 to about 45 mg, about 5 to about 40 mg, or about 15 to about 25 mg per kg of subject body weight, or at 1, 5, 10, 15, 20, 25, 30, 35, 40, or about 45 mg per kg of subject body weight.

Use of DNA Polymerase Theta (DNA POLΘ) Inhibitors

In some embodiments, DNA POLΘ inhibitors such as the FDA-approved antibiotic novobiocin can be used to effectively inhibit the same pathway as PARP inhibitors. Further in this embodiment, POLΘ inhibitors can work in combination with DNA-PKcs inhibitors and, optionally, radiation, for homologous recombination defective cancers instead of or in addition to PARP inhibitors. In one aspect, POLΘ inhibitors include, but are not limited to the FDA-approved antibiotic novobiocin, ART558, ART4215, RP-2119, or combinations thereof.

In one aspect, POLΘ inhibitors can also block the TMEJ pathway and can be used in combination with DNA-PKcs inhibitors and radiation to treat H3 mutant cancers and other cancers defective in HR mediated DNA repair.

In still another aspect, the method includes administering a POLΘ inhibitor such as, for example, novobiocin, ART558, ART4215, RP-2119, or any combination thereof. In one aspect, the POLΘ inhibitor is administered at a dosage of less than 2 grams per day, or less than 1 gram per day, or from about 50 mg to about 950 mg, from about 100 mg to about 750 mg, or from about 250 to about 500 mg per day, or at about 50, 100, 150, 200, 250, 300, 350, 400, 450, 500, 550, 600, 650, 700, 750, 800, 850, 900, or about 950 mg per day, or is administered at 20 mg or less per kg of subject body weight, or from about 1 mg to about 15 mg, about 5 mg to about 12 mg, or from about 7 mg to about 10 mg per kg of subject body weight, or at about 1, 2, 3, 4, 5, 6, 7, 8, 9, 10, 11, 12, 13, 14, 15, 16, 17, 18, or about 19 mg per kg of subject body weight.

Use of Platelet-Derived Growth Factor Receptor (PDGFR) Inhibitors

In some embodiments, PDGFR inhibitors such as, for example, the FDA-approved drugs Imatinib, Dasatinib, Nilotinib, Ponatinib, Lenvatinib, Avapritinib, Ripretinib, Sorafenib, Sunitinib, Pazopanib, Regorafenib, Nintedanib, and/or Axitinib can be used in conjunction with other drugs disclosed herein. Further in this embodiment, pediatric high-grade gliomas (pHGGs) often amplify PDGFR genes or carry activating PDGFR mutations and, as such, are expected to be sensitive to treatment with PDGFR inhibiting drugs alone and in combination with other drugs as well as with radiation.

In one aspect, Avapritinib is highly brain permeable and expected to therefore work exceptionally well at treating pHGGs and other brain tumors. In a further aspect, Dasatinib is brain permeable as well, although less so than Avapritinib. In some aspects, and without wishing to be bound by theory, Avapritinib, and to a slightly lesser extent Ripretinib, also specifically target the PDGFRA D842V mutation found in a number of pediatric high-grade gliomas. Hence, Avapritinib, Ripretinib, and Dasatinib may be especially useful in combination with the other classes of drugs disclosed herein to eliminate and prevent recurrence of pediatric high grade gliomas.

In still another aspect, the method includes administering a PDGFR inhibitor such as, for example, Imatinib, Dasatinib, Nilotinib, Ponatinib, Lenvatinib, Avapritinib, Ripretinib, Sorafenib, Sunitinib, Pazopanib, Regorafenib, Nintedanib, Axitinib, or any combination thereof. In one aspect, the PDGFR inhibitor is administered at a dosage of less than 1 gram per day, or from about 50 mg to about 950 mg, from about 100 mg to about 750 mg, or from about 250 to about 500 mg per day, or at about 50, 100, 150, 200, 250, 300, 350, 400, 450, 500, 550, 600, 650, 700, 750, 800, 850, 900, or about 950 mg per day, or is administered at 20 mg or less per kg of subject body weight, or from about 1 mg to about 15 mg, about 5 mg to about 12 mg, or from about 7 mg to about 10 mg per kg of subject body weight, or at about 1, 2, 3, 4, 5, 6, 7, 8, 9, 10, 11, 12, 13, 14, 15, 16, 17, 18, or about 19 mg per kg of subject body weight.

In an aspect, PDGFR inhibitors in combination with radiation have previously been tested for treatment of DIPG tumors and were not found to be effective. Thus, herein it has been unexpectedly discovered that use of PDGFR inhibitors, in combination with other drugs, can be useful for treating DIPG tumors and other brain tumors.

Use of DNA Alkylating Agents

In some embodiments, DNA alkylating agents such as temozolomide can be used in the compositions and methods disclosed herein.

In an aspect, temozolomide has previously been tested for treatment of DIPG tumors and was not found to be effective. Thus, herein it has been unexpectedly discovered that use of temozolomide, in combination with other drugs and/or radiation, can be useful for treating DIPG tumors. With few exceptions, clinical trials such as described for temozolomide and DIPG have been largely based on randomly testing existing drugs to see if they would work without any scientific rationale for why they should work for treating these cancers; thus, perhaps not surprisingly, these single agents were not effective with or without radiation. As opposed to the random drug screening strategy employed in most published studies, all drug choices and combinations disclosed herein are driven by strong scientific rationale based on a molecular understanding of the pathways that contribute strongly and independently to carcinogenesis. In an aspect, blocking these pathways is expected to provide therapeutic benefits by specifically killing the cancer cells while sparing the normal cells, especially when used in specific rationale-based combinations, and this is amply borne out by the data included herein.

In still another aspect, the method includes administering a DNA alkylating agent such as, for example, temozolomide or methyl methane sulfonate (MMS). In some aspects, DNA alkylating agents can be used in lieu of radiation treatment. In one aspect, the DNA alkylating agent is administered at a dosage of less than 1 gram per day, or from about 50 mg to about 950 mg, from about 100 mg to about 750 mg, or from about 250 to about 500 mg per day, or at about 50, 100, 150, 200, 250, 300, 350, 400, 450, 500, 550, 600, 650, 700, 750, 800, 850, 900, or about 950 mg per day, or is administered at 20 mg or less per kg of subject body weight, or from about 1 mg to about 15 mg, about 5 mg to about 12 mg, or from about 7 mg to about 10 mg per kg of subject body weight, or at about 1, 2, 3, 4, 5, 6, 7, 8, 9, 10, 11, 12, 13, 14, 15, 16, 17, 18, or about 19 mg per kg of subject body weight.

Radiation

In one aspect, radiation in step (c) can be administered to the subject at a dose of less than or equal to about 2 Gy, or is less than or equal to about 1.5 Gy, or less than or equal to about 1 Gy. In another aspect, radiation can be administered at least 10 times, resulting in a total dose of about 20 Gy over multiple radiation sessions. If needed, cumulative radiation doses as high as 45 Gy or 60 Gy can be delivered in thirty 1.5 Gy or 2 Gy fractions over a period of 4-6 weeks or more in coordination with the administration of NHEJ inhibiting drugs. In some aspects, the cumulative radiation dose can be up to 80 Gy.

In one aspect, radiation can be administered before, during, or after administration of the drugs. In an aspect, the NHEJ inhibiting drugs (e.g., the PARP, DNA-PK and PolΘ inhibitors) may be most effective when the radiation is delivered soon after drug administration, such as, for example, within an hour. In another aspect, for HDAC inhibitors, radiation may be best delivered few to several hours after drug administration. In still another aspect, for IDH inhibitors, radiation can be delivered one to few days after drug administration since methylation changes occur slowly. In any of these aspects, radiation times can be adjusted to best fit the combination of drugs being administered to the patient.

In one aspect, the radiation can be an ionizing radiation regimen selected from external radiation, internal radiation, systemic radiation, or any combination thereof. In a further aspect, the radiation therapy can be a fractionation regimen selected from hypofractionation, hyperfractionation, accelerated fractionation, or any combination thereof.

In any of these aspects, radiation can be delivered at a lower dose when performing the method than without performing the method. In a further aspect, a lower dose of radiation can increase patient tolerance of treatment and decrease side effects and, as part of the disclosed method, is still effective at treating cancer and preventing its recurrence.

Strategy for Histone H3 K27M and Other H3 Mutant Cancers and Homologous Recombination Deficient Cancers Using a Combination Approach In some aspects, the disclosed method includes administering a combination at least one drugs from at least two classes selected from a DNA-PKcs inhibitor, a PARP inhibitor, an IDH inhibitor, a HAT inhibitor, an HDAC inhibitor, and/or a POLΘ inhibitor, wherein the inhibitors are administered to the subject simultaneously, or sequentially in any order. In one aspect, the DNA-PKcs inhibitor and PARP inhibitor are particularly useful when the cancer has a histone H3 mutation (such as K27M, G34R/V/W/L, or K36M mutation) or is a homologous recombination-deficient (HRD) cancer, such as BRCA1 or BRCA2 mutant breast, ovarian, pancreatic and prostate cancers. In another aspect, addition of an IDH inhibitor may be beneficial when the cancer carries a histone H3 K27M mutation, and/or the cancer has low DNA methylation and/or low histone methylation. In another aspect, an HAT inhibitor may be useful when the cancer carries a histone H3 K27M mutation, and/or high histone acetylation. In still another aspect, the HDAC inhibitor may be useful when the cancer carries a histone H3 K27M mutation, and/or has high histone acetylation.

In an aspect, the method further includes administering radiation therapy to the subject before, during, and/or after administering the combination of inhibitors to the subject.

Subjects having a cancer susceptible to treatment with the combination of a DNA-PKcs inhibitor and a PARP inhibitor, an IDH inhibitor, a HAT inhibitor, an HDAC inhibitor, and/or a POLΘ inhibitor, such as a histone H3 mutation, can be identified by assaying a sample of cancer cells obtained from the subjects, as described above in connection with each of a DNA-PKcs inhibitor, a PARP inhibitor, an IDH inhibitor, a HAT inhibitor, an HDAC inhibitor, or a POLΘ inhibitor, individually.

Disclosed herein are therapeutic strategies by which these cancer cells can be specifically eliminated, while largely sparing the normal cells. First, cells carrying H3.3 mutations are defective in DNA repair via the HR pathway, making them heavily reliant on the NHEJ pathways for surviving DNA damage. This makes the H3.3 mutant cells sensitive to NHEJ inhibitors (NHEJi) combined with radiation therapy. Second, cells carrying the H3 K27M mutation have low levels of repressive epigenetic marks such as histone H3

K27 trimethylation (H3 K27me3) as well as low levels of DNA methylation. It has been shown that both the histone and DNA hypomethylation can be reversed using IDH inhibitors (IDHi) for therapeutic benefits. Third, it has been determined that H3 K27M mutant cancer cells also have high levels of histone acetylation which can be necessary for driving the expression of genes required for carcinogenesis and keeping the cancer cells alive. Hence, these cells can be eliminated by treatment with histone acetylase inhibitors (HATi) that reduce acetylation levels. Fourth, these cells can also be eliminated using histone deacetylase inhibitors (HDACi) that block the activity of the HDAC enzymes, thus leading to even higher levels of acetylation that are cytotoxic. Fifth, the highly proliferative tumor cells are known to be more sensitive to treatment with radiation due to the formation of DSBs, especially during DNA replication in S phase and it is shown that combining radiation with any of the four previous drug-based strategies results in synergistic effects leading to more efficient tumor cell killing. Finally, it is proposed to combine these four strategies for maximal therapeutic benefits using lower doses of the individual inhibitors to selectively kill the cancer cells while sparing normal cells. The combination therapeutic strategy would have the advantage of more extensive tumor cell elimination, minimal adverse effects due to reduced dosage of individual drugs, and minimal chances of development of resistance to multiple drugs used simultaneously.

In one aspect, HDACi and HATi may not be used simultaneously or combined as drugs from these two classes could neutralize each other's effects. In some aspects, the disclosed methods can include a PARP inhibitor and/or a POLΘ inhibitor. In other aspects, PARP inhibitors and POLΘ inhibitors unexpectedly exhibit synergistic effects.

Exemplary Drug Combinations

In one aspect, the disclosed method includes administering a POLΘ inhibitor such as novobiocin and an HDAC inhibitor such as, for example, valproic acid, sodium valproate, vorinostat, romidepsin, panobinostat, belinostat or a combination thereof.

In another aspect, the disclosed method includes administering an IDH inhibitor such as AG120 and a POLΘ inhibitor such as, for example novobiocin. In some aspects, an HDAC inhibitor such as, for example, vorinostat, can also be administered to the subject along with the IDH inhibitor and POLΘ inhibitor. In still other aspects, a PARP inhibitor such as, for example, Olaparib or Niraparib, can be administered to the subject along with the IDH inhibitor, POLΘ inhibitor, and HDAC inhibitor.

In yet another aspect, the disclosed method includes administering an IDH inhibitor such as AG120 and a PARP inhibitor such as, for example, Olaparib. In some aspects, an HDAC inhibitor such as, for example, vorinostat, can also be administered to the subject along with the IDH inhibitor and PARP inhibitor.

In yet another aspect, the disclosed method includes administering an IDH inhibitor such as AG120 and an HDAC inhibitor such as, for example, vorinostat.

In an alternative aspect, the disclosed method includes administering a POLΘ inhibitor such as novobiocin and a PARP inhibitor such as, for example, Olaparib. In a further aspect, an HDAC inhibitor such as vorinostat can be administered to the subject along with the POLΘ inhibitor and the HDAC inhibitor.

In yet another aspect, the disclosed method includes administering a POLΘ inhibitor such as novobiocin and an HDAC inhibitor such as, for example, vorinostat. In another aspect, the disclosed method includes administering a PARP inhibitor such as Olaparib and an HDAC inhibitor such as, for example, vorinostat.

In another aspect, the disclosed method includes administering a POLΘ inhibitor such as novobiocin and a DNA-PKcs inhibitor such as VX-984, or administering a POLΘ inhibitor such as novobiocin and a DNA-PKcs inhibitor such as NU7441. In a further aspect, the disclosed method further includes administering a PARP inhibitor along with the POLΘ inhibitor and the DNA-PKcs inhibitor. Thus, in one aspect, the disclosed method includes administering a POLΘ inhibitor such as novobiocin, a DNA-PKcs inhibitor such as VX-984, and a PARP inhibitor such as Olaparib.

In yet another aspect, the disclosed method includes administering a DNA-PKcs inhibitor such as NU7441 and a PARP inhibitor such as niraparib or talazoparib, or a DNA-PKcs inhibitor such as NU7441 and a PARP inhibitor such as Olaparib. In still another aspect, the method includes administering a DNA-PKcs inhibitor such as VX-984 and a PARP inhibitor such as Olaparib. In any of these aspects, the method can further include administering an HAT inhibitor such as, for example, curcumin (e.g., administering NU7441, talazoparib, and curcumin; or NU7441, Olaparib, and curcumin; or VX984, Olaparib, and curcumin).

In another aspect, the disclosed method includes administering a DNA alkylating agent such as temozolomide and an IDH inhibitor such as AG120.

Additional exemplary combinations include, but are not limited to, Olaparib and NU7441; AG120, novobiocin, and Olaparib; AG120, novobiocin, and vorinostat; novobiocin, Olaparib, and vorinostat; and/or AG120, novobiocin, Olaparib, and vorinostat.

Compositions and Treatment

The disclosed inhibitors (a DNA-PKcs inhibitor, a PARP inhibitor, an IDH inhibitor, a HAT inhibitor, an HDAC inhibitor, and/or a POLΘ inhibitor) can be formulated into pharmaceutically acceptable salt forms or hydrate forms. Pharmaceutically acceptable salt forms include the acid addition salts and include hydrochloric, hydrobromic, nitric, phosphoric, carbonic, sulfuric, and organic acids like acetic, propionic, benzoic, succinic, fumaric, mandelic, oxalic, citric, tartaric, maleic, and the like. Pharmaceutically acceptable base addition salts include sodium, potassium, calcium, ammonium, and magnesium salts.

Administration of one or more inhibitors can be carried out in the form of an oral tablet, capsule, or liquid formulation containing a therapeutically effective amount of the active ingredient (inhibitor). Administration is not limited to oral delivery and includes intravascular (e.g., intravenous), intramuscular, or another means known in the pharmaceutical art for administration of active pharmaceutical ingredients.

Therapeutic or prophylactic application of the inhibitors, and compositions containing them, can be accomplished by any suitable therapeutic or prophylactic method and technique presently or prospectively known to those skilled in the art. The inhibitors can be administered by any suitable route known in the art including, for example, oral, intramuscular, intraspinal, intracranial, nasal, rectal, parenteral, subcutaneous, or intravascular (e.g., intravenous) routes of administration. Administration of the inhibitors can be continuous or at distinct intervals as can be readily determined by a person skilled in the art.

In some aspects, when disclosed drugs and combinations of drugs do not typically cross the blood-brain barrier (BBB) to enter the brain, an intranasal spray can be used to deliver the drugs. In a further aspect, drugs included in the intranasal spray can be encapsulated in exosomes, liposomes, or the like, wherein the exosomes or liposomes are capable of crossing the BBB to deliver their cargo.

In some aspects, an amount of inhibitors (e.g., 100 mg-1,000 mg) are to be administered 1, 2, 3, 4, or times per day, for 1, 2, 3, 4, 5, 6, 7, or more days. Treatment can continue as needed, e.g., for several weeks. Optionally, the treatment regimen can include a loading dose, with one or more daily maintenance doses. For example, in some aspects, an initial loading dose in the range of 100 mg to 1,000 is administered, followed by a maintenance dose in the range of 100 mg to 1,000 mg every 12 hours for 1, 2, 3, 4, 5, 6, or 7, or more days. In some aspects, an initial loading dose in the range of 200 mg to 600 mg is administered, followed by a maintenance dose in the range of 100 mg to 300 mg every 12 hours for a total of 9 doses. In any of these aspects, when the inhibitors are administered in combination, lower doses are effective compared to doses for the inhibitors administered singly. Further in this aspect, lower doses of the inhibitors are associated with fewer systemic side effects and can allow for greater patient tolerance of treatment regimens.

Various cancers can be treated using the disclosed methods. In some aspects, the cancer is a hematological cancer. In some aspects, the cancer is a solid tumor. In some aspects, the cancer is a breast cancer or gynecological cancer such as ovarian cancer (e.g., serous, epithelial, or endometrial), especially of the HRD subtype. In some aspects, the cancer is a brain tumor, such as glioblastoma. In some aspects, the cancer is diffuse intrinsic pontine glioma (DIPG) carrying H3 mutations. In some aspects, the cancer is a HRD subtype of pancreatic cancer, prostate cancer, or skin cancer (e.g., melanoma).

Overall, the data presented herein suggest that NHEJ inhibitors are effective in eliminating HR deficient H3.3 mutant tumors and are also likely to be effective in the clinic. In fact, these results also suggest that simultaneous inhibition of both classic and alternative NHEJ, as well as TMEJ pathways is much more effective in eliminating HR defective cancer cells than the use of PARP inhibitors alone, since these only block the alternative NHEJ pathway. Not surprisingly, monotherapy with PARP inhibitors quickly results in the development of resistant tumors and, as such, PARP inhibitors have not yet lived up to their promise in treating a variety of cancers. Combining PARP inhibitors with an inhibitor of classic NHEJ, such as the DNA-PKcs inhibitor NU7441 or VX-984, as well as the TMEJ inhibitor Novobiocin not only kills HR defective cancer cells more effectively, but also reduces the risk of developing resistance since it is much harder to acquire mutations that that provide resistance to two or three different drugs targeting two or three different pathways simultaneously.

In one aspect, although the disclosed methods and compositions are expected to be useful against any cancer defective in homologous recombination, the disclosed methods and compositions are expected to be especially useful against cancer cells carrying a histone H3.3 mutation including pediatric high grade gliomas, such as diffuse intrinsic pontine glioma and diffuse midline gliomas; chondroblastoma, GCTB, as well as the HRD sub-type of breast cancer, ovarian cancer, pancreatic cancer, prostate cancer, melanoma. Inhibitors and compositions including them can be formulated according to known methods for preparing pharmaceutically useful compositions. Formulations are described in detail in a number of sources which are well known and readily available to those skilled in the art. For example, Remington's Pharmaceutical Science by E. W.

Martin describes formulations which can be used in connection with the disclosed method. In general, the disclosed compositions will be formulated such that an effective amount of the bioactive inhibitor is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject inhibitors include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the inhibitors can also include suspension agents, protectants, lubricants, buffers, preservatives, and stabilizers. To provide for the administration of such dosages for the desired therapeutic treatment, pharmaceutical compositions disclosed herein will advantageously include between about 0.1% and 45%, and especially, 1 and 15% by weight of the total of one or more of the inhibitor-based on the weight of the total composition including carrier or diluent.

The disclosed inhibitors can also be administered utilizing liposome technology, slow release capsules, implantable pumps, and biodegradable containers. These delivery methods can, advantageously, provide a uniform dosage over an extended period of time.

The inhibitors can also be modified by the addition of chemical groups, such as PEG (polyethylene glycol). PEGylated polypeptides typically generate less of an immunogenic response and exhibit extended half-lives in vivo in comparison to polypeptides that are not PEGylated when administered in vivo. Methods for PEGylating proteins and polypeptides known in the art. Inhibitors can also be modified to improve cell membrane permeability. In one aspect, cell membrane permeability can be improved by attaching a lipophilic moiety, such as a steroid, to the inhibitor. Other groups known in the art can be linked to the inhibitors.

Also disclosed herein is a packaged dosage formulation including, in one or more packages, packets, or containers, at least one inhibitor and/or composition as described herein, formulated in a pharmaceutically acceptable dosage. The package can contain discrete quantities of the dosage formulation, such as tablet, capsules, lozenge, and powders. The quantity of inhibitor in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg. In some aspects, the amount is in the range of 100 mg to 600 mg, to be administered 1, 2, 3, or 4 times per day, for 2, 3, 4, 5, 6, 7 or more days.

Also disclosed herein are kits including, in one or more containers, two or more inhibitors. A kit can also include one or more compounds, biological molecules, or drugs. In one aspect, a kit includes a combination of two or more inhibitors from among a DNA-PKcs inhibitor, a PARP inhibitor, an IDH inhibitor, a HAT inhibitor, an HDAC inhibitor, or a POLΘ inhibitor.

Optionally, the methods further include, prior to administering the inhibitor combination of inhibitors to the subject, identifying the subject as having the cancer. If the subject is identified as having the cancer, the inhibitor or combination of inhibitors can be administered to the subject as therapy. If the human subject is identified as not having a cancer, the inhibitor or combination of inhibitors can be withheld, or the inhibitor or combination of inhibitors can be administered as prophylaxis to prevent or delay the onset or relapse of the cancer, or an alternative agent can be administered to the subject. The identifying step can include carrying out one or both of the following: a cytology or cytopathology test of a cell sample from the subject, an assay based on the presence or level of a biomarker associated with the cancer in a biological sample from the subject (e.g., body fluid such as blood or urine, or a biopsy), or an imaging test of the subject (e.g., CT scan, MRI, nuclear scan, bone scan, PET scan, ultrasound, or x-ray).

The subject can be any age or gender. In some aspects, the subject is a human pediatric patient (ages 0-18 years).

Optionally, the disclosed methods further include administering radiation therapy to the subject before, during, and/or after administering the inhibitor or combination of inhibitors. The radiation therapy preferably includes an ionizing radiation selected from among: external radiation (e.g., external beam radiation therapy (EBRT or XRT)), internal radiation (e.g., brachytherapy), or systemic radiation (e.g., systemic radioisotope therapy), or a combination of two or more of the foregoing. The radiation therapy can include a fractionation regimen (e.g., hypofractionation, hyperfractionation, accelerated fractionation).

The administration of ionizing radiation (IR) therapy can be used to cause DNA strand breaks in combination with any of the strategies listed herein to amplify the effects of the drugs individually or in combination.

Radiation therapy by itself is an established and FDA approved treatment for a variety of cancers due to its ability to cause DSBs that need to be repaired for cell survival, failing which cells carrying unrepaired DSBs die. Hence, combining radiation therapy with NHEJ inhibitors disclosed and discussed herein that block DSB repair is expected to enhance the cell killing effect of the NHEJ inhibitors, and this is exactly what is observed. Remarkably, IDH1 inhibition also appeared to show a synergistic effect with DNA damage caused by ionizing radiation (IR) treatment in eliminating multiple patient derived H3.3 K27M mutant DIPG cancer cells. This synergy between IDH1 inhibition and radiation is not surprising at all given that DNA methylation levels are known to impact the radiation sensitivity of cells and this has been getting increasing attention in recent years as a possible target for improving the efficiency of radiation therapy for cancer. Additionally, histone modifications including methylation and acetylation have also implicated in modulating the efficiency of radiation therapy and a histone H3 demethylase inhibitor has been reported to enhance the efficacy of radiotherapy of DIPG tumors xenografted in mice. Furthermore, histones accumulate transiently upon DNA damage and the interaction between histones and IDH proteins is also enhanced upon DNA damage. Hence, it is possible that the regulation of IDH enzymes by histones and their downstream effects on histone and DNA methylation can be physiologically important for survival following DNA damage. Finally, there are numerous reports in the literature suggesting that the effects of radiation can also be potentiated by treatment with HDACi. Hence, the combined effects of treatment with HDACi and radiation were tested and found the H3.3 K27M mutant cells to be exquisitely sensitive to the combination, while the WT cells were largely unaffected. Remarkably, this combination treatment requires very low doses of Vor (10 nM) and radiation (1 Gy) to specifically eliminate H3.3 K27M DIPG cells. Overall, combining radiation therapy with any of the therapeutic strategies listed herein (e.g., treatment with a DNA-PKcs inhibitor, a PARP inhibitor, an IDH inhibitor, a HAT inhibitor, an HDAC inhibitor, PDGFR inhibitor or a combination thereof) can result in synergistic cytotoxic effects on H3 mutant, HR defective, hypomethyl-ated or hyperacetylated cancer cells, leading to more effi-cient elimination of cancer cells, while sparing the normal cells. The radiation therapy can be single dose or fraction-ated, and can be targeted or non-targeted.

In some aspects, the radiation therapy is image-guided. An image-guided device, such as the CYBERKNIFE™ device, can be used. The device combines a compact linear accelerator mounted on a robotic manipulator, and an inte-grated image guidance system. The image guidance system acquires stereoscopic kV images during treatment, tracks tumor motion, and guides the robotic manipulator to align the treatment beam to the moving tumor. The system is designed for stereotactic radiosurgery (SRS) and stereotactic body radiation therapy (SBRT). The system is also used for select 3D conformal radiotherapy (3D-CRT) and intensity modulated radiation therapy (IMRT).

Optionally, the disclosed methods further include admin-istering one or more additional biologically active agents to the subject before, during, and/or after administration of the one or more inhibitors. In some aspects, the additional biologically active agent includes one or more anti-cancer agents, such as a chemotherapeutic agent and/or an immu-nomodulatory agent such as an immune checkpoint inhibi-tor.

Also disclosed are compositions that can be used for carrying out the disclosed method. In one aspect, the com-position includes DNA-PKcs inhibitor, and a PARP inhibi-tor. Examples of DNA-PKcs inhibitors that can be used include NU7441 (2-N-morpholino-8-dibenzothiophenyl-chromen-4-one or KU-57788), NU7026 (2-(morpholin-4-yl)-benzo[h]chromen-4-one), SU11752, NK314, AZD7648, M3814, VX-984, and CC-115, or a combination of two or more of the foregoing. Examples of PARP inhibitors that can be used include olaparib, rucaparib, niraparib, talazoparib, veliparib, BGB-290 (pamiparib), CEP 9722, E7016, and 3-aminobenzamide, or a combination of two or more of the foregoing. The composition can further include a pharma-ceutically acceptable carrier or diluent.

In another aspect, the composition includes two or more of the following: a DNA-PKcs inhibitor, a PARP inhibitor, an IDH inhibitor, a HAT inhibitor, an HDAC inhibitor, a PDGFR inhibitor or a POLΘ inhibitor. Examples of DNA-PKcs inhibitors that can be used include NU7441 (2-N-morpholino-8-dibenzothiophenyl-chromen-4-one or KU-57788), NU7026 (2-(morpholin-4-yl)-benzo[h] chromen-4-one), SU11752, NK314, AZD7648, M3814, VX-984, and CC-115, or a combination of two or more of the foregoing. Examples of PARP inhibitors that can be used include olaparib, rucaparib, niraparib, talazoparib, veliparib, BGB-290 (pamiparib), CEP 9722, E7016, and 3-aminoben-zamide, or a combination of two or more of the foregoing. Examples of IDH inhibitors include AG120, IDH305, GSK321 and GSK864, or a combination thereof. The HAT inhibitor can be, for example, a natural compound, such as curcumin, garcinol, anacardic acid, or a combination of two or more of the foregoing, or a synthetic compound such as A485, C646, or CPTH2, or combination thereof. Examples of HDAC inhibitors that can be used include vorinostat, valproic acid, sodium valproate, romidepsin, panobinostat, belinostat or a combination thereof. The composition can further include a pharmaceutically acceptable carrier or diluent. Examples of POLΘ inhibitors that can be used include novobiocin, ART558, ART4215, RP-2119, or any combination thereof.

In one aspect, maximum therapeutic options are available for H3 K27M mutant brain tumors and/or other tumors with the same or a different mutation that are HR defective, and have one or more of low levels of DNA methylation, low levels of histone methylation, and/or high levels of histone acetylation. Specific exemplary aspects include, but are not limited to, the following; although many drug combinations will work without radiation, in one aspect, the drug combi-nations will be more effective in conjunction with radiation treatment: In some aspects, and without wishing to be bound by theory, when three or more drugs are used, naturally occurring DNA breaks may be enough to kill tumor cells without requiring exogenous radiation.

(a) a PARP inhibitor and a DNA-PKcs inhibitor with or without radiation;

(b) a PARP inhibitor, a DNA-PKcs inhibitor, and an IDH inhibitor with or without radiation;

(c) a PARP inhibitor, a DNA-PKcs inhibitor, and an HAT inhibitor with or without radiation;

(d) a PARP inhibitor, a DNA-PKcs inhibitor, and an HDAC inhibitor with or without radiation;

(e) a PARP inhibitor, a DNA-PKcs inhibitor, an IDH inhibitor, and an HAT inhibitor with or without radia-tion;

(f) a PARP inhibitor, a DNA-PKcs inhibitor, an IDH inhibitor, and an HDAC inhibitor with or without radiation;

(g) an IDH inhibitor and a POLΘ inhibitor with or without radiation;

(h) an IDH inhibitor and a PARP inhibitor with or without radiation;

(i) a POLΘ inhibitor and a PARP inhibitor with or without radiation;

(j) an IDH inhibitor and an HDAC inhibitor with or without radiation;

(k) a POLΘ inhibitor and an HDAC inhibitor with or without radiation;

(l) a PARP inhibitor and an HDAC inhibitor with or without radiation;

(m) an IDH inhibitor, a POLΘ inhibitor, and a PARP inhibitor with or without radiation;

(n) an IDH inhibitor, a POLΘ inhibitor, and an HDAC inhibitor with or without radiation;

(o) an IDH inhibitor, a PARP inhibitor, and an HDAC inhibitor with or without radiation;

(p) a POLΘ inhibitor, a PARP inhibitor, and an HDAC inhibitor with or without radiation;

(q) an IDH inhibitor, a POLΘ inhibitor, a PARP inhibitor, and an HDAC inhibitor with or without radiation;

(r) a POLΘ inhibitor and a DNA-PKcs inhibitor with or without radiation;

(s) a POLΘ inhibitor, a PARP inhibitor, and a DNA-PKcs inhibitor with or without radiation; and/or (t) a PARP inhibitor with radiation.

In any of the above-listed aspects, and without wishing to be bound by theory, all the combinations listed above can be augmented by including PDGFR inhibitors especially when targeting DIPG tumors that have PDGFR mutations or amplifications. In any of these aspects, ionizing radiation therapy can also be used to induce double strand breaks in DNA simultaneously with or sequentially before or after administration of the two or more compounds.

In one aspect, provided herein are pharmaceutical compositions including at least one drug from each of at least two classes selected from an inhibitor of poly-ADP ribose polymerase (PARP inhibitor), an inhibitor of DNA-dependent protein kinase catalytic subunit (DNA-PKcs inhibitor), an inhibitor of wild-type isocitrate dehydrogenase (IDH inhibitor), an inhibitor of histone acetyltransferase (HAT inhibitor), an inhibitor of histone deacetylase (HDAC inhibitor), an inhibitor of DNA polymerase Θ (POLΘ inhibitor); a platelet-derived growth factor receptor inhibitor (PDGFR inhibitor); and a DNA alkylating agent.

Exemplary pharmaceutical compositions include, but are not limited to:

(a) Valproic acid and novobiocin
(b) Sodium valproate and novobiocin
(c) AG120, novobiocin, and Olaparib
(d) Novobiocin, Olaparib, and vorinostat
(e) Novobiocin and NU7441
(f) VX-984 and Olaparib
(g) Novobiocin and Olaparib
(h) VX-984 and novobiocin
(i) VX-984, novobiocin, and Olaparib
(j) Novobiocin, NU7441, and Olaparib The disclosed pharmaceutical compositions can further include pharmaceutically acceptable excipients, carriers, diluents, preservatives, solvents, stabilizing agents, as known in the art. The disclosed pharmaceutical compositions can be administered in conjunction with radiation treatment as disclosed herein.

Also disclosed herein are kits, including one or more inhibitors and pharmaceutical formulations, packaged into suitable packaging material, optionally in combination with instructions for using the kit components, e.g., instructions for performing a method as described herein. In one aspect, a kit includes an amount of one or more inhibitors, and instructions for administering the inhibitor or combination of inhibitors to a subject in need of treatment on a label or packaging insert. In further aspects, a kit includes an article of manufacture, for delivering the inhibitor or combination of inhibitors into a subject locally, regionally, or systemically, for example.

As used herein, the term "packaging material" refers to a physical structure housing the components of the kit. The packaging material can maintain the components in a sterile state, and can be made of material commonly used for such purposes (e.g., paper, corrugated fiber, glass, plastic, foil, ampules, etc.). The label or packaging insert can include appropriate written instructions, for example, practicing a method described herein, e.g., treating cancer, an assay for identifying a subject having the cancer to be treated, etc. Thus, in additional aspects, a kit includes a label or packaging insert including instructions for practicing a disclosed method in solution, in vitro, in vivo, or ex vivo.

Instructions can therefore include instructions for practicing any of the methods described herein. For example, pharmaceutical compositions can be included in a container, pack, or dispenser together with instructions for administration to a subject to treat a cancer. Instructions can additionally include appropriate administration route, dosage information, indications of a satisfactory clinical endpoint or any adverse symptoms that can occur, storage information, expiration date, or any information required by regulatory agencies such as the Food and Drug Administration or European Medicines Agency for use in a human subject.

The instructions can be on "printed matter," e.g., on paper or cardboard within the kit, on a label affixed to the kit or packaging material, or attached to a vial or tube containing a component of the kit. Instructions can include voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Kits can additionally include a buffering agent, a preservative, or an agent for stabilizing the inhibitor or combination of inhibitors. The kit can also include control components for assaying for the presence of cancer, e.g., a control sample or a standard. Each component of the kit can be enclosed within an individual container or in a mixture and all of the various containers can be within single or multiple packages.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and can be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

Histone mutations are discussed herein. Unless otherwise specifically noted, "H3" refers to all variants of histone H3 including, but not limited to, H3.1, H3.2, H3.3, and the like.

As used in the specification and the appended claims, the singular forms "a," "an" and "the" include plural referents unless the context clearly dictates otherwise. Thus, for example, reference to "a PARP inhibitor," "a DNA-PKcs inhibitor," or "a radiation treatment," includes, but is not limited to, mixtures, combinations, or series of two or more such PARP inhibitors, DNA-PKcs inhibitors, or radiation treatments, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a drug refers to an amount that is sufficient to achieve the desired improvement in the property modulated by the formulation component, e.g. achieving the desired level of modulus. The specific level in terms of wt % in a composition required as an effective amount will depend upon a variety of factors including the stage and type of cancer being treated, amount and type of other drugs being used in a combination treatment, radiation dose, and age and body weight of the subject receiving the drug. In some aspects, the effective amount of a drug in the present compositions and methods can be less than what would be prescribed or administered if the drug were prescribed alone, due to the synergetic nature of the drug combinations and treatments described herein. In a further aspect, when the effective amount is lower, patients can exhibit fewer systemic side effects while their cancers do not become resistant to treatments.

As used herein, the terms "optional" or "optionally" means that the subsequently described event or circumstance can or cannot occur, and that the description includes instances where said event or circumstance occurs and instances where it does not.

As used herein, a subject is "in need of" a treatment if such human subject would benefit biologically, medically or in quality of life from such treatment. In some aspects, the subject has cancer and is in need of therapy. In other aspects, the subject does not have cancer and is in need of prophylaxis to prevent or delay onset or relapse of the cancer. In some aspects, the subject in need of prophylaxis is at risk of developing a cancer or relapse of a previously-treated cancer. In some aspects, the subject is at increased risk of developing a cancer or relapse of the cancer relative to others in the population.

As used herein, the terms "subject", "patient", and "individual" refer to a human or non-human animal of any age or sex. In some aspects, the subject is a mammal (human or non-human mammal).

As used herein, the term "treat", "treating" or "treatment" of any disease or disorder refers in one aspect, to ameliorating the disease or disorder (i.e., slowing or arresting or reducing the development of the disease or at least one of the clinical symptoms thereof). In another aspect, "treat", "treating" or "treatment" refers to alleviating or ameliorating at least one physical parameter including those which may not be discernible by the subject. In yet another aspect, "treat", "treating" or "treatment" refers to modulating the disease or disorder, either physically, (e.g., stabilization of a discernible symptom), physiologically, (e.g., stabilization of a physical parameter), or both. In another aspect, "treat", "treating" or "treatment" refers to reduction in tumor size, reduction in rate of tumor growth, delay in disease progression, and/or increase in the individual's disease-free survival (relapse-free survival). In yet another aspect, "treat", "treating" or "treatment" refers to prophylaxis (preventing or delaying the onset, development, progression, or relapse of the disease or disorder).

As used herein, the term "tumor" refers to all neoplastic cell growth and proliferation, whether malignant or benign, and all pre-cancerous and cancerous cells and tissues. For example, a particular cancer can be characterized by a solid mass tumor or non-solid tumor. The solid tumor mass, if present, can be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture, or weight of the tissue. However, some primary tumors are not palpable and can be detected only through medical imaging techniques such as X-rays (e.g., mammography, CAT or CT scanning), positron emission tomography (PET) scanning, magnetic resonance imaging (MRI), or by needle aspirations. The use of these imaging techniques is more common in early detection. Molecular and phenotypic analysis of cancer cells within a tissue can usually be used to confirm if the cancer is endogenous to the tissue or if the lesion is due to metastasis from another site. Some tumors are unresectable (cannot be surgically removed due to, for example the number of metastatic foci or because it is in a surgical danger zone as in the case of DIPG tumors that occur in the brain stem). The disclosed methods can be utilized for early, middle, or late stage disease, and acute or chronic disease. The disclosed methods can be used for metastatic or non-metastatic cancer.

As used herein, the term "administration" is intended to include, but is not limited to, the following delivery methods: topical, oral, parenteral, subcutaneous, transdermal, transbuccal, intravascular (e.g., intravenous or intra-arterial), intramuscular, intranasal, and intra-ocular administration. Administration can be local at a particular anatomical site, such as a site of a tumor, or systemic.

As used herein, the term "contacting" in the context of contacting a cell with at least one inhibitor or combination of inhibitors in vitro or in vivo means bringing at least one inhibitor into contact with the cell, or vice-versa, or any other manner of causing the inhibitor and the cell to come into contact.

The inhibitors administered according to the present disclosure can be provided as pharmaceutically-acceptable salt forms. Pharmaceutically-acceptable salts of the compounds can be prepared using conventional techniques. "Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts described herein are pharmaceutically acceptable acid addition salts and pharmaceutically acceptable base addition salts.

"Pharmaceutically acceptable acid addition salt" refers to those salts that retain the biological effectiveness and properties of the free bases, that are not biologically or otherwise undesirable, and that are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997), which is hereby incorporated by reference in its entirety). Acid addition salts of basic compounds can be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts can be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, a "derivative" or "pharmaceutically active derivative" refers to any compound that upon administration to the recipient, is capable of providing directly or indirectly, the activity disclosed herein (e.g., inhibitory activity). The term "indirectly" also encompasses "prodrugs," which can be converted to the active form of the drug, e.g., via endogenous enzymes or metabolism (biotransformation). The prodrug is a derivative of the inhibitors described herein according and presenting inhibitory activity that has a chemically or metabolically decomposable group, and a compound that can be converted into a pharmaceutically active inhibitor as described herein in vivo by solvolysis under physiological conditions. The prodrug is converted into a compound by a reaction with an enzyme, gastric acid, or the like under a physiological condition in the living body, e.g., by oxidation, reduction, hydrolysis, or the like, each of which is carried out enzymatically. These compounds can be produced according to well-known methods. The term "indirectly" also encompasses metabolites of compounds as described herein. Chemical reactions, reactants, and reagents useful for making derivatives can be found, for example, in March's Advanced Organic Chemistry, 7th edition, 2013, Michael B. Smith, which is incorporated herein by reference in its entirety.

More specifically, the term "prodrug" refers to a chemical compound that can be converted by the body (i.e., biotransformed) to another chemical compound that has pharmacological activity. The prodrug can itself have pharmacological activity before conversion, or be inactive before conversion and activated upon conversion. Active prodrugs or inactive prodrugs of can be administered to a subject or contacted with a cell in vitro or in vivo. Instead of administering a drug directly, a prodrug can be used instead to improve how a drug is absorbed, distributed, metabolized, and excreted (ADME). For example, a prodrug can be used to improve bioavailability when a drug itself is poorly absorbed from the gastrointestinal tract, or to improve how selectively the drug interacts with cells or processes that are not its intended target, which can reduce adverse or unintended effects of a drug. Major types of prodrugs include, but are not limited to, type I prodrugs, which are biotransformed inside cells (intracellularly), and type II prodrugs, which are biotransformed outside cells (extracellularly), such as in digestive fluids or in the body's circulatory system. These types can be further categorized into subtypes based on factors such as whether the intracellular bioactivation location is also a site of therapeutic action, or whether or not bioactivation occurs in the gastrointestinal fluids or in the circulation system (Wu, Kuei-Meng, "A New Classification of Prodrugs: Regulatory Perspectives, Pharmaceuticals, 2009, 2 (3): 77-81, which is incorporated by reference herein in its entirety).

The phrase "pharmaceutically acceptable" indicates that the substance or composition must be compatible chemically and/or toxicologically, with the other ingredients included in a formulation, and/or the mammal being treated therewith.

Pharmaceutical formulations include "pharmaceutically acceptable" and "physiologically acceptable" carriers, diluents, or excipients. In this context, the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary compounds (e.g., preservatives, antibacterial, antiviral, and antifungal agents) can also be incorporated into the compositions.

The phrase "effective amount" means an amount of an agent, such as an inhibitor, that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, a subject is "in need of" a treatment if such human or non-human animal subject would benefit biologically, medically or in quality of life from such treatment.

As used herein, the term "inhibit", "inhibition" or "inhibiting" refers to the reduction or suppression of a given condition, symptom, or disorder, or disease (e.g., cancer), or a significant decrease in the baseline activity of a biological activity or process targeted by an inhibitor.

An "inhibitor" refers to the inhibitors of DNA-Dependent Protein Kinase catalytic subunit (DNA-PKcs inhibitor), Poly-ADP Ribose Polymerase (PARP inhibitor), inhibitor of wild-type isocitrate dehydrogenase (IDH inhibitor), inhibitor of histone acetyltransferase (HAT inhibitor), inhibitor of histone deacetylase (HDAC inhibitor), inhibitor of DNA polymerase Θ (PolΘ inhibitor), inhibitor of Platelet Derived Growth Factor Receptor (PDGFR inhibitor) or any combination of two or more of the foregoing. In some aspects, a single agent (e.g., a single compound) can have properties of two or more of the aforementioned classes of inhibitors, or have properties of further classes of inhibitors. For example, CC-115 is a dual DNA-PKcs inhibitor and an mTOR inhibitor.

The inhibitor can be any agent capable of reducing or disrupting the target molecule or signaling function of the target molecule. Exemplary classes of inhibitors include, but are not limited to, small molecules, and macromolecules or biologics such as antibodies (monoclonal or polyclonal antibodies, or antigen-binding fragments thereof), inhibitory polynucleotides or oligonucleotides that reduce target molecule transcription or translation (e.g., antisense, siRNA, shRNA). Therefore, "inhibition" or "inhibiting" encompasses both pharmacological blocking of the target and genetic deletion of or interference with target molecule coding sequences.

Unless otherwise specified, temperatures referred to herein are based on atmospheric pressure (i.e. one atmosphere).

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Aspects

The present disclosure can be described in accordance with the following numbered aspects, which should not be confused with the claims.

Aspect 1. A method for treating cancer in a subject, the method comprising:

(a) administering at least one drug from each of at least two classes selected from an inhibitor of poly-ADP ribose polymerase (PARP inhibitor), an inhibitor of DNA-dependent protein kinase catalytic subunit (DNA-PKcs inhibitor), an inhibitor of wild-type isocitrate dehydrogenase (IDH inhibitor), an inhibitor of histone acetyltransferase (HAT inhibitor), an inhibitor of histone deacetylase (HDAC inhibitor), an inhibitor of DNA polymerase Θ (POLΘ inhibitor); a platelet-derived growth factor receptor inhibitor (PDGFR inhibitor); and a DNA alkylating agent to the subject; and (b) administering radiation to the subject.

Aspect 2. The method of aspect 1, wherein step (a) comprises administering a POLΘ inhibitor and a DNA-PKcs inhibitor.

Aspect 3. The method of aspect 2, wherein the POLΘ inhibitor comprises novobiocin, ART558, ART4215, RP-2119, or any combination thereof.

Aspect 4. The method of aspect 2, wherein the DNA-PKcs inhibitor comprises NU7441 (2-N-morpholino-8-dibenzothiophenyl-chromen-4-one), NU7026 (2-(morpholin-4-yl)-benzo[h]chromen-4-one), SU11752, NK314, AZD7648, M3814, VX-984, CC-115, or any combination thereof.

Aspect 5. The method of aspect 2, wherein the POLΘ inhibitor is novobiocin and the DNA-PKcs inhibitor is VX-984.

Aspect 6. The method of aspect 2, wherein the POLΘ inhibitor is novobiocin and the DNA-PKcs inhibitor is NU7441.

Aspect 7. The method of aspect 2, further comprising administering a PARP inhibitor.

Aspect 8. The method of aspect 7, wherein the PARP inhibitor comprises Olaparib, rucaparib, niraparib, talazoparib, veliparib, BGB-290 (pamiparib), CEP 9722, E7016, 3-aminobenzamide, or any combination thereof.

Aspect 9. The method of aspect 8, wherein the PARP inhibitor is Olaparib.

Aspect 10. The method of aspect 1, wherein step (a) comprises administering a POLΘ inhibitor, wherein the POLΘ inhibitor is novobiocin, administering a DNA-PKcs inhibitor, wherein the DNA-PKcs inhibitor is VX-984, and administering a PARP inhibitor, wherein the PARP inhibitor is Olaparib.

Aspect 11. The method of aspect 1, wherein in step (a) the at least two classes comprise a PARP inhibitor and a DNA-PKcs inhibitor.

Aspect 12. The method of aspect 11, wherein the PARP inhibitor comprises Olaparib, rucaparib, niraparib, talazoparib, veliparib, BGB-290 (pamiparib), CEP 9722, E7016, 3-aminobenzamide, or any combination thereof.

Aspect 13. The method of aspect 11, wherein the DNA-PKcs inhibitor comprises NU7441 (2-N-morpholino-8-dibenzothiophenyl-chromen-4-one), NU7026 (2-(morpholin-4-yl)-benzo[h]chromen-4-one), SU11752, NK314, AZD7648, M3814, VX-984, CC-115, or any combination thereof.

Aspect 14. The method of aspect 11, wherein the PARP inhibitor comprises talazoparib and the DNA-PKcs inhibitor comprises NU7441.

Aspect 15. The method of aspect 11, wherein the PARP inhibitor comprises Olaparib and the DNA-PKcs inhibitor comprises VX-984.

Aspect 16. The method of aspect 1, wherein step (a) comprises administering a POLΘ inhibitor and an HDAC inhibitor.

Aspect 17. The method of aspect 16, wherein the POLΘ inhibitor comprises novobiocin.

Aspect 18. The method of aspect 16, wherein the HDAC inhibitor comprises vorinostat, valproic acid, sodium valproate, romidepsin, panobinostat, belinostat or a combination thereof.

Aspect 19. The method of aspect 1, wherein step (a) comprises administering an IDH inhibitor and a POLΘ inhibitor.

Aspect 20. The method of aspect 19, wherein the IDH inhibitor comprises AG120 and the POLΘ inhibitor comprises novobiocin.

Aspect 21. The method of aspect 19, further comprising administering an HDAC inhibitor.

Aspect 22. The method of aspect 21, wherein the HDAC inhibitor comprises vorinostat.

Aspect 23. The method of aspect 19, further comprising administering a PARP inhibitor.

Aspect 24. The method of aspect 23, wherein the PARP inhibitor comprises Olaparib.

Aspect 25. The method of aspect 1, wherein step (a) comprises administering an IDH inhibitor and a PARP inhibitor.

Aspect 26. The method of aspect 25, wherein the IDH inhibitor comprises AG120 and the PARP inhibitor comprises Olaparib.

Aspect 27. The method of aspect 25, further comprising administering an HAT inhibitor.

Aspect 28. The method of aspect 27, wherein the HAT inhibitor comprises curcumin.

Aspect 29. The method of aspect 25, further comprising administering an HDAC inhibitor.

Aspect 30. The method of aspect 29, wherein the HDAC inhibitor comprises vorinostat.

Aspect 31. The method of aspect 1, wherein step (a) comprises administering an IDH inhibitor and an HDAC inhibitor.

Aspect 32. The method of aspect 31, wherein the IDH inhibitor comprises AG120 and the HDAC inhibitor comprises vorinostat.

Aspect 33. The method of aspect 1, wherein step (a) comprises administering a POLΘ inhibitor and a PARP inhibitor.

Aspect 34. The method of aspect 33, wherein the POLΘ inhibitor comprises novobiocin and the PARP inhibitor comprises Olaparib.

Aspect 35. The method of aspect 33, further comprising administering an HDAC inhibitor.

Aspect 36. The method of aspect 35, wherein the HDAC inhibitor comprises vorinostat.

Aspect 37. The method of aspect 1, wherein step (a) comprises administering a POLΘ inhibitor and an HDAC inhibitor.

Aspect 38. The method of aspect 37, wherein the POLΘ inhibitor comprises novobiocin and the HDAC inhibitor comprises vorinostat.

Aspect 39. The method of aspect 1, wherein step (a) comprises administering a PARP inhibitor and an HDAC inhibitor.

Aspect 40. The method of aspect 39, wherein the PARP inhibitor comprises Olaparib and the HDAC inhibitor comprises vorinostat.

Aspect 41. The method of aspect 1, wherein step (a) comprises administering a DNA alkylating agent and an IDH inhibitor.

Aspect 42. The method of aspect 41, wherein the DNA alkylating agent comprises temozolomide.

Aspect 43. The method of aspect 41, wherein the IDH inhibitor comprises AG120.

Aspect 44. The method of aspect 1, wherein step (a) comprises administering an IDH inhibitor, a POLΘ inhibitor, and a PARP inhibitor.

Aspect 45. The method of aspect 44, wherein the IDH inhibitor comprises AG120, the POLΘ inhibitor comprises novobiocin, and the PARP inhibitor comprises Olaparib.

Aspect 46. The method of aspect 1, wherein step (a) comprises administering an IDH inhibitor, a POLΘ inhibitor, and an HDAC inhibitor.

Aspect 47. The method of aspect 46, wherein the IDH inhibitor comprises AG120, the POLΘ inhibitor comprises novobiocin, and the HDAC inhibitor comprises vorinostat.

Aspect 48. The method of aspect 1, wherein step (a) comprises administering a POLΘ inhibitor, a PARP inhibitor, and an HDAC inhibitor.

Aspect 49. The method of aspect 48, wherein the POLΘ inhibitor comprises novobiocin, the PARP inhibitor comprises Olaparib, and the HDAC inhibitor comprises vorinostat.

Aspect 50. The method of aspect 1, wherein step (a) comprises administering an IDH inhibitor, a POLΘ inhibitor, a PARP inhibitor, and an HDAC inhibitor.

Aspect 51. The method of aspect 50, wherein the IDH inhibitor comprises AG120, the POLΘ inhibitor comprises novobiocin, the PARP inhibitor comprises Olaparib, and the HDAC inhibitor comprises vorinostat.

Aspect 52. The method of aspect 1, wherein step (a) comprises administering a PDGFR inhibitor.

Aspect 53. The method of aspect 52, wherein the PDGFR inhibitor comprises Imatinib, Dasatinib, Nilotinib, Ponatinib, Lenvatinib, Avapritinib, Ripretinib, Sorafenib, Sunitinib, Pazopanib, Regorafenib, Nintedanib, Axitinib, or any combination thereof.

Aspect 54. The method of aspect 52, wherein the PDGFR inhibitor is administered at 20 mg or less per kg of subject body weight.

Aspect 55. The method of aspect 52, wherein the PDGFR inhibitor is administered in a dosage of less than 1 g per day.

Aspect 56. The method of aspect 1, wherein step (a) comprises administering a DNA alkylating agent.

Aspect 57. The method of aspect 56, wherein the DNA alkylating agent comprises temozolomide.

Aspect 58. The method of aspect 56, wherein the DNA alkylating agent is administered at 20 mg or less per kg of subject body weight.

Aspect 59. The method of aspect 56, wherein the DNA alkylating agent is administered in a dosage of less than 1 g per day.

Aspect 60. The method of aspect 1, wherein the PARP inhibitor is administered in a dosage of less than 600 mg per day.

Aspect 61. The method of aspect 1, wherein the PARP inhibitor is administered at 25 mg or less per kg of subject body weight.

Aspect 62. The method of aspect 1, wherein the DNA-PKcs inhibitor is administered in a dosage of less than 400 mg per day.

Aspect 63. The method of aspect 1, wherein the DNA-PKcs inhibitor is administered at 5 mg or less per kg of subject body weight.

Aspect 64. The method of aspect 1, step (a) comprises administering an IDH inhibitor.

Aspect 65. The method of aspect 64, wherein the IDH inhibitor comprises AG120, IDH305, GSK321, GSK864, or any combination thereof.

Aspect 66. The method of aspect 64, wherein the IDH inhibitor is administered in a dosage of less than 500 mg per day.

Aspect 67. The method of aspect 64, wherein the IDH inhibitor is administered at 150 mg or less per kg of subject body weight.

Aspect 68. The method of aspect 1, wherein step (a) comprises administering an HAT inhibitor.

Aspect 69. The method of aspect 68, wherein the HAT inhibitor comprises curcumin, garcinol, anacardic acid, A485, C636, CPTH2, or any combination thereof.

Aspect 70. The method of aspect 68, wherein the HAT inhibitor is administered in a dosage of less than 400 mg per day.

Aspect 71. The method of any one of aspects 68, wherein the HAT inhibitor is administered at 5 mg or less per kg of subject body weight.

Aspect 72. The method of aspect 1, wherein step (a) comprises administering an HDAC inhibitor.

Aspect 73. The method of aspect 72, wherein the HDAC inhibitor comprises vorinostat, valproic acid, sodium valproate, romidepsin, Panobinostat, belinostat or any combination thereof.

Aspect 74. The method of aspect 72, wherein the HDAC inhibitor is administered in a dosage of less than 400 mg per day.

Aspect 75. The method of any one of aspects 72, wherein the HDAC inhibitor is administered at 50 mg or less per kg of subject body weight.

Aspect 76. The method of aspect 1, wherein step (a) comprises administering a POLΘ inhibitor.

Aspect 77. The method of aspect 76, wherein the POLΘ inhibitor comprises novobiocin, ART558, ART4215, RP-2119, or any combination thereof.

Aspect 78. The method of aspect 76, wherein the POLΘ inhibitor is administered at a dosage of less than 2 grams per day.

Aspect 79. The method of aspect 76, wherein the POLΘ inhibitor is administered at 20 mg or less per kg of subject body weight.

Aspect 80. The method of aspect 1, wherein the PARP inhibitor comprises Olaparib and wherein the DNA-PKcs inhibitor comprises NU7441.

Aspect 81. The method of aspect 1, wherein dosages for the at least one drug from each of the at least two classes are lower than individual dosages for each of the drugs when administered separately.

Aspect 82. The method of any one of aspect 1, wherein the at least one drug from each of the at least two classes are administered orally, intravenously, or any combination thereof.

Aspect 83. The method of aspect 1, wherein the at least one drug from each of the at least two classes are administered simultaneously.

Aspect 84. The method of aspect 1, wherein the at least one drug from each of the at least two classes are administered sequentially.

Aspect 85. The method of aspect 1, wherein radiation in step (b) is administered to the subject at a dose of less than or equal to about 2 Gy.

Aspect 86. The method of aspect 85, wherein radiation in step (b) is administered to the subject at a dose of less than or equal to about 1.5 Gy.

Aspect 87. The method of aspect 85, wherein radiation in step (b) is administered at least 10 times.

Aspect 88. The method of aspect 85, wherein a total dose of from about 20 Gy to about 80 Gy of radiation is administered over multiple radiation sessions.

Aspect 89. The method of aspect 1, wherein radiation is delivered in a lower dose than without performing the method.

Aspect 90. The method of aspect 1, wherein radiation is administered before, during, or after performing step (a).

Aspect 91. The method of aspect 1, wherein the radiation comprises an ionizing radiation regimen selected from external radiation, internal radiation, systemic radiation, or any combination thereof.

Aspect 92. The method of aspect 91, wherein the radiation therapy comprises a fractionation regimen selected from hypofractionation, hyperfractionation, accelerated fractionation, or any combination thereof.

Aspect 93. The method of aspect 1, wherein the cancer is associated with an H3.3 mutation.

Aspect 94. The method of aspect 93, wherein the H3.3 mutation comprises an H3.3K27M mutation, an H3.1K27M mutation, an H3.2K27M mutation, an H3.3G34V mutation, an H3.3G34R mutation, an H3.3G34W mutation, an H3.3G34L mutation, an H3.3K36M mutation, or any combination thereof.

Aspect 95. The method of aspect 1, wherein the cancer comprises acute lymphoblastic leukemia, acute myeloid leukemia, adrenocortical carcinoma, anal cancer, astrocytoma, basal cell carcinoma, bladder cancer, BRCA1 breast cancer, BRCA2 breast cancer, hormone receptor positive breast cancer, Burkitt's lymphoma, carcinoid tumor, cervical cancer, chondroblastoma, chronic lymphocytic leukemia, chronic myelogenous leukemia, colon cancer, cutaneous t-cell lymphoma, endometrial cancer, ependymoma, esophageal cancer, extrahepatic bile duct cancer, gallbladder cancer, a giant cell tumor of the bone, glioblastoma, another high-grade glioma, hairy cell leukemia, head and neck cancer, Hodgkin's lymphoma, hypopharyngeal cancer, intraocular melanoma, islet cell carcinoma, Kaposi's sarcoma, laryngeal cancer, lip and oral cavity cancer, liver cancer, medulloblastoma, melanoma (including BRCA1- or BRCA2-associated melanoma), Merkel cell carcinoma, mesothelioma, multiple myeloma, nasopharyngeal cancer, neuroblastoma, non-Hodgkin's lymphoma, non-small cell lung cancer, oropharyngeal cancer, osteosarcoma, ovarian cancer including BRCA1- or BRCA2-associated ovarian cancer, pancreatic cancer (including BRCA1- or BRCA2-associated pancreatic cancer), parathyroid cancer, penile cancer, pheochromocytoma, pituitary tumor, pleuropulmonary blastoma, primary central nervous system lymphoma, prostate cancer (including BRCA1- or BRCA2-associated prostate cancer), rectal cancer, renal cell cancer, retinoblastoma, rhabdomyosarcoma, salivary gland cancer, secondary acute myeloid leukemia (s-AML), small cell lung cancer, small intestine cancer, soft tissue sarcoma, squamous cell carcinoma, stomach cancer, testicular cancer, thymoma, thyroid cancer, uterine sarcoma, vaginal cancer, vulvar cancer, Waldenström's macroglobulinemia, Wilms' tumor, or any combination thereof.

Aspect 96. The method of aspect 95, wherein the cancer is pediatric high-grade glioma, chondroblastoma, a giant cell tumor of the bone, secondary acute myeloid leukemia; homologous recombination deficient breast cancer, ovarian cancer carrying a BRCA1 mutation, ovarian cancer carrying a BRCA2 mutation, pancreatic cancer carrying a BRCA1 mutation, pancreatic cancer carrying a BRCA2 mutation, prostate cancer carrying a BRCA1 mutation, prostate cancer carrying a BRCA2 mutation, melanoma carrying a BRCA1 mutation, melanoma carrying a BRCA2 mutation, or any combination thereof.

Aspect 97. The method of aspect 95, wherein the glioblastoma is pediatric glioblastoma.

Aspect 98. The method of aspect 1, wherein performing the method results in a reduction or elimination of at least one side effect relative to a cancer treatment not including each of steps (a) and (b).

Aspect 99. The method of aspect 98, wherein the at least one side effect comprises myelodysplastic syndrome (MDS), acute myeloid leukemia (AML), bone marrow suppression, a low white blood cell count, weakness, weight loss, fever, frequent infections, blood in urine, blood in stool, shortness of breath, fatigue, bruising more easily, bleeding more easily, shortness of breath, fever, cough, wheezing, pneumonitis, blood clots, nausea, vomiting, tiredness, weakness, low red blood cell count, diarrhea, loss of appetite, headache, changes in food taste, dizziness, indigestion, heartburn, low platelet count, QT prolongation, or any combination thereof.

Aspect 100. The method of aspect 1, wherein performing the method does not induce drug resistance in the cancer.

Aspect 101. The method of aspect 1, wherein performing the method induces partial or complete remission of the cancer.

Aspect 102. The method of aspect 1, wherein the cancer does not recur following performance of the method.

Aspect 103. The method of aspect 1, wherein performing the method selectively kills cancer cells.

Aspect 104. The method of aspect 1, wherein the subject is a mammal.

Aspect 105. The method of aspect 104, wherein the mammal is a human, cat, dog, guinea pig, rat, mouse, rabbit, horse, cattle, swine, sheep, or goat.

Aspect 106. The method of aspect 1, wherein the cancer is breast cancer, the DNA-PKcs inhibitor is VX-984, and the POLΘ inhibitor is novobiocin.

Aspect 107. The method of aspect 1, wherein the cancer is breast cancer, the PARP inhibitor is Olaparib, and the POLΘ inhibitor is novobiocin.

Aspect 108. The method of aspect 1, wherein the cancer is breast cancer, the DNA-PKcs inhibitor is VX-984, and the PARP inhibitor is Olaparib.

Aspect 109. The method of aspect 1, wherein the cancer is breast cancer, the DNA-PKcs inhibitor is VX-984, the POLΘ inhibitor is novobiocin, and the PARP inhibitor is Olaparib.

Aspect 110. The method of aspect 1, wherein the cancer is breast cancer, the DNA-PKcs inhibitor is NU7441 and the PARP inhibitor is talazoparib.

Aspect 111. The method of aspect 1, wherein the cancer is ovarian cancer, the DNA-PKcs inhibitor is VX-984, and the POLΘ inhibitor is novobiocin.

Aspect 112. The method of aspect 1, wherein the cancer is ovarian cancer, the PARP inhibitor is Olaparib, and the POLΘ inhibitor is novobiocin.

Aspect 113. The method of aspect 1, wherein the cancer is ovarian cancer, the DNA-PKcs inhibitor is VX-984, and the PARP inhibitor is Olaparib.

Aspect 114. The method of aspect 1, wherein the cancer is ovarian cancer, the DNA-PKcs inhibitor is VX-984, the POLΘ inhibitor is novobiocin, and the PARP inhibitor is Olaparib.

Aspect 115. The method of aspect 1, wherein the cancer is ovarian cancer, the DNA-PKcs inhibitor is NU7441, and the PARP inhibitor is Olaparib.

Aspect 116. The method of aspect 1, wherein the cancer is ovarian cancer, the POLΘ inhibitor is novobiocin, the DNA-PKcs inhibitor is NU7441, and the PARP inhibitor is Olaparib.

Aspect 117. The method of aspect 1, wherein the cancer is pancreatic cancer, the DNA-PKcs inhibitor is VX-984, and the POLΘ inhibitor is novobiocin.

Aspect 118. The method of aspect 1, wherein the cancer is pancreatic cancer, the PARP inhibitor is Olaparib, and the POLΘ inhibitor is novobiocin.

Aspect 119. The method of aspect 1, wherein the cancer is pancreatic cancer, the DNA-PKcs inhibitor is VX-984, and the PARP inhibitor is Olaparib.

Aspect 120. The method of aspect 1, wherein the cancer is pancreatic cancer, the DNA-PKcs inhibitor is VX-984, the POLΘ inhibitor is novobiocin, and the PARP inhibitor is Olaparib.

Aspect 121. The method of aspect 1, wherein the cancer is pancreatic cancer, the DNA-PKcs inhibitor is NU7441 and the PARP inhibitor is talazoparib.

Aspect 122. The method of aspect 1, wherein the cancer is pediatric high grade glioma, the HDAC inhibitor is valproic acid, and the POLΘ inhibitor is novobiocin.

Aspect 123. The method of aspect 1, wherein the cancer is pediatric high grade glioma, the HDAC inhibitor is sodium valproate, and the POLΘ inhibitor is novobiocin.

Aspect 124. The method of aspect 1, wherein the cancer is pediatric high grade glioma, the IDH inhibitor is AG120, the POLΘ inhibitor is novobiocin, and the PARP inhibitor is Olaparib.

Aspect 125. The method of aspect 1, wherein the cancer is pediatric high grade glioma, the IDH inhibitor is AG120, the HDAC inhibitor is vorinostat, and the PARP inhibitor is Olaparib.

Aspect 126. The method of aspect 1, wherein the cancer is pediatric high grade glioma, the POLΘ inhibitor is novobiocin, the HDAC inhibitor is vorinostat, and the PARP inhibitor is Olaparib.

Aspect 127. The method of aspect 1, wherein the cancer is pediatric high grade glioma, the POLΘ inhibitor is novobiocin and the DNA-PKcs inhibitor is NU7441.

Aspect 128. The method of aspect 1, wherein the cancer is pediatric high grade glioma, the DNA-PKcs inhibitor is VX-984, and the POLΘ inhibitor is novobiocin.

Aspect 129. The method of aspect 1, wherein the cancer is pediatric high grade glioma, the PARP inhibitor is Olaparib, and the POLΘ inhibitor is novobiocin.

Aspect 130. The method of aspect 1, wherein the cancer is pediatric high grade glioma, the DNA-PKcs inhibitor is VX-984, and the PARP inhibitor is Olaparib.

Aspect 131. The method of aspect 1, wherein the cancer is pediatric high grade glioma, the DNA-PKcs inhibitor is VX-984, the POLΘ inhibitor is novobiocin, and the PARP inhibitor is Olaparib.

Aspect 132. A pharmaceutical composition comprising at least one drug from each of at least two classes selected from an inhibitor of poly-ADP ribose polymerase (PARP inhibitor), an inhibitor of DNA-dependent protein kinase catalytic subunit (DNA-PKcs inhibitor), an inhibitor of wild-type isocitrate dehydrogenase (IDH inhibitor), an inhibitor of histone acetyltransferase (HAT inhibitor), an inhibitor of histone deacetylase (HDAC inhibitor), an inhibitor of DNA polymerase Θ (POLΘ inhibitor); a platelet-derived growth factor receptor inhibitor (PDGFR inhibitor); and a DNA alkylating agent.

Aspect 133. The pharmaceutical composition of aspect 132, wherein the HDAC inhibitor is valproic acid and the POLΘ inhibitor is novobiocin.

Aspect 134. The pharmaceutical composition of aspect 132, wherein the HDAC inhibitor is sodium valproate and the POLΘ inhibitor is novobiocin.

Aspect 135. The pharmaceutical composition of aspect 132, wherein the IDH inhibitor is AG120, the POLΘ inhibitor is novobiocin, and the PARP inhibitor is Olaparib.

Aspect 136. The pharmaceutical composition of aspect 132, wherein the POLΘ inhibitor is novobiocin, the PARP inhibitor is Olaparib, and the HDAC inhibitor is vorinostat.

Aspect 137. The pharmaceutical composition of aspect 132, wherein the POLΘ inhibitor is novobiocin and the DNA-PKcs inhibitor is NU7441.

Aspect 138. The pharmaceutical composition of aspect 132, wherein the DNA-PKcs inhibitor is VX-984 and the PARP inhibitor is Olaparib.

Aspect 139. The pharmaceutical composition of aspect 132, wherein the POLΘ inhibitor is novobiocin and the PARP inhibitor is Olaparib.

Aspect 140. The pharmaceutical composition of aspect 132, wherein the DNA-PKcs inhibitor is VX-984 and the POLΘ inhibitor is novobiocin.

Aspect 141. The pharmaceutical composition of aspect 132, wherein the DNA-PKcs inhibitor is VX-984, the POLΘ inhibitor is novobiocin, and the PARP inhibitor is Olaparib.

Aspect 142. The pharmaceutical composition of aspect 132, wherein the POLΘ inhibitor is novobiocin, the DNA-PKcs inhibitor is NU7441, and the PARP inhibitor is Olaparib.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Materials and Methods

Cell Lines and Stable shRNA Mediated H3.3 Knockdown

All cells were cultured at 37° C. and 5% $CO_2$. HCT116, KNS42, and SF8628 cells were grown in Dulbecco's Modified Eagle Medium (DMEM) with 10% fetal bovine serum (FBS: Avantor), 1× antibiotic antimycotic (Ab/Am: Corning), and 100 µg/mL Normocin (InvivoGen). SVGp12 cells were grown in a very similar manner, except that EMEM was used instead of DMEM. EJ-RFP cells, which had a DsRed reporter gene that would be expressed following doxycycline exposure, were propagated in DMEM with 10% tetracycline free FBS, 1× Ab/Am as well as 100 µg/mL Primocin (InvivoGen). pcGBM2 and DIPG 25 were cultured in Tumor Stem Medium (TSM) with the various growth factors listed below. TSM is a 1:1 mixture of Neurobasal™-A (Gibco) and DMEM/F-12 (Gibco) with 1×MEM Non-Essential Amino Acids Solution (Cytiva), 100 mM HEPES 7.4 (TEKNOVA), 1× Ab/Am (Corning), 100 µg/mL Primocin (InvivoGen), 20 mM Stable L-Glutamine Dipeptide (Cytiva), 1× B-27™ Supplement without vitamin A (Gibco), 10 ng/ml h-FGF (Shenandoah Biotech), 10 ng/ml h-EGF (Shenandoah Biotech), 10 ng/ml h-PDGF-AA (Shenandoah Biotech), 10 ng/ml h-PDGF-BB (Shenandoah Biotech) and 2 µg/mL Heparin Solution (StemCell). Human colon carcinoma cell line HCT116 and its derivatives were used in all the studies except where indicated. Transfections were carried out using 1 µg of DNA corresponding to each expression construct with Lipofectamine 2000 (Invitrogen) or jetPRIMER following the manufacturer's protocol. Transiently transfected cells were assayed between 24- and 48 hours following transfection. Where needed, stable cell lines were generated by applying the selection antibiotic 48 hours following transfection and maintaining it for at least 3 weeks until individual colonies could be picked. The EZH2−/− knockout cell line was created in the Retinal Pigment Epithelial (RPE) cell line using Zinc Finger Nucleases (ZFNs).

Mouse Xenograft Model for Testing the Effect of NHEJ Inhibitors on H3.3 Mutant Tumor Cells Animal studies were approved by the Florida State University Animal Care and Use Committee (ACUC: PROTO202100054, PROTO202200000026, and PROTO202300000039). Two strains of immunocompromised mice were obtained, namely R2G2 (B6;129-Rag2$^{tm1Fwa}$Il2rg$^{tm1Rsky}$/DwlHsd) from ENVIGO, Rag2/Il2rg double knockout (C57BL/6NTac.Cg-Rag2$^{tm1Fwa}$Il2rg$^{tm1Wjl}$) from Taconic and NIH III Nude (Crl:NIH-Lys$^{tbg-J}$Foxn1$^{nu}$Btk$^{xid}$) from Charles River. Mice were housed in autoclaved individually ventilated cages (IVCs) and fed irradiated alfalfa-free chow and acidified water (pH 2.5-3) to prevent bacterial contamination. Upon arrival, mice were allowed to acclimate to their surroundings for 1-7 days before subcutaneous (SQ) implantation with either SF8628, SF7741 or DIPG XIII (all with H3.3K27M mutation) or KNS42 (with H3.3G34V mutation) cells. A 300 µL SQ injection containing equal volumes of Matrigel (Corning) and ice-cold cell suspension (0.5-10 million cells) was injected in the right flank. Mice were also injected with ~100 mg/kg of luciferin through either intraperitoneal (IP) or SQ injection just prior or directly after the tumor cell injection and imaged in a Perkin Elmer IVIS Lumina III small animal imager to ensure the correct location of cells post-injection. Therapeutic treatments were initiated upon successful tumor engraftment (i.e., once mice showed a palpable tumor and/or a consistently increasing BLI signal). Therapeutic drug treatments were administered 5 days a week (Monday through Friday) in a 100-300 microliter IP or SQ injection composed of either 15% vehicle, or drugs diluted in sterile PBS until the end of the study. Treatments consisted of either of dimethyl sulfoxide (DMSO) vehicle or Olaparib (25-37.5 mg/kg/day; MedChemExpress); Niraparib (15 mg/kg/day; Advanced ChemBlocs Inc.); Avapritinib (15 mg/kg/day; Advanced ChemBlocs Inc.); Vorinostat (15 mg/kg/day; MedChemExpress); GSK864 (75 mg/kg/day; Excenen Pharmatech); AG120 (75 mg/kg/day; Advanced ChemBlocs Inc.); Temozolomide (15 mg/kg/day; Ambeed); Sodium Valproate (100 mg/kg/day; MP Biomedicals); Novobiocin (100 mg/kg/day; Research Products International) and/or NU7741 (5 mg/kg/day; MedChemExpress). The drugs were delivered in combination with either a total of 20 Gray (Gy) radiation administered in ten 2 Gy fractions within the first 14 days of treatment using a two day on radiation followed by one day off radiation schedule, or a total of 30 Gray (Gy) radiation administered in twenty 1.5 Gy fractions within the first 4 weeks of treatment using a five day (Monday to Friday) on radiation followed by two days off on weekends radiation schedule. Assessment of tumor size through BLI imaging or microcaliper measurements was conducted up to 3 times a week until mice met the humane or clinical endpoints.

Plasmids

Plasmids for the expression of canonical H3.1-GFP and RFP-PCNA and have been described previously. Stable H3.3 knockdown was generated by employing lentiviral mediated simultaneous transduction of HCT116 cells with different Mission shRNA constructs (Sigma-Aldrich) targeting both H3F3A and H3F3B genes followed by selection with 5 µg/mL puromycin for ~2 weeks to obtain resistant clones carrying the H3.3 knockdown. The FLAG-tagged mouse H3.3 expression construct is naturally resistant to the shRNA constructs used to knockdown H3.3 in human cells due to substantial differences in the nucleotide sequence despite identical H3.3 protein sequences between mice and humans. To construct the H3.3-mEmerald expression construct, a PCR amplified mouse H3.3 gene fused at its C-terminus to mEmerald (a brighter variant of eGFP) was ligated between the unique BglII and NotI restriction sites in a modified vector derived from pEGFP-C1 (Clontech). This expression construct is now available through Addgene (#54116).

Cell Survival Assays

Except for the viability assays performed in FIGS. 1A-1G that were scored by flow cytometry using the violet fluorescent Live/Dead cell staining kit (Invitrogen) following the manufacturer's instructions, all the remaining viability assays were performed as following. Equal number of cells were seeded in triplicate in multi-well cell culture plates at low density in the presence of the inhibitors. After the cells had reattached (usually within 3-12 hours of seeding), cells were treated radiation as indicated. The experiment was stopped before the untreated cells reached confluency by dissociating the surviving attached cells. The surviving cells were then counted on a Beckman Coulter particle and size analyzer, typically set to count all particles with a size greater than 8 µm (but was adjusted as needed based on cell size for different cell types). Significant differences between treatments was determined using ANOVA and Tukey Kramer test.

Western Blotting and Immunofluorescence (IF)

A detailed protocol for Western blotting as well as the histone H3 and H4 antibodies used here have been described previously. Home-made affinity purified rabbit polyclonal antibodies for γH2A.X were used with identical results in Western Blotting and IF as commercially available mouse monoclonal γH2A.X antibodies (Millipore).

IF was carried out using standard procedures. Cells were seeded on poly-L Lysine coated glass clover slips or collagen-coated 35 mm glass-bottom dishes. Four to 24 hours after seeding, cells at ~80% confluency were fixed in 4% formaldehyde in phosphate-buffered saline (PBS: 137 mM NaCl, 2.7 mM KCl, 8 mM $Na_2HPO_4$, 2 mM $KH_2PO_4$) for a minimum of 15 minutes, but not longer than 12 hours. Fixed cells were washed three times for 5 minutes each with PBS and then incubated in blocking buffer (1×PBS, 5% BSA, 0.3% Triton X-100 buffer) for 60 minutes at room temperature. After blocking, cells were incubated in the antibody dilution buffer (1×PBS, 1% BSA, 0.3% Triton X-100, corresponding primary antibody) for either 1 hour at room temperature or at 4° C. for up to 24 hours. Non-bound primary antibodies were removed by three washes with PBS for 5 minutes each and then incubated with fluorochrome-conjugated secondary antibodies, either Goat Anti-Rabbit IgG-TRITC (SouthernBiotech) at 1:50, or Goat Anti-Mouse-FITC (SouthernBiotech) at 1:600 for up to 1 hours, protected from light. DNA was stained with 1 µg/mL of DAPI if needed. Unbound secondary antibodies were removed with three 5-minute PBS washes before imaging.

Live Cell Imaging Following Laser Microirradiation Induced DNA Damage and FRAP

Fluorescently (mEmerald) tagged mouse wild type or mutant mouse H3.3 (which is identical to the human H3.3 protein) were transiently or stably expressed in HCT116 human colon carcinoma cells to study their recruitment to sites of laser microirradiation induced DNA damage by live cell imaging. Importantly, no chemical treatments with nucleotide analogs such as BrdU, or DNA binding dyes such as Hoechst or DAPI to pre-sensitize the cells to DNA damage were used, since these treatments could potentially interfere with these experiments and give rise to unanticipated effects due to their potential for modulating chromatin structure upon binding to DNA. For laser induced DNA damage and imaging experiments, cells were grown and transfected in collagen coated glass bottom 35 mm culture dishes (Mattek) inside a humidified chamber maintained at 5% $CO_2$ and 37° C. on the stage of an Andor Revolution spinning disk live cell imaging system equipped with a Nikon Eclipse TiE inverted confocal microscope with the Perfect Focus system. DNA damage was typically inflicted in a ~0.25 µm diffraction limited spot (or a ~0.25 µm thick line) within the nucleus using the Andor FRAPPA system to fire a 100 mW 405 nm laser at 100% power for 1 ms on a diffraction limited spot through 60× or 100× Nikon 1.49NA TIRF objectives. This was followed by rapid imaging (at least 1 frame per channel per second for the first 2 minutes and every 10-30 s thereafter) using an Andor iXON 897 EMCCD camera to follow any recruitment of the tagged proteins to the site of laser induced DNA damage. The rapid recruitment of fluorescently (Red Fluorescent Protein, RFP) tagged DNA replication factors such as PCNA and chromatin assembly factors such as CAF1 that are known to be recruited to sites of DNA damage was used as positive controls in these experiments.

FRAP experiments were essentially performed as described previously after growing the cells as described here. Fluorescent intensity over time was measured using ImageJ. These profiles were fit using QtiPlot to a FRAP recovery formula ($y=A (1-e^{(-\tau * Time)})$) where "A" signifies the amount recovered and "τ" provides information on the rate of recruitment.

Fluorescence Based DNA Repair Pathway Analyses Using Fluorescence-Activated Cell Sorting (FACS)

Fluorescent reporter systems were used to directly measure HR and mutagenic-NHEJ as described. First, cells carrying these fluorescent reporter systems were stably transfected with LUC and H3.3 shRNAs. These systems allowed direct measurement of the efficiency of an engineered DSB by both the HR and mutagenic-NHEJ pathways within these cells. For each reporter system, up to 1,000,000 cells were analyzed and measured for reporter expression (GFP for HR or DsRED for NHEJ). For the HR assay, DSB was initiated by transiently co-transfecting an I-SceI carrying plasmid with an mCherry carrying plasmid to serve as a control for transfection efficiency. To quantitate HR efficiency, the fluorescence from cells exhibiting successful HR mediated repair was quantitated 96 hours later and normalized to red fluorescence from the mCherry using FACS. For the mutagenic-NHEJ assay which primarily measured alt-NHEJ, DSB was induced by adding 100 nM triamcinolone acetonide (TA) and 1 µM Sheild1 reagent to the cells for 24 hours and the number of cells exhibiting red fluorescence due to mutagenic-NHEJ mediated repair was quantitated using FACS 48 hours post-transfection.

A simple plasmid re-ligation assay was also used to measure c-NHEJ. For this, the eGFP-C1 plasmid (Clontech) carrying an eGFP gene was cleaved with AgeI restriction endonuclease that cuts between the promoter and the coding sequence of eGFP, creating a DSB with compatible cohesive ends which prevents eGFP expression unless the DSB is repaired via c-NHEJ mediated ligation of the broken ends. The AgeI cleaved or uncleaved plasmid was co-transfected with an equimolar amount of a mCherry expressing plasmid to serve as a control for transfection efficiency in LUC and H3.3KD cells. In this strategy, eGFP expression is observed after successful c-NHEJ mediated repair. eGFP fluorescence was quantitated 24 hours after transfection using FACS and normalized to red fluorescence from the mCherry gene.

For FACS analysis of the fluorescent reporter-based DNA repair assays, cells were first dissociated using 1× 0.25% trypsin-EDTA (VWR), pelleted through centrifugation (300 g), and washed with 1×PBS. Cells were resuspended at 1 million cells per mL concentration and passed through a 50 µm nylon filter to ensure single-cell suspension. All samples were analyzed on a BD FACSCanto system. Green fluorescence was excited using 488 nm laser recorded with a FITC (530/30-A) filter while red fluorescence was excited using 561 nm laser and measured using PE Texas Red (610/20-A) filter.

Viral Transduction of Firefly Luciferase into Patient Derived H3.3 Mutant Cancer Cells The construct pHIV-iRPF720-E2A-LUC (Addgene #104587) promotes the expression of both a near-infrared fluorescent protein 720 nm (iRFP720) as well as firefly luciferase, both of which enable in vivo imaging in mice. To generate lentiviruses carrying this construct, pHIV-iRPF720-E2A-LUC was co-transfected using jetPRIMER along with pMDLg/pREE (Addgene #12251), pRSV-Rev (Addgene #12253), and pMD2.G (Addgene #122559) plasmids to enable viral packaging in HEK293T cells. Twenty-four hours after transfection, media was replaced and subsequently, the supernatant containing viral particles was collected 48- and 72-hours post-transfection. The collected supernatant was spun down ~2000 g for 10 minutes to remove any cellular debris and frozen at −80° C. H3.3 mutant cell lines KNS42 and SF8628 were seeded to ~85% confluency and were treated with 5 µg/mL polybrene and 1 mL of the lentiviral supernatant. The supernatant was removed 24-48 hours later, and successful transduction was confirmed through imaging using the PerkinElmer small animal imager to detect bioluminescence (BLI) from firefly luciferase or the Li-Cor Odyssey imager to detect iRFP720 fluorescence. All steps followed Biosafety Level 2 guidelines and safety requirements.

Quantification and Statistical Analysis

Where shown, error bars represent the standard error of the mean derived from at least 3 independent experiments for FIGS. 1A-2D. For the remaining figures, where shown, the error bars reflect the standard deviation. Multiple statistical tests were used to determine significant differences and to generate p-values as appropriate. Unless indicated otherwise in the figure legends, T-tests were used to determine the significance of observed differences in the experiments. Variations in the efficiency of recruitment of multiple DNA repair factors were analyzed using a Fisher's Exact test. Significant differences within the survival assays were determined using an ANOVA with a post hoc Tukey Honest Significant Difference test. Finally, a G-rho family of tests was used to determine the statistical significance in survival in the Kaplan-Meier plot shown in FIG. 4C.

Example 2: Results and Discussion

Histone H3.3 is Rapidly Recruited to Sites of Laser Induced DNA Damage and Cells Deficient in H3.3 Accumulate Endogenous Damage, as Well as Show Sensitivity to Exogenous DNA Damaging Agents.

Figure 1A:
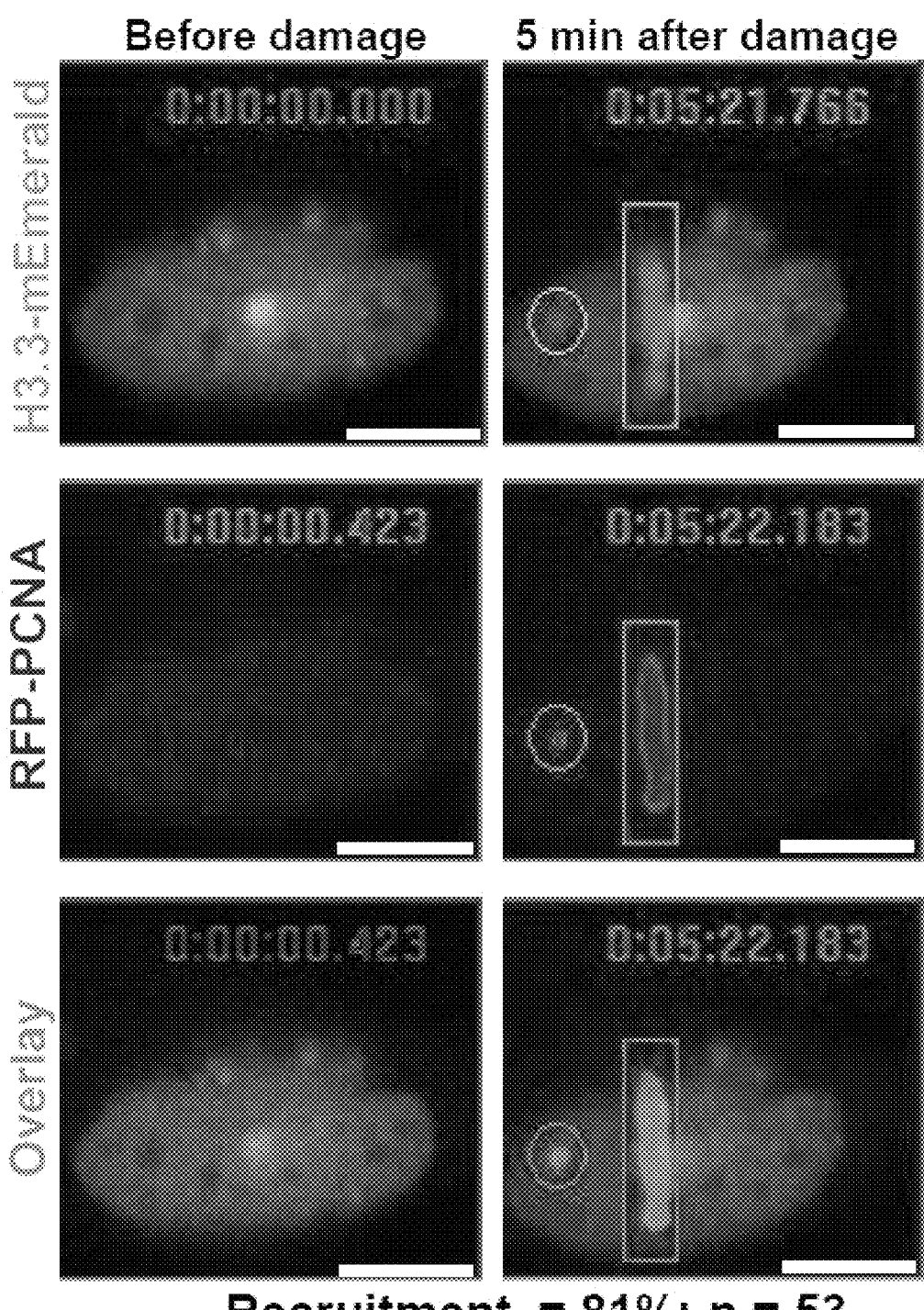
FIGS. 1A-1G show replacement histone variant H3.3 is rapidly recruited to DNA damage sites and cells deficient in H3.3 accumulate endogenous damage, while also being hypersensitive to DNA damaging agents.
Figure 1B:
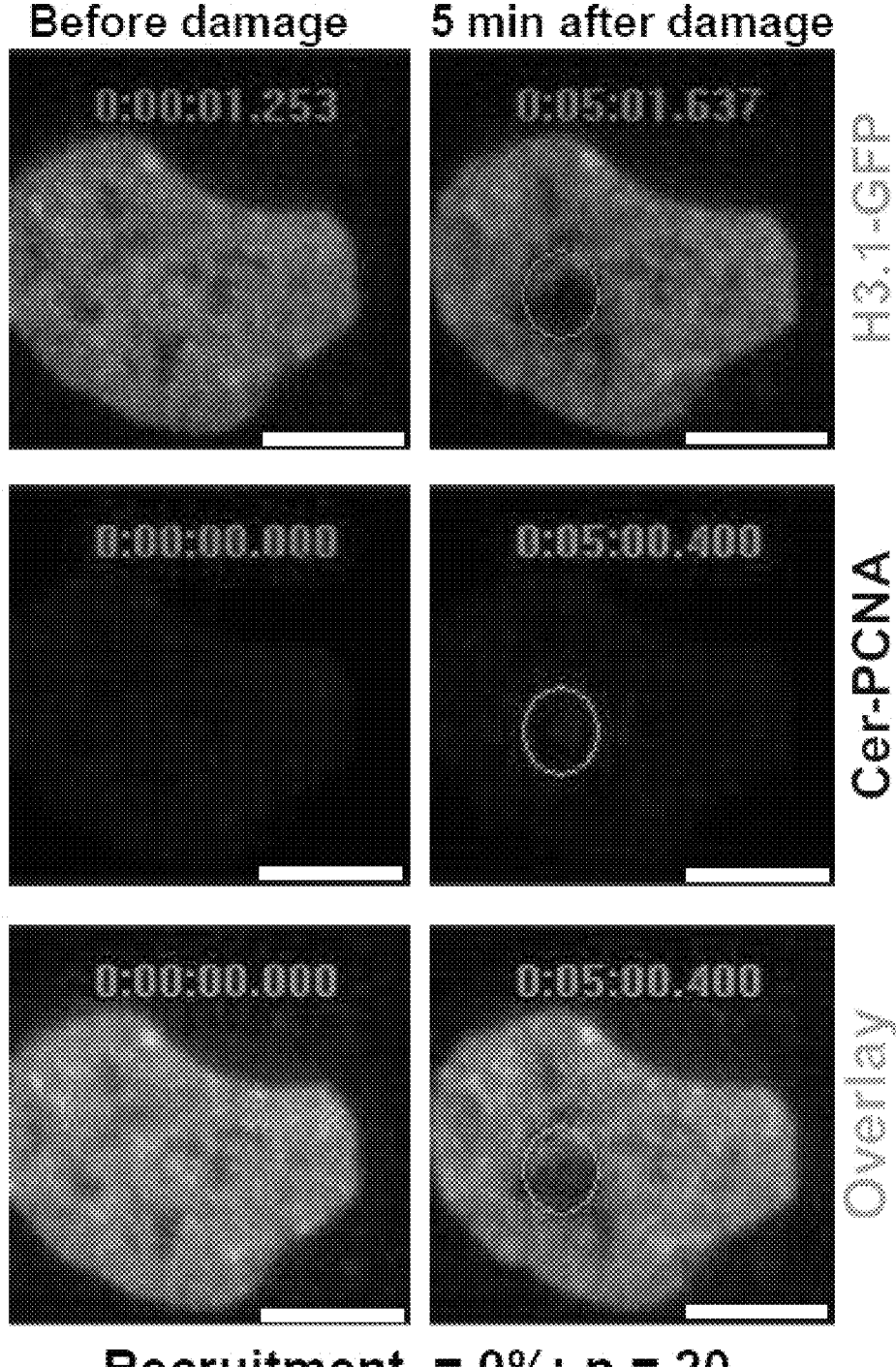
Figure 1C:
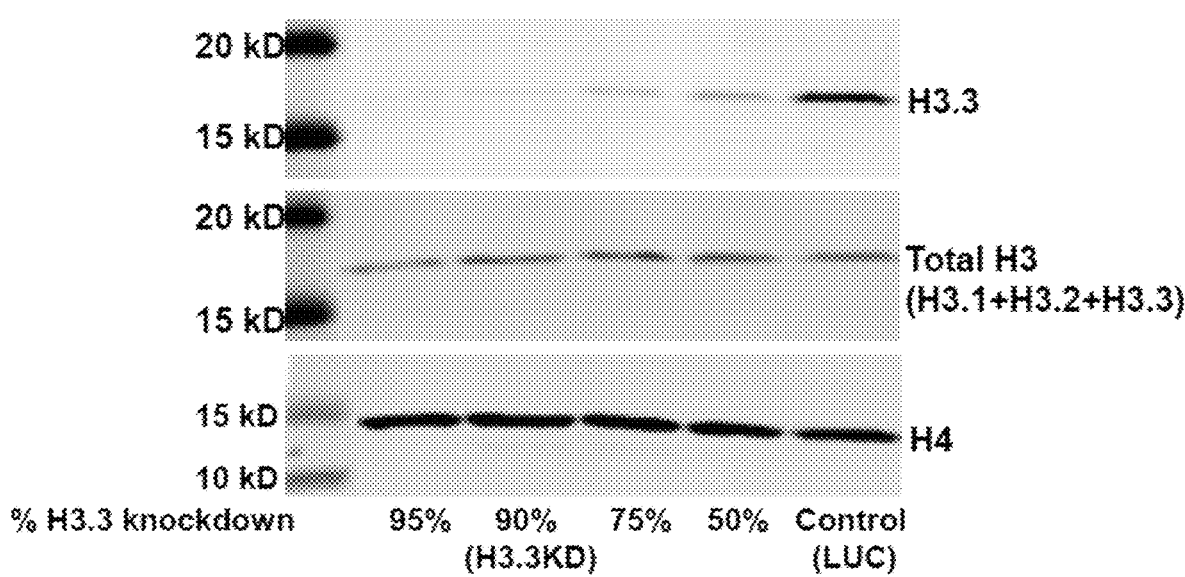

A variety of DNA damage response and repair proteins are rapidly recruited in an orderly manner to DNA repair foci. To investigate if core histone variants are involved in chromatin dynamics upon DNA damage, fluorescently tagged canonical and variant core histones were screened in HCT116 cells for recruitment to DNA damage inflicted by laser microirradiation using a 405 nm laser that generates a variety of DNA damage including single and double strand breaks (DSBs). It was found that histone H3.3 was rapidly recruited to laser induced DNA damage sites (FIG. 1A). Replication clamp Proliferating Cell Nuclear Antigen (PCNA) was also used as a marker for active repair at laser induced DNA damage sites and found it to be rapidly recruited to the DNA damage sites as has been previously demonstrated. Consistent with the extremely low mobility of canonical core histones in general, and with previously published live cell microscopy data, no recruitment of histone H3.1 (or of core histones H2A, H2B and H4; data not shown) to laser induced DNA damage sites was observed, whereas PCNA showed robust recruitment in the same cells (FIG. 1B). The recruitment of H3.3 to DNA damage sites in seconds even after prolonged transcription inhibition, combined with the fact that transcription is repressed at DNA damage sites-all suggest a potential role for H3.3 in DNA damage response independent of its role in transcription.

Figure 8A:
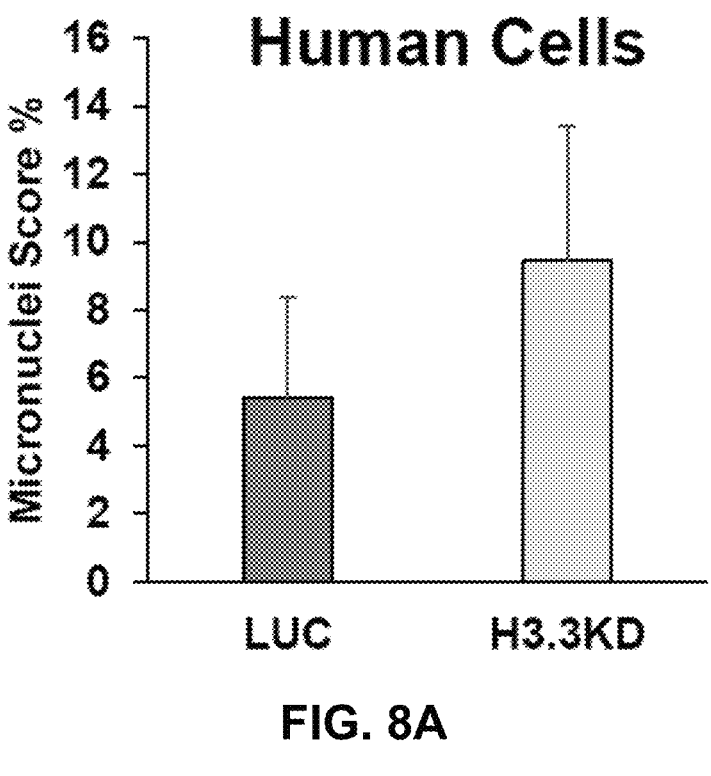
FIGS. 8A-8G show deficiency of H3.3 in cells from multiple species results in accumulation of genomic insta-bility and endogenous DNA damage, as well as hypersen-sitivity to DNA damaging agents.
Figure 8B:
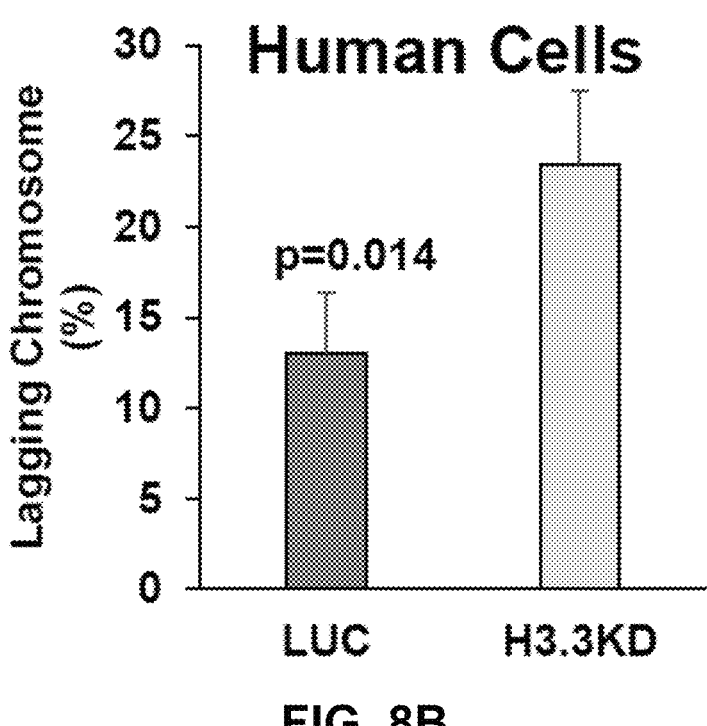
Figure 8C:
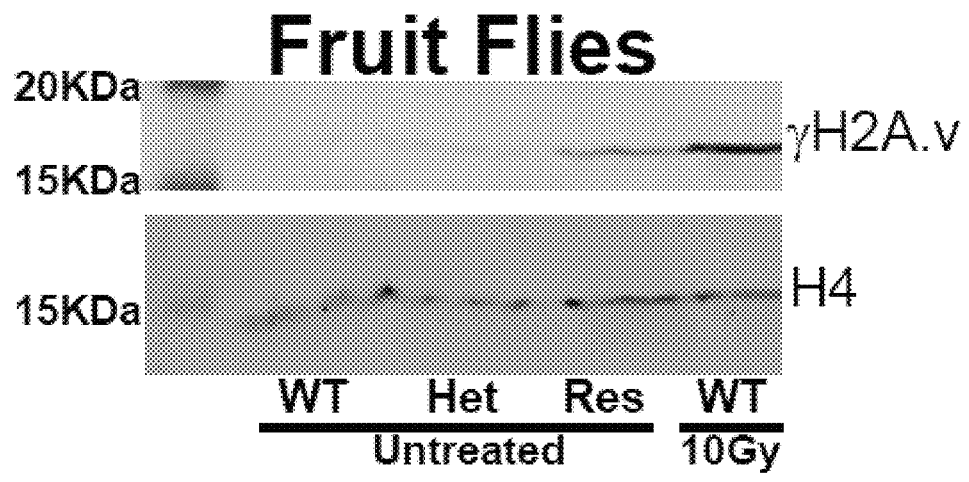

Since H3.3 is essential for viability in mammals, short-hairpin RNA (shRNA) mediated stable H3.3 knock down (H3.3 KD) cell lines expressing greatly reduced (~90%) amounts of wild type H3.3 were generated (FIG. 1C), to test if histone H3.3 indeed plays a role in DNA repair. As reported previously for H3.3 knockout (KO) embryonic stem (ES) cells, the H3.3KD cell lines grow slower than their control Luciferase (LUC) shRNA expressing cell lines, but exhibit similar cell viability. Since H3.3 was rapidly recruited to sites of DNA damage suggesting that it can play a role in DNA repair, Western blotting was used to measure the levels of phosphorylated H2A.X S139 (γH2A.X), a marker for DNA double strand breaks (DSBs), in whole cell extracts prepared from untreated LUC and H3.3KD cells. Compared to control LUC cells, the H3.3KD cells accumulated high levels of endogenous DNA damage as measured by the presence of γH2A.X (FIG. 1D), consistent with similar observations previously reported for H3.3 KO ES cells. Similar to the phenotype of H3.3 KO ES cells, a doubling of genomic instability in H3.3KD cells was also observed as measured by an enhanced rate of micronuclei formation (FIG. 8A) and the presence of lagging chromosomes (FIG. 8C). Next, the sensitivity of H3.3 KD and LUC cells to a variety of DNA damaging agents was tested. Compared to the control LUC cells, the H3.3 KD cells were very sensitive to the alkylating agent Methylmethane Sulfonate (MMS) (FIG. 1E), DNA strand breaks caused by Ionizing Radiation (IR) (FIG. 1F) and to replication inhibitors such as Mimosine (FIG. 1G).

Figure 8D:
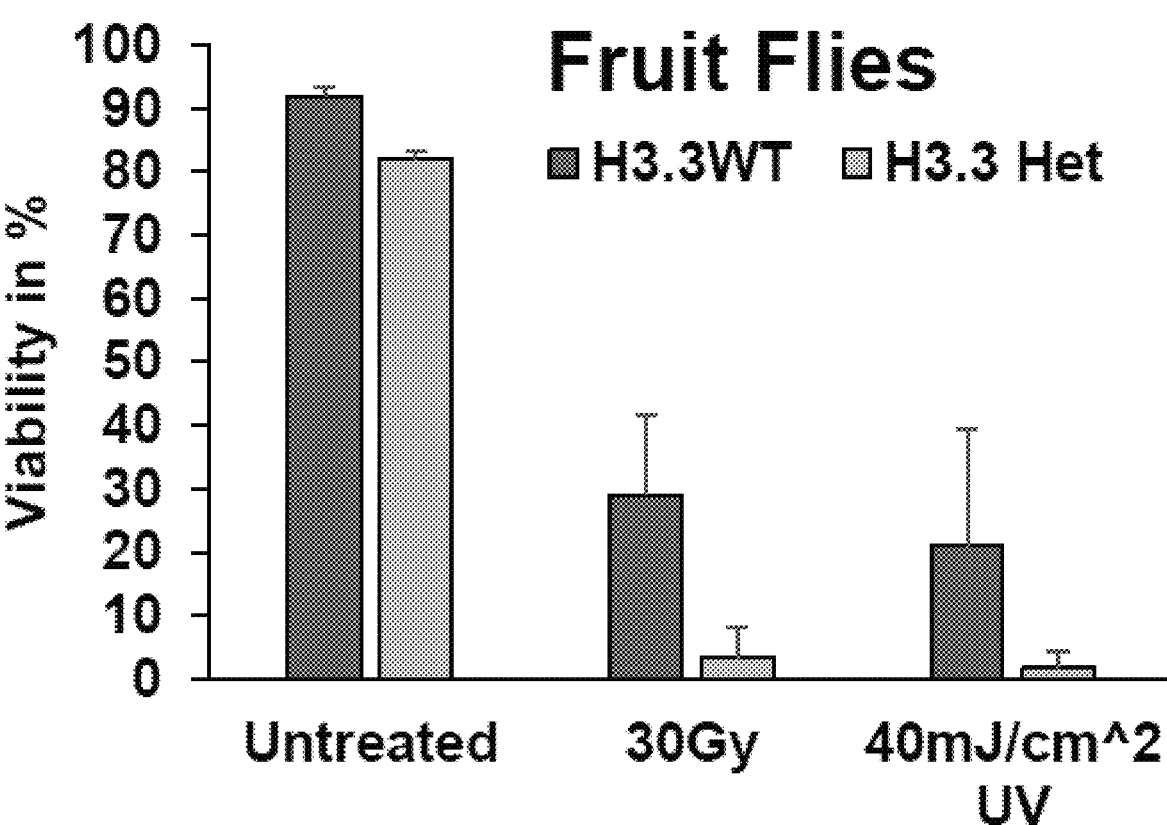
Figure 8E:
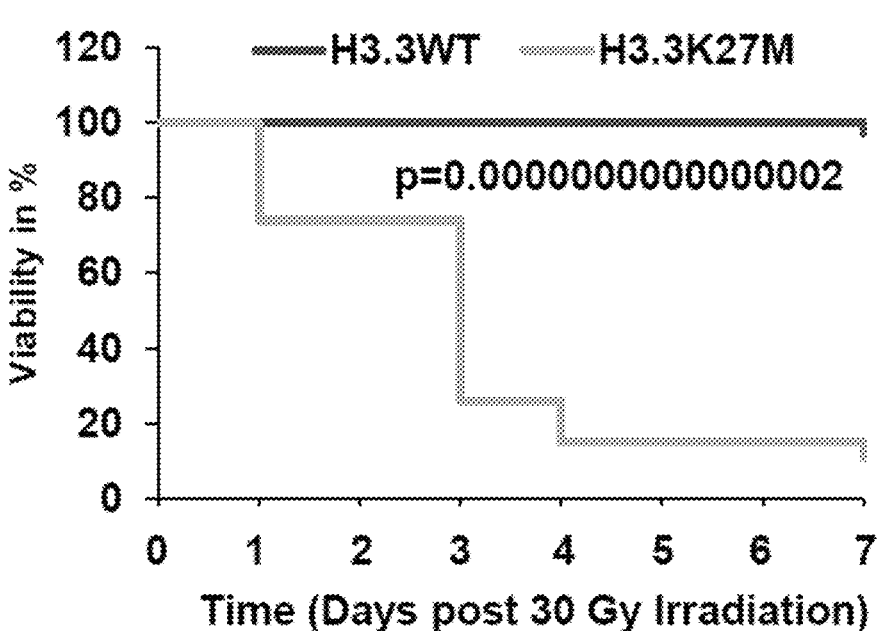

Although it has been demonstrated (FIGS. 1E-1G) that individual cells require adequate amounts of functional H3.3 to survive DNA damage, it is unclear if this requirement extends to whole multicellular organisms. To investigate this, the fruit fly *Drosophila melanogaster* which carries two H3.3 genes encoding H3.3 proteins identical to human H3.3, but which does not require H3.3 for survival was used. Although flies lacking H3.3 develop normally, they are sterile. As observed for H3.3 knockdown in human HCT116 cells, flies lacking H3.3 or with reduced H3.3 have high levels of phosphorylated H2A.v (γH2A.v, the fly equivalent of γH2A.X), indicating that they accumulate spontaneous DNA damage (FIG. 8C). Next, the DNA damage sensitivity of flies was assayed by exposing third instar fly larvae (which have completely exhausted their maternally deposited histone supplies) to different DNA damaging agents and followed their development into adult flies. Compared to wild-type controls, even heterozygous third instar larvae carrying only one of the four wild-type alleles of H3.3 (H3.3 het) were extremely sensitive to DNA damaging agents and very few developed into adult flies (FIG. 8D). No adult flies were recovered from the homozygous larvae completely lacking H3.3 following treatment with any DNA damaging agent in multiple experiments. Interestingly, introduction of an extra copy of histone H3.2 driven by the H3.3B promoter (i.e., a "rescue construct", Res) in flies lacking H3.3 alleviates their sterility, but not their DNA damage sensitivity as no adult flies with the rescue construct were recovered following DNA damage, suggesting a specific requirement for H3.3 for surviving DNA damage. Finally, flies carrying the normal complement of the H3.3 genes but expressing H3.3K27M mutant under the control of a HS70-GAL4 driver were also very sensitive to IR (FIG. 8E).

Figure 8F:
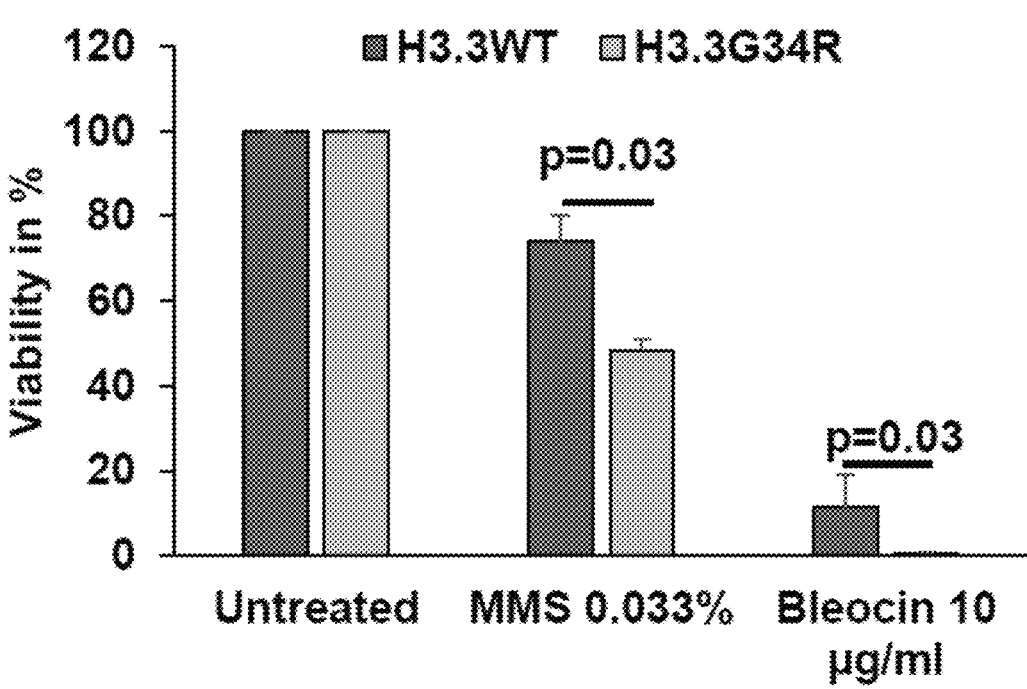
Figure 8G:
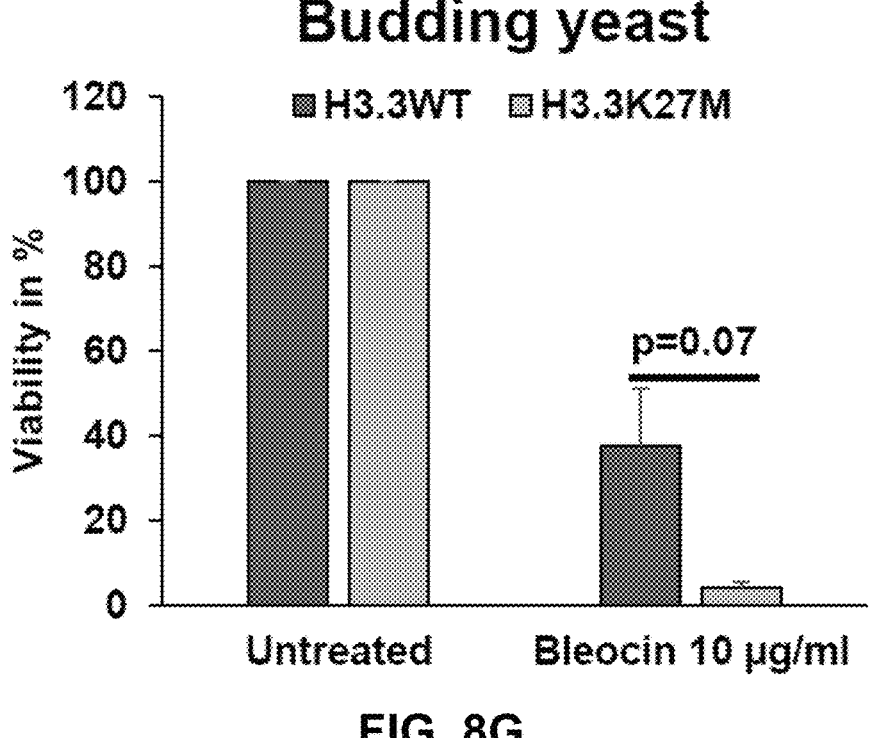

Unlike higher eukaryotes that express multiple non-centromeric H3 variants, the unicellular budding yeast express only one H3 which is very similar to human H3.3. In fact, the first 40 residues between yeast H3 and human H3.3 are identical except for one conservative change (S22 to T22). Hence, yeast was engineered to express the K27M mutation found in glioblastoma as the sole source of H3. Compared to wild-type, strains carrying the H3G34R were hypersensitive to both alkylation damage by MMS and to DNA strand-breakage by bleocin (FIG. 8F), which is consistent with data from fission yeast. Similarly, introduction of the H3K27M mutation in budding yeast also resulted in hypersensitivity to genotoxic agents such as Bleocin (FIG. 8G). Collectively, the data from yeast, flies and human cells point to an evolutionarily conserved requirement for H3.3 in individual eukaryotic cells and multicellular organisms for surviving different types of DNA damage.

Figure 2A:
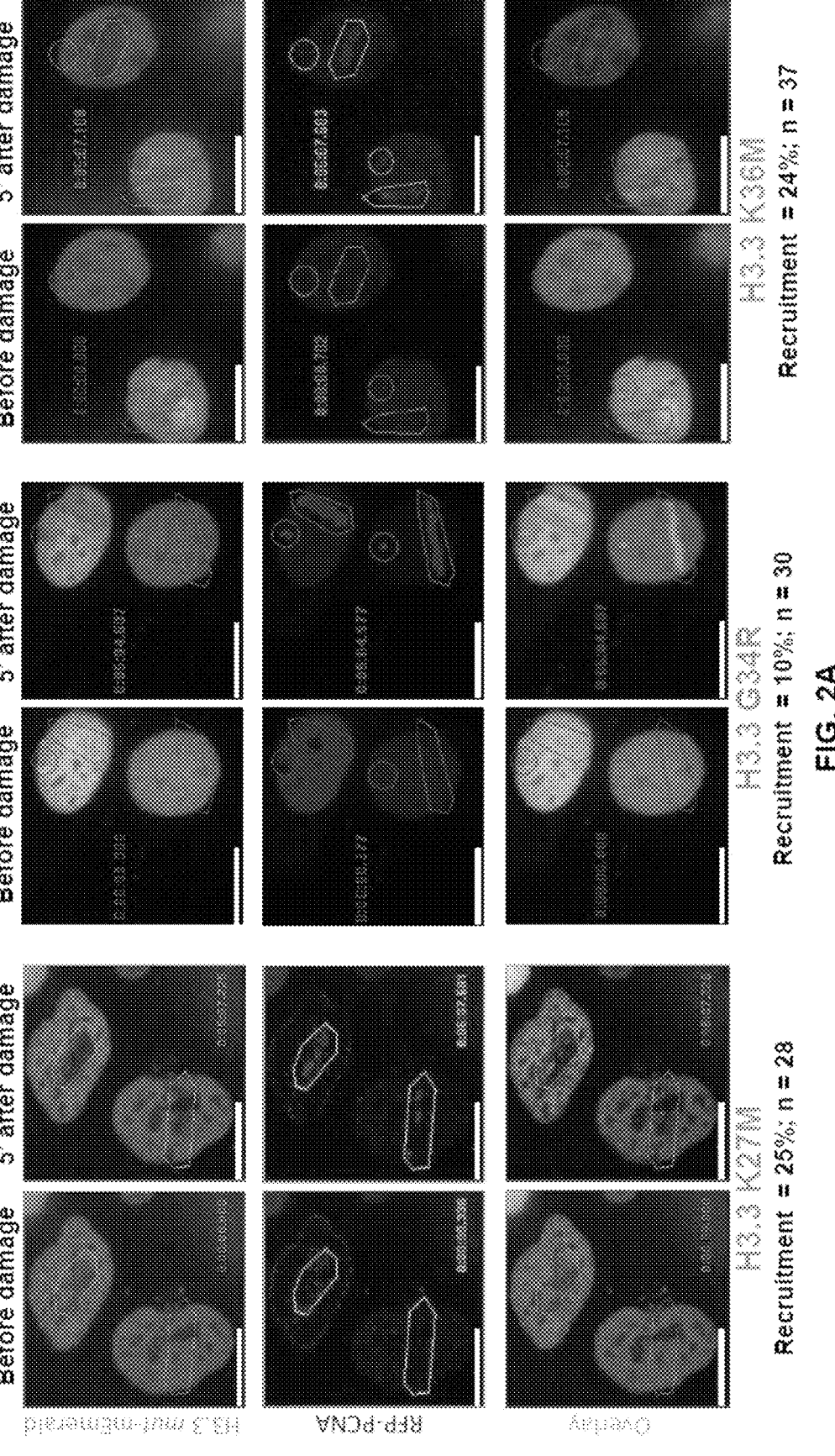
FIGS. 2A-2D show cancer-associated H3.3 mutants are defective in recruitment to DNA damage sites and accumulate spontaneous DNA damage.
Figure 9A:
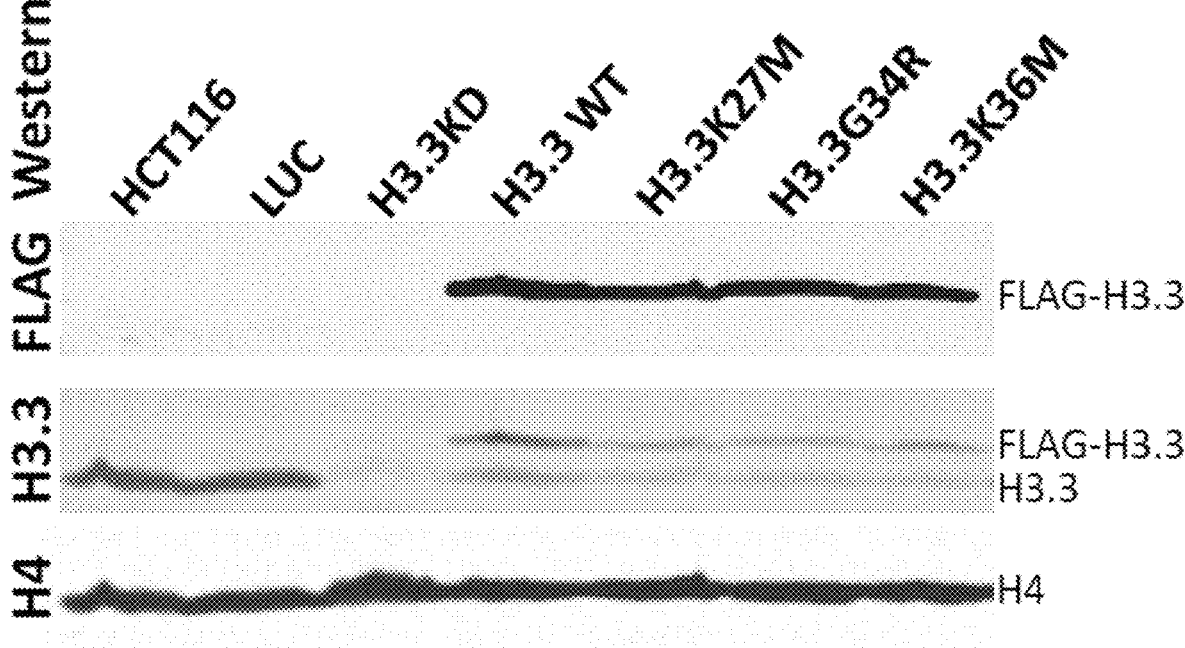
FIGS. 9A-9B show that the stability and expression levels of WT and mutant H3.3 are comparable in human cells.
Figure 9B:
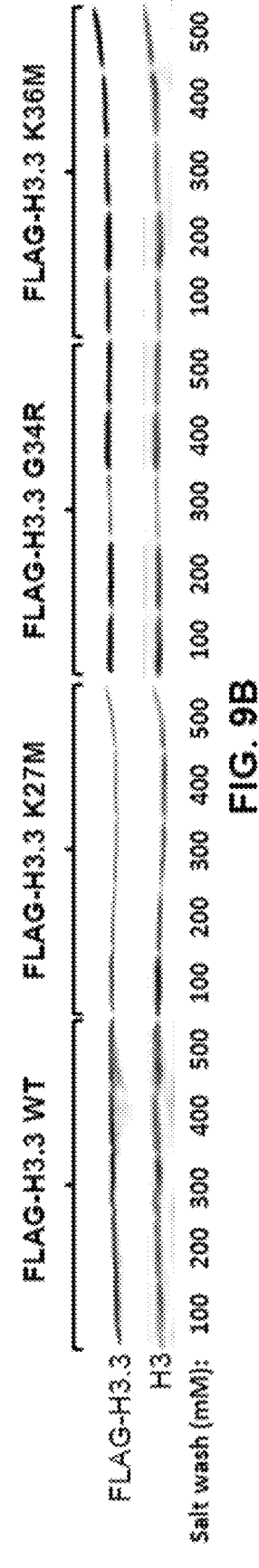

Cancer-Associated H3.3 Mutants are Defective in Recruitment to DNA Damage Sites and Accumulate Endogenous DNA Damage Since H3.3 appears to be playing an important role in the survival of cells following exposure to genotoxic insult, it was decided to investigate the effect of cancer related H3.3 mutations on the DNA damage sensitivity of cells. First, the recruitment of fluorescently tagged H3.3 K27M, G34R and K36M mutants to laser induced DNA damage sites was studied. Compared to the robust recruitment of WT H3.3, all the cancer-associated H3.3 mutants were defective in DNA damage site recruitment (FIG. 2A). The recruitment of wild type H3.3 in a cell line carrying an Enhancer of Zeste homolog 2 (EZH2) methyltransferase knockout (EZH2−/−) that is incapable of trimethylating H3K27 was also assayed and was found to be unaffected, ruling out this methylation mark as the cause of the defect in recruitment of the H3.3K27M mutant. To investigate the effects of these H3.3 mutants further, shRNA resistant FLAG epitope tagged wild type H3.3 or K27M, G34R and K36M mutants were stably reintroduced into the H3.3KD cell line and assayed them by indirect immunofluorescence (IF) for the presence of γH2A.X foci in the absence of exogenous damage. Comparable levels of exogenous WT or mutant H3.3 protein was expressed in the cells (FIG. 9A), with similar affinity for binding to chromatin in up to 0.5M salt (FIG. 9B).

Figure 1D:
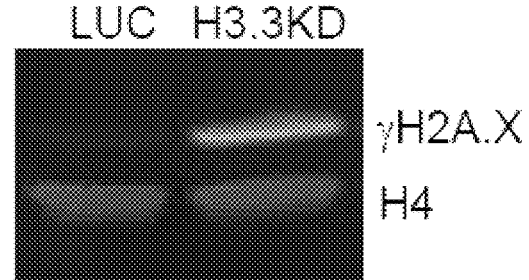
Figure 1E:
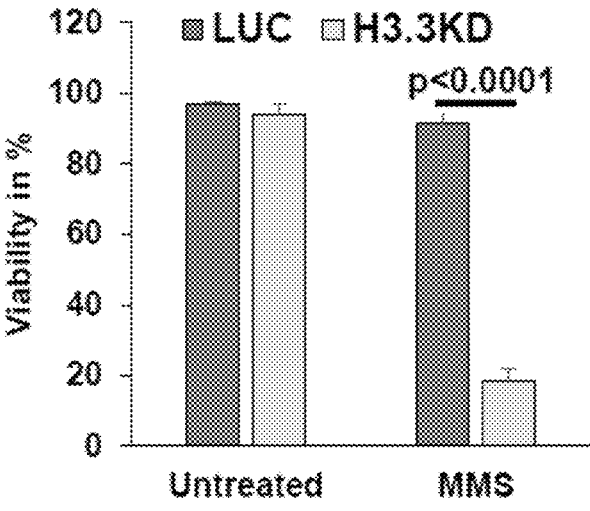
Figure 1F:
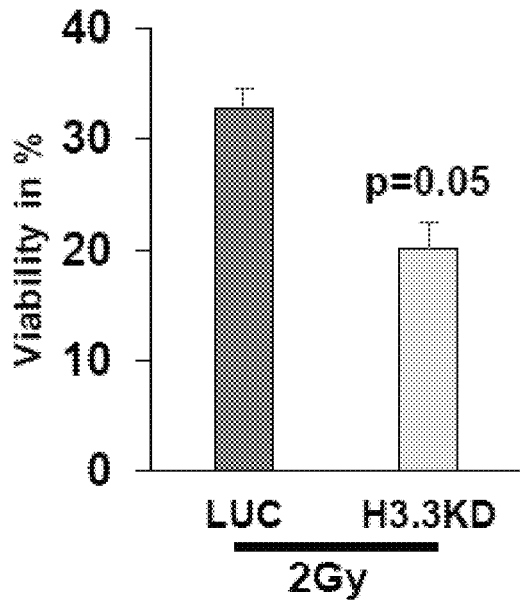
Figure 1G:
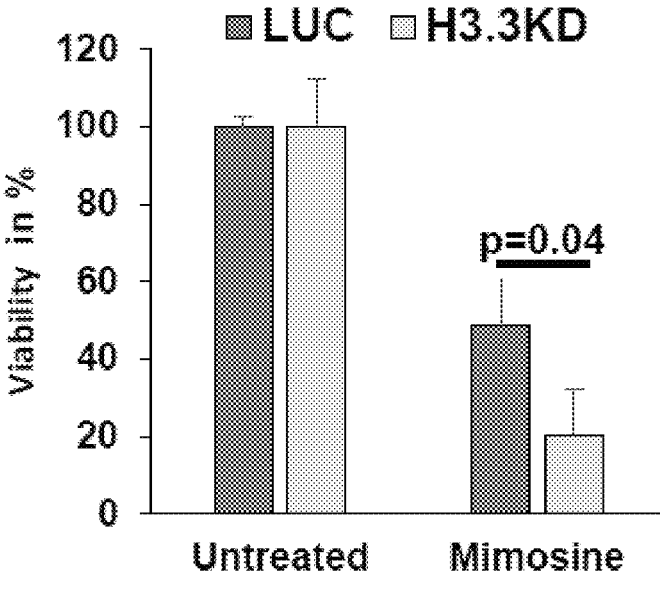
Figure 2B:
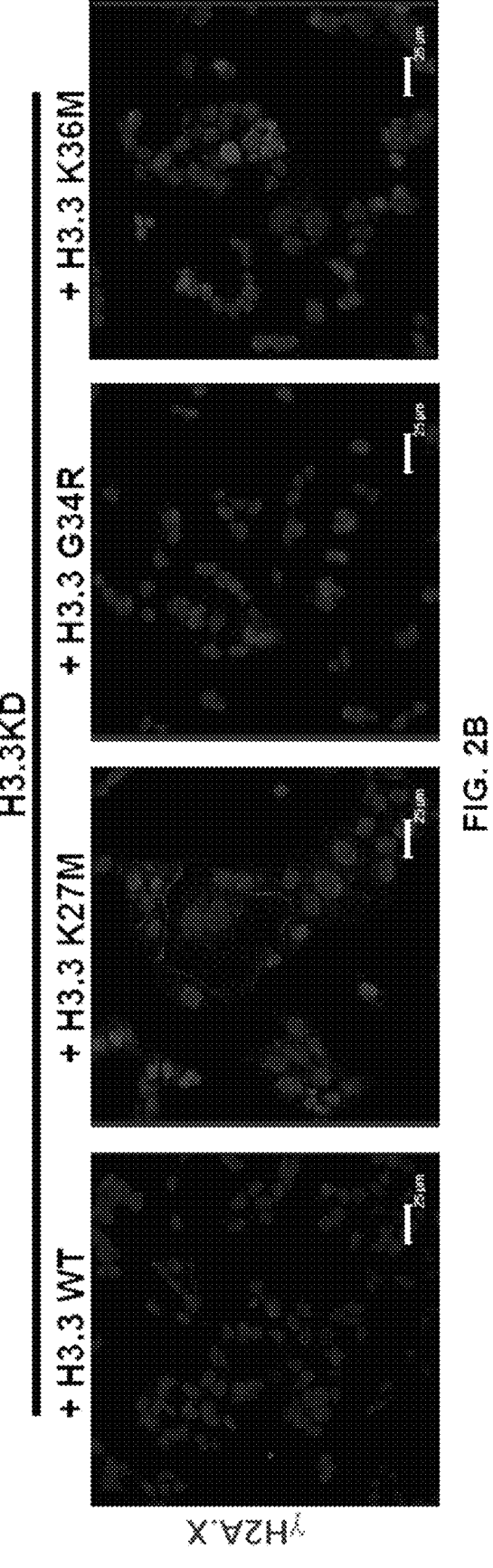
Figure 2C:
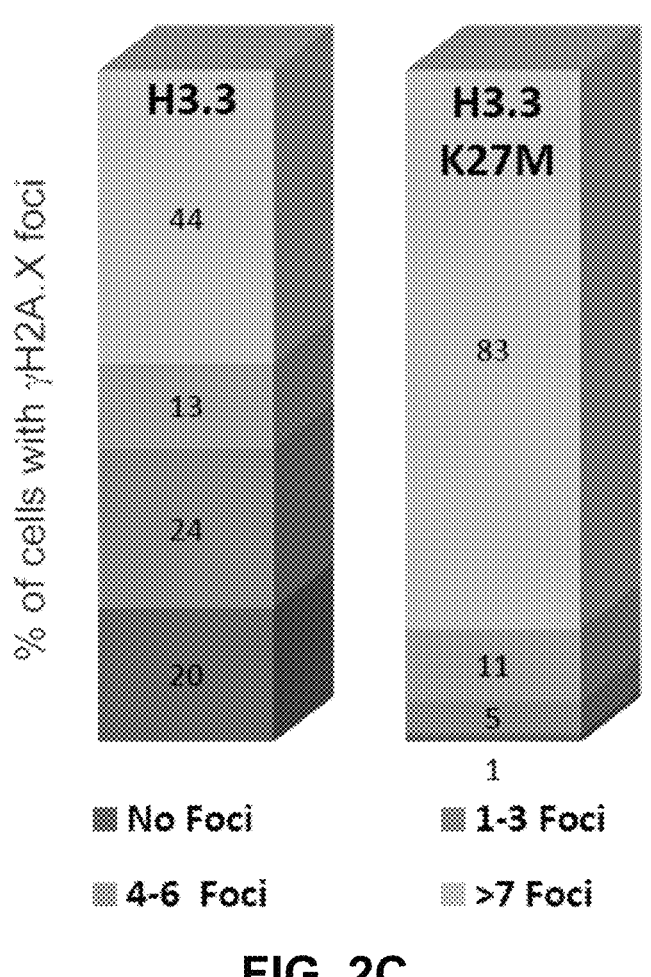
Figure 2D:
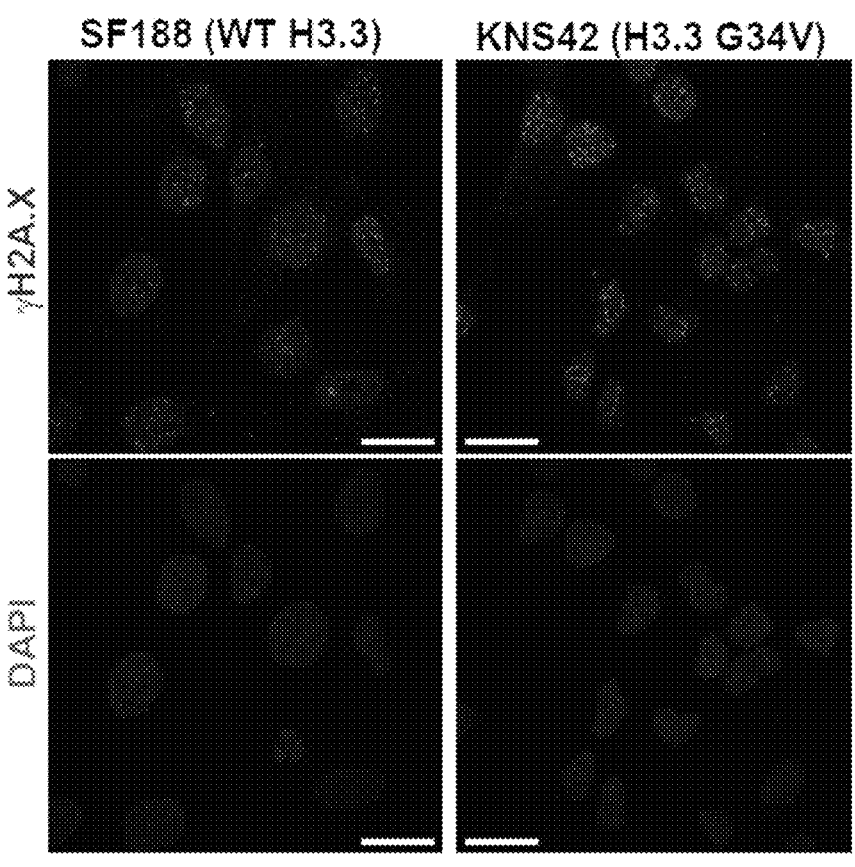

All of the cancer-associated H3.3 mutants exhibited higher spontaneous accumulation of γH2A.X foci relative to wild type H3.3 (FIG. 2B), as seen in the H3.3 KD cells (FIG. 1D). As an example, the number of H3.3K27M mutant cells with greater than seven γH2A.X foci per cell was double that of WT H3.3 cells (FIG. 2C). It was also found that the KNS42 pediatric glioblastoma patient-derived cell line, which has a H3.3G34V mutation, had increased foci of accumulated γH2A.X when compared to SF188 pediatric glioblastoma cells which have wild type H3.3 (FIG. 2C), analogous to H3.3 KD cells expressing mutant H3.3 proteins (FIG. 2B). Taken together, these results strongly suggest that the cancer-associated H3.3 mutants phenocopy H3.3KD cells and are deficient in carrying out DNA repair, which in turn likely contributes to carcinogenesis in addition to the transcriptional and epigenetic defects reported previously.

Histone H3.3 Plays a Crucial Role in HR Mediated DSB Repair

Since H3.3 deficient cells and organisms are sensitive to genotoxic agents which cause very different types of DNA lesions that are repaired by distinct repair pathways, the data suggest that H3.3 is either involved in facilitating repair via more than one pathway, or that it functions at a step that is common to multiple DNA repair pathways. Since multiple types of DNA lesions can be processed during DNA replication or by different repair machineries to ultimately generate DSBs, it is also possible that these secondary DSBs contribute to the observed sensitivity of H3.3 deficient cells to a variety of DNA damaging agents, rather than to DSB agents alone. These possibilities were explored to determine the precise role of H3.3 in DNA repair.

Figure 10A:
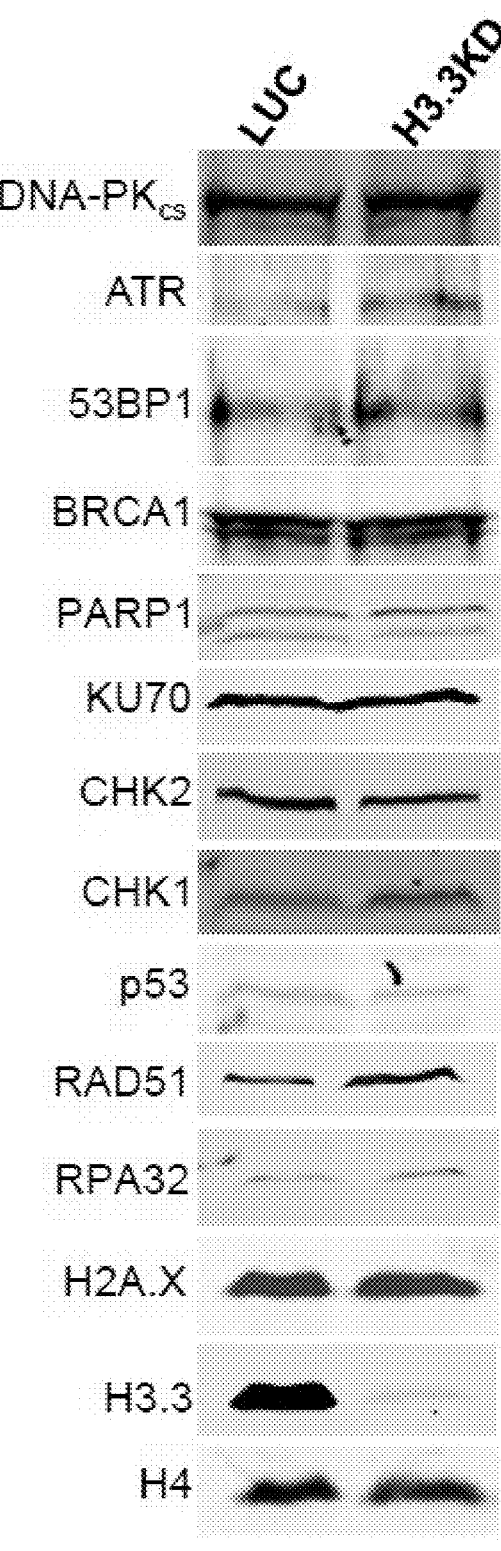
FIGS. 10A-10D show H3.3 deficiency does not affect the protein levels of major DNA repair factors or the DNA damage checkpoint responses to replication arrest and ion-izing radiation, but results in a dramatic elevation of muta-genic-NHEJ levels.

Since much of the available literature on H3.3 suggests that it regulates transcription, a potentially trivial explanation for the DNA repair defects observed in cells deficient in H3.3 is that they are simply due to alterations in the expression of DNA repair genes. However, the effects of H3.3 deficiency on genome wide transcription have been studied in multiple species and loss of H3.3 in mice (and flies) has very minor effects on gene expression, with less than 5% of the genes being affected (and counterintuitively, about two-thirds of the affected genes are upregulated rather than downregulated). Consistent with this, significant alterations were not found in the protein levels corresponding to the major DNA repair genes (FIG. 10A).

Figure 10B:
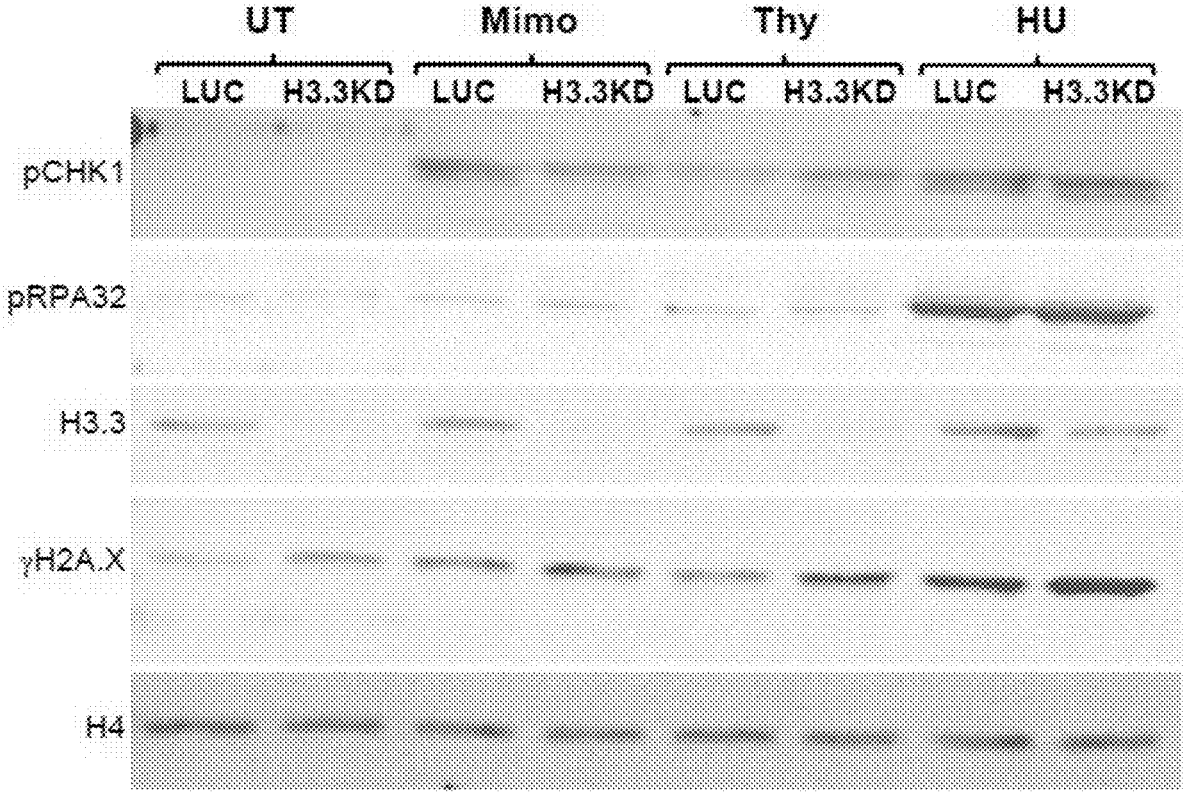
Figure 10C:
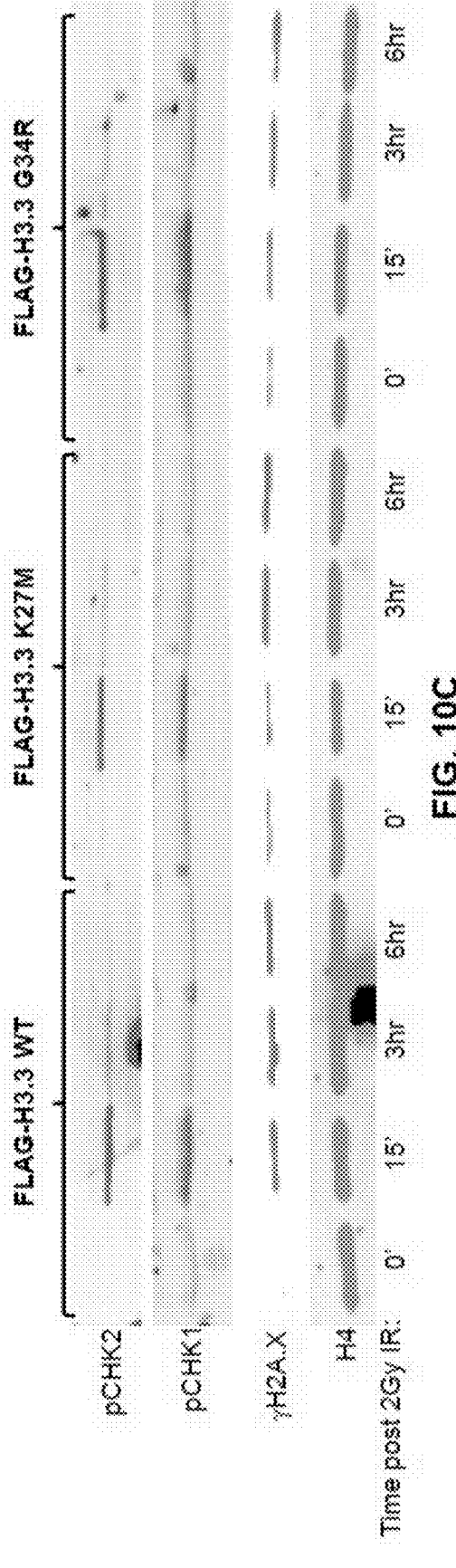

Next, it was tested whether the DNA damage checkpoint responses were altered in H3.3KD cells. For this, the phosphorylation of H2A.X, RPA32 and CHK1 was measured as markers of robust checkpoint response in LUC and H3.3KD cells following treatment with three different replication inhibitors (Mimosine, Thymidine and Hydroxyurea) that result in replicative stress and eventually DSBs (FIG. 10B). However, the phosphorylation of all three proteins was comparable between LUC and H3.3KD cells. A time course of H2A.X, CHK1 and CHK2 phosphorylation was also performed in cells expressing the cancer-associated H3.3 mutants following treatment with 2Gy IR to generate DSBs (FIG. 10C). Once again, robust phosphorylation of these checkpoint proteins was observed in cells expressing WT and cancer-associated H3.3 mutants. From this data, it is concluded that a deficiency of H3.3 does not result in any DNA damage checkpoint defects, suggesting a direct role for H3.3 in one or more DNA repair pathways.

Figure 3A:
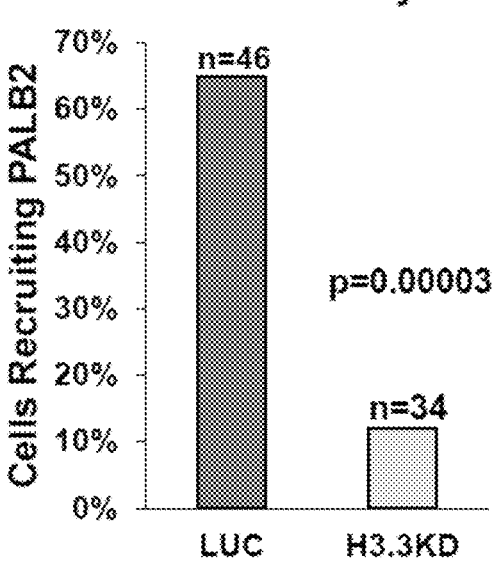
FIGS. 3A-3G show histone H3.3 deficiency results in a severe defect in HR mediated DSB repair and an overreliance on NHEJ pathways for DSB repair.
Figure 3B:
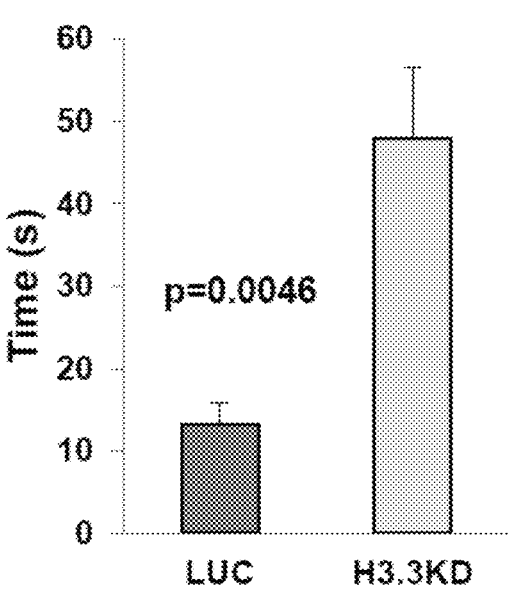
Figure 3C:
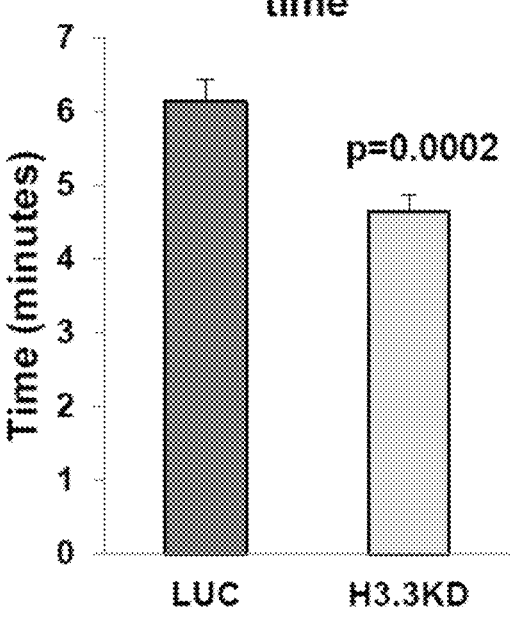

To determine the DNA repair pathway/s affected by H3.3 deficiency, the recruitment of specific repair factors involved in different DNA repair pathways was measured using the live cell imaging-based assay to follow repair at sites of laser microirradiation which generates multiple types of DNA damage. No significant differences were found between control and H3.3 knockdown cells in the recruitment efficiency of multiple repair factors involved in Base Excision Repair (BER, involved in removal of damage such as bases alkylated by MMS), Mismatch Repair (MMR, which removes mismatched base pairs due to replication errors) and NER, although the recruitment of several DSB repair factors was altered in H3.3KD cells (Table 1). In general, HR factors such as RPA70 (large subunit of the single strand DNA binding protein Replication Protein A; FIG. 3A) and PALB2 (Partner and Localizer of BRCA2; FIG. 3B) were recruited slowly or poorly in H3.3KD cells, while the recruitment of NHEJ promoting factors such as 53BP1 (53 binding protein 1; FIG. 3C) was more efficient.

TABLE 1

| Recruitment efficiency of DNA repair factors belonging to different DNA repair pathways to laser induced DNA damage sites in euchromatin in LUC versus H3.3KD cells | | | | | | |
|---|---|---|---|---|---|---|
| REPAIR PATHWAY | REPAIR FACTOR | LUC | | H3.3KD | | |
| | | % recruitment | n | % recruitment | n | p-value |
| DSB recognition | MRE11 | 96% | 26 | 95% | 20 | ns |
| DSB recognition | NBS1 | 100% | 8 | 90% | 9 | ns |

TABLE 1-continued

Recruitment efficiency of DNA repair factors belonging
to different DNA repair pathways to laser induced DNA
damage sites in euchromatin in LUC versus H3.3KD cells

| REPAIR PATHWAY | REPAIR FACTOR | LUC | | H3.3KD | | |
|---|---|---|---|---|---|---|
| | | % recruitment | n | % recruitment | n | p-value |
| SSBR/alt-NHEJ | PARP1 | 61% | 23 | 67% | 12 | ns |
| c-NHEJ | KU80 | 62% | 111 | 57% | 87 | ns |
| NHEJ | 53BP1 | 77% | 109 | 86% | 88 | ns |
| HR (ssDNA binding) | RPA70 | 69% | 36 | 44% | 34 | 0.05 |
| HR | PALB2 | 73% | 63 | 32% | 44 | 0.00003 |
| HR | BRCA1 | 83% | 36 | 58% | 31 | 0.039 |
| BER | POL-β | 100% | 9 | 100% | 9 | ns |
| BER | NTH1 | 100% | 7 | 90% | 6 | ns |
| MMR | PMS2 | 100% | 5 | 100% | 5 | ns |
| NER | DDB1 | 100% | 23 | 100% | 12 | ns |
| NER | DDB2 | 100% | 20 | 100% | 23 | ns |
| NER | XPC | 92% | 25 | 86% | 22 | ns |

LUC and H3.3KD cells were treated as described in FIG. 1A to determine the recruitment efficiency of the fluorescently-tagged DNA repair factors listed above.
p-values were determined using Fisher's Exact test.
n = number of cells analyzed.
ns = not significant.
SSBR = single strand break repair.

Figure 3D:
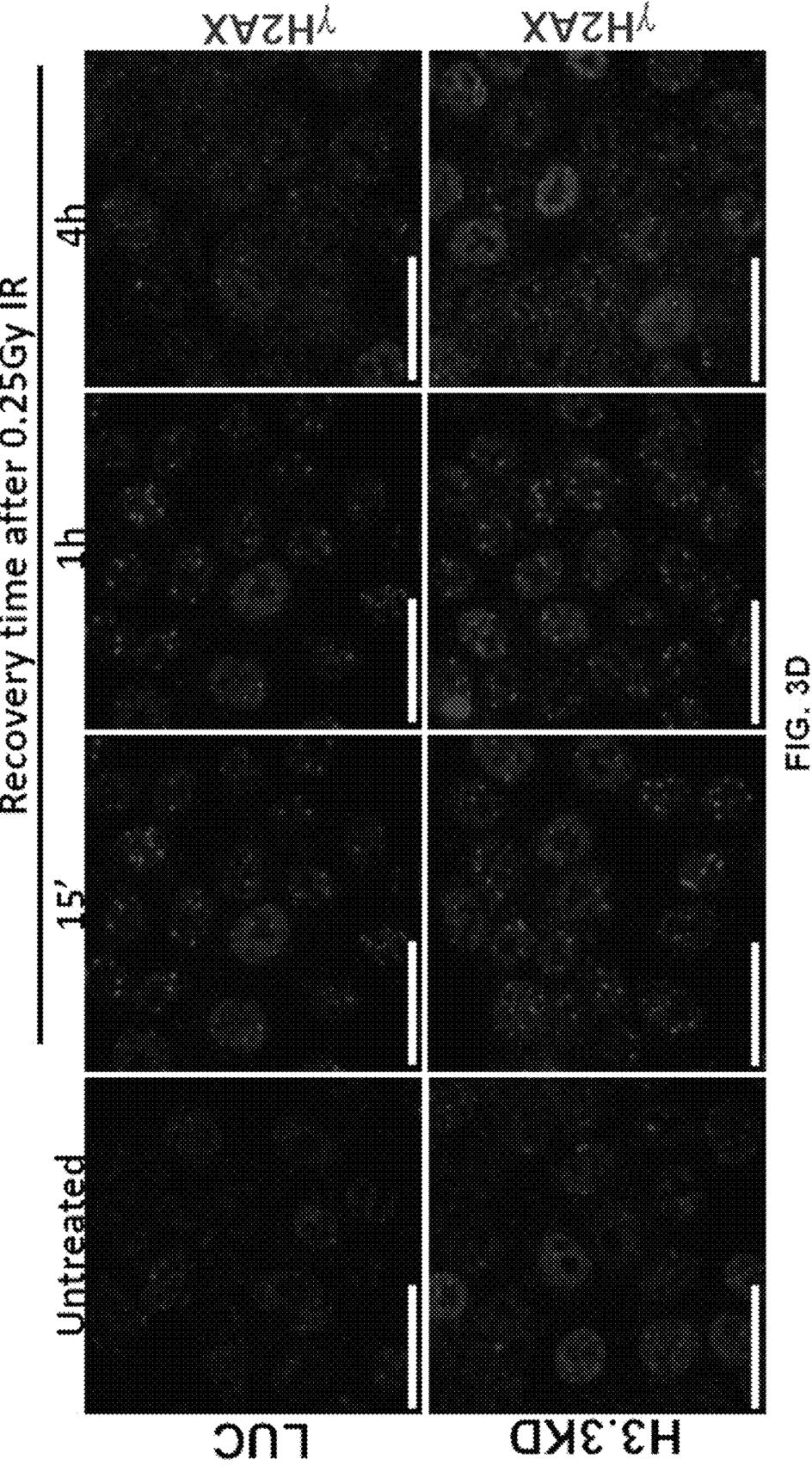
Figure 3E:
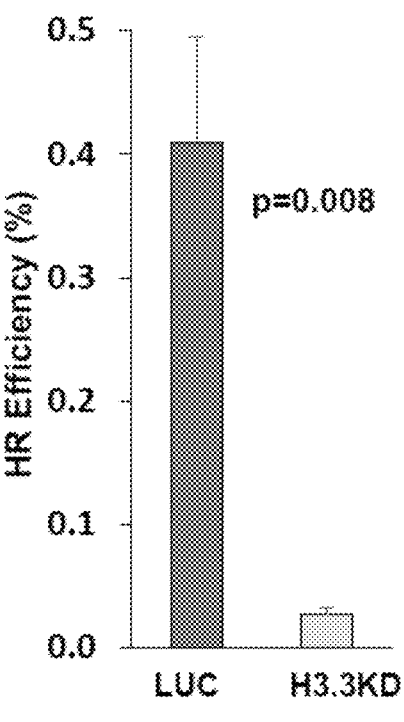

Taken together, this data on the recruitment of DNA repair factors involved in different DNA repair pathways strongly suggested that H3.3 deficient cells are likely to be primarily defective in DSB repair (Table 1). This was further confirmed by using IF to follow intranuclear γH2A.X foci as a marker for the repair of DSBs induced by IR in LUC versus H3.3KD cells (FIG. 3D). H3.3KD cells had higher γH2A.X signal in untreated cells compared to LUC as observed previously (FIG. 1D). Upon a low 0.25 Gy dose of IR, the number of γH2A.X foci increased in both LUC and H3.3 cells as expected, but while the γH2A.X signal was back to basal levels by 4 hours in the control LUC cells indicating completion of DSB repair, it persisted in H3.3KD cells (FIG. 3D), again suggesting a defect in DSB repair.

Figure 3F:
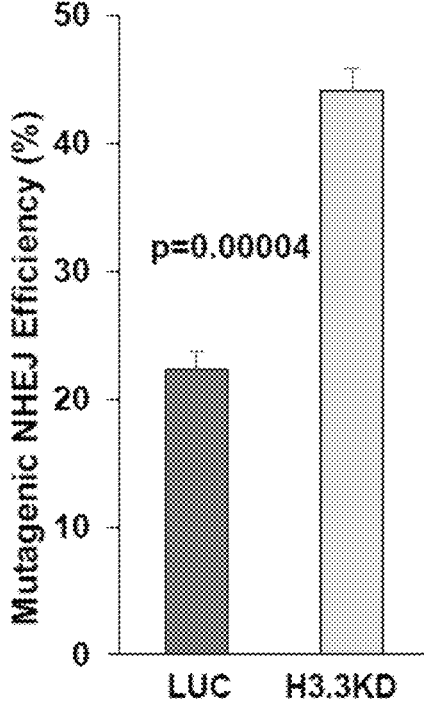
Figure 3G:
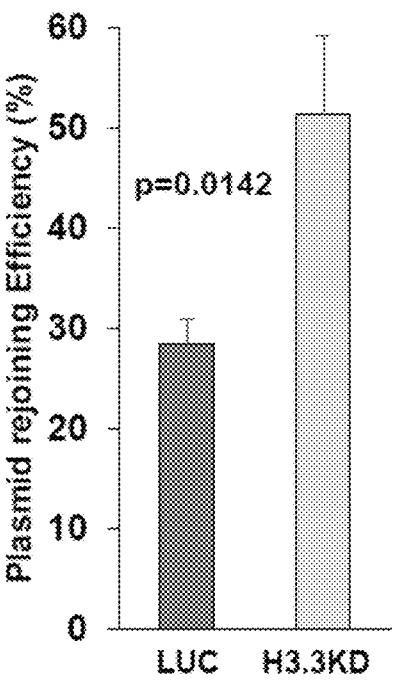
Figure 10D:
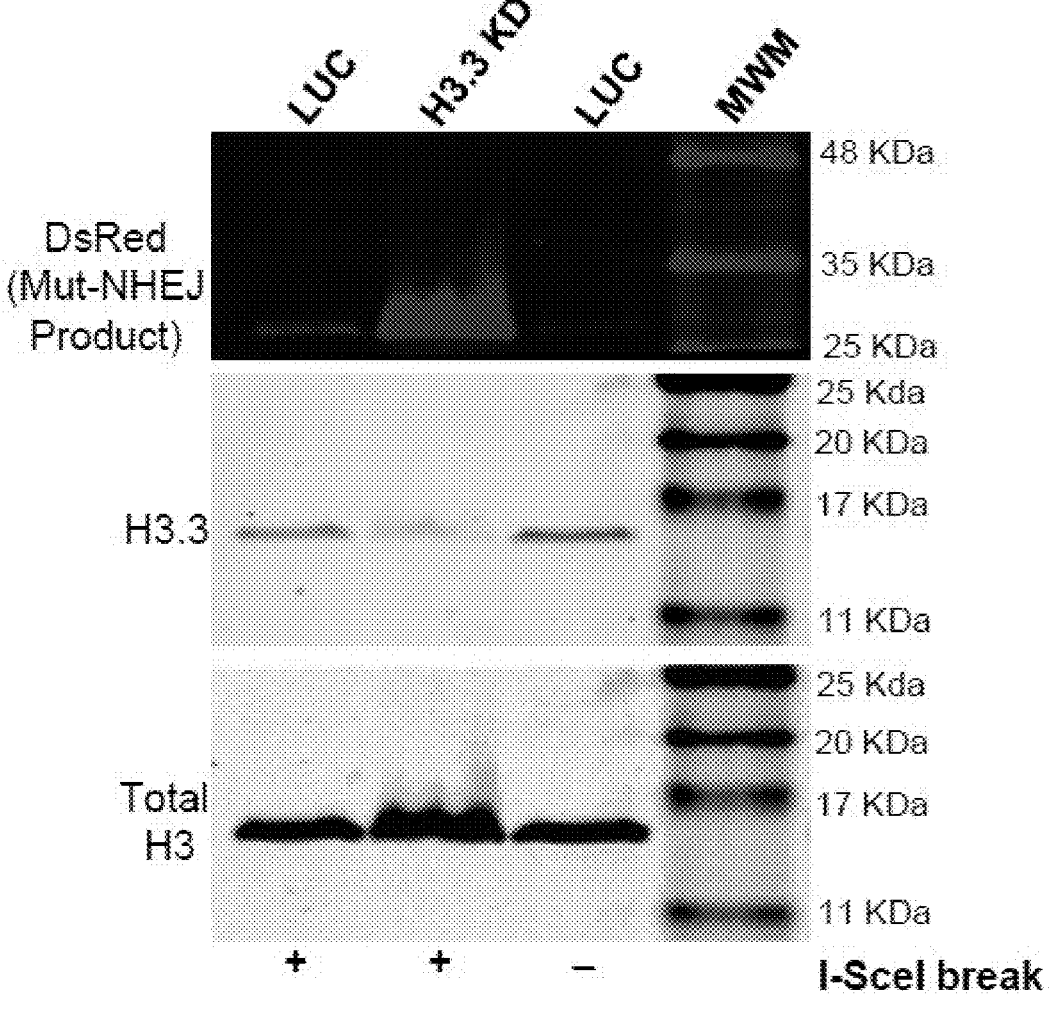

Since DSBs can be repaired by HR and NHEJ pathways and the imaging data suggested possible defects in HR with a possible increase in NHEJ efficiency in H3.3KD cells (Table 1), fluorescence-based reporter systems were used to directly measure DSB repair efficiency by HR and mutagenic NHEJ. Consistent with the imaging data (Table 1), a severe reduction was found in HR mediated repair in H3.3KD cells (FIG. 3D), while there was a compensatory increase in mutagenic-NHEJ which is mostly mediated by the alt-NHEJ pathway (FIGS. 3F, 10D). Additionally, the c-NHEJ mediated re-ligation of a restriction endonuclease cleaved plasmid was also more efficient in H3.3KD cells (FIG. 3G). Together, these data demonstrate that H3.3 plays a critical role in DSB repair by the HR pathway and its deficiency results in an overreliance on NHEJ pathways for DSB repair.

Figure 4A:
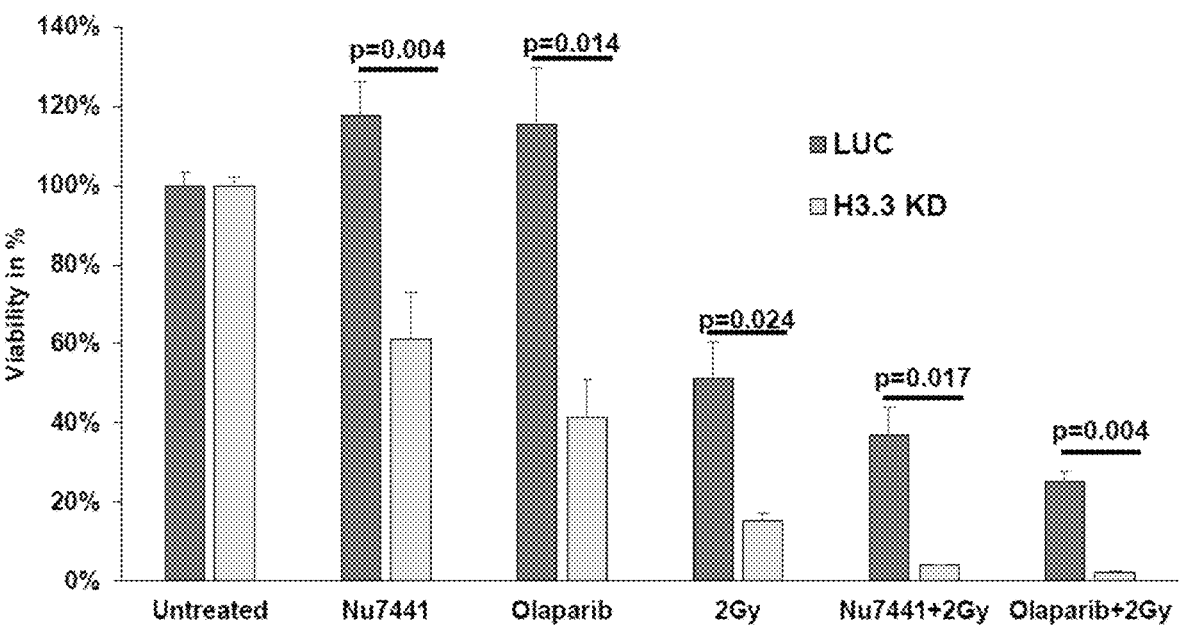
FIGS. 4A-4G show H3.3KD and pediatric patient-derived H3.3 mutant glioblastoma cells can be selectively eliminated by NHEJ inhibition in vitro and in vivo.
Figure 4B:
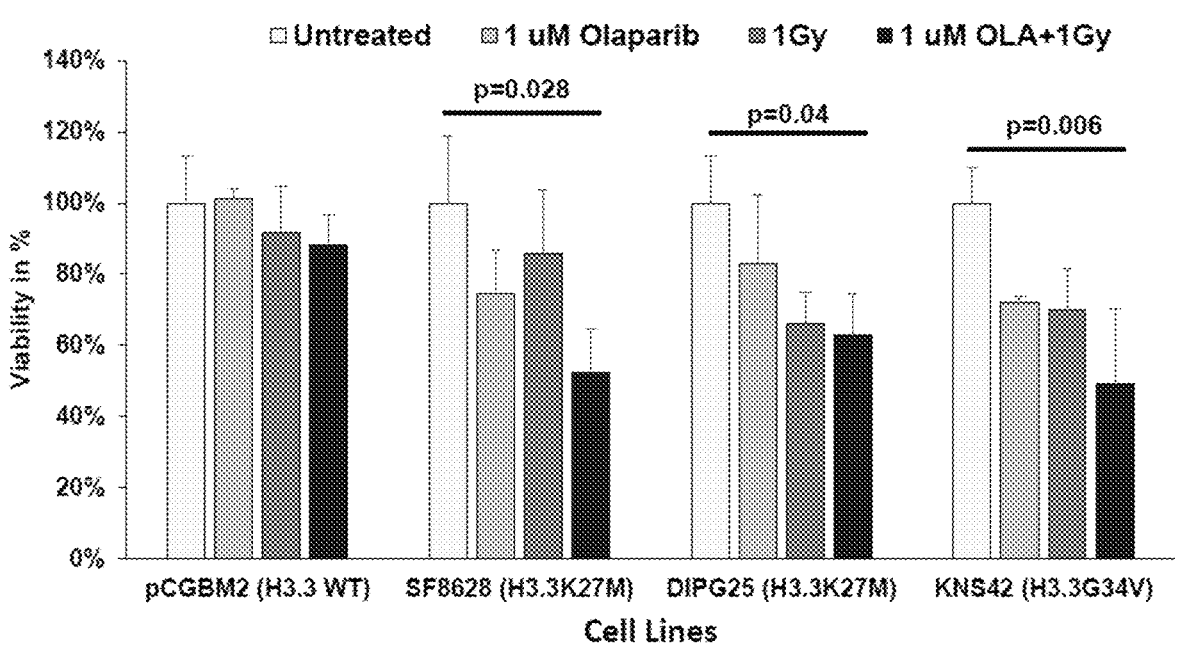
Figure 4C:
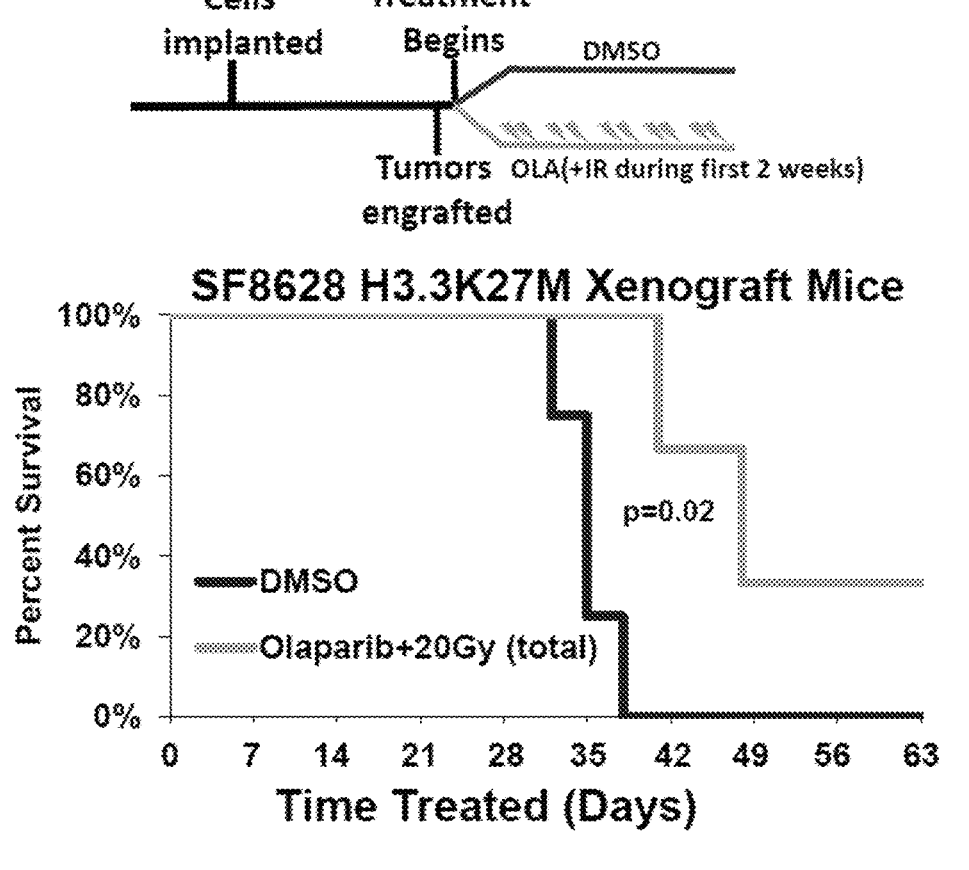
Figure 4D:
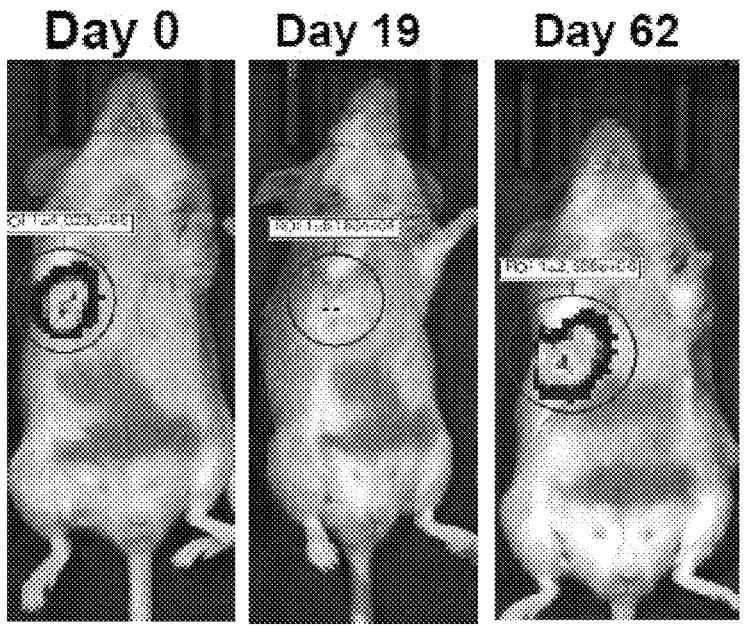
Figure 4E:
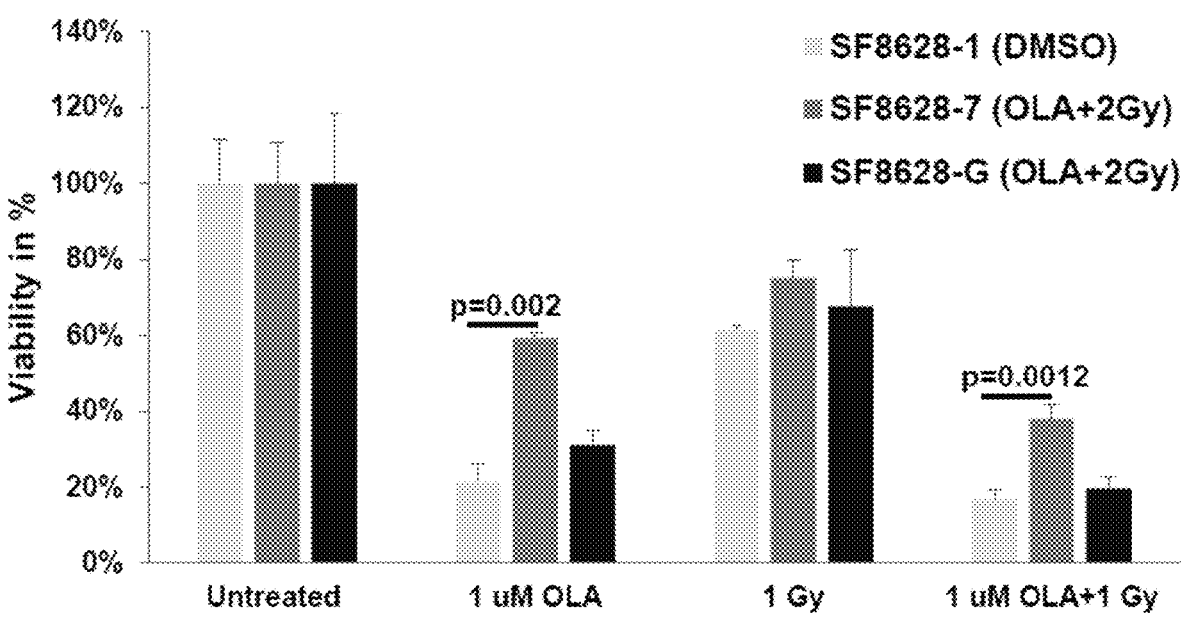
Figure 4F:
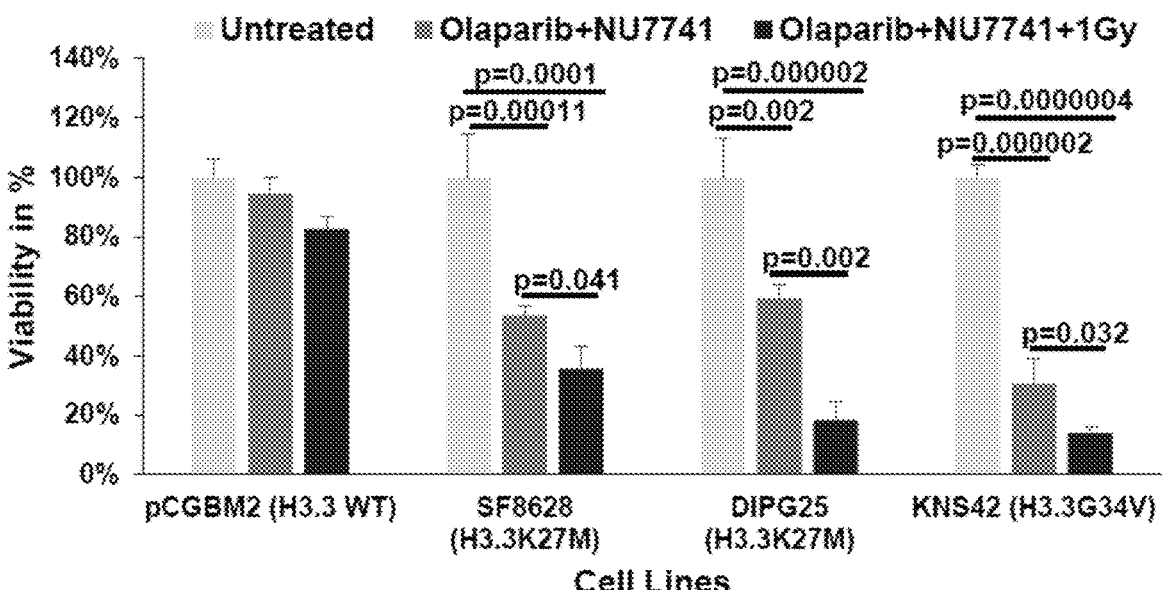
Figure 4G:
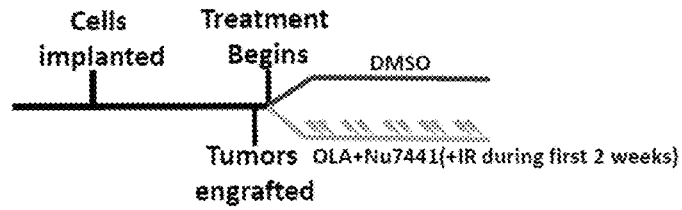
Figure 4G:
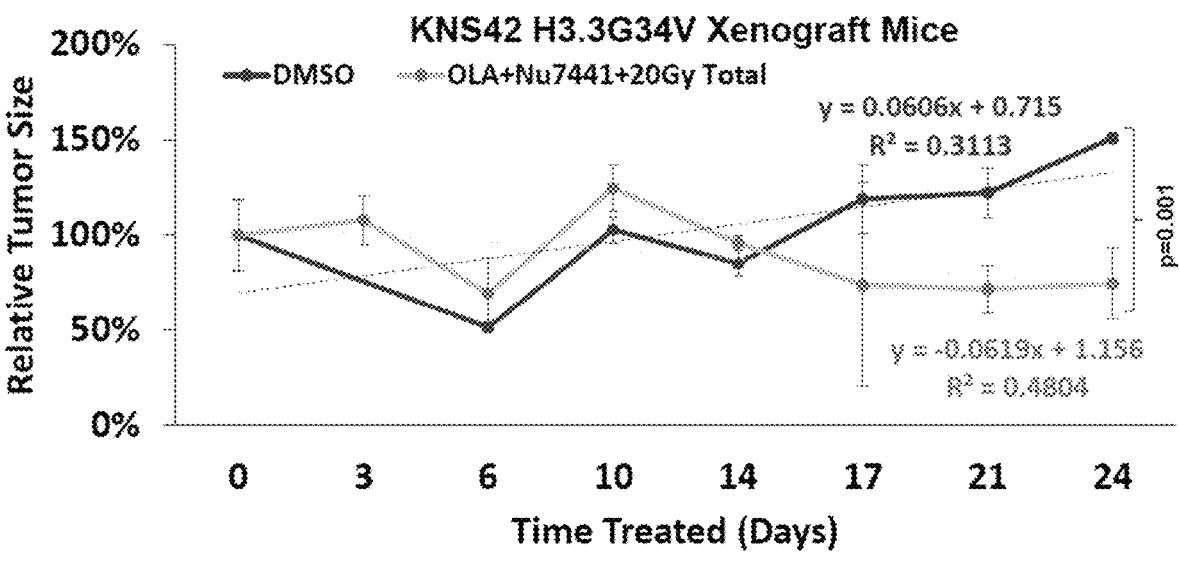

A Synthetic Lethality Based Therapeutic Strategy Involving NHEJ Inhibition and Radiation that Selectively Targets H3.3 Mutant Cancer Cells, Impairs Tumor Growth, and Improves Survival in Mouse Models The two main NHEJ pathways in mammalian cells are the DNA-dependent Protein Kinase, catalytic subunit (DNA-PKcs)-dependent classic NHEJ (c-NHEJ) and the PARP1-dependent alternative NHEJ (alt-NHEJ, also known as microhomology mediated NHEJ or backup NHEJ). More recently, a third DNA polymerase Theta (PolΘ) mediated end joining (TMEJ) pathway has been described. Given the excessive reliance of the severely HR defective H3.3KD cells on NHEJ pathways for DSB repair, it was reasoned that inhibition of these NHEJ pathways in H3.3 deficient cells in the presence of DSBs will result in synthetic lethality. Food and Drug Administration (FDA) approved PARP inhibitors (PARPi) such as Olaparib are already used in the clinic for treating HR deficient breast and ovarian cancers. There are also several pre-clinical DNA-PKcs inhibitors available, some of which are in clinical trials. Despite multiple labs working very hard to develop therapeutics for the fatal H3.3 mutant high-grade gliomas, there are no FDA approved therapies so far. Simultaneous inhibition of all NHEJ pathways has not been tested for therapeutic benefits for this cancer. Hence, it was decided to test the effects of NHEJ inhibition on H3.3 deficient cells either individually or in combination, with or without radiation. Treatment with either Olaparib (OLA) or the DNA-PKcs inhibitor NU7441 in combination with IR resulted in significant cell death of both H3.3KD (FIG. 4A) and patient-derived H3.3 mutant glioblastoma cells (FIG. 4B, FIG. 25), while cells carrying WT H3.3 were largely spared. This in vitro data was recapitulated in vivo in a mouse xenograft model where the survival of OLA plus radiation treated mice exceeded those of vehicle treated controls (FIG. 4C). However, PARPi treatment has been found to result in the development of tumor cells resistant to the PARPi from a variety of mechanisms. Resistance to PARPi was evident in one of the mice where the tumor had initially regressed to become nearly undetectable in less than 3 weeks of treatment, but rebounded by day 62 despite continued OLA administration (FIG. 4D). Evidence was also found of potential resistance to OLA by re-testing the sensitivity of the H3.3 mutant tumor cells that had been passaged through mice treated with OLA. Although the tumor cells were still sensitive to OLA, the magnitude of their sensitivity was variable (FIG. 4E). Hence, the effect of a combination treatment of OLA with NU7441 was tested, to block both c- and alt-NHEJ, concomitant with IR to induce DSBs in pediatric patient-derived WT and mutant H3.3 carrying glioblastoma cells. The combination treatment exhibited a synergistic effect in specifically targeting H3.3 mutant tumor cells for death in vitro, while cells with WT H3.3 were largely unaffected (FIG. 4F). The combination treatment was also effective in vivo in blocking the growth of H3.3 mutant tumors in xenografted mice compared to sham treated mice (FIG. 4G, FIGS. 22A-22B). Together, these data strongly suggest that combined NHEJ inhibition and radiation should be explored further for the treatment of H3.3 mutant tumors in the clinic.

Histone H3.3 Plays a Particularly Crucial Role in DSB Repair in Heterochromatin

Figure 5A:
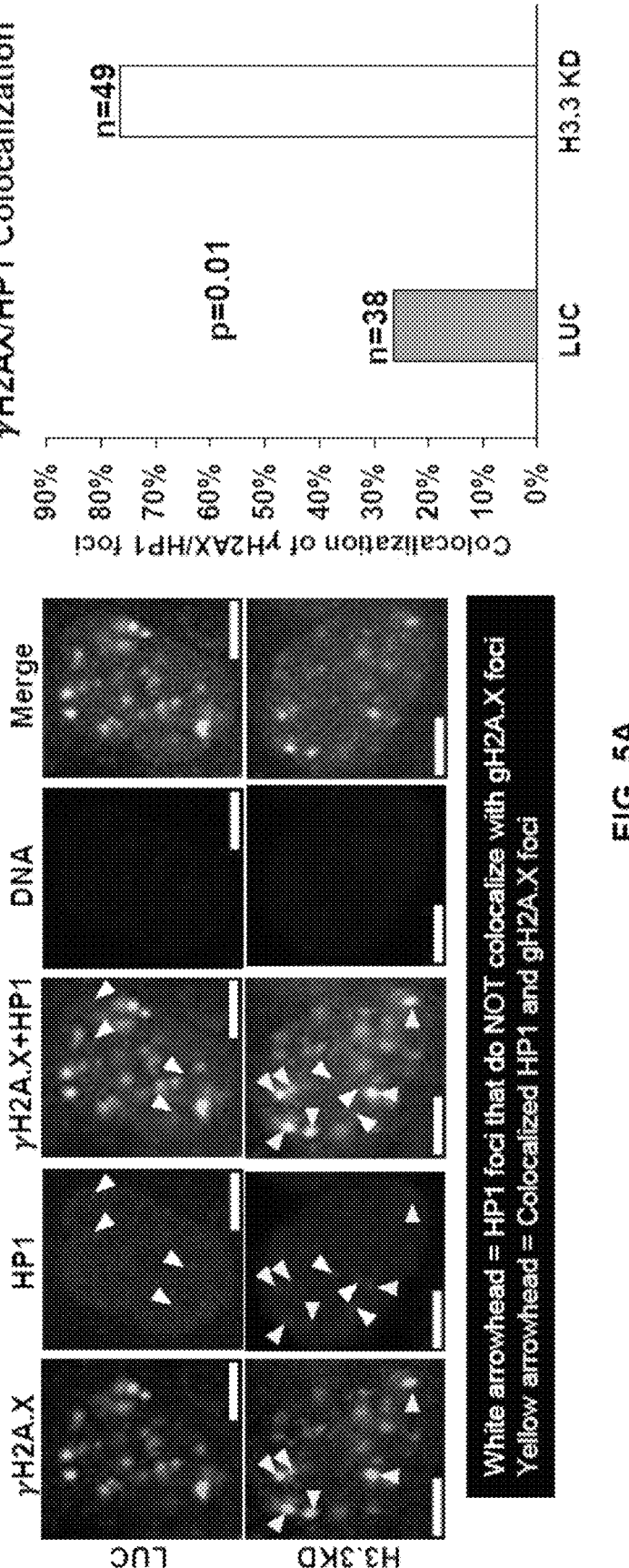
FIGS. 5A-5H show histone H3.3 is especially important for DSB repair in heterochromatin.
Figure 5B:
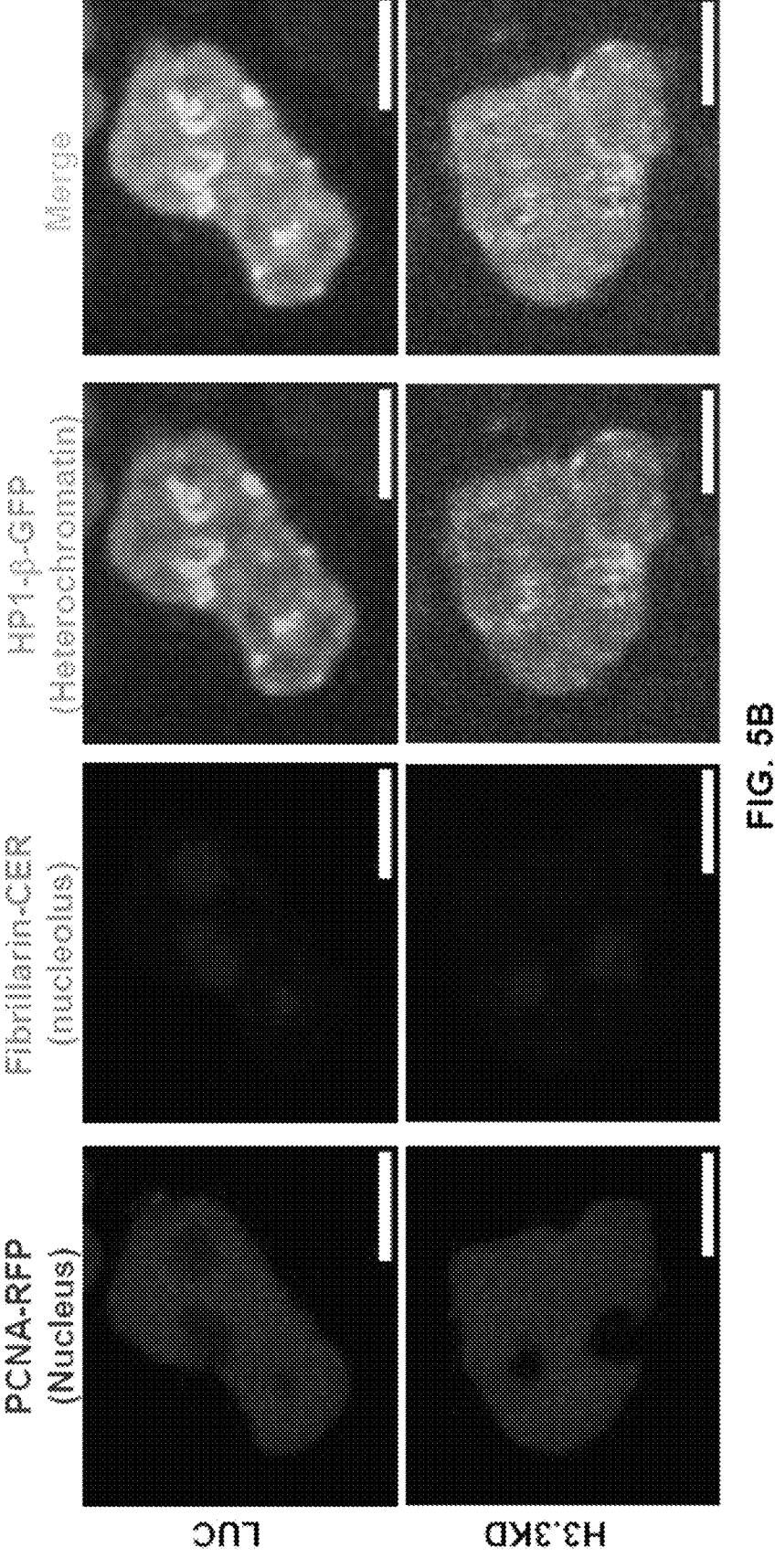
Figure 5C:
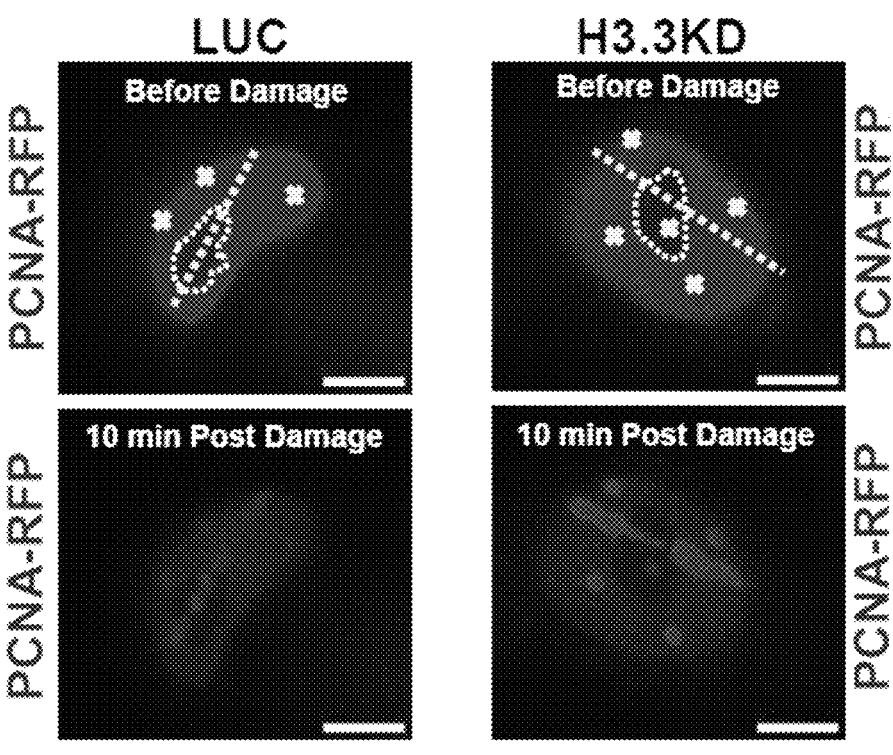
Figure 5D:
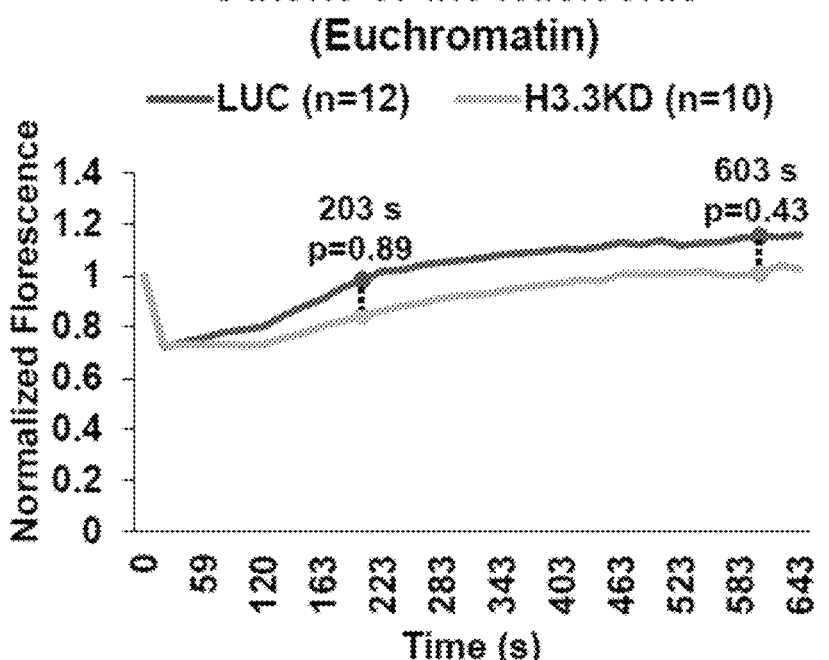
Figure 5E:
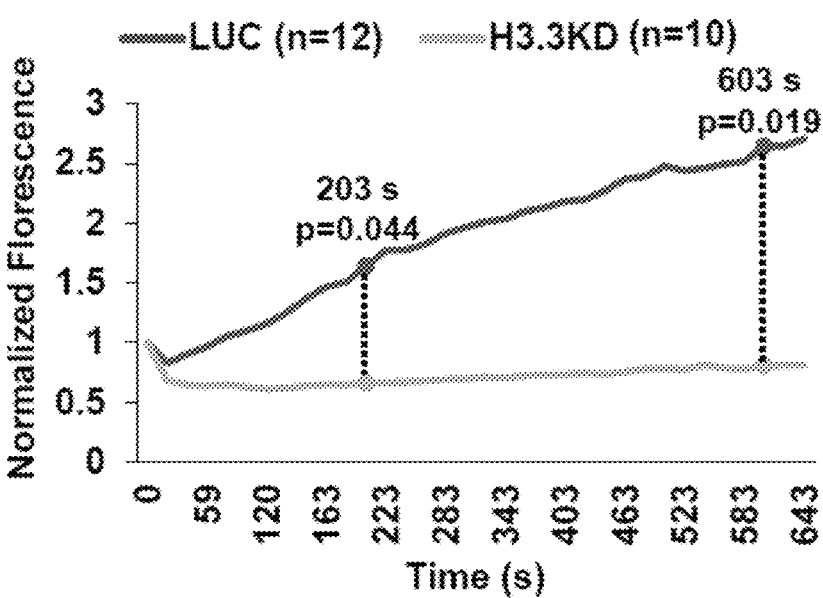

Since H3.3 is enriched both in active euchromatic regions as well as heterochromatic loci, it was decided to explore whether any of these regions were more susceptible to the formation or persistence of endogenous DSBs that accumulate in H3.3KD and H3.3 mutant cells (FIGS. 1D, 2B-2C). Given that large tracts of chromatin are involved in DSB repair via the HR pathway, the hypothesis was that H3.3 can be especially important for DSB repair within compact heterochromatin which would restrict access to repair factors. Using an IF based assay in LUC and H3.3KD cells, the endogenous DSBs using γH2A.X and heterochromatin were localized using a pan-HP1 (Heterochromatin protein 1) antibody. It was found that almost 80% of the spontaneous DSB foci in H3.3KD cells colocalized with HP1, compared to only ~25% in LUC cells (FIG. 5A), indicating that the vast majority of the persistent DSBs in H3.3 deficient cells occur in heterochromatin. To investigate the mechanisms underlying the persistence of DSBs specifically in the heterochromatin of H3.3 deficient cells, a live cell imaging-based assay was developed. It was noticed that in both control and H3.3 KD cells, PCNA was evenly distributed throughout the nucleus in non-S phase cells, but was largely excluded from the nucleolus where the rDNA (ribosomal DNA) heterochromatin resides. The localization of the rDNA heterochromatin and the dramatic reduction of signal from PCNA were further confirmed in the nucleolus using the fluorescently tagged nucleolar marker fibrillarin and the heterochromatin marker HP1β (FIG. 5B). Given the extensive amount of rDNA heterochromatin in the nucleolus, it was reasoned that laser microirradiation induced DNA damage within the nucleolus would cause a substantial amount of damage in rDNA heterochromatin and provide a convenient way to study the dynamics of DNA repair within this compartment relative to DNA repair in the euchromatin (which is loosely being defined herein as much of the nuclear region outside the nucleoli for the purpose of this experiment). The recruitment of the well-known DNA repair marker PCNA to sites of laser induced DNA damage was followed both inside and outside the nucleoli. The recruitment of PCNA to DNA damage sites within the nucleoli in H3.3 KD cells was noticeably weaker (FIG. 5C). In fact, PCNA recruitment to DNA damage within rDNA heterochromatin in nucleoli of LUC cells was also initially slower compared to DNA damage sites outside the nucleoli, however, by about 10 minutes post-damage, there was no longer any significant difference between the recruitment efficiency of PCNA to DNA damage between inside the nucleoli versus outside. There was also no significant difference between LUC and H3.3KD cells in the recruitment of PCNA to DNA damage sites in euchromatin outside the nucleoli (FIG. 5D). However, the delay in PCNA recruitment to DNA damage sites within the nucleoli in H3.3KD cells was much more pronounced (FIG. 5E). Additionally, unlike the LUC cells, this pronounced delay of PCNA recruitment to DNA damage sites persisted for all subsequent time points tested in H3.3KD cells (FIG. 11), suggesting a substantial delay in DNA repair kinetics in rDNA heterochromatin in these cells.

Figure 5F:
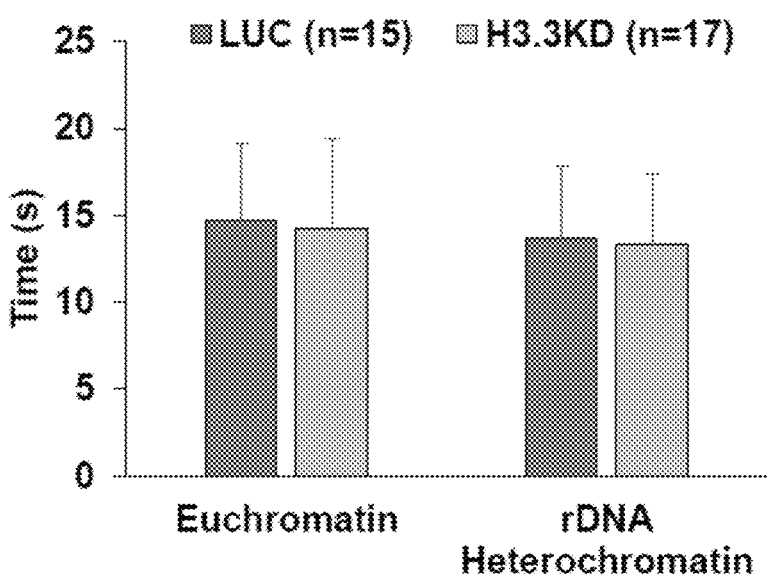

The observed delay in the recruitment of DNA repair factors to damage within the rDNA heterochromatin in nucleoli could be due to a delay in either sensing the damage or repairing it. To distinguish between these two possibilities, the recruitment efficiency of the early DSB sensor/responder MRE11 was first measured and found to be recruited in euchromatin and rDNA heterochromatin in both LUC and H3.3KD cells with similar efficiency (FIG. 5F). Similar results were obtained with NBS1, suggesting that DSB sensing was unaffected in heterochromatin. Next, the recruitment of downstream DSB repair factors such as the HR factor PALB2 and the NHEJ promoting factor 53BP1 to DNA damage within rDNA heterochromatin and euchromatin was studied. Recruitment of PALB2 to DSBs was significantly delayed in both euchromatin and rDNA heterochromatin (FIG. 5G), whereas the efficiency of 53BP1 recruitment to DSBs in heterochromatin was dramatically enhanced in the H3.3KD cells (FIG. 5H). These data suggest that cells deficient in H3.3 rely very heavily on NHEJ for DSB repair, especially in heterochromatin.

Figure 5G:
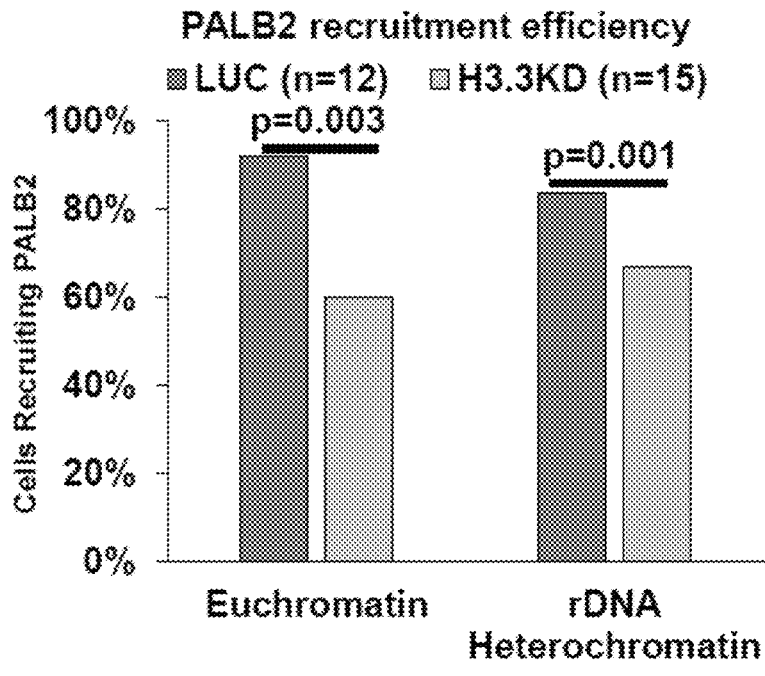
Figure 5H:
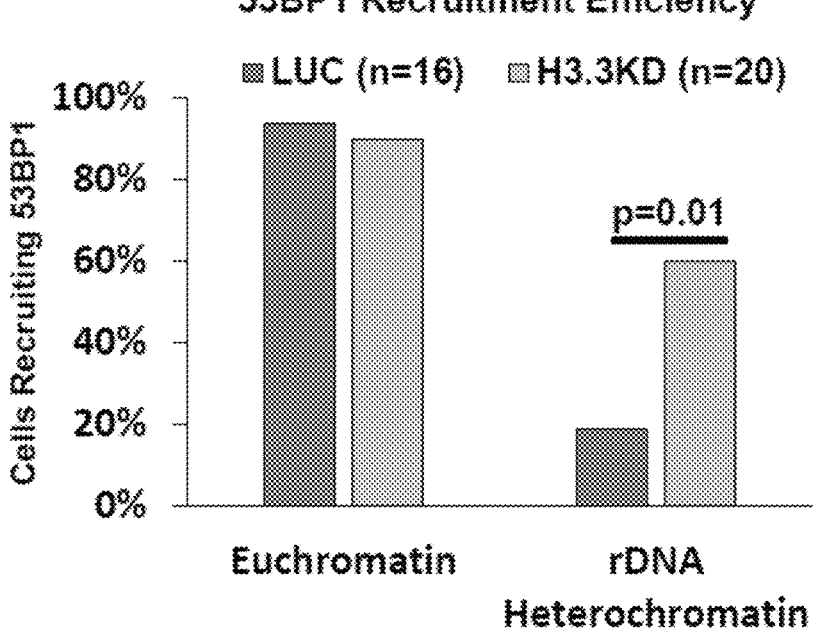
Figure 6A:
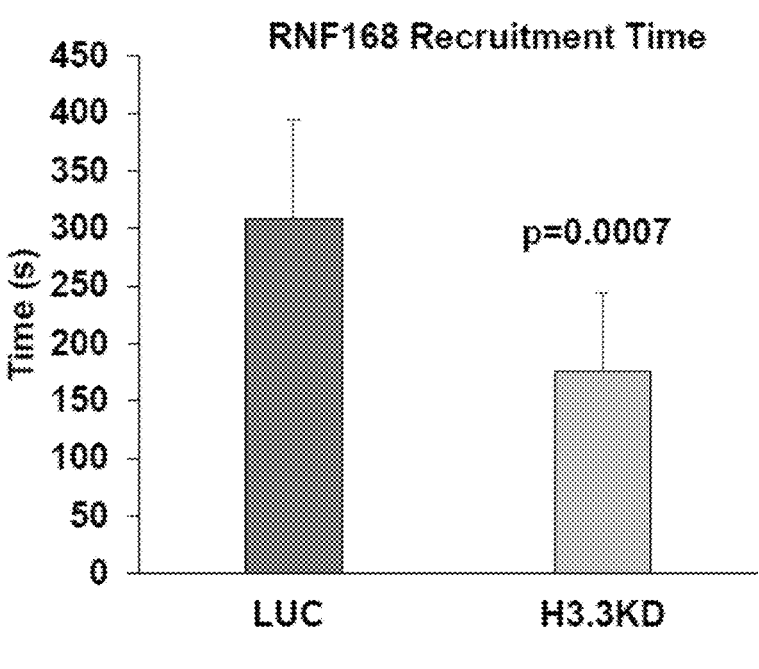
FIGS. 6A-6D show histone H3.3 promotes HR mediated DSB repair by inhibiting the binding of histone H1 in the vicinity of the DSBs.
Figure 6B:
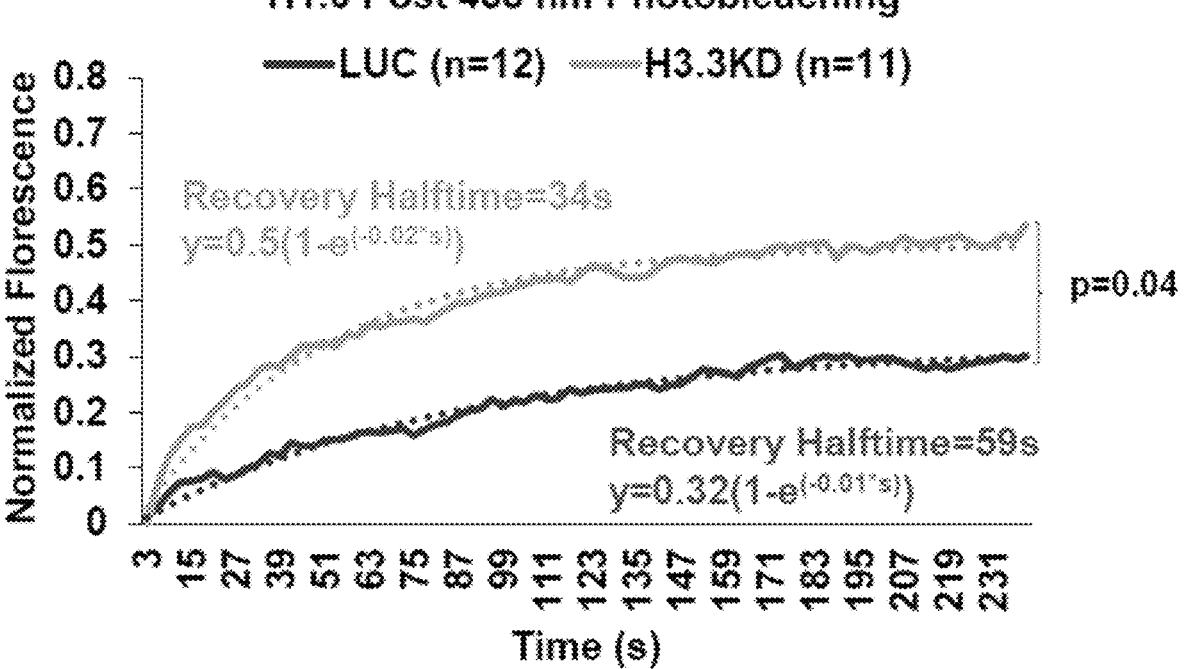
Figure 6C:
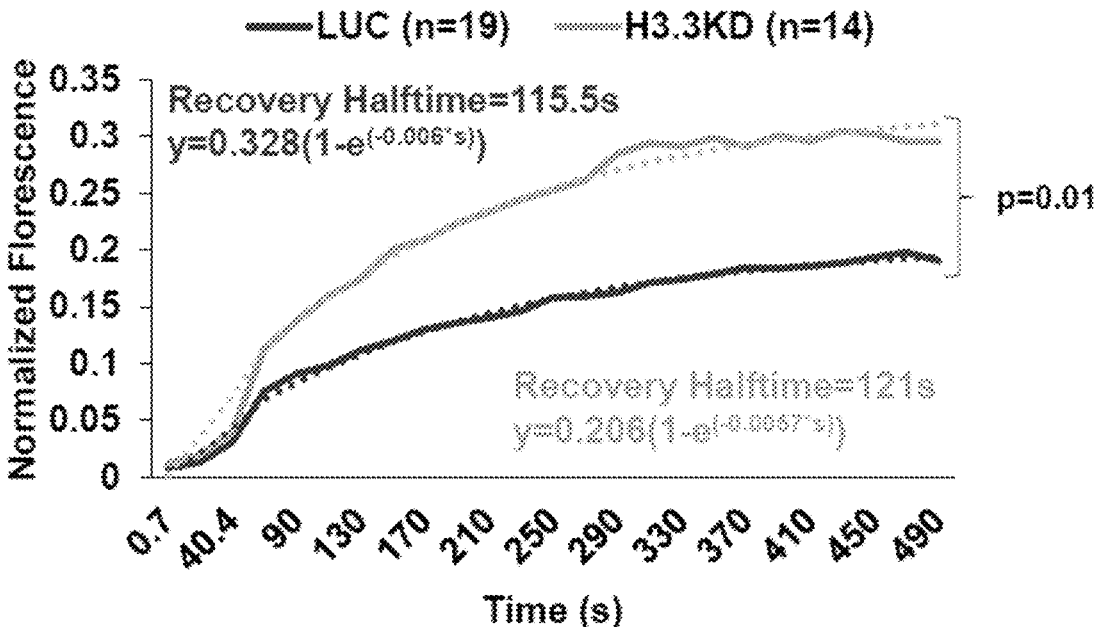
Figure 6D:
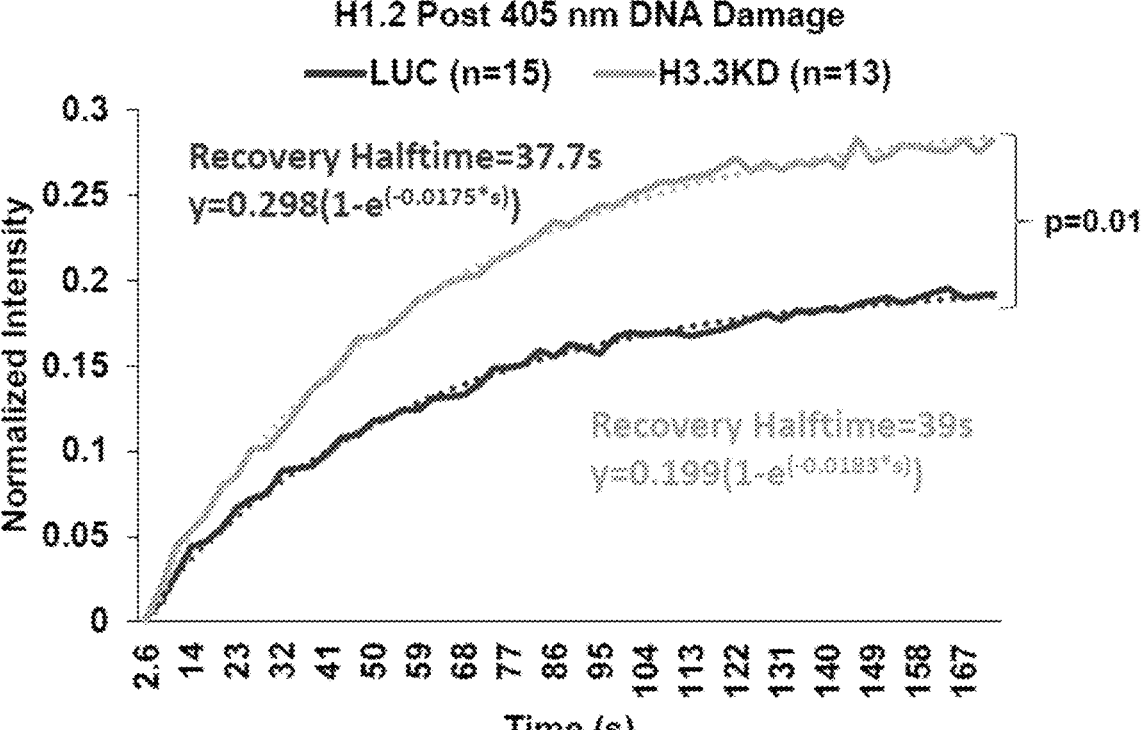

Histone H3.3 Serves as an Upstream HR Promoting DSB Repair Pathway Choice Factor and Functions by Interfering with Histone H1 Binding in the Vicinity of DSBs The underlying reasons for the dramatic increase in the recruitment of NHEJ promoting 53BP1 to DSBs in rDNA heterochromatin were probed (FIG. 5G). Recruitment of 53BP1 to DSBs requires multiple upstream steps to be completed and is primarily regulated by ubiquitylation-dependent signaling cascades. 53BP1 recruitment to DSBs depends on its ubiquitylation as well as histone H2A ubiquitylation by the ubiquitin E3 ligase RNF168. The recruitment kinetics of RNF168 itself to DSBs were measured in LUC and H3.3KD cells and were found to be significantly faster in H3.3KD cells (FIG. 6A), which is consistent with the faster recruitment of 53BP1 in these cells (FIG. 5G). This data suggests that a step upstream of RNF168 recruitment to DSBs can be enhanced in H3.3KD cells. Recruitment of RNF168 itself depends upon the activity two other E3 ubiquitin ligases, namely HUWE1 and RNF8 that ubiquitylate histone H1 to serve as a landing pad for RNF168. Interestingly, it has also been reported that the binding of histone H3.3 antagonizes the binding of histone H1. Based on these studies, it was hypothesized that in cells deficient in H3.3, histone H1 occupancy near DSBs may be higher and this in turn may increase the efficiency of HUWE1, RNF8 and RNF168 mediated ubiquitylation signaling to allow precocious 53BP1 binding to promote NHEJ. The technique of Fluorescence Recovery After Photobleaching (FRAP) was used to follow the dynamics of histone H1 in LUC and H3.3KD cells. In the absence of DNA damage, following photobleaching using a 488 nm laser, recovery of linker histone H1.0 was twice as fast and 2-fold more abundant (FIG. 6B), suggesting that linker histones are more dynamic and bind better to chromatin in cells deficient in H3.3, consistent with genome wide studies in flies. A very similar trend was observed for H1.0 recovery in the vicinity of 405 nm laser-irradiation induced DNA damage (FIG. 6C), albeit following an initial lag and there was a decrease in total H1.0 recovery compared to undamaged cells. Since human cells express eleven H1 variants, to rule out that this effect was specific to the H1.0 variant, the H1.2 variant (formerly known as H1c variant) was also studied and the same pattern of precocious linker histone recovery in H3.3KD cells at DNA damage sites was found (FIG. 6D). Overall, consistent with the hypothesis, the data show a much better recovery of histone H1 in general and at sites of DNA damage in H3.3KD cells compared to LUC cells (FIG.

6B). Higher H1 occupancy near DSBs in H3.3KD cells would be predicted to promote the H1-dependent ubiquitylation cascade that facilitates 53BP1 recruitment and NHEJ mediated repair.

Discussion

Previously published literature has suggested a role for H3.3 in DNA repair, but its precise role is unclear, with H3.3 being implicated in multiple DNA repair pathways, from the repair of UV damage to DSB repair via both HR and NHEJ. In this study, a strong evolutionarily conserved requirement was found for histone H3.3 for surviving DNA damage caused by multiple genotoxic agents (FIGS. 1A-1G, 8A-8G). In fact, in fruit flies, where H3.3 is not essential for survival or transcription, and the infertility of H3.3 KO flies can be rescued using a H3.2 gene driven by the H3.3B promoter, accumulation of endogenous DNA damage and strong sensitivity to exogenous DNA damaging agents are the most readily observable phenotypes. The fact that viable homozygous H3.3 KO flies could not be recovered following exposure to even low amounts of DNA damaging agents argues that in flies the essential role of H3.3 may be to survive DNA damage. Despite the sensitivity of H3.3 deficient cells to multiple DNA damaging agents (FIGS. 1A-1G), there was no obvious defect in DNA repair pathways such as NER, BER and MMR (Table 1). Hence, it is proposed that the accumulation of excessive amounts of endogenous DSBs in H3.3 deficient cells (FIGS. 1A-3G) is consistent with a critical role for H3.3 primarily in DSB repair since many types of DNA damage can eventually give rise to DSBs. The role of H3.3 in DNA repair has further been clarified by presenting strong evidence that a deficiency of H3.3 or cancer-associated H3.3 mutations primarily result in defective DSB repair via HR, and a compensatory overactivation of NHEJ pathways (FIGS. 3A-3G).

Previous studies have implicated epigenetic and transcriptional defects due to H3.3 mutations as the main drivers of cancer, although these do not explain their occurrence primarily in children. Given that studies in mice strongly suggest that the oncogenic H3.3K27M mutation is likely to occur during embryonic development in utero, these results provide a rationale for the occurrence of H3.3 mutant tumors predominantly in children. Based on the strong links between defective DNA repair and cancer, and the results showing that DSB repair occurs predominantly through mutagenic-NHEJ pathways in H3.3 deficient cells, it is proposed that H3.3 mutations occurring early during development result in the rapid accumulation of mutations and accelerated genomic instability, leading to cancer at a young age.

Combination therapeutics targeting DNA repair defects in H3.3 mutant cancer cells have not been tested previously. Importantly, the defect in HR mediated DSB repair coupled with a concomitant increase in NHEJ-mediated DSB repair in H3.3 mutant cancer cells has been exploited to devise a therapeutic strategy based on synthetic lethality, using a combination of FDA approved and pre-clinical drugs to selectively eliminate these cancer cells in vitro and in vivo, while sparing normal cells (FIGS. 4A-4G). Although multiple groups have been working over the past decade towards developing effective therapies for H3.3K27M mutant pediatric high-grade glioblastomas, these tumors currently lack any approved or efficacious therapies and are 100% fatal. Importantly, these results show that all the three cancer-associated H3.3 mutants are likely to have similar DNA repair defects, and it is demonstrated that pediatric high-grade glioma cells carrying either H3.3K27M and H3.3G34R are susceptible to NHEJ inhibition. Hence, targeting the HR defect in combination with the elevated rates of NHEJ in these tumors can be a promising avenue to pursue to provide therapeutic benefits in patients with a variety of H3.3 mutant cancers, rather than just the high-grade gliomas. Results from a clinical trial employing Olaparib and radiation for treating high-grade gliomas are still awaited, although a different clinical trial involving the use of PARP inhibitor Veliparib with radiation did not improve survival of DIPG patients. Meanwhile, the in vivo mice xenograft experiments that were designed to mimic major aspects of this clinical trial suggest that there are likely to be significant benefits of combining the FDA approved PARP inhibiting drug Olaparib (or the brain penetrant PARP inhibitor Niraparib) with radiation, especially since the majority of pediatric high-grade glioma patients already receive radiation. However, development of resistance to PARP inhibitors such as Olaparib can be a potential problem (FIGS. 4A-4G). Although the DNA-PKcs inhibitor used in these proof-of-principle studies is still a preclinical drug and resistance to DNA-PKcs inhibitors has not been reported, at least two other DNA-PKcs inhibitors are undergoing phase I/II trials for different cancers and could be exploited for therapeutic purposes. More importantly, the synthetic lethality-based strategy designed to inhibit both c-NHEJ with a DNA-PKcs inhibitor and alt-NHEJ with Olaparib in combination with radiation to induce DSBs provided very promising results. This combination therapeutic strategy is likely to succeed, as it would be harder for the tumor cells to acquire simultaneous mutations in response to inhibition of two different pathways to develop resistance to both. An additional benefit of this combination therapy is that lower doses of the individual drugs were required to selectively target H3.3 cancer cells, which would reduce the risk of toxicity and adverse effects associated with this therapy in patients. Not surprisingly, no signs of bone marrow suppression, which is commonly observed for the standard doses of PARP inhibitor monotherapy in human patients, was observed for the lower doses of PARP inhibitors used in the disclosed combination therapies in mice. It should also be feasible to combine the NHEJ inhibition therapeutic strategy with additional drugs that target other aberrant pathways in pediatric high-grade gliomas, such as using histone deacetylase or demethylase inhibitors to further minimize the chances of resistance and maximize therapeutic benefits. Finally, since resistance to PARP inhibitors is a problem in the treatment of other HR deficient cancers such as BRCA1/BRCA2 mutant breast cancers, it is possible that this combination treatment can also be applied to other such HR defective cancers, or cancers with upregulated NHEJ.

Evidence is provided herein that H3.3 is particularly important for the repair of DSBs in heterochromatin (FIGS. 5A-5H). DSBs located within heterochromatin are more challenging to repair and require additional mechanisms to alleviate the barrier presented by its compact structure. Consistent with this, DSB repair in heterochromatin generally proceeds slower than in euchromatin and heterochromatic regions are also associated with higher mutation rates in cancer cells. Importantly, the HR pathway is preferentially used to repair DSBs within heterochromatin in flies, rDNA heterochromatin in yeast and human cells, as well as within centromeric heterochromatin in mouse cells throughout the cell cycle. HR mediated DSB repair in heterochromatin typically involves the relocalization of the DSBs outside heterochromatin in mammalian cells and flies, while DSBs accumulate in heterochromatin upon depletion of HR components. Consistent with a role for H3.3 in HR mediated DSB repair especially in heterochromatin, it is found that cells deficient in histone H3.3 accumulate endogenous DSBs that colocalize predominantly with HP1 containing heterochromatic foci (FIGS. 5A-5H). Further, it is shown that H3.3 deficient cells are slow to recruit HR factors to DSBs, but precociously recruit the NHEJ promoting DSB repair pathway choice factor 53BP1 to rDNA heterochromatin. Since the core HR factors such as Rad51 are not loaded onto DSBs in heterochromatin until after resection and relocation of the DSBs outside the heterochromatin, the recruitment of H3.3 to DSBs is likely playing an upstream role in promoting DSB repair by HR, possibly by facilitating chromatin access to the resection machinery, due in part to the unstable nature of H3.3 containing nucleosomes. Indeed, histone loss following DSB formation in the budding yeast has been shown to promote HR by facilitating homology search through increased chromatin mobility.

Figure 7:
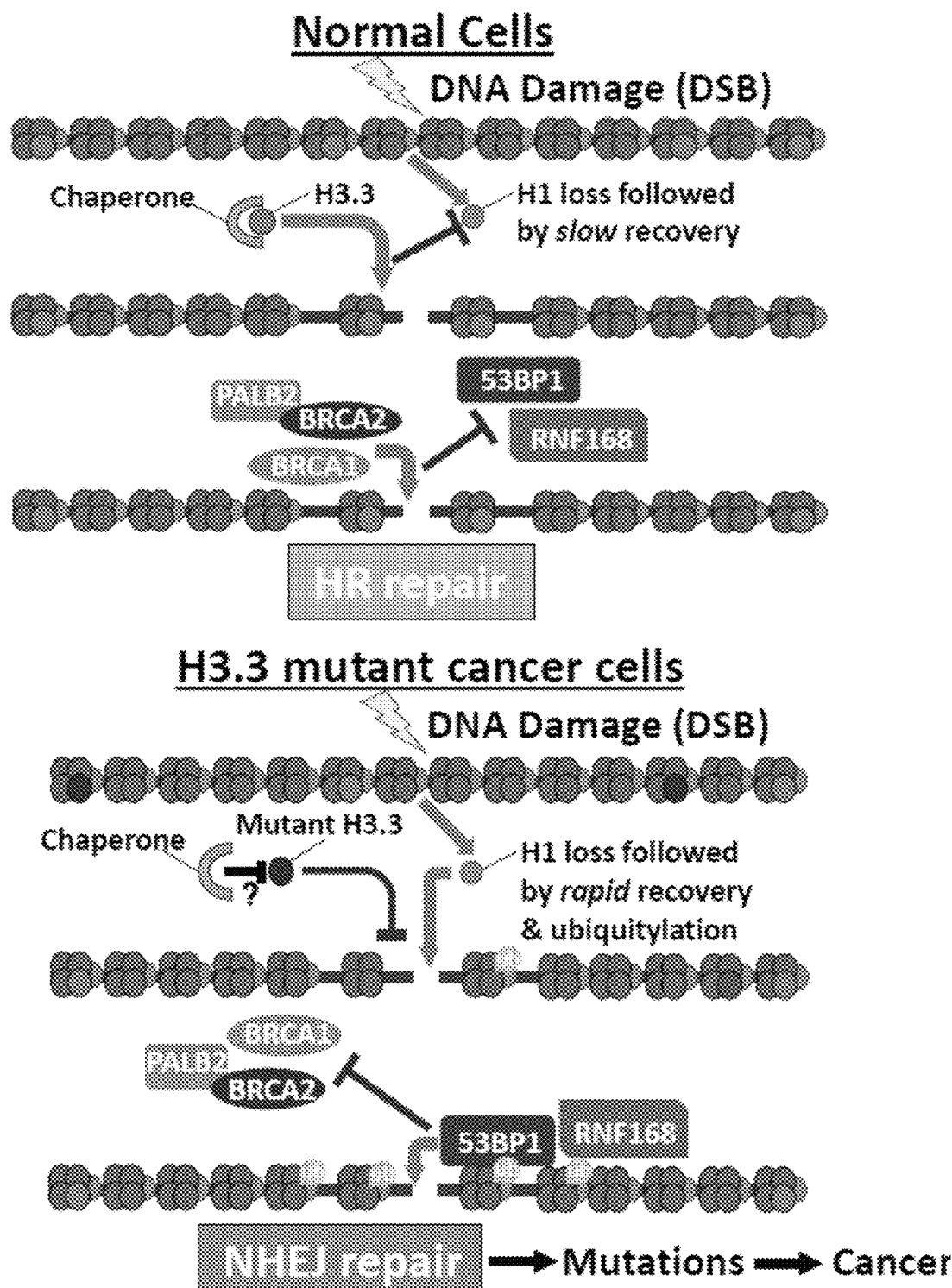
FIG. 7 shows H3.3 serves as an upstream DSB repair pathway choice factor by interfering with H1 binding to block NHEJ and promote HR. WT cells recruit H3.3 to DSBs to block the binding of histone H1 in the vicinity of DSBs, thus preventing the H1-dependent ubiquitylation cascade that promotes subsequent 53BP1 recruitment for driving repair via NHEJ. This allows the binding of HR factors like BRCA1 and subsequently RPA, PALB2 and BRCA2 to DSBs to promote HR mediated DSB repair. However, cancer-associated mutant H3.3 are deficient in recruitment to DSBs, presumably due to unidentified DNA repair specific chaperone(s) (indicated by the question mark) that cannot interact with the H3.3 mutants. Due to this deficient recruitment of mutant H3.3 to DSBs in H3.3 mutant cancer cells, histone H1 binds precociously to the sites of DSBs, thereby prematurely initiating the ubiquity-lation cascade that drives 53BP1 recruitment. This blocks the recruitment of BRCA1 and other downstream HR factors, resulting in the repair of the DSBs via NHEJ. Therefore, H3.3 may be serving as an upstream DSB repair pathway choice factor that promotes HR. ub=ubiquitylated histones.

Histone H1 is concentrated in heterochromatin, and exhibits a higher immobile fraction in heterochromatin compared to euchromatin. Histone H1 has also been shown to suppress HR in both budding yeast and mammalian cells, while promoting DSB repair by NHEJ. Furthermore, in budding yeast, DSB induced degradation of histones including histone H1, promotes HR mediated repair by facilitating homology search through an increase in chromatin mobility. In mammalian cells, following DNA damage, histone H1 is rapidly but transiently displaced from damaged DNA in a PARP1-dependent manner. Interestingly, the binding of histone H1 to chromatin has shown to be antagonized by histone H3.3, suggesting that H3.3 can affect H1 binding in the context of DNA repair. Consistent with these studies, a precocious recovery of histone H1 was observed at DNA damage sites in cells deficient in H3.3 (FIGS. 6A-6D), upon which it could be rapidly ubiquitylated by different E3 ligases to promote 53BP1 recruitment for NHEJ mediated DSB repair. This led to the proposal of a model whereby H3.3 promotes HR mediated DSB repair by blocking the premature return of the NHEJ-promoting histone H1 at DNA damage sites following its initial displacement (FIG. 7). It is suggested that H3.3 functions fairly upstream as a HR promoting DSB repair pathway choice factor. H3.3 deficiency or mutations therefore result in the use of error prone NHEJ pathways for DSB repair, leading to accelerated accumulation of mutations and genomic instability, which in turn drive cancer at a young age.

Example 3: Sensitivity of H3.3K27M Mutant Cells to Combination Treatments

Surprisingly, H3.3K27M mutant cells such as, for example, pediatric high grade glioma (pHGG) cells are especially sensitive to combinations of drugs, with and without radiation.

FIGS. 12A-12B show that only H3.3K27M mutant pediatric high grade glioma (pHGG) cells (cell line SF8628) are specifically sensitive to combinations of older FDA-approved drugs such as the histone deacetylase (HDAC) inhibitors sodium valproate or valproic acid, and the antibiotic Novobiocin which is also a DNA Polymerase theta (POLΘ) inhibitor, in combination with ionizing radiation (IR). Wild-type (WT) or H3.3K27M mutant pediatric high grade glioma cells were seeded at about 5500 cells per well in well plates and treated with the indicated concentrations of the different inhibitors with or without 1.5 Gy IR treatment prior to counting surviving cells after 7 days (similar data was also obtained in FIG. 25). Error bars represent standard deviation. VPA=Valproic Acid and VAL=Sodium Valproate, both of which are HDAC inhibitors;

Novo=Novobiocin, a POLΘ inhibitor. Experiments were repeated in triplicate. Additional experimental details are provided in the section "Cell Survival Assays" of Example 1.

This data clearly shows that HDAC inhibitors specifically target the H3.3K27M mutant pediatric high grade glioma cells, while the pediatric gliomas carrying wild-type H3.3 are not appreciably affected. Furthermore, although both the WT and H3.3K27M mutant cells showed similar sensitivity to the POLΘ inhibitor, a synergistic killing effect was only observed for the H3.3K27M mutant cells when POLΘ and HDAC inhibitors were combined (FIGS. 12A-12B). Note that this assay cannot accurately determine cell survival below ~20% due to the presence of significant numbers of senescent cells that are still alive, but which are not capable of proliferating or dividing any more.

FIG. 13 shows that H3.3K27M mutant pediatric high grade glioma (pHGG) cells are increasingly sensitive to combinations of different classes of FDA-approved drugs. H3.3K27M mutant SF8628 pHGG cells were treated with the indicated concentrations of the different inhibitors for 7 days prior to counting the surviving cells. Error bars represent standard deviation. Ag120=Ivosidenib, an Isocitrate Dehydrogenase 1 (IDH1) inhibitor; Ola=Olaparib, a Poly-ADP Ribose Polymerase (PARP) inhibitor; Novo=Novobiocin, a DNA Polymerase Theta (POLΘ) inhibitor; Vor=Vorinostat, a histone deacetylase (HDAC) inhibitor. This data clearly shows that, in general, H3.3K27M mutant cells show increasing sensitivity to treatment with each additional inhibitor from a different class, for combinations of at least three, and possibly four, different inhibitors. Experiments were repeated in triplicate. Additional experimental details are provided in the section "Cell Survival Assays" of Example 1.

As seen in FIGS. 12-13, 25, 27 and 28, different combinations of two or more drugs, with or without radiation, have different levels of effectiveness. Some of the most effective combinations include drugs that are not significantly better than untreated controls when used individually. See, for example, AG120, which performs worst among all drugs tested against pHGG cells when administered alone. However, when used in combination with Olaparib, Vorinostat, or both Olaparib and Vorinostat, is much more effective at killing pHGG cells than when used alone. These results are surprising and unexpected based on current knowledge regarding pHGG treatment of H3.3 K27M and other H3 mutant cancers.

Example 4: Combination Treatments are Effective on Multiple Cell Types

DIPG

FIGS. 16A-16C show patient derived H3.3 K27M mutant Diffuse Intrinsic Pontine Glioma (DIPG) cells exhibit high levels of histone acetylation and can be specifically eliminated following treatment with histone deacetylase inhibitors (HDACi). (FIG. 16A) H3.3 K27M mutant DIPG cells exhibit high levels of acetylation that can be enhanced even further to cytotoxic levels upon treatment with HDACi. Patient derived glioblastoma cells carrying either wild type (WT) H3.3 or the H3.3 K27M mutant were either left untreated (UT) or treated with 75 nM Vorinostat (Vor) for 16 hours before harvesting them, acid extracting total histones and processing them for Western blotting using antibodies specific to the indicated acetylated (Ac) histones. Ponceau staining of the total histones is shown as a loading control. (FIG. 16B) Treatment of cells with HDACi specifically kills the H3.3 K27M mutant DIPG cells, while largely sparing the cells carrying WT H3.3. The indicated cells were either left untreated or treated with 75 nM of the FDA approved HDACi Vorinostat (Vor; trade name Zolinza) for 7 days before counting the surviving cells. The structure of Vor is also shown. (FIG. 16C) The cytotoxic effects of HDACi synergizes with radiation in specifically eliminating H3.3K27M mutant DIPG cells. The indicated cells were either left untreated or treated with a very low dose of Vor (10 nM) either with or without a low 1 Gy dose of radiation and surviving cells were counted one week later. Error bars represent standard deviation and significant differences between treatments are indicated by the p values.

FIGS. 17A-17B show only H3.3K27M mutant pediatric glioma cells are specifically sensitive to IDH1 inhibitors. (FIG. 17A) Patient derived H3.3K27M mutant Diffuse Intrinsic Pontine Glioma (DIPG) cells are sensitive to treatment with IDH1 inhibitors (IDHi) in a manner that is synergistic with ionizing radiation (IR). The indicated human patient derived WT or H3.3K27M mutant pediatric high grade glioma cells were exposed for 7 days to the indicated concentrations of the IDH inhibitors with or without IR treatment prior to measuring survival as described in FIGS. 16A-16C. Error bars represent standard deviation. (FIG. 17B) Pediatric glioblastoma cells such as KNS42 carrying the H3.3G34V mutant or SF188 cells carrying wild type H3.3 are not sensitive to IDH inhibition. Experiment was performed as in FIG. 17A. IDH1i=IDH1 inhibitor. This data clearly shows that IDH1 inhibitors specifically target the H3.3K27M mutant pediatric high grade glioma cells, while the pediatric gliomas carrying H3.3G34V or wild type H3.3 are not appreciably affected. On the other hand, combinations of DNA repair inhibitors that target non-homologous end-joining (NHEJ) pathways eliminate all H3.3 mutant pediatric high grade gliomas.

FIGS. 18A-18B show inhibition of IDH1 using the pre-clinical (and possibly brain penetrant) inhibitor GSK864 in combination with radiation completely blocks the growth of H3.3K27M mutant human DIPG XIII tumors xenografted in mice. Immunocompromised R2G2 mice (Envigo) were engrafted subcutaneously in the flank with the pediatric patient derived DIPGXIII H3.3K27M mutant tumors and were treated as described in and scheme shown at top, except that the drug treated mice received 75 mg/kg GSK864 plus 30 Gy ionizing radiation (IR, delivered over the first four weeks of treatment in twenty 1.5 Gy fractions indicated by lightning bolts) following which only drug administration was continued until the humane or clinical endpoint was met. Microcaliper measurement based relative tumor volumes are plotted. Error bars show standard deviation.

FIGS. 19A-19B show inhibition of IDH1 using the FDA approved inhibitor AG120 (Ivosidenib) in combination with radiation completely blocks the growth of H3.3K27M mutant human DIPG XIII tumors xenografted in mice. Immunocompromised Rag2/IL2rg double knockout mice (Taconic) were engrafted subcutaneously in the flank with the pediatric patient derived DIPGXIII H3.3K27M mutant tumors and were treated as described in and scheme shown at top. The drug treated mice received either mg/kg of Temozolomide (TMZ, which failed to provide benefits for DIPG patients in clinical trials) or 75 mg/kg AG120 along with 30 Gy ionizing radiation (IR, delivered over the first four weeks of treatment in twenty 1.5 Gy fractions indicated by lightning bolts) following which only drug administration was continued until the humane or clinical endpoint was met. Microcaliper measurement based relative tumor volumes are plotted. Error bars show standard deviation.

FIG. 20 shows inhibition of IDH1 using the FDA approved inhibitor AG120 (Ivosidenib) in combination with radiation completely blocks the growth of H3.3K27M mutant human DIPG XIII tumors xenografted in mice. Immunocompromised Rag2/IL2rg double knockout mice (Taconic) were engrafted subcutaneously in the flank with the pediatric patient derived DIPGXIII H3.3K27M mutant tumors and were treated as described in and scheme shown at top, except that the drug treated mice received 75 mg/kg AG120 plus 30 Gy radiation (delivered over the first four weeks of treatment in twenty 1.5 Gy fractions indicated by lightning bolts) following which only drug administration was continued until the humane or clinical endpoint was met. Microcaliper measurement based relative tumor volumes are plotted. Error bars show standard deviation.

FIG. 21 shows dissemination of human patient derived DIPG XIII H3.3K27M cancer cells in untreated mice. Bio-luminescence images of the side and belly of a representative mouse at the time of engraftment with H3.3K27M mutant tumor on the flank, followed by vehicle injections for two months by which time the tumor had disseminated extensively in the abdominal area and elsewhere (DIPG tumors within the brain are not typically known to metastasize). The original site of engraftment in the flank is indicated by the arrow. Overall, up to 30% of the mice in multiple untreated groups developed disseminated tumors compared to none in the treatment groups so far. Up to 30% of the untreated mice in multiple cohorts also developed lower body paralysis presumably due to invasion of the spinal cord by the DIPG tumor cells engrafted in the flank. The poor outcomes in untreated mice harboring human H3.3 mutant DIPG tumors further highlight the effectiveness of the disclosed therapeutic approaches.

FIGS. 22A-22B show combination treatment with c-NHEJ inhibitor Olaparib and alt-NHEJ inhibitor NU7441 along with radiation completely blocks the growth of DIPG XIII H3.3K27M mutant tumors in mice. Immunocompromised R2G2 mice (Envigo) were engrafted subcutaneously in the flank with the pediatric patient derived DIPGXIII H3.3K27M mutant tumors and were treated as described in and scheme shown at top, except that the drug treated mice received 37.5 mg/kg Olaparib (OLA) and 5 mg/kg NU7441 (NU) plus 20 Gy radiation (delivered over the first two weeks of treatment in ten 2 Gy fractions indicated by lightning bolts) following which only OLA and NU administration was continued until the humane or clinical endpoint was met. Microcaliper measurement based relative tumor volumes are plotted. No symptoms of bone marrow suppression due to the treatment with the low doses of OLA and NU was observed in any mice and more detailed analyses are awaited. Error bars show standard deviation.

FIG. 23 shows patient derived H3.3K27M mutant DIPG cells are exquisitely sensitive to treatment with another FDA approved PARP inhibitor Talazoparib (Talzenna). The indicated human patient derived WT or H3.3K27M pediatric glioblastoma cells were exposed to a triple combination of the indicated concentration of the FDA approved PARP inhibitor drug Talazoparib for 7 days prior to measuring survival by counting viable cells. The H3.3 K27M mutant cancer cells are very sensitive to Talazoparib. Error bars represent standard deviation.

FIG. 24 shows DNA polymerase Theta inhibitor Novo-biocin synergizes with c-NHEJ inhibitor NU7441 in killing patient derived SF7761 H3.3K27M mutant DIPG cells in culture. The indicated human patient derived H3.3K27M pediatric glioblastoma cells were exposed to the indicated concentration of the FDA approved Pole inhibitor Novobiocin (Novo) or the DNA-PK inhibitor NU7441 for 7 days prior to measuring survival by counting viable cells. Error bars represent standard deviation.

FIG. 25 shows patient derived H3.3K27M mutant DIPG cells are exquisitely sensitive to combination treatment with FDA approved NHEJ inhibiting drugs. The indicated human patient derived WT or H3.3K27M pediatric glioblastoma cells were exposed to a triple combination of the indicated concentrations of the FDA approved drugs Olaparib (OLA), Novobiocin (Novo) and the preclinical, brain permeable DNA-PK inhibitor Vx-984 for 7 days prior to measuring survival as described in FIGS. 16A-16C. Additive/synergistic effects are clearly visible when the drugs are used in combination. Error bars represent standard deviation.

FIG. 26 shows combination treatment with c-NHEJ inhibitor Olaparib and alt-NHEJ inhibitor NU7441 along with radiation completely blocks the growth of DIPG XIII H3.3K27M mutant tumors in mice. Immunocompromised BRG mice (Jackson Laboratories) were engrafted subcutaneously in the flank with the pediatric patient derived, luciferase carrying H3.3K27M mutant SF7761 DIPG tumor cells. The drug treated mice received 100 mg/kg of Novobiocin (Novo) and Sodium Valproate (Val), plus 30 Gy ionizing radiation (IR, delivered over the first four weeks of treatment in twenty 1.5 Gy fractions indicated by lightning bolts), following which only drug administration was continued 5 days per week (Monday through Friday, with no treatments on weekends) for a total of 90 days (~13 weeks), after which all treatments were stopped. Bioluminescent images of the mice from the indicated weeks are shown. Since no signals from tumor cells have been detected in the treated mice for over 24 weeks now (which is equivalent to nearly 10 years in human lifespan), it is believed that this treatment was curative for these mice.

FIG. 27 shows patient derived H3.3K27M mutant DIPG cells are exquisitely sensitive to combination treatment with FDA approved drugs. The indicated human patient derived WT or H3.3K27M pediatric glioblastoma cells were exposed to a triple combination of the indicated concentrations of the FDA approved drugs Olaparib (OLA), AG120 (Ivosidenib) and Vorinostat (Vor) for 7 days prior to measuring survival as described in FIGS. 16A-16C. Error bars represent standard deviation.

FIG. 28 shows patient derived H3.3K27M mutant DIPG cells are exquisitely sensitive to combination treatment with FDA approved drugs Olaparib (Lynparza), AG120 (Ivosidenib, Tibsovo) and Vorinostat (Zolinza), or health supplements like Curcumin. The indicated human patient derived WT or H3.3K27M pediatric glioblastoma cells were exposed to a triple combination of the indicated concentrations of the FDA approved drugs Olaparib (OLA), AG120 (Ivosidenib, Tibsovo) and Vorinostat (Vor), or the commonly used health supplement Curcumin (Cur, which is a natural inhibitor of histone acetyltransferases) for 7 days prior to measuring survival as described in FIGS. 16A-16C. Error bars represent standard deviation.

FIG. 29 shows inhibition of NHEJ pathways kills H3.3K27M mutant human tumor cells within 3D neurospheres. Compared to 2D cultures of cells in vitro, cultured 3D tumor spheroids, organoids or neurospheres are much better mimics of the 3D tumors in vivo. H3.3K27M mutant SF7761 DIPG neurospheres expressing luciferase were cultured in vitro. Bioluminescence from the organoids was measured daily to determine survival upon treatment with or without a combination of 100 UM Novobiocin (Novo) to block Pole mediated Theta Mediated End Joining (TMEJ), 2 μM OLA (Olaparib) to block Poly-ADP Ribose Polymerase 1 (PARP1) mediated alternative-End Joining (a-EJ), and 2 μM VX-984, a DNA-PK inhibitor to block classic Non-Homologous End Joining (c-NHEJ).

FIG. 30 shows inhibition of NHEJ pathways kills H3.3K27M mutant human tumor cells within 3D neurospheres. H3.3K27M mutant SF7761 DIPG neurospheres expressing luciferase were cultured in vitro and treated with or without a combination of 100 UM Novo to block Pole mediated TMEJ, 2 μM OLA to block PARP1 mediated a-EJ, and 2 μM VX-984, a DNA-PK inhibitor to block c-NHEJ. On day 5 of treatment, organoids were stained with the live cell permeable dye Hoechst 33342 (blue, to stain DNA in all cells) and live-cell impermeable propidium iodide (red, to stain nucleic acids in dead or dying cells only). Images were collected at 10× magnification on a Keyence microscope. Bioluminescence measurements from an experiment performed in triplicate is plotted. Composite overlay of images including brightfield of representative organoids are shown. Unlike the bioluminescence data shown previously in FIG. 25, the microscopy images shown here provide data from individual cells within the neurospheres, which is more informative regarding the relative efficacy of single and combination treatments.

Breast Cancer

FIG. 31 shows breast cancer cells deficient in homologous recombination (HR) due to mutations in the BRCA1 gene are very sensitive to inhibition of Non-Homologous End Joining (NHEJ) pathways by simultaneous treatment with both DNA-PKcs, PARP and Pole inhibitors. Wild type (WT) breast cancer (MCF7), BRCA1 mutant breast cancer (HCC1937) cells were either left untreated or treated with the DNA-PKcs inhibitor Vx-984 (Vx, 0.5 μM), FDA approved PARP inhibitor Olaparib (Ola, 0.5 μM), and the Pole inhibitor Novobiocin (Novo, 25 μM) and surviving cells were counted one week later. Additive/synergistic effects can be seen when the drugs are used in combination. Error bars represent standard deviation.

FIG. 32 shows breast and ovarian cancer cells deficient in homologous recombination (HR) due to mutations in the BRCA1 gene are very sensitive to inhibition of Non-Homologous End Joining (NHEJ) pathways by simultaneous treatment with both DNA-PKcs and PARP inhibitors. Wild type (WT) breast cancer (MCF7), BRCA1 mutant breast cancer (HCC1937), BRCA1 mutated ovarian cancer (UWB1.289) and its isogenic WT reconstituted control (UWB1.289+BRCA1) cells were either left untreated or treated with the DNA-PKcs inhibitor NU7441 (NU, 1 μM) or the FDA approved PARP inhibitor Talazoparib (Talazo, 50 nM) and surviving cells were counted one week later. Error bars represent standard deviation. This data suggests that the use of lower doses of Talazoparib will allow for better visualization of the synergistic effect on cell killing when combined with NU7441, which is predicted to increase even further when combined with radiation to cause DNA strand breaks.

Ovarian Cancer

FIG. 33 shows ovarian cancer cells deficient in homologous recombination (HR) due to mutations in the BRCA1 gene are very sensitive to inhibition of Non-Homologous End Joining (NHEJ) pathways by simultaneous treatment with combinations of DNA-PKcs, PARP inhibitors and Pole inhibitors. Wild type (WT) ovarian cancer OVCAR-5, hemizygous (IGR-OV1) and homozygous (UWB1.289) BRCA1 mutated ovarian cancer, and its isogenic WT reconstituted control (UWB1.289+BRCA1) cells were either left untreated or treated with the DNA-PKcs inhibitor Vx-984 (Vx, 0.5 UM), FDA approved PARP inhibitor Olaparib (Ola, 0.5 µM), and the Pole inhibitor Novobiocin (Novo, 25 UM) and surviving cells were counted one week later. Error bars represent standard deviation. Note: The lower detection limit of this assay is about 10% survival. Nevertheless, additive/synergistic effects are apparent when the drugs are used in combination.

FIG. 34 shows homologous recombination deficient (HRD) ovarian cancer cells that carry either a mutant or epigenetically silenced BRCA1 gene are very sensitive to inhibition of Non-Homologous End Joining (NHEJ) pathways upon combination treatment with PARP, DNA-PK and Pole inhibitors. The indicated WT or BRCA1 deficient ovarian cancer cells were either left untreated (UT) or treated with different combinations of the DNA-PK inhibitor Nu7441 (1 µM), the FDA approved PARP inhibitor Olaparib (OLA; 1 µM), and the FDA approved antibiotic Novobiocin (NOVO; 50 µM) which is also a Pole inhibitor. Surviving cells were counted one week later. Error bars represent standard deviation.

Pancreatic Cancer

FIG. 35 shows pancreatic cancer cells deficient in homologous recombination (HR) due to mutations in the BRCA2 gene are very sensitive to inhibition of Non-Homologous End Joining (NHEJ) pathways by simultaneous treatment with both DNA-PKcs, PARP and Pole inhibitor inhibitors in the presence of radiation. The indicated wild type or BRCA2 mutant pancreatic cancer cells were either left untreated or treated with the DNA-PKcs inhibitor Vx-984 (1 µM), the FDA approved PARP inhibitor Olaparib (0.75 UM), and the Pole inhibitor Novobiocin (Novo, 37.5 UM), either with or without a low 1 Gy dose of radiation to cause DNA stand breaks and surviving cells were counted one week later. Additive/synergistic effects are clear when the drugs are used in combination. Error bars represent standard deviation.

FIG. 36 shows pancreatic cancer cells deficient in homologous recombination (HR) due to mutations in the BRCA2 gene are very sensitive to inhibition of Non-Homologous End Joining (NHEJ) pathways by simultaneous treatment with both DNA-PKcs and PARP inhibitors in the presence of radiation. The indicated wild type or BRCA2 mutant pancreatic cancer cells were either left untreated or treated with the DNA-PKcs inhibitor NU7441 (Nu; 1 µM), a very low dose of the FDA approved PARP inhibitor Talazoparib (10 nM), either with or without a low 1.5 Gy dose of radiation to cause DNA stand breaks and surviving cells were counted one week later. Error bars represent standard deviation.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Adam S, et al (2013) Transcription recovery after DNA damage requires chromatin priming by the H3.3 histone chaperone HIRA. Cell 155: 94-106

2. Adam S, et al (2014) Blurring the line between the DNA damage response and transcription: the importance of chromatin dynamics. Experimental cell research 329: 148-153

3. Adams, D. J., et al. (2020). Melanoma predisposition-A limited role for germline BRCA1 and BRCA2 variants. Pigment Cell & Melanoma Research 33: 6-7.

4. Alhmoud J F, et al (2020) DNA Damage/Repair Management in Cancers. Cancers (Basel) 12

5. Amary, M. F., et al. (2011). IDH1 and IDH2 mutations are frequent events in central chondrosarcoma and central and periosteal chondromas but not in other mesenchymal tumours. The Journal of Pathology 224: 334-343.

6. Apostolou, P., et al. (2013). Hereditary breast cancer: the era of new susceptibility genes. Biomed Research International 2013: 747318.

7. Audia, J. E., et al. (2016). Histone Modifications and Cancer. Cold Spring Harb Perspect Biol. 8: a019521.

8. Aziz-Bose R, et al (2019) Diffuse intrinsic pontine glioma: molecular landscape and emerging therapeutic targets. Curr Opin Oncol 31: 522-530

9. Barber L, et al (2013) Secondary mutations in BRCA2 associated with clinical resistance to a PARP inhibitor. J Pathol 229: 422-4290.

10. Baxter P A, et al. A phase I/II study of veliparib (ABT-888) with radiation and temozolomide in newly diagnosed diffuse pontine glioma: a Pediatric Brain Tumor Consortium study. Neuro Oncol. 2020 Jun. 9; 22 (6): 875-885.

11. Behjati S, et al (2013) Distinct H3F3A and H3F3B driver mutations define chondroblastoma and giant cell tumor of bone. Nature genetics 45: 1479-1482

12. Belzile J P, et al (2007) HIV-1 Vpr-mediated G2 arrest involves the DDB1-CUL4AVPRBP E3 ubiquitin ligase. PLoS Pathog 3: e85

13. Bender, S., et al. (2013). Reduced H3K27me3 and DNA hypomethylation are major drivers of gene expression in K27M mutant pediatric high-grade gliomas. Cancer Cell 24: 660-672.

14. Bennett, C. B., et al. (1996). A double-strand break within a yeast artificial chromosome (YAC) containing human DNA can result in YAC loss, deletion or cell lethality. Mol. Cell. Biol. 16: 4414-4425.

15. Bindra R S, et al (2013) Development of an assay to measure mutagenic non-homologous end-joining repair activity in mammalian cells. Nucleic acids research 41: e115

16. Bjerke L, et al et al (2013a) Histone H3.3 Mutations Drive Pediatric Glioblastoma through Upregulation of MYCN. Cancer discovery 17. Bleuyard J Y, et al (2012) ChAM, a novel motif that mediates PALB2 intrinsic chromatin binding and facilitates DNA repair. EMBO Rep 13: 135-141

18. Bohgaki M, et al (2013) RNF168 ubiquitylates 53BP1 and controls its response to DNA double-strand breaks. Proceedings of the National Academy of Sciences of the United States of America 110: 20982-20987

19. Bonner, W. M., et al. (2008). GammaH2AX and cancer. Nature Reviews Cancer 8: 957-967.

20. Boursi, B., et al. (2023). Analysis of BRCA1- and BRCA2-Related Pancreatic Cancer and Survival. JAMA Network Open 6: e2345013.

21. Braunschweig U, et al (2009) Histone H1 binding is inhibited by histone variant H3.3. The EMBO journal 28: 3635-3645

22. Brieger A, et al (2012) C-terminal fluorescent labeling impairs functionality of DNA mismatch repair proteins. PloS one 7: e31863

23. Britton S, et al (2013) A new method for high-resolution imaging of Ku foci to decipher mechanisms of DNA double-strand break repair. The Journal of cell biology 202: 579-595

24. Brown D T, et al (2006) Mapping the interaction surface of linker histone H1 (0) with the nucleosome of native chromatin in vivo. Nature structural & molecular biology 13: 250-255

25. Brown, D. T. (2003). Histone H1 and the dynamic regulation of chromatin function. Biochem. Cell Biol. 81: 221-227.

26. Bush K M, et al (2013) Endogenous mammalian histone H3.3 exhibits chromatin-related functions during development. Epigenetics & chromatin 6: 7

27. Cairns, R. A., et al. (2013). Oncogenic isocitrate dehydrogenase mutations: mechanisms, models, and clinical opportunities. Cancer Discovery 3: 730-741.

28. Calvert, A. E., et al. (2017). Cancer-Associated IDH1 Promotes Growth and Resistance to Targeted Therapies in the Absence of Mutation. Cell Reports 19: 1858-1873.

29. Camenisch U, et al (2009) Two-stage dynamic DNA quality check by xeroderma pigmentosum group C protein. The EMBO journal 28: 2387-2399

30. Caron P, et al (2021) DNA Double-Strand Break Repair: All Roads Lead to HeterochROMAtin Marks. Front Genet 12: 730696

31. Casolino, R., et al. (2023). Treatment of pancreatic cancer in 2022. Cambridge Prisms Precision Medicine 1: e14.

32. Casolino, R., et al. (2021). Homologous Recombination Deficiency in Pancreatic Cancer: A Systematic Review and Prevalence Meta-Analysis. Journal of Clinical Oncology 39: 2617-2631.

33. Ceccaldi, R., et al. (2015). Homologous-recombination-deficient tumours are dependent on Pole-mediated repair. Nature 518: 258-262.

34. Celeste, A., et al. (2003). H2AX haploinsufficiency modifies genomic stability and tumor susceptibility. Cell 114: 371-383.

35. Challa K, et al (2021) Damage-induced chromatome dynamics link Ubiquitin ligase and proteasome recruitment to histone loss and efficient DNA repair. Molecular cell 81: 811-829 e816

36. Chan K M, et al (2013) The histone H3.3K27M mutation in pediatric glioma reprograms H3K27 methylation and gene expression. Genes & development 27: 985-990

37. Chang F T, et al (2015) CHK1-driven histone H3.3 serine 31 phosphorylation is important for chromatin maintenance and cell survival in human ALT cancer cells. Nucleic acids research 43: 2603-2614

38. Chatwin H V, et al (2021) Pediatric high-grade glioma: moving toward subtype-specific multimodal therapy. The FEBS journal 288: 6127-6141

39. Cheblal A, et al (2020) DNA Damage-Induced Nucleosome Depletion Enhances Homology Search Independently of Local Break Movement. Molecular cell 80: 311-326 e314

40. Chen X. S., et al. (2021). DNA Polymerase θ: A Cancer Drug Target with Reverse Transcriptase Activity. Genes (Basel) 12: 1146.

41. Cheutin T, et al (2003) Maintenance of stable heterochromatin domains by dynamic HP1 binding. Science 299: 721-725

42. Chi, H. C., et al. (2018). Impact of DNA and RNA Methylation on Radiobiology and Cancer Progression. Int J Mol Sci, 19: 555.

43. Chiolo I, et al (2011) Double-strand breaks in heterochromatin move outside of a dynamic HP1a domain to complete recombinational repair. Cell 144: 732-744

44. Cho, Y. S., et al. (2017). Discovery and Evaluation of Clinical Candidate IDH305, a Brain Penetrant Mutant IDH1 Inhibitor. ACS Med Chem Lett 8: 1116-1121.

45. Chornenkyy, Y., et al. (2015). Poly-ADP-Ribose Polymerase as a Therapeutic Target in Pediatric Diffuse Intrinsic Pontine Glioma and Pediatric High-Grade Astrocytoma. Mol Cancer Ther. 14: 2560-2568.

46. Chou, T.-C. (2008). Preclinical versus clinical drug combination studies. Leukemia & Lymphoma 49: 2059-2080.

47. Ciccia, A., et al. (2010). The DNA damage response: making it safe to play with knives. Molecular Cell 40: 179-204.

48. Cohen, K. J., et al. (2011). Temozolomide in the treatment of children with newly diagnosed diffuse intrinsic pontine gliomas: a report from the Children's Oncology Group. Neuro Oncol 13: 410-416.

49. Comenge J, et al (2018) Multimodal cell tracking from systemic administration to tumour growth by combining gold nanorods and reporter genes. Elife 7

50. Cook, A. J., et al. (2011). A specific function for the histone chaperone NASP to fine-tune a reservoir of soluble H3-H4 in the histone supply chain. Molecular Cell 44: 918-927.

51. Cornford, E. M., et al. (1985). Blood-brain barrier transport of valproic acid. J Neurochem 44: 1541-1550.

52. Dang, L., et al. (2009). Cancer-associated IDH1 mutations produce 2-hydroxyglutarate. Nature 462: 739-744.

53. Davis, M. I., et al. (2014). Biochemical, cellular, and biophysical characterization of a potent inhibitor of mutant isocitrate dehydrogenase IDH1. The Journal of Biological Chemistry 289: 13717-13725.

54. den Brok, W. D., et al. (2017). Homologous Recombination Deficiency in Breast Cancer: A Clinical Review. JCO Precision Oncology 1: 1-13.

55. Dillon K M, et al. (2022). PALB2 or BARD1 loss confers homologous recombination deficiency and PARP inhibitor sensitivity in prostate cancer. NPJ Precis Oncol 6: 49.

56. Dinant C, et al (2007) Activation of multiple DNA repair pathways by sub-nuclear damage induction methods. Journal of cell science 120: 2731-2740

57. Doles, J. D., et al. (2018). Does the Poly (ADP-Ribose) Polymerase Inhibitor Veliparib Merit Further Study for Cancer-Associated Weight Loss? Observations and Conclusions from Sixty Prospectively Treated Patients. Journal of Palliative Medicine 21: 1334-1338.

58. Downs J A, et al (2003) Suppression of homologous recombination by the Saccharomyces cerevisiae linker histone. Molecular cell 11: 1685-1692

59. Drost, J., et al. (2018). Organoids in cancer research. Nature Reviews Cancer 18: 407-418.

60. Dryhurst, D., et al. (2012). Histone H2A.Z prepares the prostate specific antigen (PSA) gene for androgen receptor-mediated transcription and is upregulated in a model of prostate cancer progression. Cancer Lett. 315: 38-47.

61. Duan, P., et al. (2009). Novobiocin is a potent inhibitor for human organic anion transporters. Drug Metabolism and Disposition 37: 1203-10.

62. Dull T, et al (1998) A third-generation lentivirus vector with a conditional packaging system. J Virol 72: 8463-8471

63. Economopoulou, M., et al. (2009). Histone H2AX is integral to hypoxia-driven neovascularization. Nat. Med. 15: 553-558.

64. Elbakry A, et al (2018) DNA repair synthesis and histone deposition partner during homologous recombination. Mol Cell Oncol 5: e1511210

65. Elsaesser S J, et al (2010) New functions for an old variant: no substitute for histone H3.3. Curr Opin Genet Dev 20: 110-117

66. Essers J, et al (2005) Nuclear dynamics of PCNA in DNA replication and repair. Molecular and cellular biology 25: 9350-9359

67. Fan Y, et al. (2024) Homologous Recombination Repair Gene Mutations in Prostate Cancer: Prevalence and Clinical Value. Adv Ther 41: 2196-2216.

68. Feiersinger G E, et al. (2018). Olaparib is effective in combination with, and as maintenance therapy after, first-line endocrine therapy in prostate cancer cells. Mol Oncol 12: 561-576.

69. Fenech M, et al (2003) Intra- and inter-laboratory variation in the scoring of micronuclei and nucleoplasmic bridges in binucleated human lymphocytes. Results of an international slide-scoring exercise by the HUMN project. Mutat Res 534: 45-64

70. Fields, E. C., et al. (2017). Radiation Treatment in Women with Ovarian Cancer: Past, Present, and Future. Frontiers in Oncology 7: 177.

71. Filbin M G, et al (2018) Developmental and oncogenic programs in H3K27M gliomas dissected by single-cell RNA-seq. Science 360: 331-335

72. Flanagan T W, et al (2016) Molecular dynamics of histone H1. Biochimica et biophysica acta 1859: 468-475

73. Fontebasso, A. M., et al. (2013). Chromatin remodeling defects in pediatric and young adult glioblastoma: a tale of a variant histone 3 tail. Brain Pathology 23: 210-216.

74. Frey A, et al (2014) Histone H3.3 is required to maintain replication fork progression after UV damage. Current biology: CB 24: 2195-2201

75. Frit, P., et al. (2014). Alternative end-joining pathway(s): bricolage at DNA breaks. DNA Repair (Amst) 17: 81-97.

76. Fung H, et al (2011) Repair at single targeted DNA double-strand breaks in pluripotent and differentiated human cells. PloS one 6: e20514

77. Gallinari, P., et al. (2007). HDACs, histone deacetylation and gene transcription: from molecular biology to cancer therapeutics. Cell Res. 17: 195-211.

78. Gil del Alcazar, et al. (2014). Inhibition of DNA double-strand break repair by the dual PI3K/mTOR inhibitor NVP-BEZ235 as a strategy for radiosensitization of glioblastoma. Clinical Cancer Research 20: 1235-1248.

79. Ginsburg, O. M., et al. (2010). Hereditary Breast Cancer Clinical Study Group. BRCA1 and BRCA2 families and the risk of skin cancer. Familial Cancer 9: 489-93.

80. Golan, T., et al. (2019). Maintenance Olaparib for Germline BRCA-Mutated Metastatic Pancreatic Cancer. New England Journal of Medicine 381: 317-327.

81. Goldberg A D, et al (2010) Distinct factors control histone variant H3.3 localization at specific genomic regions. Cell 140: 678-691

82. Goodarzi A A, et al (2008) ATM signaling facilitates repair of DNA double-strand breaks associated with heterochromatin. Molecular cell 31: 167-177

83. Goodarzi A A, et al (2012) The heterochromatic barrier to DNA double strand break repair: how to get the entry visa. Int J Mol Sci 13: 11844-11860

84. Grasso C S, et al (2015) Functionally defined therapeutic targets in diffuse intrinsic pontine glioma. Nat Med 21: 827

85. Gumaste, P. V., et al. (2015). Skin cancer risk in BRCA1/2 mutation carriers. British Journal of Dermatology 172: 1498-1506.

86. Gunjan A, et al (1999) Effects of H1 histone variant overexpression on chromatin structure. J Biol Chem 274: 37950-37956

87. Gunjan A, et al (2003) A Rad53 kinase-dependent surveillance mechanism that regulates histone protein levels in S. cerevisiae. Cell 115: 537-549

88. Gursoy-Yuzugullu, O., et al. (2017). Epigenetic therapy with inhibitors of histone methylation suppresses DNA damage signaling and increases glioma cell radiosensitivity. Oncotarget 8: 24518-24532.

89. Haince J F, et al (2008) PARP1-dependent kinetics of recruitment of MRE11 and NBS1 proteins to multiple DNA damage sites. J Biol Chem 283: 1197-1208

90. Halsall, J. A., et al. (2015). Cells adapt to the epigenomic disruption caused by histone deacetylase inhibitors through a coordinated, chromatin-mediated transcriptional response. Epigenetics Chromatin 8: 29.

91. Hamiche, A., et al. (2012). Chaperoning the histone H3 family. Biochimica et Biophysica acta 1819: 230-237.

92. Hanna, C., et al. (2020) Pharmacokinetics, safety, and tolerability of olaparib and temozolomide for recurrent glioblastoma: results of the phase I OPARATIC trial. Neuro Oncol. 22: 1840-1850.

93. Haring S J, et al (2008) Cellular functions of human RPA1. Multiple roles of domains in replication, repair, and checkpoints. J Biol Chem 283: 19095-19111

94. Harper, J. W., et al. (2007). The DNA damage response: ten years after. Molecular Cell 28: 739-745.

95. Hashizume R, et al (2014) Pharmacologic inhibition of histone demethylation as a therapy for pediatric brainstem glioma. Nat Med 20: 1394-1396

96. Hegi, M. E., et al. (2005). MGMT gene silencing and benefit from temozolomide in glioblastoma. N Engl J Med 352: 997-1003.

97. Henikoff S, et al (2009) Genome-wide profiling of salt fractions maps physical properties of chromatin. Genome research 19: 460-469

98. Hennika T, et al (2017) Pre-Clinical Study of Panobinostat in Xenograft and Genetically Engineered Murine Diffuse Intrinsic Pontine Glioma Models. PloS one 12: e0169485

99. Hernandez, L., et al. (2016). Characterization of ovarian cancer cell lines as in vivo models for preclinical studies. Gynecologic Oncology 142: 332-340.

100. Herz H M, et al (2014) Histone H3 lysine-to-methionine mutants as a paradigm to study chromatin signaling. Science 345: 1065-1070

101. Hodl M, et al (2009) Transcription in the absence of histone H3.3. Current biology: CB 19: 1221-1226

102. Hodl M, et al (2012) Transcription in the absence of histone H3.2 and H3K4 methylation. Current biology: CB 22: 2253-2257

103. Huang, X. Z., et al. (2020). Efficacy and Prognostic Factors for PARP Inhibitors in Patients With Ovarian Cancer. Frontiers in Oncology 10: 958.

104. Hut H M, et al (2005) Dysfunctional BRCA1 is only indirectly linked to multiple centrosomes. Oncogene 24: 7619-7623

105. Jakob B, et al (2011) DNA double-strand breaks in heterochromatin elicit fast repair protein recruitment, histone H2AX phosphorylation and relocation to euchromatin. Nucleic acids research 39: 6489-6499

106. Jakob, C. G., et al. (2018). Novel Modes of Inhibition of Wild-Type Isocitrate Dehydrogenase 1 (IDH1): Direct Covalent Modification of His315. J Med Chem 61: 6647-6657.

107. Jang C W, et al (2015) Histone H3.3 maintains genome integrity during mammalian development. Genes & development 29: 1377-1392

108. Jaspers J E, et al (2013) Loss of 53BP1 causes PARP inhibitor resistance in Brca1-mutated mouse mammary tumors. Cancer discovery 3: 68-81

109. Jin C, et al (2007) Nucleosome stability mediated by histone variants H3.3 and H2A.Z. Genes & development 21: 1519-1529

110. Jones C, et al (2014) Unique genetic and epigenetic mechanisms driving paediatric diffuse high-grade glioma. Nature reviews Cancer 14

111. Jones C, et al (2017) Pediatric high-grade glioma: biologically and clinically in need of new thinking. Neuro Oncol 19: 153-161

112. Juhasz S, et al (2018) ATRX Promotes DNA Repair Synthesis and Sister Chromatid Exchange during Homologous Recombination. Molecular cell 71: 11-24 e17

113. Jung, K., et al. (2023). Comprehensive genomic analysis for homologous recombination deficiency in pancreatic cancer. Journal of Clinical Oncology 41: 16_supplement.

114. Kapoor, A., et al. (2010). The histone variant macroH2A suppresses melanoma progression through regulation of CDK8. Nature 468: 1105-1109.

115. Karagiannis, T. C., et al. (2006). Modulation of cellular radiation responses by histone deacetylase inhibitors. Oncogene. 25: 3885-93.

116. Katagi, H., et al. (2019). Radiosensitization by Histone H3 Demethylase Inhibition in Diffuse Intrinsic Pontine Glioma. Clin Cancer Res 25: 5572-5583.

117. Khan, A. J., et al. (2018). VX-984 is a selective inhibitor of non-homologous end joining, with possible preferential activity in transformed cells. Oncotarget 9: 25833-25841.

118. Kholosy, W. M., et al. (2021). Neuroblastoma and DIPG Organoid Coculture System for Personalized Assessment of Novel Anticancer Immunotherapies. J Pers Med. 11: 869.

119. Kijas A W, et al (2015) ATM-dependent phosphorylation of MRE11 controls extent of resection during homology directed repair by signalling through Exonuclease 1. Nucleic acids research 43: 8352-8367

120. Kimura H, et al (2001) Kinetics of core histones in living human cells: little exchange of H3 and H4 and some rapid exchange of H2B. The Journal of cell biology 153: 1341-1353

121. Kindler, H. L., et al. (2022). Overall Survival Results From the POLΘ Trial: A Phase III Study of Active Maintenance Olaparib Versus Placebo for Germline BRCA-Mutated Metastatic Pancreatic Cancer. Journal of Clinical Oncology 40: 3929-3939.

122. Kocatürk, B., et al. (2015). Orthotopic injection of breast cancer cells into the mammary fat pad of mice to study tumor growth. Journal of Visualized Experiments. 96: 51967.

123. Kumar A, et al (2004) DNA intercalators differentially affect chromatin structure and DNA replication in *Xenopus* egg extract. Anticancer Drugs 15: 633-639

124. Kyriazis, A. P., et al. (1982). Human pancreatic adenocarcinoma line Capan-1 in tissue culture and the nude mouse: morphologic, biologic, and biochemical characteristics. American Journal of Pathology 106: 250-60.

125. Lan L, et al (2014) Novel method for site-specific induction of oxidative DNA damage reveals differences in recruitment of repair proteins to heterochromatin and euchromatin. Nucleic acids research 42: 2330-2345

126. Ledermann, J., et al. (2014). Olaparib maintenance therapy in patients with platinum-sensitive relapsed serous ovarian cancer: a preplanned retrospective analysis of outcomes by BRCA status in a randomised phase 2 trial. The Lancet Oncology 15: 852-861.

127. Lesueur P, et al (2019) Phase I/IIa study of concomitant radiotherapy with olaparib and temozolomide in unresectable or partially resectable glioblastoma: OLA-TMZ-RTE-01 trial protocol. BMC Cancer 19: 198

128. Levkoff, L. H., et al. (2008). Bromodeoxyuridine inhibits cancer cell proliferation in vitro and in vivo. Neoplasia 10: 804-816.

129. Lewis P W, et al (2013) Inhibition of PRC2 activity by a gain-of-function H3 mutation found in pediatric glioblastoma. Science 340: 857-861

130. Li Z, et al (2018) Destabilization of linker histone H1.2 is essential for ATM activation and DNA damage repair. Cell research 28: 756-770

131. Liang S, et al (2022) Structural insights into inhibitor regulation of the DNA repair protein DNA-PKcs. Nature 601: 643-648

132. Liang, D., et al. (2012). Core histone gene dosage regulates DNA damage sensitivity in a checkpoint independent manner. Nucleic Acids Res. 40: 9604-9620.

133. Lin G L, et al (2019) Therapeutic strategies for diffuse midline glioma from high-throughput combination drug screening. Sci Transl Med 11

134. Losman, J. A., et al. (2013). (R)-2-hydroxyglutarate is sufficient to promote leukemogenesis and its effects are reversible. Science 339: 1621-1625.

135. Lowe B R, et al (2019) Histone H3 Mutations: An Updated View of Their Role in Chromatin Deregulation and Cancer. Cancers (Basel) 11

136. Lu, C., et al. (2012). IDH mutation impairs histone demethylation and results in a block to cell differentiation. Nature 483: 474-478.

137. Luedeman M E, et al. (2022). Poly (ADP) ribose polymerase promotes DNA polymerase theta-mediated end joining by activation of end resection. Nature Communications 13: 4547.

138. Luijsterburg M S, et al (2016) PARP1 Links CHD2-Mediated Chromatin Expansion and H3.3 Deposition to DNA Repair by Non-homologous End-Joining. Molecular cell 61: 547-562

139. Lukas C, et al (2011) 53BP1 nuclear bodies form around DNA lesions generated by mitotic transmission of chromosomes under replication stress. Nature cell biology 13: 243-253

140. Lutz K, et al (2022) Essential Management of Pediatric Brain Tumors. Children (Basel) 9

141. MacDonald, T. J., et al. (2011). Treatment of high-grade glioma in children and adolescents. Neuro-oncology 13: 1049-1058.

142. Malla, M., et al. (2023). The evolving role of radiation in pancreatic cancer. Frontiers in Oncology 12: 1060885.

143. Manchana, T., et al. (2019). BRCA mutation in high grade epithelial ovarian cancers. Gynecology and Oncology Reports 29: 102-105.

144. Mandemaker I K, et al (2017) DNA damage-induced histone H1 ubiquitylation is mediated by HUWE1 and stimulates the RNF8-RNF168 pathway. Sci Rep 7: 15353

145. Maru, Y., et al. (2019). Efficient use of patient-derived organoids as a preclinical model for gynecologic tumors. Gynecological Oncology 154: 189-198.

146. Marzluff W F, et al (2002) The human and mouse replication-dependent histone genes. Genomics 80: 487-498

147. Mckinnon P J, et al (2007) DNA strand break repair and human genetic disease. Annu Rev Genomics Hum Genet 8: 37-55

148. Mekonnen, N. et al. (2022). Homologous Recombination Deficiency in Ovarian, Breast, Colorectal, Pancreatic, Non-Small Cell Lung and Prostate Cancers, and the Mechanisms of Resistance to PARP Inhibitors. Frontiers in Oncology 12: 880643.

149. Meng, J., et al. (2010). Combination treatment with MEK and AKT inhibitors is more effective than each drug alone in human non-small cell lung cancer in vitro and in vivo. PloS one 5: e14124.

150. Merigliano C, et al (2021) Multi-scale dynamics of heterochromatin repair. Curr Opin Genet Dev 71: 206-215

151. Mirzayans, R., et al. (2007). A sensitive assay for the evaluation of cytotoxicity and its pharmacologic modulation in human solid tumor-derived cell lines exposed to cancer-therapeutic agents. Journal of Pharmacy & Pharmaceutical Sciences 10: 298s-311s.

152. Misteli T, et al (2000) Dynamic binding of histone H1 to chromatin in living cells. Nature 408: 877-881

153. Mito Y, et al (2005) Genome-scale profiling of histone H3.3 replacement patterns. Nature genetics 37: 1090-1097

154. Mokhtari, R. B., et al. (2017). Combination therapy in combating cancer. Oncotarget 8: 38022-38043.

155. Moore, S. (2009). Pancreatic cancer deaths in Texas veterans. Texas Medical Center Dissertations AAI1470201. https://digitalcommons.library.tmc.edu/dissertations/AAI1470201

156. Moschetta, M., et al. (2016). BRCA somatic mutations and epigenetic BRCA modifications in serous ovarian cancer. Annals of Oncology 27: 1449-55.

157. Mount C W, et al (2018) Potent antitumor efficacy of anti-GD2 CAR T cells in H3-K27M(+) diffuse midline gliomas. Nat Med 24: 572-579

158. Murga M, et al (2007) Global chromatin compaction limits the strength of the DNA damage response. The Journal of cell biology 178: 1101-1108

159. Myung, K., et al. (2003). *Saccharomyces cerevisiae* chromatin assembly factors that act during DNA replication function in the maintenance of genome stability. Proc. Natl. Acad. Sci. USA 100: 6640-6645.

160. Nagaraja S, et al (2017) Transcriptional Dependencies in Diffuse Intrinsic Pontine Glioma. Cancer cell 31: 635-652 e636

161. Nagaraja S, et al (2019) Histone Variant and Cell Context Determine H3K27M Reprogramming of the Enhancer Landscape and Oncogenic State. Molecular cell 76: 965-980 e912

162. Narod, S. A., et al. (2024). Hereditary Breast Cancer Clinical Research Group. The risk of skin cancer in women who carry BRCA1 or BRCA2 mutations. Hereditary Cancer in Clinical Practice 22: 7.

163. Navsaria, L. J., et al. (2024). Skin cancer risk in patients with BRCA mutations. Journal of American Academy of Dermatology International 17: 175-177.

164. Neve, R. M., et al. (2006). A collection of breast cancer cell lines for the study of functionally distinct cancer subtypes. Cancer Cell 10: 515-527.

165. Nijman, S. M. (2011). Synthetic lethality: general principles, utility and detection using genetic screens in human cells. FEBS Letters 585: 1-6.

166. Nyberg, T., et al. 2020. Prostate Cancer Risks for Male BRCA1 and BRCA2 Mutation Carriers: A Prospective Cohort Study. Eur Urol 77: 24-35.

167. Okoye-Okafor, U. C., et al. (2015). New IDH1 mutant inhibitors for treatment of acute myeloid leukemia. Nat Chem Biol 11: 878-886.

168. Ou, Y., et al. (2018). DNA methylation enzyme inhibitor RG108 suppresses the radioresistance of esophageal cancer. Oncol Rep 39: 993-1002.

169. Owens, S., et al. (2020). Incidence Rates of Gynecologic Cancers in the U.S. Active Duty Military Population. Military Medicine 185: e1590-e1595.

170. Paik, E. S., et al. (2023). Prevalence of Homologous Recombination Deficiency in First-Line PARP Inhibitor Maintenance Clinical Trials and Further Implication of Personalized Treatment in Ovarian Cancer. Cancers (Basel) 15: 3095.

171. Palmieri, D., et al. (2009). Vorinostat inhibits brain metastatic colonization in a model of triple-negative breast cancer and induces DNA double-strand breaks. Clin Cancer Res. 15: 6148-6157.

172. Park, S. Y., et al. (2020). A short guide to histone deacetylases including recent progress on class II enzymes. Exp Mol Med. 52: 204-212.

173. Pathania M, et al (2017) H3.3 (K27M) Cooperates with Trp53 Loss and PDGFRA Gain in Mouse Embryonic Neural Progenitor Cells to Induce Invasive High-Grade Gliomas. Cancer cell 32: 684-700 e689

174. Paugh, B. S. et al. (2013). Novel oncogenic PDGFRA mutations in pediatric high-grade gliomas. Cancer Res 73: 6219-6229.

175. Pearson, T., et al. (2008). Non-obese diabetic-recombination activating gene-1 (NOD-Rag1 null) interleukin (IL)-2 receptor common gamma chain (IL2r gamma null) null mice: a radioresistant model for human lymphohematopoietic engraftment. Clinical and Experimental Immunology 154: 270-284.

176. Phillips E O N, et al (2022) Histone variants: The unsung guardians of the genome. DNA repair 112: 103301

177. Phillips, E., et al. (2025). Histone variant H3.3 plays an evolutionarily conserved role in DNA repair that can be targeted for cancer therapy. The EMBO Journal. UNDER REVISON.

178. Piombino C, et al. (2024). Homologous Recombination Repair Deficiency in Metastatic Prostate Cancer: New Therapeutic Opportunities. Int J Mol Sci 25: 4624.

179. Polo S E, et al (2006) New histone incorporation marks sites of UV repair in human cells. Cell 127: 481-493

180. Polo S E, et al (2011) Dynamics of DNA damage response proteins at DNA breaks: a focus on protein modifications. Genes & development 25: 409-433

181. Popovici-Muller, J., et al. (2018). Discovery of AG-120 (Ivosidenib): A First-in-Class Mutant IDH1 Inhibitor for the Treatment of IDH1 Mutant Cancers. ACS Med Chem Lett. 9: 300-305.

182. Prado, F. et al. (2005). Partial depletion of histone H4 increases homologous recombination-mediated genetic instability. Mol. Cell. Biol. 25: 1526-1536.

183. Prado, F., et al. (2004). The absence of the yeast chromatin assembly factor Asf1 increases genomic instability and sister chromatid exchange. EMBO Rep. 5: 497-502.

184. Puleo J., et al. (2021). The MCF10 Model of Breast Tumor Progression. Cancer Research. 81: 4183-4185.

185. Puumalainen M R, et al (2014) Chromatin retention of DNA damage sensors DDB2 and XPC through loss of p97 segregase causes genotoxicity. Nat Commun 5: 3695

186. Richmond T J, et al (2003) The structure of DNA in the nucleosome core. Nature 423: 145-150

187. Rodriguez-Berriguete, G., et al. (2023). Small-molecule Pole inhibitors provide safe and effective tumor radiosensitization in preclinical models. Clinical Cancer Research 23: CCR-22-2977.

188. Rodríguez-Cerrato, V., et al. (2010). Comparative efficacy of novobiocin and amoxicillin in experimental sepsis caused by beta-lactam-susceptible and highly resistant pneumococci. International Journal of Antimicrobial Agents 35: 544-9.

189. Rohle, D., et al. (2013). An inhibitor of mutant IDH1 delays growth and promotes differentiation of glioma cells. Science 340: 626-630.

190. Rosen, M. N., et al. (2021). BRCA mutated pancreatic cancer: A change is coming. World Journal of Gastroenterology 27: 1943-1958.

191. Rosidi B, et al (2008) Histone H1 functions as a stimulatory factor in backup pathways of NHEJ. Nucleic acids research 36: 1610-1623

192. Ross, H. H., et al. (2012). In vivo intermittent hypoxia elicits enhanced expansion and neuronal differentiation in cultured neural progenitors. Experimental Neurology 235: 238-245.

193. Ruis, B. L., et al. (2008). The catalytic subunit of DNA-dependent protein kinase regulates proliferation, telomere length, and genomic stability in human somatic cells. Mol. Cell. Biol. 20: 6182-6195.

194. Sakai A, et al (2009) Transcriptional and developmental functions of the H3.3 histone variant in *Drosophila*. Current biology: CB 19: 1816-1820

195. Sansoni, V., et al. (2014). The histone variant H2A.Bbd is enriched at sites of DNA synthesis. Nucleic Acids Research 42: 6405-6420.

196. Schimmel, J., et al. (2019). Templated Insertions: A Smoking Gun for Polymerase Theta-Mediated End Joining. Trends in Genetics 35: 632-644.

197. Schindelin J, et al (2012) Fiji: an open-source platform for biological-image analysis. Nat Methods 9: 676-682

198. Schnaiter, S., et al. (2024). Stratification of Homologous Recombination Deficiency-Negative High-Grade Ovarian Cancer by the Type of Peritoneal Spread into Two Groups with Distinct Survival Outcomes. Cancers (Basel) 16: 2129.

199. Schuster-Bockler B, et al (2012) Chromatin organization is a major influence on regional mutation rates in human cancer cells. Nature 488: 504-507

200. Schwartzentruber J, et al (2012) Driver mutations in histone H3.3 and chromatin remodelling genes in paediatric glioblastoma. Nature 482: 226-231

201. Scully, R, et al. (2002). BRCA1 and BRCA2 in hereditary breast cancer. Biochimie 84: 95-102.

202. Senra, J. M., et al. (2011). Inhibition of PARP-1 by olaparib (AZD2281) increases the radiosensitivity of a lung tumor xenograft. Molecular Cancer Therapeutics 10: 1949-1958.

203. Shih, A. H., et al. (2012). IDH1 mutations disrupt blood, brain, and barriers. Cancer Cell 22: 285-287.

204. Shu, Y., et al. (2023). Hematological toxicities in PARP inhibitors: A real-world study using FDA adverse event reporting system (FAERS) database. Cancer Medicine 12: 3365-3375.

205. Singh R K, et al (2009) Histone levels are regulated by phosphorylation and ubiquitylation-dependent proteolysis. Nature cell biology 11: 925-933

206. Singh, R. K., et al. (2010). Epigenetic therapy: Targeting histones and their modifications in human disease. Future Med. Chem. 2: 543-548.

207. Singh, R. K., et al. (2012). Novel E3 ubiquitin ligases that regulate histone protein levels in the budding yeast *Saccharomyces cerevisiae*. PloS One 7: e36295.

208. Smits, K. M., et al. (2014). Epigenetics in radiotherapy: where are we heading? Radiother Oncol 111: 168-177.

209. Son, Y., et al. (2020). Treatment of keloids with a single dose of low energy superficial X-ray radiation to prevent recurrence after surgical excision: an in vitro and in vivo study. Journal of American Academy of Dermatology 83: 1304-1314.

210. Sporbert A, et al (2005) PCNA acts as a stationary loading platform for transiently interacting Okazaki fragment maturation proteins. Nucleic acids research 33: 3521-3528

211. Sprague B L, et al (2005) FRAP analysis of binding: proper and fitting. Trends Cell Biol 15: 84-91

212. Stafford, J. M., et al. (2018). Multiple modes of PRC2 inhibition elicit global chromatin alterations in H3K27M pediatric glioma. Sci Adv 4: eaau5935.

213. Stewart G S, et al (2009) The RIDDLE syndrome protein mediates a ubiquitin-dependent signaling cascade at sites of DNA damage. Cell 136: 420-434

214. Stordal, B., et al. (2013). BRCA1/2 mutation analysis in 41 ovarian cell lines reveals only one functionally deleterious BRCA1 mutation. Molecular Oncology 7: 567-579.

215. Strickfaden H, et al (2016) Poly(ADP-ribosyl)ation-dependent Transient Chromatin Decondensation and Histone Displacement following Laser Microirradiation. J Biol Chem 291: 1789-1802.

216. Su, J M et al, Phase I/II trial of vorinostat and radiation and maintenance vorinostat in children with diffuse intrinsic pontine glioma: A Children's Oncology Group report, Neuro-Oncology, Volume 24, Issue 4, April 2022, Pages 655-644.

217. Suijker, J., et al. (2015). The oncometabolite D-2-hydroxyglutarate induced by mutant IDH1 or -2 blocks osteoblast differentiation in vitro and in vivo. Oncotarget 6: 14832-14842.

218. Sun, K., et al. (2018). A comparative pharmacokinetic study of PARP inhibitors demonstrates favorable properties for niraparib efficacy in preclinical tumor models. Oncotarget 9: 37080-37096.

219. Sunada S, et al (2018) Crosstalk of DNA double-strand break repair pathways in poly (ADP-ribose) polymerase inhibitor treatment of breast cancer susceptibility gene 1/2-mutated cancer. Cancer Sci 109: 893-899

220. Szenker E, et al (2011) The double face of the histone variant H3.3. Cell research 21: 421-434

221. Tagami H, et al (2004) Histone H3.1 and H3.3 complexes mediate nucleosome assembly pathways dependent or independent of DNA synthesis. Cell 116: 51-61

222. Takamatsu, S., et al. (2022). Utility of Homologous Recombination Deficiency Biomarkers Across Cancer Types. Journal of Clinical Oncology-Precision Oncology 6: e2200085.

223. Talbert, P. B., et al. (2010). Histone variants—ancient wrap artists of the epigenome. Nat Rev Mol. Cell Biol. 11: 264-275.

224. Tang M C, et al (2015) Contribution of the two genes encoding histone variant h3.3 to viability and fertility in mice. PLoS genetics 11: e1004964

225. Taylor R A, et al. (2019). The influence of BRCA2 mutation on localized prostate cancer. Nat Rev Urol 16: 281-290.

226. Teuber, A., et al. (2024). Avapritinib-based SAR studies unveil a binding pocket in KIT and PDGFRA. Nat Commun 15: 63.

227. Thorslund T, et al (2015) Histone H1 couples initiation and amplification of ubiquitin signalling after DNA damage. Nature 527: 389-393.

228. Timme, C. R., et al. (2018). The DNA-PK Inhibitor VX-984 Enhances the Radiosensitivity of Glioblastoma Cells Grown In Vitro and as Orthotopic Xenografts. Molecular Cancer Therapeutics 17: 1207-1216.

229. Tinkle C L, et al. Phase I study using crenolanib to target PDGFR kinase in children and young adults with newly diagnosed DIPG or recurrent high-grade glioma, including DIPG. Neurooncol Adv. 2021 Dec. 1; 3(1): vdab179.

230. Toh, M., et al. (2021). Homologous Recombination Deficiency: Cancer Predispositions and Treatment Implications. Oncologist 26: e1526-e1537.

231. Tomayko, M. M. et al. (1989). Determination of subcutaneous tumor size in athymic (nude) mice. Cancer. Chemother. Pharmacol. 24: 148-154.

232. Tommasini-Ghelfi, S., et al. (2019). Cancer-associated mutation and beyond: The emerging biology of isocitrate dehydrogenases in human disease. Sci Adv 5: eaaw4543.

233. Torres-Esquius, S., et al. (2024). Prevalence of Homologous Recombination Deficiency Among Patients With Germline RAD51C/D Breast or Ovarian Cancer. JAMA Network Open 7: e247811.

234. Torres-Rosell J, et al (2007) The Smc5-Smc6 complex and SUMO modification of Rad52 regulates recombinational repair at the ribosomal gene locus. Nature cell biology 9: 923-931

235. Tsouroula K, et al (2016) Temporal and Spatial Uncoupling of DNA Double Strand Break Repair Pathways within Mammalian Heterochromatin. Molecular cell 63: 293-305

236. Tung, N., et al. (2022). PARP inhibition in breast cancer: progress made and future hopes. NPJ Breast Cancer 8: 47.

237. Turcan, S., et al. (2012). IDH1 mutation is sufficient to establish the glioma hypermethylator phenotype. Nature 483: 479-483.

238. Urban, D. J., et al. (2017). Assessing inhibitors of mutant isocitrate dehydrogenase using a suite of preclinical discovery assays. Sci Rep 7: 12758.

239. Usman, O. H., et al. (2022). Genomic heterogeneity in pancreatic cancer organoids and its stability with culture. NPJ Genomic Medicine 7: 71.

240. Usman, O. H., et al. (2023) Differential modulation of cellular phenotype and drug sensitivity by extracellular matrix proteins in primary and metastatic pancreatic cancer cells. Molecular Biology of the Cell. 34: ar130.

241. Vahteristo, P., et al. (2001). P53, Chk2, and Chk1 genes in Finnish families with Li Fraumeni syndrome: further evidence of Chk2 in inherited cancer predisposition. Cancer Research 61: 5718-5722.

242. van Bussel M T J, et al (2021) A first-in-man phase 1 study of the DNA-dependent protein kinase inhibitor peposertib (formerly M3814) in patients with advanced solid tumours. Br J Cancer 124: 728-735

243. van der Noll, R., et al. (2015). Long-term safety and anti-tumour activity of olaparib monotherapy after combination with carboplatin and paclitaxel in patients with advanced breast, ovarian or fallopian tube cancer. British Journal of Cancer 113: 396-402.

244. van Holde, K. E. (1988). Chromatin, Springer-Verlag, New York.

245. van Sluis M, et al (2015) A localized nucleolar DNA damage response facilitates recruitment of the homology-directed repair machinery independent of cell cycle stage. Genes & development 29: 1151-1163

246. Venkitaraman, A. R. (2002). Cancer susceptibility and the functions of BRCA1 and BRCA2. Cell 108: 171-82.

247. Venneti, S., et al. (2013). Evaluation of histone 3 lysine 27 trimethylation (H3K27me3) and enhancer of Zest 2 (EZH2) in pediatric glial and glioneuronal tumors shows decreased H3K27me3 in H3F3A K27M mutant glioblastomas. Brain Pathology 23: 558-564.

248. Wang, F., et al. (2013). Targeted inhibition of mutant IDH2 in leukemia cells induces cellular differentiation. Science 340: 622-626.

249. Wang, N., et al. (2022). PARP inhibitor resistance in breast and gynecological cancer: Resistance mechanisms and combination therapy strategies. Frontiers in Pharmacology 13: 967633

250. Watts F Z (2016) Repair of DNA Double-Strand Breaks in Heterochromatin. Biomolecules 6

251. Wen H, et al (2014) ZMYND11 links histone H3.3K36me3 to transcription elongation and tumour suppression. Nature 508: 263-268

252. Willmore, E., et al. (2004). A novel DNA-dependent protein kinase inhibitor, NU7026, potentiates the cytotoxicity of topoisomerase II poisons used in the treatment of leukemia. Blood. 103: 4659-4665.

253. Wittschieben B O, et al (2000) Overlapping roles for the histone acetyltransferase activities of SAGA and elongator in vivo. The EMBO journal 19: 3060-3068

254. Wlodkowic D, et al (2008) Please do not disturb: destruction of chromatin structure by supravital nucleic acid probes revealed by a novel assay of DNA-histone interaction. Cytometry A 73: 877-879

255. Wolffe, A. (1995). Chromatin structure and function, Second Edition, Academic Press, San Diego, CA.

256. Wong L H, et al (2009) Histone H3.3 incorporation provides a unique and functionally essential telomeric chromatin in embryonic stem cells. Genome research 19: 404-414

257. Wong, W., et al. (2020). BRCA Mutations in Pancreas Cancer: Spectrum, Current Management, Challenges and Future Prospects. Cancer Management and Research 12: 2731-2742.

258. Wu G, et al (2012) Somatic histone H3 alterations in pediatric diffuse intrinsic pontine gliomas and non-brainstem glioblastomas. Nature genetics 44: 251-253

259. Xie, G., et al. (2024). Phenotypic, Genomic, and Transcriptomic Heterogeneity in a Pancreatic Cancer Cell Line. Pancreas 53: e748-e759.

260. Xu G, et al (2015) REV7 counteracts DNA double-strand break resection and affects PARP inhibition. Nature 521: 541-544

261. Xu, Y., et al. (2012). Histone H2A.Z controls a critical chromatin remodeling step required for DNA double-strand break repair. Mol. Cell 48: 723-733.

262. Yadav R K, et al (2017) Histone H3G34R mutation causes replication stress, homologous recombination defects and genomic instability in *S. pombe*. Elife 6

263. Yan, H., et al. (2009). IDH1 and IDH2 mutations in gliomas. The New England Journal of Medicine 360: 765-773.

264. Yang X, et al (2013) Histone acetyltransferase 1 promotes homologous recombination in DNA repair by facilitating histone turnover. J Biol Chem 288: 18271-18282

265. Yang, Y., et al. (2022) The roles of histone modifications in tumorigenesis and associated inhibitors in cancer therapy. Journal of the National Cancer Center 2: 277-290.

266. Yang, H., et al. (2012). IDH1 and IDH2 Mutations in Tumorigenesis: Mechanistic Insights and Clinical Perspectives. Clinical Cancer Research 18: 5562-5571.

267. Ye, X., et al. (2003). Defective S phase chromatin assembly causes DNA damage, activation of the S phase checkpoint and S phase arrest. Mol. Cell 11: 341-351.

268. Yoon. S., et al. (2016). HDAC and HDAC Inhibitor: From Cancer to Cardiovascular Diseases. Chonnam Med J. 52: 1-11.

269. Yu, J. R., et al. (2019). PRC2 is high maintenance. Genes Dev 33: 903-935.

270. Zaid, O. et al. (2005). Histones as tumour suppressor genes. Cell Mol Life Sci 62: 1653-1656.

271. Zeitlin S G, et al (2009) Double-strand DNA breaks recruit the centromeric histone CENP-A. Proceedings of the National Academy of Sciences of the United States of America 106: 15762-15767

272. Zhang, X., et al. (2019). Oncohistone Mutations in Diffuse Intrinsic Pontine Glioma. Trends Cancer 5: 799-808.

273. Zhao Y, et al (2006) Preclinical evaluation of a potent novel DNA-dependent protein kinase inhibitor NU7441. Cancer research 66: 5354-5362

274. Zhao, Q., et al. (2018). Optimization of 3-Pyrimidin-4-yl-oxazolidin-2-ones as Orally Bioavailable and Brain Penetrant Mutant IDH1 Inhibitors. ACS Med Chem Lett 9: 746-751.

275. Zheng. L., et al. (2003). S phase activation of the histone H2B promoter by OCA-S, a coactivator complex that contains GAPDH as a key component. Cell 114: 255-66.

276. Zhou, J., et al. (2021). A first-in-class Polymerase Theta Inhibitor selectively targets Homologous-Recombination-Deficient Tumors. Nature Cancer 2: 598-610.

277. Zhu, X., et al. (2018). The pivotal role of DNA methylation in the radio-sensitivity of tumor radiotherapy. Cancer Med 7: 3812-3819.

278. Zielske, S. P. (2015). Epigenetic DNA methylation in radiation biology: on the field or on the sidelines? J Cell Biochem 116: 212-217.

What is claimed is:

1. A method for treating cancer in a subject, the method comprising: (a) administering at least one drug from each of at least three classes selected from an inhibitor of poly-ADP ribose polymerase (PARP inhibitor), an inhibitor of histone deacetylase (HDAC inhibitor) and a platelet-derived growth factor receptor inhibitor (PDGFR inhibitor) to the subject; and (b) administering radiation to the subject;

wherein the PDGFR inhibitor is Avapritinib, the PARP inhibitor is niraparib, and the HDAC inhibitor is vorinostat; and wherein the cancer comprises glioma, breast cancer, ovarian cancer, pancreatic cancer, prostate cancer, or a combination thereof.

2. The method of claim 1, wherein dosages for the at least one drug from each of the at least three classes are lower than individual dosages for each of the drugs when administered separately.

3. The method of claim 1, wherein the at least one drug from each of the at least three classes are administered orally, intravenously, or any combination thereof.

4. The method of claim 1, wherein radiation in step (b) is administered to the subject at a dose of less than or equal to about 2 Gy.

5. The method of claim 4, wherein radiation in step (b) is administered at least 10 times.

6. The method of claim 1, wherein radiation is delivered in a lower dose than without performing the method.

7. The method of claim 1, wherein performing the method results in a reduction or elimination of at least one side effect relative to a cancer treatment not including each of steps (a) and (b).

8. The method of claim 7, wherein the at least one side effect comprises myelodysplastic syndrome (MDS), acute myeloid leukemia (AML), bone marrow suppression, a low white blood cell count, weakness, weight loss, fever, frequent infections, blood in urine, blood in stool, shortness of breath, fatigue, bruising more easily, bleeding more easily, shortness of breath, fever, cough, wheezing, pneumonitis, blood clots, nausea, vomiting, tiredness, weakness, low red blood cell count, diarrhea, loss of appetite, headache, changes in food taste, dizziness, indigestion, heartburn, low platelet count, QT prolongation, or any combination thereof.

9. The method of claim 1, wherein performing the method does not induce drug resistance in the cancer.

10. The method of claim 1, wherein performing the method induces partial or complete remission of the cancer.

11. The method of claim 1, wherein the PARP inhibitor is niraparib.

12. The method of claim 1, wherein the PDGFR inhibitor is Avapritinib.

13. The method of claim 1, wherein the HDAC inhibitor is vorinostat.

* * * * *